United States Patent
Amberg et al.

(10) Patent No.: US 8,957,089 B2
(45) Date of Patent: Feb. 17, 2015

(54) TETRAHYDROISOQUINOLINES, PHARMACEUTICAL COMPOSITIONS CONTAINING THEM, AND THEIR USE IN THERAPY

(71) Applicants: AbbVie Deutschland GmbH & Co. KG, Wiesbaden (DE); AbbVie Inc., North Chicago, IL (US)

(72) Inventors: Wilhelm Amberg, Wiesbaden (DE); Michael Ochse, Wiesbaden (DE); Udo Lange, Mannheim (DE); Wilfried Braje, Wiesbaden (DE); Berthold Behl, Wiesbaden (DE); Wilfried Hornberger, Wiesbaden (DE); Mario Mezler, Wiesbaden (DE); Charles Hutchins, Green Oaks, IL (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 13/792,105

(22) Filed: Mar. 10, 2013

(65) Prior Publication Data

US 2013/0203749 A1    Aug. 8, 2013

Related U.S. Application Data

(62) Division of application No. 12/933,326, filed as application No. PCT/EP2009/053800 on Mar. 31, 2009, now Pat. No. 8,653,100.

(60) Provisional application No. 61/041,313, filed on Apr. 1, 2008.

(51) Int. Cl.
| | |
|---|---|
| C07D 217/18 | (2006.01) |
| C07D 401/04 | (2006.01) |
| A61K 31/44 | (2006.01) |
| C07D 401/06 | (2006.01) |
| C07D 401/12 | (2006.01) |
| C07D 409/12 | (2006.01) |
| C07D 409/14 | (2006.01) |
| C07D 413/12 | (2006.01) |
| C07D 413/14 | (2006.01) |
| C07D 417/12 | (2006.01) |
| C07D 498/04 | (2006.01) |
| C07D 513/04 | (2006.01) |
| C07D 401/08 | (2006.01) |

(52) U.S. Cl.
CPC ............ *C07D 217/18* (2013.01); *C07D 401/04* (2013.01); *C07D 401/06* (2013.01); *C07D 401/12* (2013.01); *C07D 409/12* (2013.01); *C07D 409/14* (2013.01); *C07D 413/12* (2013.01); *C07D 413/14* (2013.01); *C07D 417/12* (2013.01); *C07D 498/04* (2013.01); *C07D 513/04* (2013.01); *C07D 401/08* (2013.01)
USPC ............................ 514/307; 546/148; 546/149

(58) Field of Classification Search
None
See application file for complete search history.

(56) References Cited

U.S. PATENT DOCUMENTS

| | | | |
|---|---|---|---|
| 4,927,838 | A | 5/1990 | Guthrie et al. |
| 5,506,246 | A | 4/1996 | Junge et al. |
| 5,519,034 | A | 5/1996 | Kozlik et al. |
| 5,545,755 | A | 8/1996 | Lin et al. |
| 6,057,357 | A | 5/2000 | Horwell et al. |
| 6,331,636 | B1 | 12/2001 | Romero et al. |
| 6,426,346 | B1 | 7/2002 | Pruitt et al. |
| 7,189,850 | B2 | 3/2007 | Ceccarelli et al. |
| 7,427,612 | B2 | 9/2008 | Alberati-giani et al. |
| 7,462,617 | B2 | 12/2008 | Alberati-giani et al. |
| 7,511,013 | B2 | 3/2009 | Molino et al. |
| 7,514,068 | B2 | 4/2009 | Tung |
| 7,521,421 | B2 | 4/2009 | Naicker et al. |
| 7,528,131 | B2 | 5/2009 | Persichetti et al. |

(Continued)

FOREIGN PATENT DOCUMENTS

| | | |
|---|---|---|
| DE | 10315570 | 10/2004 |
| EP | 0091241 | 10/1983 |

(Continued)

OTHER PUBLICATIONS

Bermejo, A. et al., "Syntheses and antitumor targeting G1 phase of the cell cycle of benzoyldihydroisoquinolines and related 1-substituted isoquinolines," J. Med. Chem. (2002) 45:5058-5068.

(Continued)

*Primary Examiner* — Zinna Northington Davis
(74) *Attorney, Agent, or Firm* — Lisa V. Mueller; Michael Best & Friedrich LLP

(57) ABSTRACT

The present invention relates to tetrahydroisoquinoline of the formula (I)

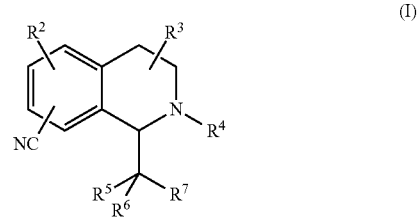

or a physiologically tolerated salt thereof.
The invention relates to pharmaceutical compositions comprising such tetrahydroisoquinolines, and the use of such tetrahydroisoquinolines for therapeutic purposes. The tetrahydroisoquinolines are GlyT1 inhibitors.

15 Claims, No Drawings

(56) References Cited

U.S. PATENT DOCUMENTS

| | | |
|---|---|---|
| 7,531,685 B2 | 5/2009 | Czarnik |
| 7,534,814 B2 | 5/2009 | Ascher et al. |
| 7,538,189 B2 | 5/2009 | Naicker et al. |
| 8,420,670 B2 | 4/2013 | Amberg et al. |
| 8,563,617 B2 | 10/2013 | Amberg et al. |
| 8,642,587 B2 | 2/2014 | Lange et al. |
| 8,653,100 B2 | 2/2014 | Amberg et al. |
| 2002/0169197 A1 | 11/2002 | Egle et al. |
| 2003/0083359 A1 | 5/2003 | Lee et al. |
| 2004/0026364 A1 | 2/2004 | Kihara et al. |
| 2005/0124627 A1 | 6/2005 | Schadt et al. |
| 2005/0153963 A1 | 7/2005 | Dargazanli et al. |
| 2005/0153980 A1 | 7/2005 | Schadt et al. |
| 2005/0159450 A1 | 7/2005 | Dargazanli et al. |
| 2005/0267152 A1 | 12/2005 | Bloomfield et al. |
| 2006/0074105 A1 | 4/2006 | Ware et al. |
| 2006/0223802 A1 | 10/2006 | Dargazanli et al. |
| 2006/0223861 A1 | 10/2006 | Dargazanli et al. |
| 2006/0223885 A1 | 10/2006 | Dargazanli et al. |
| 2006/0223886 A1 | 10/2006 | Dargazanli et al. |
| 2007/0021408 A1 | 1/2007 | Molino et al. |
| 2007/0155753 A1 | 7/2007 | Ye et al. |
| 2007/0214087 A1 | 9/2007 | Kawaguchi et al. |
| 2008/0070941 A1 | 3/2008 | Dargazanli et al. |
| 2008/0119486 A1 | 5/2008 | Jolidon et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0222346 A1 | 9/2010 | Amberg et al. |
| 2010/0273739 A1 | 10/2010 | Amberg et al. |
| 2011/0009378 A1 | 1/2011 | Lange et al. |
| 2012/0077796 A1 | 3/2012 | Pohlki et al. |
| 2012/0088790 A1 | 4/2012 | Pohlki et al. |
| 2012/0316153 A1 | 12/2012 | Amberg et al. |
| 2013/0035323 A1 | 2/2013 | Amberg et al. |
| 2013/0131132 A1 | 5/2013 | Amberg et al. |
| 2013/0184238 A1 | 7/2013 | Amberg et al. |
| 2013/0210880 A1 | 8/2013 | Amberg et al. |

FOREIGN PATENT DOCUMENTS

| | | |
|---|---|---|
| EP | 0258755 | 3/1988 |
| EP | 0303961 | 2/1989 |
| EP | 0420064 | 4/1991 |
| EP | 1199306 | 4/2002 |
| EP | 1254662 | 11/2002 |
| EP | 1284257 | 2/2003 |
| EP | 2246331 | 11/2010 |
| WO | WO 81/03491 | 12/1981 |
| WO | WO 90/15047 | 12/1990 |
| WO | WO 92/06967 | 4/1992 |
| WO | WO 92/19234 | 11/1992 |
| WO | WO 92/22533 | 12/1992 |
| WO | 93/13073 | 7/1993 |
| WO | WO 93/13073 | 7/1993 |
| WO | WO 95/07271 | 3/1995 |
| WO | WO 97/10223 | 3/1997 |
| WO | WO 97/45115 | 12/1997 |
| WO | WO 98/04521 | 2/1998 |
| WO | WO 98/56757 | 12/1998 |
| WO | WO 00/20376 | 4/2000 |
| WO | WO 01/09120 | 2/2001 |
| WO | WO 02/076979 A1 * | 10/2002 |
| WO | 03031435 | 4/2003 |
| WO | WO 03/045924 | 6/2003 |
| WO | 03053942 | 7/2003 |
| WO | 03055478 | 7/2003 |
| WO | 03076420 | 9/2003 |
| WO | 03087086 | 10/2003 |
| WO | 03089411 | 10/2003 |
| WO | WO 03/097586 | 11/2003 |
| WO | WO 2004/007468 | 1/2004 |
| WO | 2004013100 | 2/2004 |
| WO | 2004013101 | 2/2004 |
| WO | 2004022528 | 3/2004 |
| WO | 2004072034 | 8/2004 |
| WO | WO 2004/071445 | 8/2004 |
| WO | WO 2004/080968 | 9/2004 |
| WO | 2004096761 | 11/2004 |
| WO | 2004112787 | 12/2004 |
| WO | 2004113280 | 12/2004 |
| WO | 2004113301 | 12/2004 |
| WO | WO 2004/110149 | 12/2004 |
| WO | 2005014563 | 2/2005 |
| WO | 2005023260 | 3/2005 |
| WO | 2005023261 | 3/2005 |
| WO | 2005037781 | 4/2005 |
| WO | 2005037782 | 4/2005 |
| WO | 2005037783 | 4/2005 |
| WO | 2005037785 | 4/2005 |
| WO | 2005037792 | 4/2005 |
| WO | 2005040166 | 5/2005 |
| WO | 2005046601 | 5/2005 |
| WO | 2005049023 | 6/2005 |
| WO | 2005058317 | 6/2005 |
| WO | 2005058882 | 6/2005 |
| WO | 2005058885 | 6/2005 |
| WO | WO 2005/099353 | 10/2005 |
| WO | WO 2005/123681 | 12/2005 |
| WO | WO 2006/008754 | 1/2006 |
| WO | WO 2006/034235 | 3/2006 |
| WO | WO 2006/063709 | 6/2006 |
| WO | WO 2006/082001 | 8/2006 |
| WO | WO 2006/102760 | 10/2006 |
| WO | WO 2006/121767 | 11/2006 |
| WO | WO 2007/143823 | 12/2007 |
| WO | WO 2008/038053 | 4/2008 |
| WO | WO 2008/148755 | 12/2008 |
| WO | WO 2009/024611 | 2/2009 |
| WO | WO 2009/121872 | 10/2009 |
| WO | WO 2010/020548 | 2/2010 |
| WO | WO 2010/025856 | 3/2010 |
| WO | WO 2010/029180 | 8/2010 |
| WO | WO 2010/092181 | 8/2010 |
| WO | WO 2010/138901 | 12/2010 |
| WO | WO 2012/020130 | 2/2012 |
| WO | WO 2012/020131 | 2/2012 |
| WO | WO 2012/020133 | 2/2012 |
| WO | WO 2012/152915 | 11/2012 |

OTHER PUBLICATIONS

Ashby, E.C. et al., "Single electron transfer in reactions of alkyl halides with lithium thiolates," J. Org. Chem. (1985) 50(25):5184-5193.

Barbasiewicz, M. et al., "Intermolecular reactions of chlorohydrine anions: acetalization of carbonyl compounds under basic conditions," Org. Lett. (2006) 8(17):3745-3748.

Belliotti, T.R. et al., "Structure-activity relationships of pregabalin and analogues that target the alpha(2)-delta protein," J. Med. Chem. (2005) 48(7):2294-2307.

Beylot, M. et al., "In vivo studies of intrahepatic metabolic pathways," Diabetes Metabolism (1997) 23(3):251-257.

Bishop, D.C., "Analgetics based on the azetidine ring," Azetidine Analgetics (1968) 11:466-470.

Blagojevic, N. et al., "Role of heavy water in boron neutron capture therapy," Topics in Dosimetry and Treatment Planning for Neutron Capture Thearpy (1994) 125-134.

Blake, M.I. et al., "Studies with deuterated drugs," J. Pharm. Sci. (1975) 64(3):367-391.

Boulay, D. et al., "Characterization of SSR 103800, a selective inhibitor of the glycine transporter-1 in models predictive of therapeutic activity in schizophrenia," Pharmacology, Biochemistry and Behavior (2008) 91:47-58.

(56) References Cited

OTHER PUBLICATIONS

Brickner, S.J. et al., "Synthesis and antibacterial activity of U-100592 and U-100766, two oxazolidinone antibacterial agents for the potential treatment of multidrug-resistant gram-positive bacterial infections," J. Med. Chem. (1996) 39(3):673-679.

Burn, D., "Alkylation with the vilsmeier reagent," Chem. And Industry (1973) 870-873.

Burns, N.Z. et al., "Total synthesis of haouamine A: the indeno-tetrahydropyridine core," Tetrahedron (2009) 65(33):6600-6610.

Butte, N.F. et al., "Measurement of milk intake: tracer-to-infant deuterium dilution method," Br. J. Nutrition (1991) 65:3-14.

Cheng, Y. et al., "Relationship between the inhibition constant (KI) and the concentration of inhibitor which causes 50 percent inhibition ($I_{50}$) of an enzymatic reaction," Biochem. Pharmacol. (1973) 22:3099-3108.

Cheung, F.K. et al., "The use of a [4+2] cycloadditional reaction for the preparation of a series of 'tethered' Ru(II)-diamine and aminoalcohol complexes," Org. & Biomol. Chem. (2007) 5(7):1093-1103.

Chrzanowska, M. et al., "Asymmetric synthesis of isoquinoline alkaloids," Chem. Rev. (2004) 104(7):3341-3370.

Clayden et al., Tetra. Lett. (2003) 44(15):3059-3062.

Clezy, P.S. et al., "Preparation of a deuterated analogue of tetrahydropapaveroline suitable for use as an internal standard for G.C./M.S. analysis of this alkaloid: retro pictet-spengler condensation," Australian J. Chem. (1998) 41:483-491.

Colandrea, V.J. et al., "Synthesis and regioselective alkylation of 1.6- and 1.7-naphthyridines," Tetra. Lett. (2000) 41:8053-8057.

Coward, W.A. et al., "New method for measuring milk intakes in breast-fed babies," The Lancet (1979) 13-14.

Czajka, D.M. et al., "Effect of deuterium oxide on the reproductive potential of mice," Annals of the New York Academy of Sciences (1960) 84:770-779.

Czajka, D.M. et al., "Physiological effects of deuterium on dogs," Am. J. Physiology (1961) 201(2):357-362.

Denkewalter, R.G. et al., Progress of Pharmaceutical Research, Drug Research (1966) 10:223-226.

Di, L. et al., "Optimization of a higher throughput microsomal stability screening assay for profiling drug discovery candidates," J. Biomol. Screening (2003) 8(4):453-462.

Dohi, T. et al., "Glycine transporter inhibitors as a novel drug discovery strategy for neuropathic pain," Pharma. & Therapeutics (2009) 123(1):54-79.

Duan, Z.C. et al., "Highly enantioselective Rh-catalyzed hydrogenation of beta gamma-unsaturated phosphonates with chiral ferrocene-based monophosphoramidite ligands," J. Org. Chem. (2009) 74(23):9191-9194.

Erhunmwunse, M.O. et al., "A novel rearrangement reaction of beta-diaxo-alpha-ketoacetals," Tetra. Lett. (2009) 50:3568-3570.

Ferles, M. et al., "Reduction of 1-isoquinolyl-dimethylmethanol and 1-(1-isoquinolyl)cyclohexanon," Collection of Czechoslovak Chem. Comm. (1981) 46(1):262-265.

Fiedler, H.B., "Lexikon der hilfsstoffe fur pharmazie, Kosmetik und angrenzende Gebiete," (1996) 4th Edition, Table of Contents.

Foster, A.B. et al., "Deuterium isotope effects in the metabolism of drugs and xenobiotics: implications for drug design," Advances in Drug Research (1985) 14:2-36.

Fraser et al., Canadian Journal of Chemistry (1971) 49(5):800-802.

Grant & Hackh's Chemical Dictionary, 5th Edition (1987), p. 148.

Green, G.M. et al., "Polystyrene-supported benzenesulfonyl azide: a diazo transfer reagent that is both efficient and safe," J. Org. Chem. (2001) 66(7):2509-2511.

Greene, T.W. et al., in Protective Groups in Organic Synthesis, 2nd Edition, John Wiley & Sons, Inc., (1991) Table of Contents.

Greene, T.W. et al., in Protective Groups in Organic Synthesis, 3rd Edition, John Wiley & Sons, Inc., (1999) Preface, Table of Contents and Abbreviations.

Guillonneau, C. et al., "Synthesis of 9-O-substituted derivatives of 9-hydroxy-5, 6-dimethyl-6H-pyrido[4,3- b]carbazole-1-carboxylic acid (2-(dimethylamino)ethyl)amide and their 10- and 11-methyl analogues with improved antitumor activity," J. Med. Chem. (1999) 42(12):2191-2203.

Gupta, A. et al., "Simple and efficient synthesis of steroidal hybrids of estrogen and vitamin D3," Synthetic Comm. (2009) 39:61-69.

Hashimoto, K. "Glycerine transport inhibitors for the treatment of schizophrenia," The Open Medicinal Chemistry Journal (2010) 4:10-19.

Hashimoto, K. et al., "Phencyclidine-induced cognitive deficits in mice are improved by subsequent subchronic administration of the glycine transporter-1 inhibitor NFPS and D-serine," Eurp. Neuropsychopharmacology (2008) 18:414-421.

Hillier, M.C. et al., "A one-pot preparation of 1,3-disubstituted azetidines," J. Org. Chem. (2006) 71(20):7885-7887.

Ikunaka, M. et al., "The highly selective equatorial hydride delivery by biocatalysis: chemoenzymatic synthesis of trans-2-(4-propylcyclohexyl)-1,3-propanediol via cis-4-propylcyclohexanol," Organic Process Research and Development (2004) 8(3):389-395.

Jellimann, C. et al., "Synthesis of phenalene and acenaphthene derivatives as new conformationally restricted ligands for melatonin receptors," J. Med. Chem. (2000) 43(22):4051-4062.

Jensen, B.L. et al., "Total synthesis of 4,5,7a,8-tetrahydro-1,2-dimethoxyphenanthro[10,1-bc]-azepin-6(7H)-one: a photochemical approach," J. Heterocyclic Chem. (1986) 23:343-347.

Jetter, M.C. et al., "Heteroaryl beta-tetralin ureas as novel antagonists of human TRPV1," Bioorg. Med. Chem. Lett. (2007) 17(22):6160-6163.

Jutz, C. et al., "The Vilsmeier-Haackarnold acylations. C-C bond-forming reactions of chloromethyleniminium ions," Adv. Org. Chem. (1976) 9(1):225-342.

Kaiser, C. et al., "6,7-dichloro-1-(3,4,5-trimethyoxygenzyl)-1,2,3,4-tetrahydroisoquinoline. A structurally novel beta-adrenergic receptor blocking agent," J. Med. Chem. (1986) 29(11):2381-2384.

Kato, S. et al., "Synthesis of deuterated mosapride citrate," J. Labelled Compounds and Radiopharmaceuticals (1995) 36(10):927-932.

King, F.D., editor "Bioisosteres, conformational restriction and pro-drugs—case history: an example of a conformational restriction approach," Medical Chemistry: Principles and Practice (1994), Chapter 14, 206-209.

Kinney, G.G. et al., "The glycerine transporter type 1 inhibitor N-[3-(4'-fluorophenyl)-3-(4'-phenylphenoxy) propyl] sarcosine potentiates NMDA receptor-mediated responses in vivo and produces an antipsychotic profile in rodent behavior," The Journal of Neurosci. (2003) 23(20):7586-7591.

Kocienski, P.J., Protective Groups, Georg Thieme Verlag Stuttgart, Germany, Table of Contents (1994).

Kreher, R.P., Hetarene II, Georg Thieme Verlag Stuttgart, Germany (1991) 583-726.

Kuhakarn, C. et al., "Synthesis of alkylated indolizidine alkaloids via pummerer mediated cyclization: synthesis of indolizidine 167B, 5-butylindolizidine and monomorine I," Tetrahedron (2008) 64(8):1663-1670.

Kushner et al., "Pharmacological uses and perspectives of heavy water and deuterated compounds," Canadian J. Physiol. Pharmacol. (1999) 77(2):79-88.

Lindsley, C.W. et al., "Design, synthesis, and in vivo efficacy of glycine transporter-1 (GlyT1) inhibitors derived from a series of [4-phenyl-1-(propylsulfonyl)piperidin-4-yl]methyl benzamides," Chem. Med. Chem. (2006) 1(8):807-811.

Lizondo, J. et al., "Linezolid: oxazolindinone antibacterial," Drugs of the Future (1996) 21(11):1116-1123.

Lowe, J. et al., "A novel-nonsubstrate-based series of glycine type 1 transporter inhibitors derived from high-throughput screening," Bioorg. Med. Chem. Lett. (2007) 17(6):1675-1678.

Maclennan, A.H. et al., "Neonatal body water turnover: a putative index of perinatal morbidity," Amer. J. Obstetrics & Gynecology (1981) 139(8):948-952.

Mai, K. et al., "A fast n-substituted alpha-aminonitrile synthesis," Synthetic Commun. (1985) 15(2):157-163.

Mallesham, B. et al., "Highly efficient cul-catalyzed coupline of aryl bromides with oxazolidinones using Buchwald's protocol: a short route to linezolid and toloxatone," Org. Lett. (2003) 5(7):963-965.

(56) References Cited

OTHER PUBLICATIONS

McOmie, J.F.W., ed., Protective Groups in Organic Chemistry, Plenum Press (1973) Table of Contents.
Meek, J.S. et al., "Diels-Alder reactions of 9-substituted anthracenes.1 II. 9-cyanoanthracene," J. Amer. Chem. Soc. (1956) 78(20):5413-5416.
Memetzidis, G. et al., "Synthesis of aromatic chloroberbines," Heterocycles (1990) 31(2):341-351.
Mezler, M. et al., "Inhibitors of GlyT1 affect glycine transport via discrete binding sites," Mol. Pharmacol. (2008) 74(6):1705-1715.
Munson, P.J. et al., "Ligand: a versatile computerized approach for characterization of ligand-binding systems," Anal. Biochem. (1980) 107(1):220-239.
Nunez, E. et al., "Differential effects of the tricyclic antidepressant amoxapine on glycine uptake mediated by the recombinant GLYT1 and CLYT2 glycine transporters," Br. J. Pharm. (2000) 129(1):200-206.
Obach, R.S., "Prediction of human clearance of twenty-nine drugs from hepatic microsomal intrinsic clearance data: an examination of in vitro half-life approach and nonspecific binding to microsomes," Drug Metabolism and Disposition (1999) 27(11):1350-1359.
Obach, R.S., "The prediction of human clearance from hepatic microsomal metabolism data," Curr. Opin. Drug Disc. & Development (2001) 4(1):36-44.
Paal, T.A. et al., "Lipase-catalyzed kinetic and dynamic kinetic resolution of 1,2,3,4-tetrahydroisoquinoline-1-carboxylic acid," Tetrahedron: asymmetry (2007) 18(12):1428-1433.
Papageorgiou, C. et al., "163 synthesis of hydroxy-and methoxy-substituted octahydrobenzo[g]isoquinolines as potential ligands for serotonin receptors," Helvetica Chimica Acta (1989) 72:1463-1470.
Pinard, E. et al., "Selective gly T1 inhibitors: discovery of [4-(3-fluoro-5-trifluoremethylpyridin-2-yl)piperazin-1-yl]-][5-methanesulfonyl-2-((S)-2,2,2-trifluoro-1-methylethoxy)phenyl)methanone (RG1678), a promising novel medicine to treat schizophrenia," J. Med. Chem. (2010) 53:4603-4614.
Pitts, M.R. et al., "Indium metal as a reducing agent in organic synthesis," J. Chem Soc. Perkin Transactions (2001) 1:955-977.
Pons, G. et al., "Stable isotopes labeling of drugs in pediatric clinical pharmacology," Pediatrics (1999) 104(3-2):633-639.
Prout, F.S. et al., "3-Benzyl-3-Methylpentanoic acid," Organic Syntheses, Coll. (1963) 4:93; (1955) 35:6.
Quirante, J. et al., "Synthesis of diazatricyclic core of magangamines from Cis-perhydroisoquinolines," J. Org. Chem. (2008) 73(7):768-771.
Rand et al., "Indium (III) chloride-promoted rearrangement of epoxides: a selective synthesis of substituted benzylic aldehydes and ketones," J. Org. Chem. (1998) 8212-8216.
Reddy, K.S. et al., "Synthesis of a 9-fluorenone derived beta-amino alcohol ligand depicting high catalytic activity and pronounced nonlinear stereochemical effects," Synthesis (2000) 1:165-176.
Reddy, M.P. et al., "Applications of the Vilsmeier reaction. 13. Vilsmeier approach to polycyclic aromatic hydrocarbons," J. Org. Chem. (1981) 46:5371-5373.
Reimann, E. et al., "A convenient synthesis of 1-benzyl-1,2,3,4-tetrahydroisoquinolines by combined Strecker/Bruylants reaction," Monatshefte fur Chemie/Chemical Monthly (2004) 135(10):1289-1295.
Rodewald, L.E. et al., "Deuterium oxide as a tracer for measurement of compliance in pediatric clinical drug trials," J. Pediatrics (1989) 114(5):885-891.
Schwarcz, H.P., "Use of stable isotopes to determine compliance," Controlled Clinical Trials (1984) 5(Supp 4):573-575.
Schwarz, J.B. et al., "Novel cyclopropyl beta-amino acid analogues of pregabalin and gabapentin that target the alpha2-delta protein," J. Med. Chem. (2005) 48(8):3026-3035.
Sharma, S.D. et al., "Phosphorous oxychloride (POCl3): a key molecule in organic synthesis," Indian J. Chem. (1998) 37B:965-978.
Sur, C. et al., "Glycine transporter 1 inhibitors and modulation of NMDA receptor-mediated excitatory neurotransmission," Curr. Drug Targets (2007) 8:643-649.
Taber, D.F. et al., "Enantioselective ring construction: synthesis of (+)-alpha-cuparenone," J. Amer. Chem. Soc. (1985) 107:196-199.
Tavares, F.X. et al., "Potent, selective, and orally efficacious antagonists of melanin-concentrating hormone receptor 1," J. Med. Chem. (2006) 49(24):7095-7107.
Thompson, H.W. et al., "Stereochemical control of reductions. 9. Haptophilicity studies with 1,1-disubstituted 2-methyleneacenaphthenes," J. Org. Chem. (2002) 67(9):2813-2825.
Thomson, J.F., "Physiological effects of D20 in mammals," Annals of the N.Y. Academy of Sci. (1960) 84:736-744.
Ting, P.C. et al., "The synthesis of substituted bipiperidine amide compounds as CCR3 antagonists," Bioorg. Med. Chem. Lett. (2005) 15(5):1375-1378.
Tsai, G. et al., "Gene knockout of glycine transporter 1: characterization of the behavioral phenotype," PNAS (2004) 101(22):8485-8490.
Vogel, S. et al., "Palladium-catalyzed intramolecular allylic alkylation of alpha-sulfinyl carbanions: a new asymmetric route to enantiopure gamma-lactams," Tetra. Lett. (2010) 51(11):1459-1461.
White, J.D. et al., "Catalyzed asymmetric diels-alder reaction of benzoquinone. Total synthesis of (−)-ibogamine," Org. Lett. (2000) 2(15):2373-2376.
Zhao, Z. et al., "Synthesis and SAR of GlyT1 inhibitors derived from a series of N-(4-(morpholine-4-carbonyl)-1-(propylsulfonyl) piperidin-4-yl) methyl) benzamindes," Bioorg. Med. Chem. Lett. (2006) 16(23):5968-5972.
Zhou, D. et al., "Studies toward the discovery of the next generation of antidepressants. Part 5: 3,4-dihydro-2H-benzo[1,4]oxazine derivatives with dual 5-HT1A receptor and serotonin transporter affinity," Bioorg. Med. Chem. Lett. (2006) 16(5):1338-1341.
United States Patent Office Notice of Allowance for U.S. Appl. No. 12/706,326 dated Jun. 11, 2013 (10 pages).
United States Patent Office Notice of Allowance for U.S. Appl. No. 12/706,326 dated Feb. 21, 2013 (9 pages).
United States Patent Office Action for U.S. Appl. No. 12/706,326 dated Sep. 21, 2012 (7 pages).
United States Patent Office Notice of Allowance for U.S. Appl. No. 12/666,629 dated Dec. 11, 2012 (5 pages).
United States Patent Office Action for U.S. Appl. No. 12/666,629 dated Jul. 5, 2012 (11 pages).
United States Patent Office Notice of Allowance for U.S. Appl. No. 12/706,321 dated Sep. 30, 2013 (10 pages).
United States Patent Office Action for U.S. Appl. No. 12/706,321 dated Jul. 19, 2012 (7 pages).
United States Patent Office Action for U.S. Appl. No. 12/706,321 dated Mar. 27, 2012 (11 pages).
United States Patent Office Notice of Allowance for U.S. Appl. No. 12/933,326 dated Jan. 9, 2014 (2 pages).
United States Patent Office Notice of Allowance for U.S. Appl. No. 12/933,326 dated Dec. 9, 2013 (4 pages).
United States Patent Office Notice of Allowance for U.S. Appl. No. 12/933,326 dated Oct. 1, 2013 (8 pages).
United States Patent Office Notice of Allowance for U.S. Appl. No. 12/933,326 dated Jan. 11, 2013 (5 pages).
United States Patent Office Action for U.S. Appl. No. 12/933,326 dated Oct. 29, 2012 (6 pages).
United States Patent Office Notice of Allowance for U.S. Appl. No. 13/206,937 dated Feb. 21, 2014 (9 pages).
United States Patent Office Action for U.S. Appl. No. 13/206,937 dated Aug. 28, 2013 (6 pages).
United States Patent Office Action for U.S. Appl. No. 13/206,750 dated Feb. 19, 2014 (6 pages).
United States Patent Office Notice of Allowance for U.S. Appl. No. 13/207,030 dated Mar. 11, 2014 (9 pages).
United States Patent Office Notice of Allowance for U.S. Appl. No. 13/207,160 dated Mar. 17, 2014 (9 pages).
United States Patent Office Action for U.S. Appl. No. 13/566,051 dated Sep. 16, 2013 (15 pages).
United States Patent Office Action for U.S. Appl. No. 13/680,488 dated Dec. 5, 2013 (17 pages).

(56) References Cited

OTHER PUBLICATIONS

United States Patent Office Action for U.S. Appl. No. 13/680,488 dated Jun. 21, 2013 (43 pages).
International Search Report for Application No. PCT/EP2010/051903, mailed May 26, 2010.
International Search Report for Application No. PCT/EP2008/061007 dated Aug. 10, 2009 (6 pages).
International Search Report for Application No. PCT/EP2009/053800 dated Nov. 20, 2009 (6 pages).
International Search Report for Application No. PCT/EP2012/058760 dated Aug. 27, 2012 (4 pages).
International Search Report for Application No. PCT/EP2012/065294 dated Sep. 21, 2012 (4 pages).
Written Opinion for Application No. PCT/EP2010/051903, mailed Aug. 16, 2011.
Written Opinion for Application No. PCT/EP2008/061007 dated Aug. 10, 2009 (7 pages).
Written Opinion for Application No. PCT/EP2009/053800 dated Nov. 20, 2009 (7 pages).
Written Opinion for Application No. PCT/EP2012/058760 dated Aug. 27, 2012 (4 pages).
Hashimoto, Kenji, "Glycine transporter inhibitors as therapeutic agents for schizophrenia," Recent Patents on CNS Drug Discovery (2006) 1:43-53.
Harsing, L.G. et al., "Glycine transporter Type-1 and its inhibitors," Curr. Med. Chem. (2006) 13:1017-1044.
Javitt, D.C., "Glutamate as a therapeutic target in psychiatric disorders," Mol. Psychiatry (2004) 9:984-997.
Lindsley, C.W. et al., "Progress towards validating the NMDA receptor hypofunction hypothesis of schizophrenia," Curr. Topics Med. Chem. (2006) 6:771-785.
Lindsley, C.W. et al., "Progress in the preparation and testing of glycine transporter Type-1 (GlyT1) inhibitors," Current Topics Med. Chem. (2006) 6:1883-1896.
United States Patent Office Notice of Allowance for U.S. Appl. No. 13/207,160 dated Jun. 6, 2014 (9 pages).
United States Patent Office Notice of Allowance for U.S. Appl. No. 13/566,051 dated May 29, 2014 (8 pages).
United States Patent Office Corrected Notice of Allowance for U.S. Appl. No. 13/680,488 dated Jun. 12, 2014 (7 pages).
United States Patent Office Action for U.S. Appl. No. 13/546,434 dated Apr. 14, 2014 (12 pages).
United States Patent Office Action for U.S. Appl. No. 14/031,265 dated Apr. 15, 2014 (14 pages).
United States Patent Office Action for U.S. Appl. No. 13/789,967 dated Apr. 1, 2014 (11 pages).
United States Patent Office Notice of Allowance for U.S. Appl. No. 13/206,937 dated May 15, 2014 (9 pages).
United States Patent Office Notice of Allowance for U.S. Appl. No. 13/680,488 dated Apr. 28, 2014 (13 pages).
United States Patent Office Notice of Allowance for U.S. Appl. No. 13/207,030 dated May 13, 2014 (9 pages).
Kamitani, T. et al., "Studies on the syntheses of heterocyclic compounds. Part DLXXVII. Synthesis of 2,3,4,5-tetrahydro-1H-benzazepine derivatives by phenolic cyclisation," J. Chem. Soc. Perkin Trans. (1974) 22:2602-2604.
Registry No. 1025812-32-1; entered in STN Jun. 5, 2008, "4-morpholineacetamide, N-[2-[[1-[2,4-dihydroxy-5-(1-methylethyl)benzoyl]-2,3-dihydro-1H-isoindol-5-yl]oxy]ethyl".
United States Patent Office Action for U.S. Appl. No. 14/317,104 dated Nov. 5, 2014 (11 pages).
United States Patent Office Action for U.S. Appl. No. 14/282,712 dated Oct. 3, 2014 (12 pages).
United States Patent Office Action for U.S. Appl. No. 13/468,682 dated Sep. 10, 2014 (12 pages).
United States Patent Office Action for U.S. Appl. No. 13/764,454 dated Sep. 30, 2014 (11 pages).
United States Patent Office Notice of Allowance for U.S. Appl. No. 13/206,750 dated Nov. 7, 2014 (8 pages).

* cited by examiner

TETRAHYDROISOQUINOLINES, PHARMACEUTICAL COMPOSITIONS CONTAINING THEM, AND THEIR USE IN THERAPY

CROSS-REFERENCE TO RELATED APPLICATIONS

This is a divisional of U.S. Pat. No. 12/933,326, filed on Dec. 20, 2010, now U.S. Pat. No. 8,653,100, which is a U.S. National Stage Entry of International Patent Application No. PCT/EP2009/053800, filed on Mar. 31, 2009, which claims priority to U.S. Pat. No. 61/041,313, filed on Apr. 1, 2008, the entire contents of all of which are fully incorporated herein by reference.

BACKGROUND OF THE INVENTION

The present invention relates to tetrahydroisoquinolines, pharmaceutical compositions comprising such quinolines, and the use of such quinolines for therapeutic purposes. The quinolines are GlyT1 inhibitors.

Dysfunction of glutamatergic pathways has been implicated in a number of disease states in the human central nervous system (CNS) including but not limited to schizophrenia, cognitive deficits, dementia, Parkinson disease, Alzheimer disease and bipolar disorder. A large number of studies in animal models lend support to the NMDA hypofunction hypothesis of schizophrenia.

NMDA receptor function can be modulated by altering the availability of the co-agonist glycine. This approach has the critical advantage of maintaining activity-dependent activation of the NMDA receptor because an increase in the synaptic concentration of glycine will not produce an activation of NMDA receptors in the absence of glutamate. Since synaptic glutamate levels are tightly maintained by high affinity transport mechanisms, an increased activation of the glycine site will only enhance the NMDA component of activated synapses.

Two specific glycine transporters, GlyT1 and GlyT2 have been identified and shown to belong to the Na/Cl-dependent family of neurotransmitter transporters which includes taurine, gamma-aminobutyric acid (GABA), proline, monoamines and orphan transporters. GlyT1 and GlyT2 have been isolated from different species and shown to have only 50% identity at the amino acid level. They also have a different pattern of expression in mammalian central nervous system, with GlyT2 being expressed in spinal cord, brainstem and cerebellum and GlyT1 present in these regions as well as forebrain areas such as cortex, hippocampus, septum and thalamus. At the cellular level, GlyT2 has been reported to be expressed by glycinergic nerve endings in rat spinal cord whereas GlyT1 appears to be preferentially expressed by glial cells. These expression studies have led to the suggestion that GlyT2 is predominantly responsible for glycine uptake at glycinergic synapses whereas GlyT1 is involved in monitoring glycine concentration in the vicinity of NMDA receptor expressing synapses. Recent functional studies in rat have shown that blockade of GlyT1 with the potent inhibitor (N-[3-(4'-fluorophenyl)-3-(4'-phenylphenoxy)propyl])-sarcosine (NFPS) potentiates NMDA receptor activity and NMDA receptor-dependent long-term potentiation in rat.

Molecular cloning has further revealed the existence of three variants of GlyT1, termed GlyT-1a, GlyT-1b and GlyT-1c, each of which displays a unique distribution in the brain and peripheral tissues. The variants arise by differential splicing and exon usage, and differ in their N-terminal regions.

The physiological effects of GlyT1 in forebrain regions together with clinical reports showing the beneficial effects of GlyT1 inhibitor sarcosine in improving symptoms in schizophrenia patients suggest that selective GlyT1 inhibitors represent a new class of antipsychotic drugs.

Glycine transporter inhibitors are already known in the art, for example:

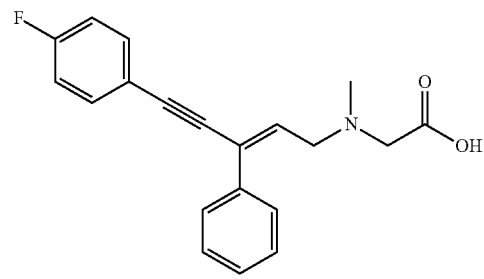

US 200426364

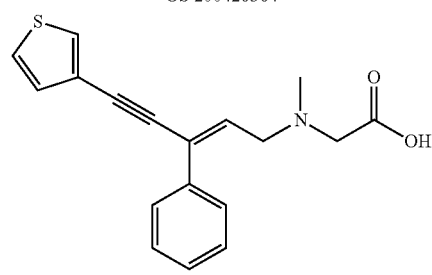

US 2002169197

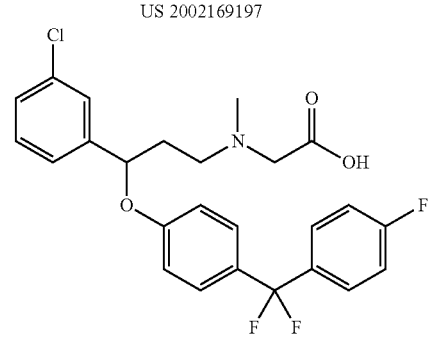

EP 1 284 257

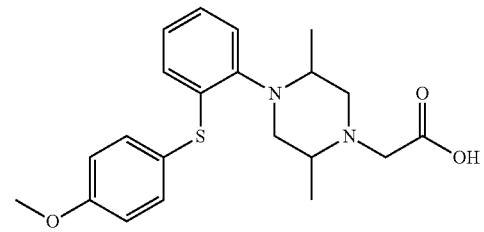

WO 2003053942

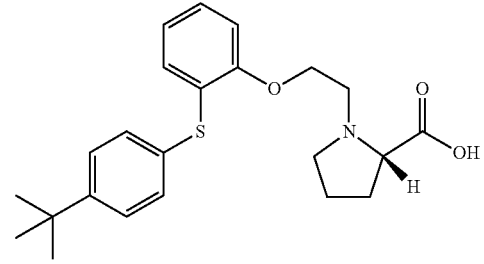

WO 20040966761

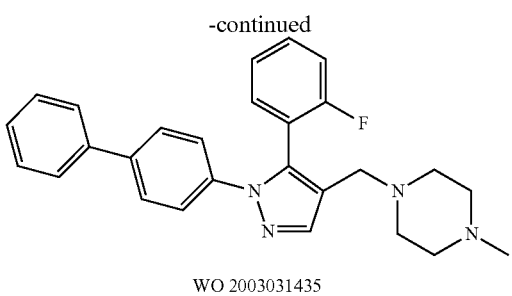
WO 2003031435
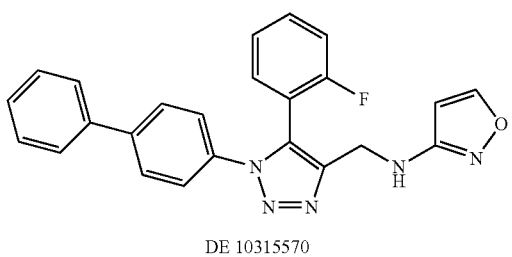
DE 10315570
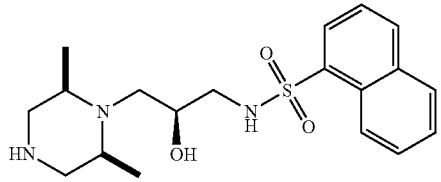
WO 2003055478
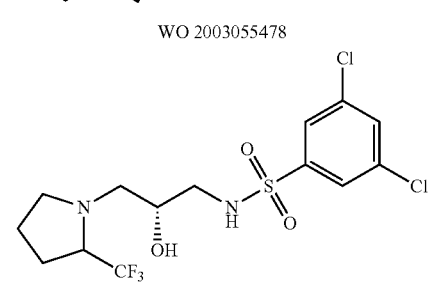
WO 2004113280
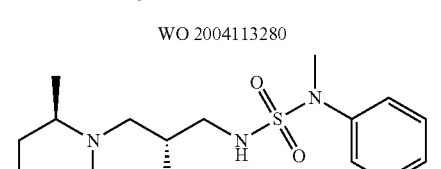
WO 2004112787
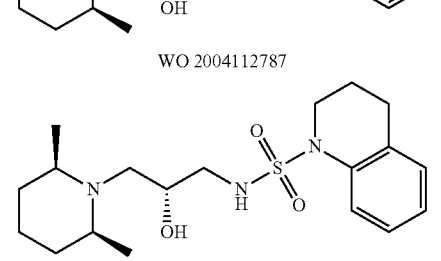
WO 2004113301
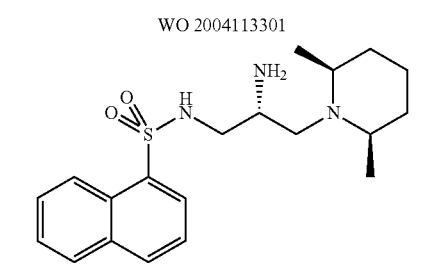
WO 2005049023
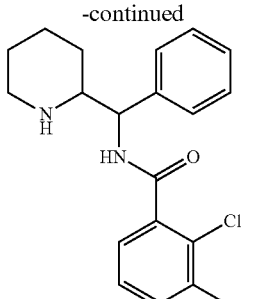
WO 2003089411
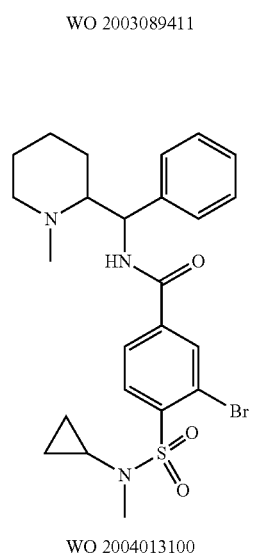
WO 2004013100
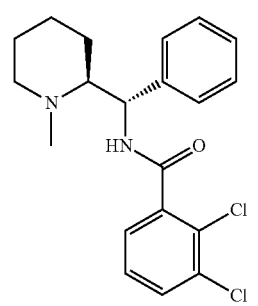
WO 2004013101
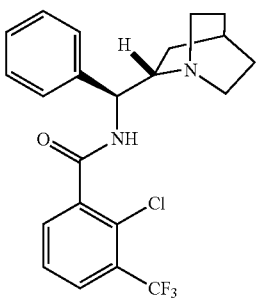
WO 2005037783

-continued
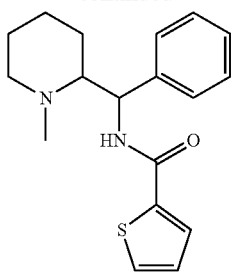
WO 2005037792
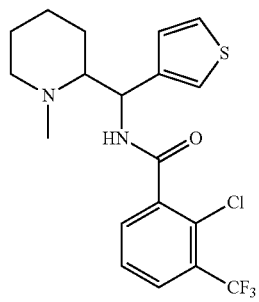
WO 2005037781
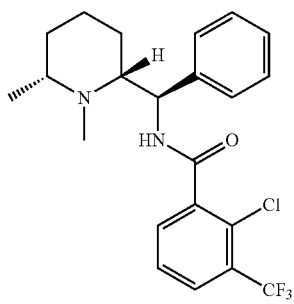
WO 2005037782
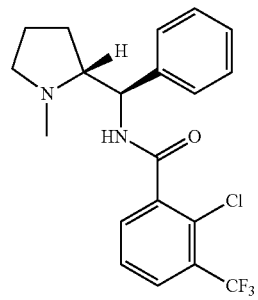
WO 2005037785
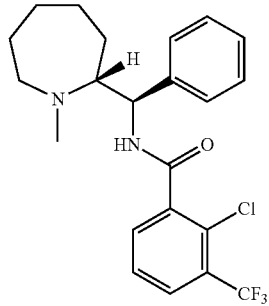
WO 2005037785
-continued
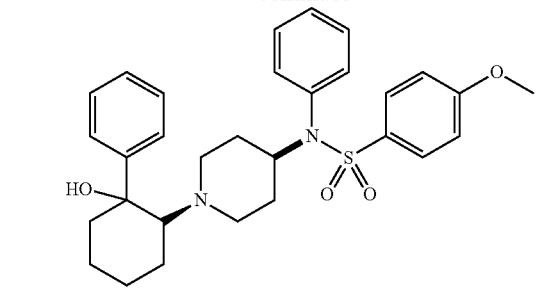
WO 2004072034
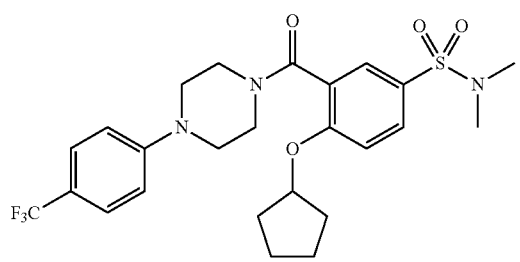
WO 2005014563
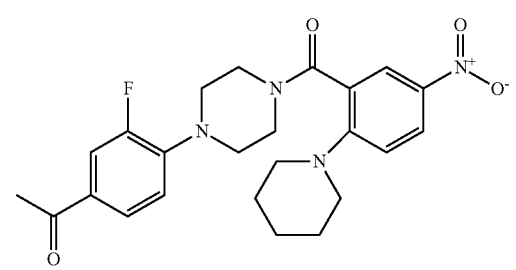
WO 2005023260
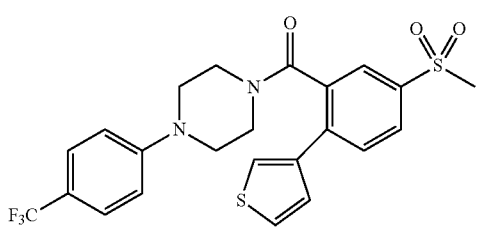
WO 2005023261
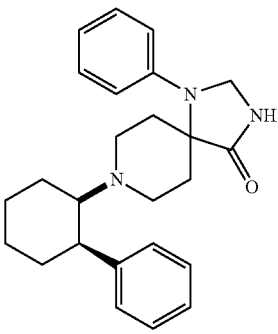
WO 2005040166

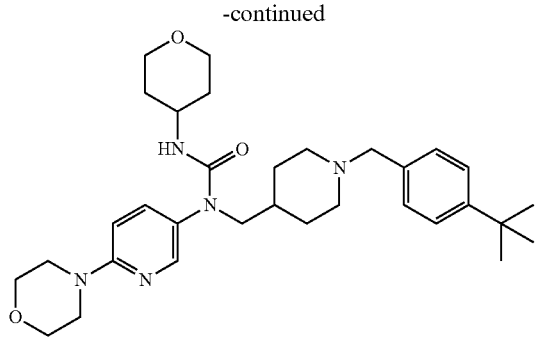

WO 2005058882

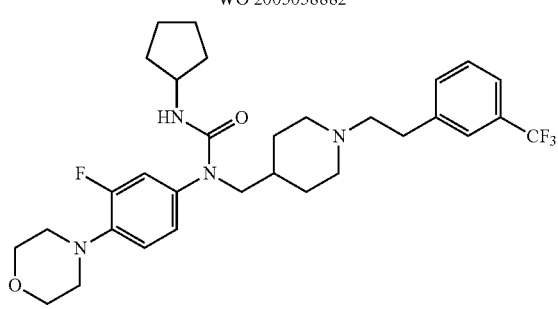

WO 2005058885

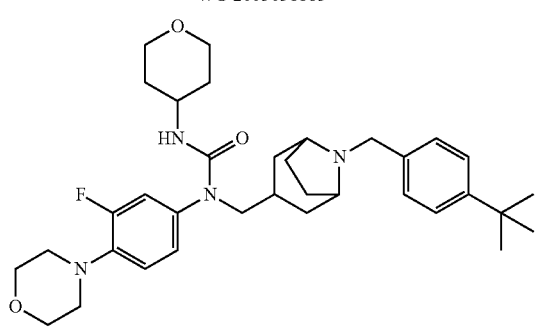

WO 2005058317

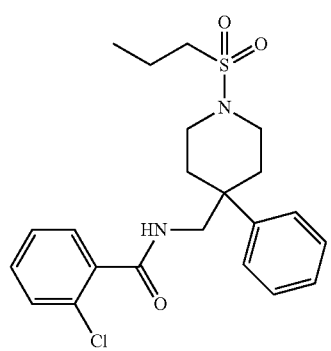

WO2005046601

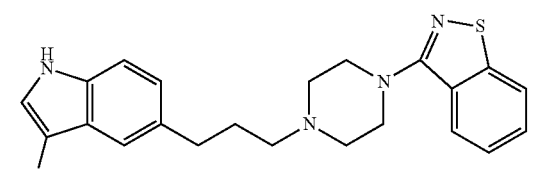

WO 2003087086

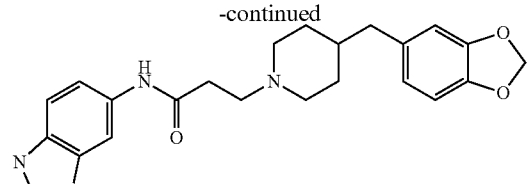

WO 20030766420

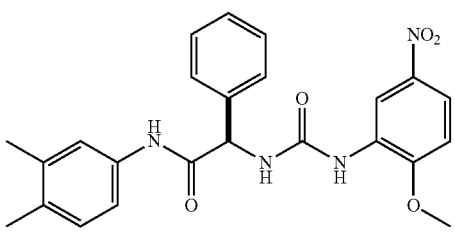

WO 2004022528

(see also Hashimoto K., Recent Patents on CNS Drug Discovery, 2006, 1, 43-53; Harsing L. G. et al., Current Medicinal Chemistry, 2006, 13, 1017-1044; Javitt D. C., Molecular Psychiatry (2004) 9, 984-997; Lindsley, C. W. et al., Current Topics in Medicinal Chemistry, 2006, 6, 771-785; Lindsley C. W. et al., Current Topics in Medicinal Chemistry, 2006, 6, 1883-1896).

It was one object of the present invention to provide further glycine transporter inhibitors.

SUMMARY OF THE INVENTION

The present invention relates to tetrahydroisoquinolines of the formula (Ia)

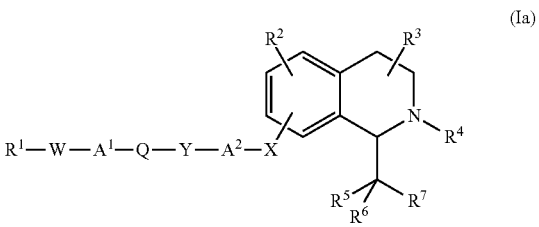

(Ia)

wherein

R$^1$ is hydrogen, alkyl, halogenated alkyl, hydroxyalkyl, alkoxyalkyl, aminoalkyl, alkylaminoalkyl, dialkylaminoalkyl, alkylcarbonylaminoalkyl, alkyloxycarbonylaminoalkyl, alkylaminocarbonylaminoalkyl, dialkylaminocarbonylaminoalkyl, alkylsulfonyl-aminoalkyl, arylalkylaminoalkyl, optionally substituted arylalkyl, optionally substituted heterocyclylalkyl, cycloalkyl, alkylcarbonyl, halogenated alkylcarbonyl, alkoxycarbonyl, halogenated alkoxycarbonyl, aryloxycarbonyl, aminocarbonyl, alkylaminocarbonyl, (halogenated alkyl)aminocarbonyl, arylaminocarbonyl, alkenyl, alkynyl, optionally substituted aryl, hydroxy, alkoxy, halogenated alkoxy, alkylcarbonyloxy, hydroxyalkoxy, alkoxyalkoxy, aminoalkoxy, alkylaminoalkoxy, dialkylaminoalkoxy, alkylcarbonylaminoalkoxy, arylcarbonylaminoalkoxy, alkoxycarbonylaminoalkoxy, arylalkoxy, alkylsulfonylaminoalkoxy, (halogenated alkyl)sulfonylaminoalkoxy, aryl-sulfonylaminoalkoxy, (arylalkyl)sulfonylaminoalkoxy, heterocyclylsulfonylaminoalkoxy, heterocyclylalkoxy, aryloxy, heterocyclyloxy, alkylthio, halogenated alkylthio, alkylamino, (halogenated alkyl)amino, dialkylamino, di-(halogenated alkyl)amino, alkylcarbonylamino, (halogenated alkyl)carbonylamino, arylcarbonylamino, alkylsulfonylamino, (halogenated alkyl)sulfonylamino, arylsulfonylamino or optionally substituted heterocyclyl;

W is —NR$^8$— or a bond;
A$^1$ is optionally substituted alkylene or a bond;
Q is —S(O)$_2$— or —C(O)—;
Y is —NR$^9$— or a bond;
A$^2$ is optionally substituted alkylene, alkylene-O-alkylene, alkylene-NR$^{10}$-alkylene, optionally substituted arylene, optionally substituted heteroarylene or a bond;
X is —O—, —NR$^{11}$—, —S— or optionally substituted alkylene;
R$^2$ is hydrogen, halogen, alkyl, halogenated alkyl, hydroxyalkyl, alkenyl, alkynyl, —CN, optionally substituted aryl, hydroxy, alkoxy, halogenated alkoxy, alkenyloxy, arylalkoxy, alkylcarbonyloxy, alkylthio, alkylsulfinyl, alkylsulfonyl, aminosulfonyl, amino, alkylamino, alkenylamino or optionally substituted heterocyclyl;
R$^3$ is hydrogen, halogen, alkyl or alkoxy, or two radicals R$^3$ together with the carbon atom to which they are attached form a carbonyl group;
R$^4$ is hydrogen, alkyl, halogenated alkyl, hydroxyalkyl, alkoxyalkyl, aminoalkyl, CH$_2$CN, —CHO, alkylcarbonyl, (halogenated alkyl)carbonyl, arylcarbonyl, alkylaminocarbonyl, alkenyl, —C(=NH)NH$_2$, —C(=NH)NHCN, alkylsulfonyl, arylsulfonyl, amino, —NO or heterocyclyl;
R$^5$ is optionally substituted alkyl, alkylaminoalkyl, dialkylaminoalkyl, heterocyclylalkyl, optionally substituted aryl or hydroxy;
R$^6$ is hydrogen, optionally substituted alkyl or hydroxy, or R$^5$, R$^6$
  together are carbonyl or optionally substituted alkylene, wherein one —CH$_2$— of alkylene may be replaced by an oxygen atom or —NR$^{12}$—;
R$^7$ is optionally substituted aryl, optionally substituted cycloalkyl or optionally substituted heterocyclyl;
R$^8$ is hydrogen or alkyl;
R$^9$ is hydrogen, alkyl or aminoalkyl;
R$^{10}$ is hydrogen, alkyl or alkylsulfonyl;
R$^{11}$ is hydrogen or alkyl; or
R$^9$, R$^{11}$
  together are alkylene, and
R$^{12}$ is hydrogen or alkyl;
or a physiologically tolerated salt thereof.

The present invention further relates to tetrahydroisoquinolines of the formula (Ib)

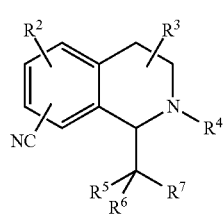

(Ib)

wherein R$^2$, R$^3$, R$^4$, R$^5$, R$^6$ and R$^7$ are as defined herein.

Said compounds, i.e., the tetrahydroisoquinolines and their physiologically tolerated acid addition salts, are glycine transporter inhibitors and thus useful as pharmaceuticals.

The present invention thus further relates to the compounds of formula (Ia) or (Ib) for use in therapy.

The present invention also relates to pharmaceutical compositions which comprise a carrier and a compound of formula (Ia) or (Ib).

In particular, said compounds, i.e., the tetrahydroisoquinolines and their physiologically tolerated acid addition salts, are inhibitors of the glycine transporter GlyT1.

The present invention thus further relates to the compounds of formula (Ia) or (Ib) for use in inhibiting the glycine transporter.

The present invention also relates to the use of the compounds of formula (Ia) or (Ib) in the manufacture of a medicament for inhibiting the glycine transporter GlyT1 and corresponding methods of inhibiting the glycine transporter GlyT1.

Glycine transport inhibitors and in particular inhibitors of the glycine transporter GlyT1 are known to be useful in treating a variety of neurologic and psychiatric disorders.

The present invention thus further relates to the compounds of formula (Ia) or (Ib) for use in treating a neurologic or psychiatric disorder.

The present invention also relates to the use of the compounds of formula (Ia) or (Ib) in the manufacture of a medicament for treating a neurologic or psychiatric disorder and corresponding methods of treating said disorders.

The present invention further relates to dihydroisoquinolines of formula (IIa)

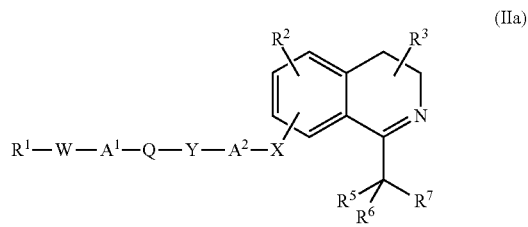

(IIa)

wherein R$^1$, W, A$^1$, Q, Y, A$^2$, X, R$^2$, R$^3$, R$^5$, R$^6$ and R$^7$ are defined as herein.

The present invention further relates to dihydroisoquinolines of formula (IIb)

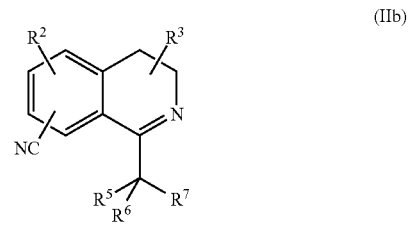

(IIb)

wherein R$^2$, R$^3$, R$^5$, R$^6$ and R$^7$ are defined as herein.

The dihydroisoquinolines of formula (IIa) and (IIb) are useful as intermediates in the preparation of GlyT1 inhibitors, in particular those of formula (Ia) and (Ib), respectively.

DETAILED DESCRIPTION OF THE INVENTION

Provided that the tetrahydroisoquinolines of the formula (Ia) and (Ib) of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula (Ia) and (Ib) and/or of their salts.

According to one embodiment, an enantiomer of the tetrahydroisoquinolines of the present invention has the following formula:

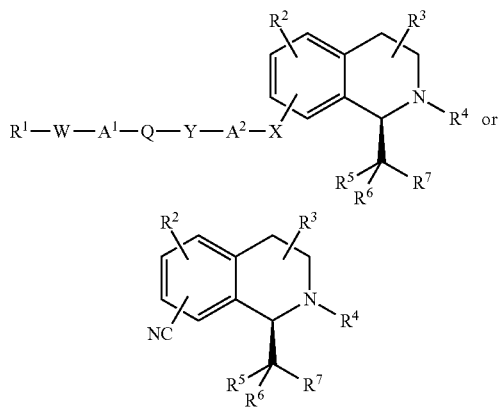

wherein $R^1$, W, $A^1$, Q, Y, $A^2$, X, $R^2$, $R^3$, $R^4$, $R^5$, $R^6$ and $R^7$ are as defined herein.

According to another embodiment, an enantiomer of the tetrahydroisoquinolines of the present invention has the following formula:

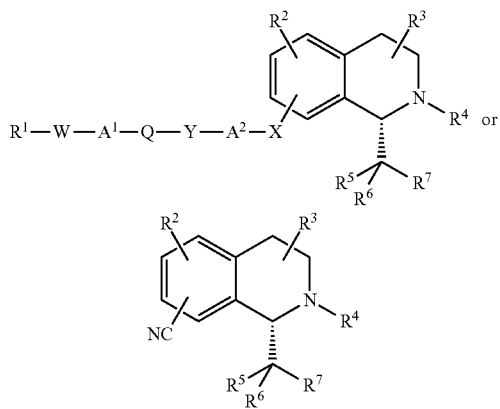

wherein $R^1$, W, $A^1$, Q, Y, $A^2$, X, $R^2$, $R^3$, $R^4$, $R^5$, $R^6$ and $R^7$ are as defined herein.

The physiologically tolerated salts of the tetrahydroisoquinolines of the formula (Ia) and (Ib) are especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, cycloaliphatic sulfonic acids, such as S-(+)-10-campher sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966.

The organic moieties mentioned in the above definitions of the variables are—like the term halogen—collective terms for individual listings of the individual group members. The prefix $C_n$-$C_m$ indicates in each case the possible number of carbon atoms in the group.

Unless indicated otherwise, the term "substituted" means that a radical is substituted with 1, 2 or 3, especially 1, substituent which are in particular selected from the group consisting of halogen, $C_1$-$C_4$-alkyl, hydroxy-$C_1$-$C_4$-alkyl, $C_3$-$C_{12}$-heterocyclyl-alkyl, $C_1$-$C_4$-alkoxy-$C_1$-$C_4$-alkyl, amino-$C_1$-$C_4$-alkyl, $C_1$-$C_4$-alkenyl, OH, SH, CN, $CF_3$, O—$CF_3$, COOH, O—$CH_2$—COOH, $C_1$-$C_6$-alkoxy, $C_1$-$C_6$-alkylthio, $C_3$-$C_7$-cycloalkyl, COO—$C_1$-$C_6$-alkyl, $CONH_2$, CONH—$C_1$-$C_6$-alkyl, $SO_2$NH—$C_1$-$C_6$-alkyl, CON—($C_1$-$C_6$-alkyl)$_2$, $SO_2$N—($C_1$-$C_6$-alkyl)$_2$, $NH_2$, NH—$C_1$-$C_6$-alkyl, N—($C_1$-$C_6$-alkyl)$_2$, NH—($C_1$-$C_4$-alkyl-$C_6$-$C_{12}$-aryl), NH—CO—$C_1$-$C_6$-alkyl, NH—$SO_2$—$C_1$-$C_6$-alkyl, $SO_2$—$C_1$-$C_6$-alkyl, $C_6$-$C_{12}$-aryl, O—$C_6$-$C_{12}$-aryl, O—$CH_2$—$C_6$-$C_{12}$-aryl, CONH—$C_6$-$C_{12}$-aryl, $SO_2$NH—$C_6$-$C_{12}$-aryl, CONH—$C_3$-$C_{12}$-heterocyclyl, $SO_2$NH—$C_3$-$C_{12}$-heterocyclyl, $SO_2$—$C_6$-$C_{12}$-aryl, NH—$SO_2$—$C_6$-$C_{12}$-aryl, NH—CO—$C_6$-$C_{12}$-aryl, NH—$SO_2$—$C_3$-$C_{12}$-heterocyclyl, NH—CO—$C_3$-$C_{12}$-heterocyclyl and $C_3$-$C_{12}$-heterocyclyl ($C_1$-$C_4$-haloalkyl, $C_3$-$C_{12}$-aryl-alkyl, CO—$C_1$-$C_6$-alkyl, COO—$C_1$-$C_4$-alkyl-$C_3$-$C_{12}$-aryl, COO—$C_1$-$C_4$-alkyl-$C_3$-$C_{12}$-heterocyclyl, $C_1$-$C_4$-haloalkoxy and carbamoylamino being further examples of such substituents), wherein aryl and heterocyclyl in turn may be unsubstituted or substituted with 1, 2 or 3 substituents selected from the group consisting of halogen, $C_1$-$C_4$-alkyl, $C_1$-$C_4$-haloalkyl, $C_1$-$C_4$-alkoxy and $C_1$-$C_4$-haloalkoxy.

The term halogen denotes in each case fluorine, bromine, chlorine or iodine, in particular fluorine or chlorine.

$C_1$-$C_4$-Alkyl is a straight-chain or branched alkyl group having from 1 to 4 carbon atoms. Examples of an alkyl group are methyl, $C_2$-$C_4$-alkyl such as ethyl, n-propyl, iso-propyl, n-butyl, 2-butyl, iso-butyl or tert-butyl. $C_1$-$C_2$-Alkyl is methyl or ethyl, $C_1$-$C_3$-alkyl is additionally n-propyl or iso-propyl.

$C_1$-$C_6$-Alkyl is a straight-chain or branched alkyl group having from 1 to 6 carbon atoms. Examples include methyl, $C_2$-$C_4$-alkyl as mentioned herein and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogenated $C_1$-$C_4$-alkyl is a straight-chain or branched alkyl group having 1 to 4 carbon atoms, preferably 1 to 3 carbon atoms, more preferably 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethyl, dihalogenomethyl, trihalogenomethyl, (R)-1-halogenoethyl, (S)-1-halogenoethyl, 2-halogenoethyl, 1,1-dihalogenoethyl, 2,2-dihalogenoethyl, 2,2,2-trihalogenoethyl, (R)-1-halogenopropyl, (S)-1-halogenopropyl, 2-halogenopropyl, 3-halogenopropyl, 1,1-dihalogenopropyl, 2,2-dihalogenopropyl, 3,3-dihalogenopropyl, 3,3,3-trihalogenopropyl, (R)-2-halogeno-1-methylethyl, (S)-2-halogeno-1-methylethyl, (R)-2,2-dihalogeno-1-methylethyl, (S)-2,2-dihalogeno-1- methylethyl, (R)-1,2-dihalogeno-1-methylethyl, (S)-1,2-dihalogeno-1-methylethyl, (R)-2,2,2-trihalogeno-1-methylethyl, (S)-2,2,2-trihalogeno-1-methylethyl, 2-halogeno-1-(halogenomethyl)ethyl, 1-(dihalogenomethyl)-2,2-dihalogenoethyl, (R)-1-halogenobutyl, (S)-1-halogenobutyl, 2-halogenobutyl, 3-halogenobutyl, 4-halogenobutyl, 1,1-dihalogenobutyl, 2,2-dihalogenobutyl, 3,3-dihalogenobutyl, 4,4-dihalogenobutyl, 4,4,4-trihalogenobutyl, etc. Particular examples include the fluorinated $C_1$-$C_4$ alkyl groups as defined, such as trifluoromethyl.

$C_6$-$C_{12}$-Aryl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_6$-$C_{12}$-aryl, such as in benzyl.

Hydroxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two hydroxyl groups, such as in hydroxymethyl, (R)-1-hydroxyethyl, (S)-1-hydroxyethyl, 2-hydroxyethyl, (R)-1-hydroxypropyl, (S)-1-hydroxypropyl, 2-hydroxypropyl, 3-hydroxypropyl, (R)-2-hydroxy-1-methylethyl, (S)-2-hydroxy-1-methylethyl, 2-hydroxy-1-(hydroxymethyl)ethyl, (R)-1-hydroxybutyl, (S)-1-hydroxybutyl, 2-hydroxybutyl, 3-hydroxybutyl, 4-hydroxybutyl.

$C_1$-$C_6$-Alkoxy-$C_1$-$C_4$-alkyl is a straight-chain or branched alkyl group having 1 to 4 carbon atoms, preferably 1 to 3 carbon atoms, more preferably 1 or 2 carbon atoms, wherein one or two hydrogen atoms are replaced by one or two alkoxy groups having 1 to 6, preferably 1 to 4, in particular 1 or 2 carbon atoms, such as in methoxymethyl, (R)-1-methoxyethyl, (S)-1-methoxyethyl, 2-methoxyethyl, (R)-1-methoxypropyl, (S)-1-methoxypropyl, 2-methoxypropyl, 3-methoxypropyl, (R)-2-methoxy-1-methylethyl, (S)-2-methoxy-1-methylethyl, 2-methoxy-1-(methoxymethyl)ethyl, (R)-1-methoxybutyl, (S)-1-methoxybutyl, 2-methoxybutyl, 3-methoxybutyl, 4-methoxybutyl, ethoxymethyl, (R)-1-ethoxyethyl, (S)-1-ethoxyethyl, 2-ethoxyethyl, (R)-1-ethoxypropyl, (S)-1-ethoxypropyl, 2-ethoxypropyl, 3-ethoxypropyl, (R)-2-ethoxy-1-methylethyl, (S)-2-ethoxy-1-methylethyl, 2-ethoxy-1-(ethoxymethyl)ethyl, (R)-1-ethoxybutyl, (S)-1-ethoxybutyl, 2-ethoxybutyl, 3-ethoxybutyl, 4-ethoxybutyl.

Amino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by an amino group, such as in aminomethyl, 2-aminoethyl.

$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylamino group, in particular by a $C_1$-$C_4$-alkylamino group, such as in methylaminomethyl, ethylaminomethyl, n-propylaminomethyl, iso-propylaminomethyl, n-butylaminomethyl, 2-butylaminomethyl, iso-butylaminomethyl or tert-butylaminomethyl.

Di-$C_1$-$C_6$-Alkylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylamino group, in particular by a di-$C_1$-$C_4$-alkylamino group, such as in dimethylaminomethyl.

$C_1$-$C_6$-Alkylcarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylcarbonylamino group, in particular by a $C_1$-$C_4$-alkylcarbonylamino group, such as in methylcarbonylaminomethyl, ethylcarbonylaminomethyl, n-propylcarbonylaminomethyl, iso-propylcarbonylaminomethyl, n-butylcarbonylaminomethyl, 2-butylcarbonylaminomethyl, iso-butylcarbonylaminomethyl or tert-butylcarbonylaminomethyl.

$C_1$-$C_6$-Alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylaminocarbonylamino group, in particular by a $C_1$-$C_4$-alkylaminocarbonylamino group, such as in methylaminocarbonylaminomethyl, ethylaminocarbonylaminomethyl, n-propylaminocarbonylaminomethyl, iso-propylaminocarbonylaminomethyl, n-butylaminocarbonylaminomethyl, 2-butylaminocarbonylaminomethyl, iso-butylaminocarbonylaminomethyl or tert-butylaminocarbonylaminomethyl.

Di-$C_1$-$C_6$-alkylaminocarbonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a di-$C_1$-$C_6$-alkylaminocarbonylamino group, in particular by a di-$C_1$-$C_4$-alkylaminocarbonylamino group, such as in dimethylaminocarbonylaminomethyl, dimethylaminocarbonyl aminoethyl, dimethylaminocarbonylaminon-propyl.

$C_1$-$C_6$-Alkylsulfonylamino-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a $C_1$-$C_6$-alkylsulfonylamino group, in particular by a $C_1$-$C_4$-alkylsulfonylamino group, such as in methylsulfonylaminomethyl, ethylsulfonylaminomethyl, n-propylsulfonylaminomethyl, iso-propylsulfonylaminomethyl, n-butylsulfonylaminomethyl, 2-butylsulfonylaminomethyl, iso-butylsulfonylaminomethyl or tert-butylsulfonylaminomethyl.

($C_6$-$C_{12}$-Aryl-$C_1$-$C_6$-alkyl)amino-$C_1$-$C_4$ alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by a ($C_6$-$C_{12}$-aryl-$C_1$-$C_6$-alkyl)amino group, in particular a ($C_6$-$C_{12}$-aryl-$C_1$-$C_2$-alkyl) amino group, such as in benzylaminomethyl.

$C_3$-$C_{12}$-Heterocyclyl-$C_1$-$C_4$-alkyl is a straight-chain or branched alkyl group having 1 to 4 carbon atoms, preferably 1 to 3 carbon atoms, more preferably 1 or 2 carbon atoms, in particular 1 or two carbon atoms, wherein one hydrogen atom is replaced by $C_3$-$C_{12}$-heterocyclyl, such as in N-pyrrolidinylmethyl, N-piperidinylmethyl, N-morpholinylmethyl.

$C_3$-$C_{12}$-Cycloalkyl is a cycloaliphatic radical having from 3 to 12 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

$C_1$-$C_6$-Alkylcarbonyl is a radical of the formula R—C(O)—, wherein R is an alkyl radical having from 1 to 6, preferably from 1 to 4, in particular 1 or 2 carbon atoms as defined herein. Examples include acetyl, propionyl, n-butyryl, 2-methylpropionyl, pivaloyl.

Halogenated $C_1$-$C_6$-alkylcarbonyl is $C_1$-$C_6$-alkylcarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonyl is a radical of the formula R—C(O)—, wherein R is an aryl radical having from 6 to 12 carbon atoms as defined herein. Examples include benzoyl.

$C_1$-$C_6$-Alkoxycarbonyl is a radical of the formula R—O—C(O)—, wherein R is an alkyl radical having from 1 to 6, preferably from 1 to 4, in particular 1 or 2 carbon atoms as defined herein. Examples include methoxycarbonyl.

Halogenated $C_1$-$C_6$-alkoxycarbonyl is a $C_1$-$C_6$-alkoxycarbonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Aryloxycarbonyl is a radical of the formula R—O—C(O)—, wherein R is an aryl radical having from 6 to 12 carbon atoms as defined herein. Examples include phenoxycarbonyl.

Cyano is —C≡N.

Aminocarbonyl is $NH_2C(O)$—.

$C_1$-$C_6$-Alkylaminocarbonyl is a radical of the formula R—NH—C(O)—, wherein R is an alkyl radical having from 1 to 6, preferably from 1 to 4, in particular 1 or 2 carbon atoms as defined herein. Examples include methylaminocarbonyl.

(Halogenated $C_1$-$C_4$-alkyl)aminocarbonyl is a $C_1$-$C_4$-alkylaminocarbonyl as defined herein, wherein at least one, e.g. 1, 2, 3, 4 or all of the hydrogen atoms are replaced by 1, 2, 3, 4 or a corresponding number of identical or different hydrogen atoms.

$C_6$-$C_{12}$-Arylaminocarbonyl is a radical of the formula R—NH—C(O)—, wherein R is an aryl radical having from 6 to 12 carbon atoms as defined herein. Examples include phenylaminocarbonyl.

$C_2$-$C_6$-Alkenyl is a singly unsaturated hydrocarbon radical having 2, 3, 4, 5 or 6 carbon atoms, e.g. vinyl, allyl (2-propen-1-yl), 1-propen-1-yl, 2-propen-2-yl, methallyl(2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_2$-$C_6$-Alkynyl is a singly unsaturated hydrocarbon radical having 2, 3, 4, 5 or 6 carbon atoms, e.g. ethynyl, 2-propyn-1-yl, 1-propyn-1-yl, 2-propyn-2-yl and the like. $C_3$-$C_5$-Alkynyl is, in particular, 2-propyn-1-yl, 2-butyn-1-yl, 3-butyn-1-yl, 2-pentyn-1-yl, 3-pentyn-1-yl, 4-pentyn-1-yl.

$C_1$-$C_4$-Alkylene is straight-chain or branched alkylene group having from 1 to 4 carbon atoms. Examples include methylene and ethylene.

$C_6$-$C_{12}$-Aryl is a 6- to 12-membered, in particular 6- to 10-membered, aromatic cyclic radical. Examples include phenyl and naphthyl.

$C_3$-$C_{12}$-Arylene is an aryl diradical. Examples include phen-1,4-ylene and phen-1,3-ylene. A further example is phen-1,2-ylene.

Hydroxy is —OH.

$C_1$-$C_6$-Alkoxy is a radical of the formula R—O—, wherein R is a straight-chain or branched alkyl group having from 1 to 6, in particular 1 to 4 carbon atoms. Examples include methoxy, ethoxy, n-propoxy, isopropoxy, n-butoxy, 2-butoxy, isobutoxy(2-methylpropoxy), tert.-butoxy pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy is a straight-chain or branched alkoxy group having from 1 to 6, preferably from 1 to 4, in particular 1 or 2 carbon atoms, wherein at least one, e.g. 1, 2, 3, 4 or all of the hydrogen atoms are replaced by 1, 2, 3, 4 or a corresponding number of identical or different halogen atoms, such as in halogenomethoxy, dihalogenomethoxy, trihalogenomethoxy, (R)-1-halogenoethoxy, (S)-1-halogenoethoxy, 2-halogenoethoxy, 1,1-dihalogenoethoxy, 2,2-dihalogenoethoxy, 2,2,2-trihalogenoethoxy, (R)-1-halogenopropoxy, (S)-1-halogenopropoxy, 2-halogenopropoxy, 3-halogenopropoxy, 1,1-dihalogenopropoxy, 2,2-dihalogenopropoxy, 3,3-dihalogenopropoxy, 3,3,3-trihalogenopropoxy, (R)-2-halogeno-1-methylethoxy, (S)-2-halogeno-1-methylethoxy, (R)-2,2-dihalogeno-1-methylethoxy, (S)-2,2-dihalogeno-1-methylethoxy, (R)-1,2-dihalogeno-1-methylethoxy, (S)-1,2-dihalogeno-1-methylethoxy, (R)-2,2,2-trihalogeno-1-methylethoxy, (S)-2,2,2-trihalogeno-1-methylethoxy, 2-halogeno-1-(halogenomethyl)ethoxy, 1-(dihalogenomethyl)-2,2-dihalogenoethoxy, (R)-1-halogenobutoxy, (S)-1-halogenobutoxy, 2-halogenobutoxy, 3-halogenobutoxy, 4-halogenobutoxy, 1,1-dihalogenobutoxy, 2,2-dihalogenobutoxy, 3,3-dihalogenobutoxy, 4,4-dihalogenobutoxy, 4,4,4-trihalogenobutoxy, etc. Particular examples include the fluorinated $C_1$-$C_4$ alkoxy groups as defined, such as trifluoromethoxy.

$C_1$-$C_6$-Alkylcarbonyloxy is a radical of the formula R—C(O)—O—, wherein R is an alkyl radical having from 1 to 6, preferably from 1 to 4, in particular 1 or 2 carbon atoms as defined herein. Examples include acetyloxy, propionyloxy, n-butyryloxy, 2-methylpropionyloxy, pivaloyloxy.

$C_1$-$C_6$-Hydroxyalkoxy is an alkoxy radical having from 1 to 6, preferably from 1 to 4 carbon atoms as defined herein, wherein one or two hydrogen atoms are replaced by hydroxy. Examples include 2-hydroxyethoxy, 3-hydroxypropoxy, 2-hydroxypropoxy, 1-methyl-2-hydroxyethoxy and the like.

$C_1$-$C_6$-Alkoxy-$C_1$-$C_4$-alkoxy is an alkoxy radical having from 1 to 4 carbon atoms, preferably 1 or 2 carbon atoms as defined herein, wherein one or two hydrogen atoms are replaced by one or two alkoxy radicals having from 1 to 6, preferably from 1 to 4 carbon atoms as defined herein. Examples include methoxymethoxy, 2-methoxyethoxy, 1-methoxyethoxy, 3-methoxypropoxy, 2-methoxypropoxy, 1-methyl-1-methoxyethoxy, ethoxymethoxy, 2-ethoxyethoxy, 1-ethoxyethoxy, 3-ethoxypropoxy, 2-ethoxypropoxy, 1-methyl-1-ethoxyethoxy and the like.

Amino-$C_1$-$C_4$-alkoxy is an alkoxy radical having from 1 to 4, preferably 1 or 2 carbon atoms as defined herein, wherein one hydrogen atom is replaced by an amino group. Examples include 2-aminoethoxy.

$C_1$-$C_6$-Alkylamino-$C_1$-$C_4$-alkoxy is an alkoxy radical having from 1 to 4, preferably 1 or 2 carbon atoms as defined herein, wherein one hydrogen atom is replaced by an alkylamino group having from 1 to 6, preferably from 1 to 4 carbon atoms as defined herein. Examples include methylaminomethoxy, ethylaminomethoxy, n-propylaminomethoxy, iso-propylaminomethoxy, n-butylaminomethoxy, 2-butylaminomethoxy, iso-butylaminomethoxy, tert-butylaminomethoxy, 2-(methylamino)ethoxy, 2-(ethylamino)ethoxy, 2-(n-propylamino)ethoxy, 2-(iso-propylamino)ethoxy, 2-(n-butylamino)ethoxy, 2-(2-butylamino)ethoxy, 2-(iso-butylamino)ethoxy, 2-(tert-butylamino)ethoxy.

Di-$C_1$-$C_6$-alkylamino-$C_1$-$C_4$-alkoxy is an alkoxy radical having from 1 to 4, preferably 1 or 2 carbon atoms as defined herein, wherein one hydrogen atom is replaced by a dialkylamino group having from 1 to 6, preferably from 1 to 4 carbon atoms as defined herein. Examples include dimethylaminomethoxy, diethylaminomethoxy, N-methyl-N-ethylamino)ethoxy, 2-(dimethylamino)ethoxy, 2-(diethylamino)ethoxy, 2-(N-methyl-N-ethylamino)ethoxy.

$C_1$-$C_6$-Alkylcarbonylamino-$C_1$-$C_4$-alkoxy is an alkoxy radical having from 1 to 4, preferably 1 or 2 carbon atoms as defined herein, wherein one hydrogen atom is replaced by an alkylcarbonylamino group wherein the alkyl group has from 1 to 6, preferably from 1 to 4 carbon atoms as defined herein. Examples include methylcarbonylaminomethoxy, ethylcarbonylaminomethoxy, n-propylcarbonylaminomethoxy, iso-propylcarbonylaminomethoxy, n-butylcarbonylaminomethoxy, 2-butylcarbonylaminomethoxy, iso-butylcarbonylaminomethoxy, tert-butylcarbonylaminomethoxy, 2-(methylcarbonylamino)ethoxy, 2-(ethylcarbonylamino)ethoxy, 2-(n-propylcarbonylamino)ethoxy, 2-(iso-propylcarbonylamino)ethoxy, 2-(n-butylcarbonylamino)ethoxy, 2-(2-butylcarbonylamino)ethoxy, 2-(iso-butylcarbonylamino)ethoxy, 2-(tert-butylcarbonylamino)ethoxy.

$C_6$-$C_{12}$-Arylcarbonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylcarbonylamino group as defined herein. Examples include 2-(benzoylamino)ethoxy.

$C_1$-$C_6$-Alkoxycarbonylamino-$C_1$-$C_4$-alkoxy is an alkoxy radical having from 1 to 4, preferably 1 or 2 carbon atoms as defined herein, wherein one hydrogen atom is replaced by an alkoxycarbonylamino group wherein the alkoxy group has from 1 to 6, preferably from 1 to 4 carbon atoms as defined herein. Examples include methoxycarbonylaminomethoxy, ethoxycarbonylaminomethoxy, n-propoxycarbonylaminomethoxy, iso-propoxycarbonylaminomethoxy, n-butoxycarbonylaminomethoxy, 2-butoxycarbonylaminomethoxy, iso-butoxycarbonylaminomethoxy, tert-butoxycarbonylaminomethoxy, 2-(methoxycarbonylamino)ethoxy, 2-(ethoxycarbonylamino)ethoxy, 2-(n-propoxycarbonylamino)ethoxy, 2-(iso-propoxycarbonylamino)ethoxy, 2-(n-butoxycarbonylamino)ethoxy, 2-(2-butoxycarbonylamino)ethoxy, 2-(iso-butoxycarbonylamino)ethoxy, 2-(tert-butoxycarbonylamino)ethoxy.

$C_2$-$C_6$-Alkenyloxy is a radical of the formula R—O—, wherein R is a straight-chain or branched alkenyl group having from 2 to 6, in particular 2 to 4 carbon atoms. Examples include vinyloxy, allyloxy(2-propen-1-yloxy), 1-propen-1-yloxy, 2-propen-2-yloxy, methallyloxy(2-methylprop-2-en-1-yloxy) and the like. $C_3$-$C_5$-Alkenyloxy is, in particular, allyloxy, 1-methylprop-2-en-1-yloxy, 2-buten-1-yloxy, 3-buten-1-yloxy, methallyloxy, 2-penten-1-yloxy, 3-penten-1-yloxy, 4-penten-1-yloxy, 1-methylbut-2-en-1-yloxy or 2-ethylprop-2-en-1-yloxy.

$C_6$-$C_{12}$-Aryl-$C_1$-$C_4$-alkoxy is an alkoxy radical having from 1 to 4, preferably 1 or 2 carbon atoms as defined herein, wherein one hydrogen atom is replaced by a $C_6$-$C_{12}$-aryl group as defined herein. Examples include benzyloxy.

$C_1$-$C_6$-Alkylsulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein. Examples include 2-(methylsulfonylamino)ethoxy, 2-(ethylsulfonylamino)ethoxy, 2-[(2-methylpropyl)sulfonylamino]ethoxy.

(Halogenated $C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by an alkylsulfonylamino group having from 1 to 6, preferably from 1 to 4 carbon atoms as defined herein, wherein the alkyl group is halogenated. Examples include 2-(trifluoromethylsulfonylamino)ethoxy.

$C_6$-$C_{12}$-Arylsulfonylamino-$C_1$-$C_4$-alkoxy is an alkoxy radical having from 1 to 4, preferably 1 or 2 carbon atoms as defined herein, wherein one hydrogen atom is replaced by a $C_6$-$C_{12}$-arylsulfonylamino group as defined herein. Examples include 2-(phenylsulfonylamino)ethoxy, 2-(naphthylsulfonylamino)ethoxy.

($C_6$-$C_{12}$-Aryl-$C_1$-$C_6$-alkyl)sulfonylamino-$C_1$-$C_4$-alkoxy is an alkoxy radical having from 1 to 4, preferably 1 or 2 carbon atoms as defined herein, wherein one hydrogen atom is replaced by a ($C_6$-$C_{12}$-aryl-$C_1$-$C_6$-alkyl)sulfonylamino group, preferably by a ($C_6$-$C_{12}$-aryl-$C_1$-$C_2$-alkyl)sulfonylamino group. Examples include 2-(benzylsulfonylamino)ethoxy.

$C_3$-$C_{12}$-Heterocyclylsulfonylamino-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclylsulfonylamino group as defined herein. Examples include 2-(pyridin-3-yl-sulfonylamino)ethoxy.

$C_3$-$C_{12}$-Heterocyclyl-$C_1$-$C_4$-alkoxy is an alkoxy radical having from 1 to 4, preferably 1 or 2 carbon atoms as defined herein, wherein one hydrogen atom is replaced by a $C_3$-$C_{12}$-heterocyclyl group as defined herein. Examples include 2-(N-pyrrolidinyl)ethoxy, 2-(N-morpholinyl)ethoxy and 2-(N-imidazolyl)ethoxy.

$C_1$-$C_2$-Alkylenedioxo is a radical of the formula —O—R—O—, wherein R is a straight-chain or branched alkylene group having from 1 or 2 carbon atoms as defined herein. Examples include methylenedioxo.

$C_6$-$C_{12}$-Aryloxy is a radical of the formula R—O—, wherein R is an aryl group having from 6 to 12, in particular 6 carbon atoms as defined herein. Examples include phenoxy.

$C_3$-$C_{12}$-Heterocyclyloxy is a radical of the formula R—O—, wherein R is a $C_3$-$C_{12}$-heterocyclyl group having from 3 to 12, in particular from 3 to 7 carbon atoms as defined herein. Examples include pyridin-2-yloxy.

$C_1$-$C_6$-Alkylthio is a radical of the formula R—S—, wherein R is an alkyl radical having from 1 to 6, preferably from 1 to 4 carbon atoms as defined herein. Examples include methylthio, ethylthio, propylthio, butylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropyl and 1-ethyl-2-methylpropyl.

Halogenated $C_1$-$C_6$-alkylthio is a radical of the formula R—S—, wherein R is a halogenated alkyl radical having from 1 to 6, preferably from 1 to 4 carbon atoms as defined herein. Examples include halogenomethylthio, dihalogenomethylthio, trihalogenomethylthio, (R)-1-halogenoethylthio, (S)-1-halogenoethylthio, 2-halogenoethylthio, 1,1-dihalogenoethylthio, 2,2-dihalogenoethylthio, 2,2,2-trihalogenoethylthio, (R)-1-halogenopropylthio, (S)-1-halogenopropylthio, 2-halogenopropylthio, 3-halogenopropylthio, 1,1-dihalogenopropylthio, 2,2-dihalogenopropylthio, 3,3-dihalogenopropylthio, 3,3,3-trihalogenopropylthio, (R)-2-halogeno-1- methylethylthio, (S)-2-halogeno-1-methylethylthio, (R)-2,2-dihalogeno-1-methylethylthio, (S)-2,2-dihalogeno-1-methylethylthio, (R)-1,2-dihalogeno-1-methylethylthio, (S)-1,2-dihalogeno-1-methylethylthio, (R)-2,2,2-trihalogeno-1-methylethylthio, (S)-2,2,2-trihalogeno-1-methylethylthio, 2-halogeno-1-(halogenomethyl)ethylthio, 1-(dihalogenomethyl)-2,2-dihalogenoethylthio, (R)-1-halogenobutylthio, (S)-1-halogenobutylthio, 2-halogenobutylthio, 3-halogenobutylthio, 4-halogenobutylthio, 1,1-dihalogenobutylthio, 2,2-dihalogenobutylthio, 3,3-dihalogenobutylthio, 4,4-dihalogenobutylthio, 4,4,4-trihalogenobutylthio, etc. Particular examples include the fluorinated $C_1$-$C_4$ alkylthio groups as defined, such as trifluoromethylthio.

$C_1$-$C_6$-Alkylsulfinyl is a radical of the formula R—S(O)—, wherein R is an alkyl radical having from 1 to 6, preferably from 1 to 4 carbon atoms as defined herein. Examples include methylsulfinyl, ethylsulfinyl, propylsulfinyl, butylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, hexylsulfinyl, 1,1-dimethylpropylsulfinyl, 1,2-dimethylpropylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl and 1-ethyl-2-methylpropyl.

$C_1$-$C_6$-Alkylsulfonyl is a radical of the formula R—S(O)$_2$—, wherein R is an alkyl radical having from 1 to 6, preferably from 1 to 4 carbon atoms as defined herein. Examples include methylsulfonyl, ethylsulfonyl, propylsulfonyl, butylsulfonyl, pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, hexylsulfonyl, 1,1-dimethylpropylsulfonyl, 1,2-dimethylpropylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl and 1-ethyl-2-methylpropyl.

(Halogenated $C_1$-$C_6$-alkyl)sulfonyl is a $C_1$-$C_6$-alkylsulfonyl as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonyl is a radical of the formula R—S(O)$_2$—, wherein R is an aryl radical having from 6 to 12 carbon atoms as defined herein. Examples include phenylsulfonyl.

($C_6$-$C_{12}$-Aryl-$C_1$-$C_4$-alkyl)sulfonyl is a radical of the formula R—S(O)$_2$—, wherein R is a $C_6$-$C_{12}$-aryl-$C_1$-$C_4$-alkyl radical, in particular a $C_6$-$C_{12}$-aryl-$C_1$-$C_2$-alkyl radical as defined herein. Examples include benzylsulfonyl.

$C_3$-$C_{12}$-Heterocyclylsulfonyl is a radical of the formula R—S(O)$_2$—, wherein R is $C_3$-$C_{12}$-heterocyclyl as defined herein.

Aminosulfonyl is NH$_2$—S(O)$_2$—.

$C_1$-$C_6$-Alkylaminosulfonyl is a radical of the formula R—NH—S(O)$_2$— wherein R is an alkyl radical having from 1 to 6, preferably from 1 to 4 carbon atoms as defined herein. Examples include methylaminosulfonyl, ethylaminosulfonyl, n-propylaminosulfonyl, iso-propylaminosulfonyl, n-butylaminosulfonyl, 2-butylaminosulfonyl, iso-butylaminosulfonyl, tert-butylaminosulfonyl.

Di-$C_1$-$C_6$-alkylaminosulfonyl is a radical of the formula RR'N—S(O)$_2$— wherein R and R' are independently of each other an alkyl radical having from 1 to 6, preferably from 1 to 4 carbon atoms as defined herein. Examples include dimethylaminosulfonyl, diethylaminosulfonyl, N-methyl-N-ethylaminosulfonyl.

$C_6$-$C_{12}$-Arylaminosulfonyl is a radical of the formula R—NH—S(O)$_2$— wherein R is an aryl radical having from 6 to 12, preferably 6 carbon atoms as defined herein.

Amino is NH$_2$.

$C_1$-$C_6$-Alkylamino is a radical of the formula R—NH— wherein R is an alkyl radical having from 1 to 6, in particular from 1 to 4 carbon atoms as defined herein. Examples include methylamino, ethylamino, n-propylamino, iso-propylamino, n-butylamino, 2-butylamino, iso-butylamino, tert-butylamino.

(Halogenated $C_1$-$C_6$-alkyl)amino is a $C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

Di-$C_1$-$C_6$-alkylamino is a radical of the formula RR'N— wherein R and R' are independently of each other an alkyl radical having from 1 to 6, in particular from 1 to 4 carbon atoms as defined herein. Examples include dimethylamino, diethylamino, N-methyl-N-ethylamino.

Di-(halogenated $C_1$-$C_6$-alkyl)amino is a di-$C_1$-$C_6$-alkylamino as defined herein, wherein at least one, e.g. 1, 2, 3, 4 or all of the hydrogen atoms are replaced by 1, 2, 3, 4 or a corresponding number of identical or different halogen atoms.

$C_1$-$C_6$-Alkylcarbonylamino is a radical of the formula R—C(O)—NH—, wherein R is an alkyl radical having from 1 to 6, in particular from 1 to 4 carbon atoms as defined herein. Examples include acetamido(methylcarbonylamino), propionamido, n-butyramido, 2-methylpropionamido(isopropylcarbonylamino), 2,2-dimethylpropionamido and the like.

(Halogenated $C_1$-$C_6$-alkyl)carbonylamino is a $C_1$-$C_6$-alkylcarbonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylcarbonylamino is a radical of the formula R—C(O)—NH—, wherein R is an aryl radical having from 6 to 12 carbon atoms as defined herein. Examples include phenylcarbonylamino.

$C_2$-$C_6$-Alkenylamino is a radical of the formula R—NH—, wherein R is a straight-chain or branched alkenyl group having from 2 to 6, in particular 2 to 4 carbon atoms. Examples include vinylamino, allylamino(2-propen-1-ylamino), 1-propen-1-ylamino, 2-propen-2-ylamino, methallylamino(2-methylprop-2-en-1-ylamino) and the like. $C_3$-$C_5$-Alkenylamino is, in particular, allylamino, 1-methylprop-2-en-1-ylamino, 2-buten-1-ylamino, 3-buten-1-ylamino, methallylamino, 2-penten-1-ylamino, 3-penten-1-ylamino, 4-penten-1-ylamino, 1-methylbut-2-en-1-ylamino or 2-ethylprop-2-en-1-ylamino.

$C_1$-$C_6$-Alkylsulfonylamino is a radical of the formula R—S(O)$_2$—NH—, wherein R is an alkyl radical having from 1 to 6, in particular from 1 to 4 carbon atoms as defined herein. Examples include methylsulfonylamino, ethylsulfonylamino, n-propylsulfonylamino, iso-propylsulfonylamino, n-butylsulfonylamino, 2-butylsulfonylamino, iso-butylsulfonylamino, tert-butylsulfonylamino.

(Halogenated $C_1$-$C_6$ alkyl)sulfonylamino is a $C_1$-$C_6$-alkylsulfonylamino as defined herein, wherein at least one, e.g. 1, 2, 3, 4 or all of the hydrogen atoms are replaced by 1, 2, 3, 4 or a corresponding number of identical or different halogen atoms.

$C_6$-$C_{12}$-Arylsulfonylamino is a radical of the formula R—S(O)$_2$—NH—, wherein R is an aryl radical having from 6 to 12 carbon atoms as defined herein. Examples include phenylsulfonylamino.

Nitro is —NO$_2$.

$C_3$-$C_{12}$-Heterocyclyl is a 3- to 12-membered heterocyclic radical including a saturated heterocyclic radical, which generally has 3, 4, 5, 6, or 7 ring forming atoms (ring members), an unsaturated non-aromatic heterocyclic radical, which generally has 5, 6 or 7 ring forming atoms, and a heteroaromatic radical (hetaryl), which generally has 5, 6 or 7 ring forming atoms. The heterocyclic radicals may be bound via a carbon atom (C-bound) or a nitrogen atom (N-bound). Preferred heterocyclic radicals comprise 1 nitrogen atom as ring member atom and optionally 1, 2 or 3 further heteroatoms as ring members, which are selected, independently of each other from O, S and N. Likewise preferred heterocyclic radicals comprise 1 heteroatom as ring member, which is selected from O, S and N, and optionally 1, 2 or 3 further nitrogen atoms as ring members.

Examples of $C_3$-$C_{12}$-heterocyclyl include:

C-bound 3-4-membered, saturated rings, such as 2-oxiranyl, 2-oxetanyl, 3-oxetanyl, 2-aziridinyl, 3-thiethanyl, 1-azetidinyl, 2-azetidinyl;

C-bound, 5-membered, saturated rings, such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as tetrahydropyrrol-1-yl(pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as piperidin-1-yl, hexahydropyrimidin-1-yl, hexahydropyrazin-1-yl(piperazin-1-yl), hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl(morpholin-1-yl), tetrahydro-1,2-oxazin-2-yl;

C-bound, 5-membered, partially unsaturated rings, such as 2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4, 5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

C-bound, 5-membered, heteroaromatic rings, such as 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings, such as pyridin-2-yl, pyridin-3-yl, pyridin-4-yl (4-pyridyl), pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings, such as pyrrol-1-yl, pyrazol-1-yl, imidazol-1-yl, 1,2,3-triazol-1-yl, 1,2,4-triazol-1-yl, tetrazol-1-yl.

Heterocyclyl also includes bicyclic heterocycles, which comprise one of the described 5- or 6-membered heterocyclic rings and a further anellated, saturated or unsaturated or aromatic carbocycle, such as a benzene, cyclohexane, cyclohexene or cyclohexadiene ring, or a further anellated 5- or 6-membered heterocyclic ring, this heterocyclic ring being saturated or unsaturated or aromatic. These include quinolinyl, isoquinolinyl, indolyl, indolizinyl, isoindolyl, indazolyl, benzofuryl, benzthienyl, benzo[b]thiazolyl, benzoxazolyl, benzthiazolyl and benzimidazolyl. Examples of 5- or 6-membered heteroaromatic compounds comprising an anellated cycloalkenyl ring include dihydroindolyl, dihydroindolizinyl, dihydroisoindolyl, dihydrochinolinyl, dihydroisoquinolinyl, chromenyl and chromanyl.

$C_3$-$C_{12}$-Heteroarylene is a heteroaryl diradical. Examples include pyrid-2,5-ylene and pyrid-2,4-ylene. A further example is pyrid-2,3-ylene.

With respect to compounds' capability of inhibiting glycine transporter 1, the variables R, $R^1$, W, $A^1$, Q, Y, $A^2$, X, $R^2$, $R^3$, $R^4$, $R^5$, $R^6$, $R^7$, $R^8$, $R^9$, $R^{19}$, $R^{11}$, $R^{12}$ preferably have the following meanings which, when taken alone or in combination, represent particular embodiments of the tetrahydroisoquinolines of the formula (I):

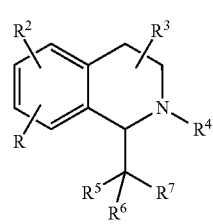

(I)

In said formula (I), there may be one or more than one substituent R, $R^2$ and/or $R^3$. More particularly, there may be up to 3 substituents $R^2$, and up to 5 substituents $R^3$. Preferably there is one substituent R and 1, 2 or 3 substituents $R^2$. Formula (I) may thus be depicted as follows:

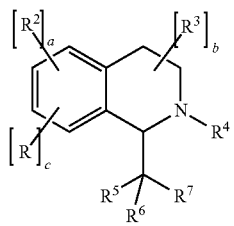

wherein a is 1, 2 or 3, b is 1, 2, 3, 4 or 5 and c is 1. If there is more than one radical $R^2$, these may be the same or different radicals. If there is more than one radical $R^3$, these may be the same or different radicals.

According to one embodiment, R is cyano.

Preferably, R is $R^1$—W-$A^1$-Q-Y-$A^2$-X—, wherein $R^1$, W, $A^1$, Q, Y, $A^2$, X are as defined herein.

$R^1$ is hydrogen, $C_1$-$C_6$-alkyl (e.g. methyl, n-propyl, isopropyl, n-butyl, isobutyl or 2,2-dimethylpropyl), halogenated $C_1$-$C_6$-alkyl (e.g. trifluormethyl, a further example being 3-fluoropropyl or 3,3,3-trifluoropropyl), hydroxy-$C_1$-$C_4$-alkyl (e.g. 2-hydroxyethyl or 2-hydroxy-2-methylpropyl), $C_1$-$C_6$-alkoxy-$C_1$-$C_4$-alkyl (e.g. methoxyethyl), amino-$C_1$-$C_4$-alkyl (e.g. aminoethyl, a further example being 3-amino-n-propyl or 4-amino-n-butyl), $C_1$-$C_6$-alkylamino-$C_1$-$C_4$-alkyl (e.g. ethylamino-n-propyl, n-propylamino-n-propyl or isopropylamino-n-propyl, a further example being isopropylaminoethyl or methylamino-n-propyl), di-$C_1$-$C_6$-alkylamino-$C_1$-$C_4$-alkyl (e.g. dimethylamino-n-propyl or diethylamino-n-propyl, a further example being dimethylaminoethyl), $C_1$-$C_6$-alkylcarbonylamino-$C_1$-$C_4$-alkyl, $C_1$-$C_6$-alkyloxycarbonylamino-$C_1$-$C_4$-alkyl (e.g. t-butoxycarbonylaminoethyl), $C_1$-$C_6$-alkylaminocarbonylamino-$C_1$-$C_4$-alkyl (e.g. n-propylaminocarbonylaminoethyl), di-$C_1$-$C_6$-alkylaminocarbonylamino-$C_1$-$C_4$-alkyl, $C_1$-$C_6$-alkylsulfonylamino-$C_1$-$C_4$-alkyl, ($C_6$-$C_{12}$-aryl-$C_1$-$C_6$-alkyl)amino-$C_1$-$C_4$ alkyl, optionally substituted $C_6$-$C_{12}$-aryl-$C_1$-$C_4$-alkyl (e.g. benzyl), optionally substituted $C_3$-$C_{12}$-heterocyclyl-$C_1$-$C_4$-alkyl (e.g. 2-(1-piperidinyl)ethyl), $C_3$-$C_{12}$-cycloalkyl (e.g. cyclopropyl), $C_1$-$C_6$-alkylcarbonyl, $C_1$-$C_6$-alkoxycarbonyl (e.g. tert-butyloxycarbonyl), halogenated $C_1$-$C_6$-alkoxycarbonyl, $C_6$-$C_{12}$-aryloxycarbonyl, aminocarbonyl, $C_1$-$C_6$-alkylaminocarbonyl (e.g. ethylaminocarbonyl), (halogenated $C_1$-$C_4$-alkyl)aminocarbonyl, $C_6$-$C_{12}$-arylaminocarbonyl, $C_2$-$C_6$-alkenyl (e.g. prop-1-en-1-yl), $C_2$-$C_6$-alkynyl, optionally substituted $C_6$-$C_{12}$-aryl (e.g. phenyl, naphthyl, 2-CN-phenyl, 3-CN-phenyl, 2-Cl-phenyl, 3-Cl-phenyl, 4-Cl-phenyl, 2,4-di-Cl-phenyl, 2-MeO-phenyl, 3-MeO-phenyl or 4-MeO-phenyl, a further example being 4-(2-fluoroethyl)-phenyl, 3-$NH_2$-phenyl, 4-$NH_2$-phenyl or 4-aminocarbonylaminophenyl), hydroxy, $C_1$-$C_6$-alkoxy, halogenated $C_1$-$C_6$-alkoxy, $C_1$-$C_6$-hydroxyalkoxy, $C_1$-$C_6$-alkoxy-$C_1$-$C_4$-alkoxy, amino-$C_1$-$C_4$ alkoxy, $C_1$-$C_6$-alkylamino-$C_1$-$C_4$-alkoxy, di-$C_1$-$C_6$-alkylamino-$C_1$-$C_4$-alkoxy, $C_1$-$C_6$-alkylcarbonylamino-$C_1$-$C_4$-alkoxy, $C_6$-$C_{12}$-arylcarbonylamino-$C_1$-$C_4$-alkoxy, $C_1$-$C_6$-alkoxycarbonylamino-$C_1$-$C_4$-alkoxy, $C_6$-$C_{12}$-aryl-$C_1$-$C_4$-alkoxy, $C_1$-$C_6$-alkylsulfonylamino-$C_1$-$C_4$-alkoxy, (halogenated $C_1$-$C_6$-alkyl)sulfonylamino-$C_1$-$C_4$-alkoxy, $C_6$-$C_{12}$-arylsulfonylamino-$C_1$-$C_4$-alkoxy, ($C_6$-$C_{12}$-aryl-$C_1$-$C_6$-alkyl)sulfonylamino-$C_1$-$C_4$-alkoxy, $C_3$-$C_{12}$-heterocyclylsulfonylamino-$C_1$-$C_4$-alkoxy, $C_3$-$C_{12}$-heterocyclyl-$C_1$-$C_4$-alkoxy, $C_6$-$C_{12}$-aryloxy, $C_3$-$C_{12}$-heterocyclyloxy, $C_1$-$C_6$-alkylthio, halogenated $C_1$-$C_6$-alkylthio, $C_1$-$C_6$-alkylamino (e.g. isopropylamino or t-butylamino), (halogenated $C_1$-$C_6$-alkyl)amino, di-$C_1$-$C_6$-alkylamino (e.g. diethylamino, a further example being dimethylamino), di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$ alkyl)sulfonylamino, $C_6$-$C_{12}$-arylsulfonylamino or optionally substituted $C_3$-$C_{12}$-heterocyclyl (e.g. 3-pyridyl, 6-chloro-3-pyridyl, 6-amino-3-pyridyl, 6-propylamino-3-pyridyl, 6-benzylamino-3-pyridyl, 2-thienyl, 5-(3-isoxazolyl)-2-thienyl, 1-methyl-1,2-diazol-4-yl, 1,3-dimethyl-1,2-diazol-4-yl, 1,3-diazol-4-yl, 1-methyl-1,3-diazol-4-yl, 1,2-dimethyl-1,3-diazol-4-yl, 8-quinolinyl, piperidin-1-yl, piperidin-3-yl, 1,4-piperazinyl, 1-ethoxycarbonyl-1,4-piperazinyl, 1-t-butoxycarbonyl-1,4-piperazinyl, 1-propyl-1,4-piperazinyl, 1-propylsulfonyl-1,4-piperazinyl, morpholinyl, 1,3-dioxo-1,3-dihydro-2H-isoindol-2-yl or 6-chloro-imidazo[2,1-b][1,3]thiazole-5-yl, a further example being 3-azetidinyl, 1-methylcarbonyl-azetidin-3-yl, 3-pyrrolidinyl, 1-benzyloxycarbonylpyrrolidin-3-yl, 1,2-diazol-4-yl, 1,2,4-triazol-5-yl, 3-amino-1,2,4-triazol-5-yl, 5-methyl-1,2-oxazol-4-yl, 2-amino-1,3-thiazol-5-yl, 2-acetylamino-1,3-thiazol-5-yl, 5-methylamino-1,3,4-thiadiazol-2-yl, 4-methyl-3,4-dihydro-2H-pyrido[3,2-b][1,4]oxazin-7-yl, 2-pyridyl, 6-methoxy-3-pyridyl, 3-phenoxy-3-pyridyl, 6-amino-3-pyridyl, 6-morpholin-4-yl-3-pyridyl, 2-amino-1,3-pyrimidin-5-yl, 4-piperidinyl or 1-benzyl-piperidin-4-yl). Further, $R^1$ may also be halogenated $C_1$-$C_6$-alkylcarbonyl or $C_1$-$C_6$-alkylcarbonyloxy.

Preferably, $R^1$ is $C_1$-$C_6$-alkyl (e.g. methyl, n-propyl, isopropyl, n-butyl, isobutyl or 2,2-dimethylpropyl), halogenated $C_1$-$C_6$-alkyl (e.g. trifluormethyl, a further example being 3-fluoropropyl or 3,3,3-trifluoropropyl), hydroxy-$C_1$-$C_4$-alkyl (e.g. 2-hydroxyethyl or 2-hydroxy-2-methylpropyl), $C_1$-$C_6$-alkoxy-$C_1$-$C_4$-alkyl (e.g. methoxyethyl), amino-$C_1$-$C_4$-alkyl (e.g. aminoethyl, a further example being 3-amino-n-propyl or 4-amino-n-butyl), $C_1$-$C_6$-alkylamino-$C_1$-$C_4$-alkyl (e.g. ethylamino-n-propyl, n-propylamino-n-propyl or isopropylamino-n-propyl, a further example being isopropylaminoethyl or methylamino-n-propyl), di-$C_1$-$C_6$-alkylamino-$C_1$-$C_4$-alkyl (e.g. dimethylamino-n-propyl or diethylamino-n-propyl, a further example being dimethylaminoethyl), $C_1$-$C_6$-alkylcarbonylamino-$C_1$-$C_4$-alkyl, $C_1$-$C_6$-alkyloxycarbonylamino-$C_1$-$C_4$-alkyl (e.g. t-butoxycarbonylaminoethyl), $C_1$-$C_6$-alkylaminocarbonylamino-$C_1$-$C_4$-alkyl (e.g. n-propylaminocarbonylaminoethyl), di-$C_1$-$C_6$-alkylaminocarbonylamino-$C_1$-$C_4$-alkyl, $C_6$-$C_{12}$-aryl-$C_1$-$C_4$-alkyl (e.g. benzyl), $C_3$-$C_{12}$-heterocyclyl-$C_1$-$C_4$-alkyl (e.g. 2-(1-piperidinyl)ethyl), $C_3$-$C_{12}$-cycloalkyl (e.g. cyclopropyl), optionally substituted $C_6$-$C_{12}$-aryl (e.g. phenyl, naphthyl, 2-CN-phenyl, 3-CN-phenyl, 2-Cl-phenyl, 3-Cl-phenyl, 4-Cl-phenyl, 2,4-di-Cl-phenyl, 2-MeO-phenyl, 3-MeO-phenyl or 4-MeO-phenyl, a further example being 4-(2-fluoroethyl)-phenyl, 3-NH$_2$-phenyl, 4-NH$_2$-phenyl or 4-aminocarbonylamino-phenyl), hydroxy, $C_1$-$C_6$-alkylamino (e.g. isopropylamino or t-butylamino), (halogenated $C_1$-$C_6$-alkyl)amino, di-$C_1$-$C_6$-alkylamino (e.g. diethylamino, a further example being dimethylamino), di-(halogenated $C_1$-$C_6$-alkyl)amino, $C_1$-$C_6$-alkylcarbonylamino, (halogenated $C_1$-$C_6$-alkyl)carbonylamino, $C_6$-$C_{12}$-arylcarbonylamino, $C_1$-$C_6$-alkylsulfonylamino, (halogenated $C_1$-$C_6$ alkyl)sulfonylamino, $C_6$-$C_{12}$-arylsulfonylamino or optionally substituted $C_3$-$C_{12}$-heterocyclyl (e.g. 3-pyridyl, 6-chloro-3-pyridyl, 6-amino-3-pyridyl, 6-propylamino-3-pyridyl, 6-benzylamino-3-pyridyl, 2-thienyl, 5-(3-isoxazolyl)-2-thienyl, 1-methyl-1,2-diazol-4-yl, 1,3-dimethyl-1,2-diazol-4-yl, 1,3-diazol-4-yl, 1-methyl-1,3-diazol-4-yl, 1,2-dimethyl-1,3-diazol-4-yl, 8-quinolinyl, piperidin-1-yl, piperidin-3-yl, 1,4-piperazinyl, 1-ethoxycarbonyl-1,4-piperazinyl, 1-t-butoxycarbonyl-1,4-piperazinyl, 1-propyl-1,4-piperazinyl, 1-propylsulfonyl-1,4-piperazinyl, morpholinyl, 1,3-dioxo-1,3-dihydro-2H-isoindol-2-yl or 6-chloro-imidazo[2,1-b][1,3]thiazole-5-yl, a further example being 3-azetidinyl, 1-methylcarbonyl-azetidin-3-yl, 3-pyrrolidinyl, 1-benzyloxycarbonylpyrrolidin-3-yl, 1,2-diazol-4-yl, 1,2,4-triazol-5-yl, 3-amino-1,2,4-triazol-5-yl, 5-methyl-1,2-oxazol-4-yl, 2-amino-1,3-thiazol-5-yl, 2-acetylamino-1,3-thiazol-5-yl, 5-methylamino-1,3,4-thiadiazol-2-yl, 4-methyl-3,4-dihydro-2H-pyrido[3,2-b][1,4]oxazin-7-yl, 2-pyridyl, 6-methoxy-3-pyridyl, 3-phenoxy-3-pyridyl, 6-amino-3-pyridyl, 6-morpholin-4-yl-3-pyridyl, 2-amino-1,3-pyrimidin-5-yl, 4-piperidinyl or 1-benzyl-piperidin-4-yl). It is further preferred if $R^1$ is $C_1$-$C_6$-alkoxycarbonyl (e.g. tert-butyloxycarbonyl), $C_1$-$C_6$-alkylaminocarbonyl (e.g. ethylaminocarbonyl) or $C_2$-$C_6$-alkenyl (e.g. prop-1-en-1-yl).

In particular, $R^1$ is hydrogen, $C_1$-$C_6$-alkyl (e.g. methyl, n-propyl, isopropyl, n-butyl, isobutyl or 2,2-dimethylpropyl), halogenated $C_1$-$C_6$-alkyl (e.g. trifluormethyl, a further example being 3-fluoropropyl or 3,3,3-trifluoropropyl), $C_1$-$C_6$-alkoxy-$C_1$-$C_4$-alkyl (e.g. methoxyethyl, amino-$C_1$-$C_4$-alkyl (e.g. aminoethyl, a further example being 3-amino-n-propyl or 4-amino-n-butyl), $C_1$-$C_6$-alkylamino-$C_1$-$C_4$-alkyl (e.g. ethylamino-n-propyl, n-propylamino-n-propyl or isopropylamino-n-propyl, a further example being isopropylaminoethyl or methylamino-n-propyl), di-$C_1$-$C_6$-alkylamino-$C_1$-$C_4$-alkyl (e.g. dimethylamino-n-propyl or diethylamino-n-propyl, a further example being dimethylaminoethyl), $C_1$-$C_6$-alkyloxycarbonylamino-$C_1$-$C_4$-alkyl (e.g. t-butoxycarbonylaminoethyl), $C_1$-$C_6$-alkylaminocarbonylamino-$C_1$-$C_4$-alkyl (e.g. n-propylaminocarbonylaminoethyl), $C_6$-$C_{12}$-aryl-$C_1$-$C_4$-alkyl (e.g. benzyl), $C_3$-$C_{12}$-heterocyclyl-$C_1$-$C_4$-alkyl (e.g. 2-(1-piperidinyl)ethyl), $C_3$-$C_{12}$-cycloalkyl (e.g. cyclopropyl), optionally substituted $C_6$-$C_{12}$-aryl (e.g. phenyl, naphthyl, 2-CN-phenyl, 3-CN-phenyl, 2-Cl-phenyl, 3-Cl-phenyl, 4-Cl-phenyl, 2,4-di-Cl-phenyl, 2-MeO-phenyl, 3-MeO-phenyl or 4-MeO-phenyl, a further example being 4-(2-fluoroethyl)-phenyl, 3-NH$_2$-phenyl, 4-NH$_2$-phenyl or 4-aminocarbonylamino-phenyl), hydroxy, $C_1$-$C_6$-alkylamino (e.g. isopropylamino or t-butylamino), di-$C_1$-$C_6$-alkylamino (e.g. diethylamino, a further example being dimethylamino), or optionally substituted $C_3$-$C_{12}$-heterocyclyl (e.g. 3-pyridyl, 6-chloro-3-pyridyl, 6-amino-3-pyridyl, 6-propylamino-3-pyridyl, 6-benzylamino-3-pyridyl, 2-thienyl, 5-(3-isoxazolyl)-2-thienyl, 1-methyl-1,2-diazol-4-yl, 1,3-dimethyl-1,2-diazol-4-yl, 1,3-diazol-4-yl, 1-methyl-1,3-diazol-4-yl, 1,2-dimethyl-1,3-diazol-4-yl, 8-quinolinyl, piperidin-1-yl, piperidin-3-yl, 1,4-piperazinyl, 1-ethoxycarbonyl-1,4-piperazinyl, 1-t-butoxycarbonyl-1,4-piperazinyl, 1-propyl-1,4-piperazinyl, 1-propylsulfonyl-1,4-piperazinyl, morpholinyl, 1,3-dioxo-1,3-dihydro-2H-isoindol-2-yl or 6-chloro-imidazo[2,1-b][1,3]thiazole-5-yl, a further example being 3-azetidinyl, 1-methylcarbonyl-azetidin-3-yl, 3-pyrrolidinyl, 1-benzyloxycarbonylpyrrolidin-3-yl, 1,2-diazol-4-yl, 1,2,4-triazol-5-yl, 3-amino-1,2,4-triazol-5-yl, 5-methyl-1,2-oxazol-4-yl, 2-amino-1,3-thiazol-5-yl, 2-acetylamino-1,3-thiazol-5-yl, 5-methylamino-1,3,4-thiadiazol-2-yl, 4-methyl-3,4-dihydro-2H-pyrido[3,2-b][1,4]oxazin-7-yl, 2-pyridyl, 6-methoxy-3-pyridyl, 3-phenoxy-3-pyridyl, 6-amino-3-pyridyl, 6-morpholin-4-yl-3-pyridyl, 2-amino-1,3-pyrimidin-5-yl, 4-piperidinyl or 1-benzyl-piperidin-4-yl).

In connection with $R^1$, substituted $C_6$-$C_{12}$-aryl in particular includes $C_6$-$C_{12}$-aryl, such as phenyl or naphthyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy, $C_1$-$C_4$-haloalkoxy, amino, $C_1$-$C_4$-alkylamino, $C_1$-$C_4$-dialkylamino, morpholino and piperidinyl, aminocarbonylamino being a further example of such substituents. The same applies to substituted $C_6$-$C_{12}$-aryl in substituted $C_6$-$C_{12}$-aryl-$C_1$-$C_4$-alkyl.

In connection with $R^1$, substituted $C_3$-$C_{12}$-heterocyclyl in particular includes $C_3$-$C_{12}$-heterocyclyl, such as pyridyl, thienyl, diazolyl, quinolinyl, piperidinyl, piperazinyl or morpholinyl (azetidinyl, triazolyl, thiazolyl, thiadiazolyl and pyrimidinyl being further examples of such $C_3$-$C_{12}$-heterocyclyl), substituted with 1, 2 or 3 substituents selected from the group consisting of halogen, $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl), $C_3$-$C_{12}$-aryl-$C_1$-$C_4$-alkyl, $C_1$-$C_4$-alkylcarbonyl, $C_3$-$C_{12}$-aryloxycarbonyl, $C_3$-$C_{12}$-aryloxy and $C_1$-$C_4$-alkylcarbonylamino being further examples of such substituents. The same applies to substituted $C_3$-$C_{12}$-heteroaryl in substituted $C_3$-$C_{12}$-heteroaryl-$C_1$-$C_4$-alkyl.

According to one embodiment, W is —NR$^8$— and Y is a bond. According to an alternative embodiment, W is a bond and Y is —NR$^9$—. According to a further alternative embodiment, W is a bond and Y is a bond, especially if $R^1$ is a nitrogen-bound radical, e.g. nitrogen-bound heterocyclyl such as piperazinyl or morpholinyl.

According to one embodiment, Q is —S(O)$_2$—. According to an alternative embodiment, Q is —C(O)—.

According to a particular embodiment, —W-A$^1$-Q-Y— is —W-A$^1$-S(O)$_2$—NR$^9$—, —NR$^8$—S(O)$_2$—, -A$^1$-S(O)$_2$— or —S(O)$_2$—.

$A^1$ is optionally substituted $C_1$-$C_4$-alkylene (e.g. 1,2-ethylene or 1,3-propylene) or a bond. In connection with $A^1$, substituted $C_1$-$C_4$-alkylene in particular includes $C_1$-$C_4$-alkylene substituted with 1, 2 or 3 substituents selected from the group consisting of halogen, $C_1$-$C_4$-alkyl and cyano. Preferably, $A^1$ is a bond. If $A^1$ is $C_1$-$C_4$-alkylene, W is preferably —NR$^8$—.

$A^2$ is optionally substituted $C_1$-$C_4$-alkylene (e.g. methylene or ethylene), $C_1$-$C_4$-alkylene-O—$C_1$-$C_4$-alkylene, $C_1$-$C_4$-alkylene-$NR^{10}$—$C_1$-$C_4$-alkylene (e.g. ethylene-N(propylsulfonyl)-ethylene), optionally substituted $C_6$-$C_{12}$-arylene (e.g. 1,4-phenylene or 1,2-phenylene), optionally substituted $C_6$-$C_{12}$-heteroarylene (2,5-pyridylene or 2,3-pyridylene) or a bond. Preferably, $A^2$ is optionally substituted $C_1$-$C_4$-alkylene (e.g. methylene or ethylene), $C_1$-$C_4$-alkylene-O—$C_1$-$C_4$-alkylene or —$C_4$-alkylene-$NR^{10}$—$C_1$-$C_4$-alkylene (e.g. ethylene-N(propylsulfonyl)-ethylene). More preferably, $A^2$ is $C_1$-$C_4$-alkylene (e.g. methylene or ethylene). Alternatively, it is preferred that $A^2$ is optionally substituted $C_6$-$C_{12}$-arylene, in particular $C_6$-$C_{12}$-arylene selected from the group consisting of phen-1,4-ylene and phen-1,3-ylene, or optionally substituted $C_6$-$C_{12}$-heteroarylene, in particular $C_6$-$C_{12}$-heteroarylene selected from the group consisting of pyrid-2,5-ylene and pyrid-2,4-ylene. If $A^2$ is a bond, X is preferably optionally substituted $C_1$-$C_4$-alkylene.

In connection with $A^2$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano.

In connection with $A^2$, substituted $C_6$-$C_{12}$-arylene in particular includes $C_6$-$C_{12}$-arylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

In connection with $A^2$, substituted $C_6$-$C_{12}$-heteroarylene in particular includes $C_6$-$C_{12}$-heteroarylene substituted with 1, 2 or 3 substituents selected from the group consisting of $C_1$-$C_4$-alkyl, $C_1$-$C_4$-haloalkyl, $C_1$-$C_4$-alkoxycarbonyl, cyano, $C_1$-$C_4$-alkoxy, $C_1$-$C_4$-haloalkoxy, $C_1$-$C_4$-alkylsulfonyl, amino, $C_1$-$C_4$-alkylamino, $C_1$-$C_4$-dialkylamino, $C_6$-$C_{12}$-arylamino and $C_3$-$C_{12}$-heterocyclyl (e.g., morpholino or piperidinyl).

X is —O—, —$NR^{11}$—, —S— or optionally substituted $C_1$-$C_4$-alkylene (e.g. —$CH_2$—). In connection with X, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl and cyano. Preferably, X is —O—, —$NR^{11}$— or —S—. More preferably, X is —O— or —$NR^{11}$—.

According to a particular embodiment, $A^2$ is a bond and X is optionally substituted $C_1$-$C_4$-alkylene.

According to a further particular embodiment, —Y-$A^2$-X— is —$NR^9$—$C_1$-$C_4$-alkylene-O— (e.g. —NH—$(CH_2)_2$—O—), —$C_1$-$C_4$-alkylene-O— (e.g. —$(CH_2)_3$—O—), —$NR^9$—$C_1$-$C_4$-alkylene-NH— (e.g. —NH—$(CH_2)_2$—NH—), —$NR^9$—$CH_2CO$—NH— (e.g. —NH—$CH_2CO$—NH—), —$NR^9$—$C_1$-$C_4$-alkylene- (e.g. —NH—$CH_2$—), —$NR^9$-1,4-phenylene-O— (e.g. —NH-1,4-phenylene-O—), —$NR^9$-1,2-phenylene-O— (e.g. —NH-1,2-phenylene-O—), —$NR^9$-2,5-pyridylene-O— (e.g. —NH-2,5-pyridylene-O—), —$NR^9$-2,3-pyridylene-O— (e.g. —NH-2,3-pyridylene-O—) or —O—, with —Y-$A^2$-X— preferably having 2 to 6, 3 to 5 and especially 4 atoms in the main chain.

According to a particular embodiment, $R^1$—W-$A^1$-Q-Y-$A^2$-X— is $R^1$—$S(O)_2$—NH-$A^2$-X—, $R^1$—NH—$S(O)_2$-$A^2$-X—, $R^1$—C(O)—NH-$A^2$-X— or $R^1$—NH—C(O)-$A^2$-X—.

According to a further particular embodiment, —Y-$A^2$-X— is —$C_1$-$C_4$-alkylene-O— or —$NR^9$—$C_1$-$C_4$-alkylene-O—, with —Y-$A^2$-X— preferably having 2 to 6, 3 to 5 and especially 4 atoms in the main chain. Particular examples of —Y-$A^2$-X— include —$(CH_2)_3$—O— and —$NR^9$—$(CH_2)_2$—O—.

The radical $R^1$—W-$A^1$-Q-Y-$A^2$-X— (or the radical —CN) may, in principle, be bound to the 5-, 6-, 7- or 8-position of the tetrahydroisoquinoline skeleton:

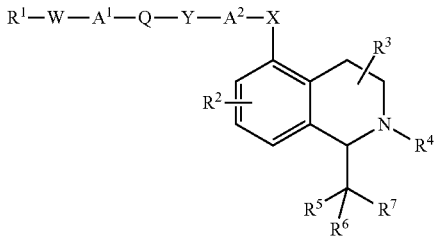

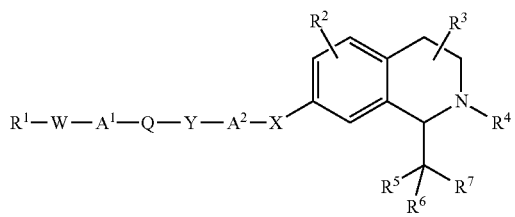

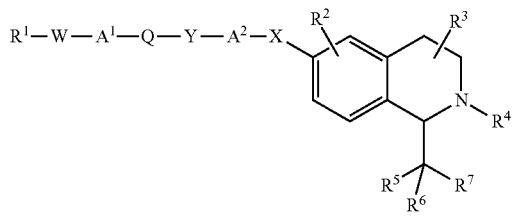

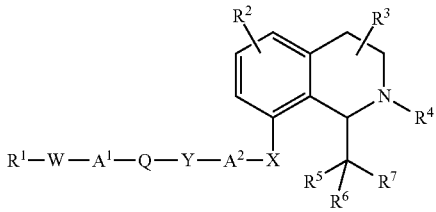

In said formulae, $R^1$, W, $A^1$, Q, Y, $A^2$, X, $R^2$, $R^3$, $R^4$, $R^5$, $R^6$, $R^7$ are as defined herein.

Tetrahydroisoquinolines having the radical $R^1$—W-$A^1$-Q-Y-$A^2$-X— (or the radical —CN) in the 5-, 6-, 7-position are preferred.

Particularly preferred are tetrahydroisoquinolines having the radical $R^1$—W-$A^1$-Q-Y-$A^2$-X— (or the radical —CN) in the 7-position.

In addition to the radical $R^1$—W-$A^1$-Q-Y-$A^2$-X— (or the radical —CN), the tetrahydroisoquinolines of the invention may have one or more than one further substituent bound to the 5-, 6-, 7- or 8-position of the tetrahydroisoquinoline skeleton. In 5-, 6-, 7- and/or 8-position, the tetrahydroisoquinoline skeleton may thus be substituted with one or more than one radical $R^2$. If there is more than one radical $R^2$, these may be the same or different radicals. In particular, in 5-, 6-, 7- and/or 8-position, the tetrahydroisoquinoline skeleton may be substituted with one or more than one radical $R^2$. The tetrahydroisoquinolines of the invention may therefore be represented by one of the following formulae:

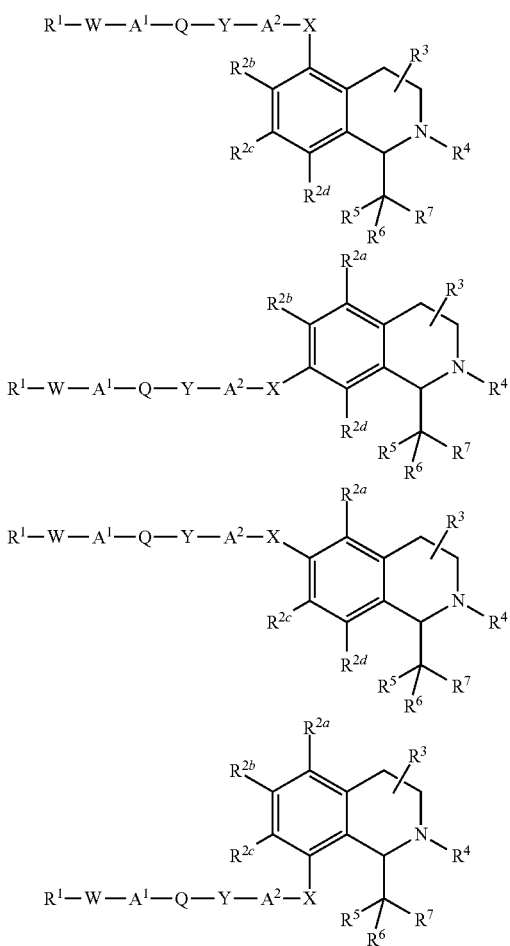

or by corresponding formulae wherein the radical $R^1$—W-$A^1$-Q-Y-$A^2$-X— is replaced by the radical —CN,
wherein $R^{2a}$, $R^{2b}$, $R^{2c}$, $R^{2d}$ independently have the meaning of $R^2$ and $R^1$, W, $A^1$, Q, Y, $A^2$, X, $R^2$, $R^3$, $R^4$, $R^5$, $R^6$, $R^7$ are as defined herein.

$R^2$ is hydrogen, halogen (e.g. fluoro, chloro or bromo), $C_1$-$C_6$-alkyl (e.g. methyl), halogenated $C_1$-$C_4$-alkyl (e.g. trifluoromethyl), hydroxy-$C_1$-$C_4$-alkyl, —CN, $C_2$-$C_6$-alkenyl, $C_2$-$C_6$-alkynyl, optionally substituted $C_6$-$C_{12}$-aryl (e.g. phenyl, 4-F-phenyl, 4-Cl-phenyl, 2-Me-phenyl, 4-Me-phenyl or 4-isopropyl-phenyl), hydroxy, $C_1$-$C_6$-alkoxy (e.g. methoxy), halogenated $C_1$-$C_6$-alkoxy, $C_2$-$C_6$-alkenyloxy, $C_6$-$C_{12}$-aryl-$C_1$-$C_4$-alkoxy (e.g. benzyloxy), $C_1$-$C_6$-alkylcarbonyloxy (e.g. methylcarbonyloxy), $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino or optionally substituted $C_3$-$C_{12}$-heterocyclyl.

In connection with $R^2$, substituted $C_6$-$C_{12}$-aryl in particular includes $C_6$-$C_{12}$-aryl, such as phenyl, substituted with 1, 2 or 3 substituents selected from the group consisting of halogen and $C_1$-$C_4$-alkyl, $C_1$-$C_4$-haloalkyl, cyano, $C_1$-$C_4$-alkoxy and $C_1$-$C_4$-haloalkoxy.

In connection with $R^2$, substituted $C_3$-$C_{12}$-heterocyclyl in particular includes $C_3$-$C_{12}$-heterocyclyl, such as morpholinyl, pyrrolidinyl and piperidinyl, substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

Preferably, $R^2$ is hydrogen, halogen (e.g. fluoro or bromo), or $C_1$-$C_6$-alkoxy (e.g. methoxy).

According to a particular embodiment, the tetrahydroisoquinolines of the invention have one of the following formulae:

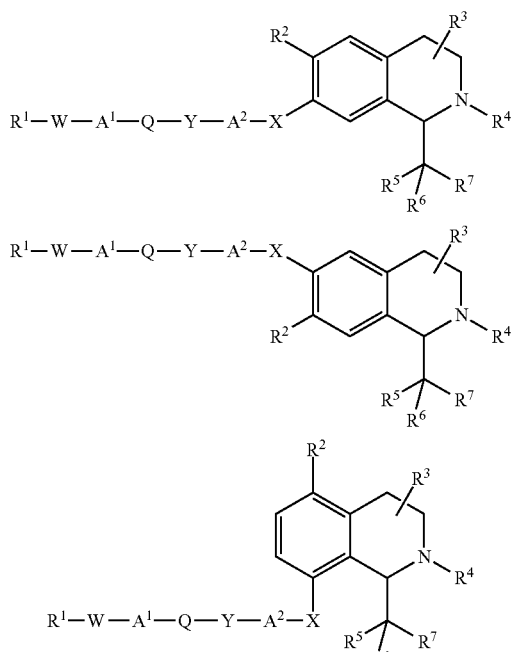

or one of the corresponding formulae wherein the radical $R^1$—W-$A^1$-Q-Y-$A^2$-X— is replaced by the radical —CN,
wherein $R^1$, W, $A^1$, Q, Y, $A^2$, X, $R^2$, $R^3$, $R^4$, $R^5$, $R^6$, $R^7$ are as defined herein.

In 1-, 3- and/or 4-position, the tetrahydroisoquinolines of the invention may be substituted with one or more than one radical $R^3$. If there is more than one radical $R^3$, these may be the same or different radicals. The tetrahydroisoquinolines of the invention may therefore be represented by the following formula:

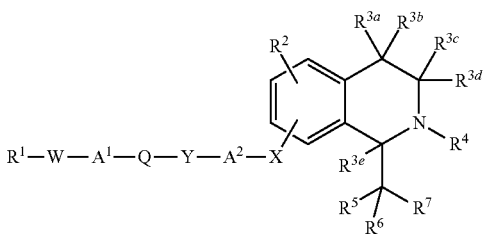

or by the corresponding formula wherein the radical $R^1$—W-$A^1$-Q-Y-$A^2$-X— is replaced by the radical —CN,
wherein $R^{3a}$, $R^{3b}$, $R^{3c}$, $R^{3d}$, $R^{3e}$ independently have the meaning of $R^3$ and $R^1$, W, $A^1$, Q, Y, $A^2$, X, $R^2$, $R^3$, $R^4$, $R^5$, $R^6$, $R^7$ are as defined herein.

According to a particular embodiment, the tetrahydroisoquinolines of the invention have one of the following formulae:

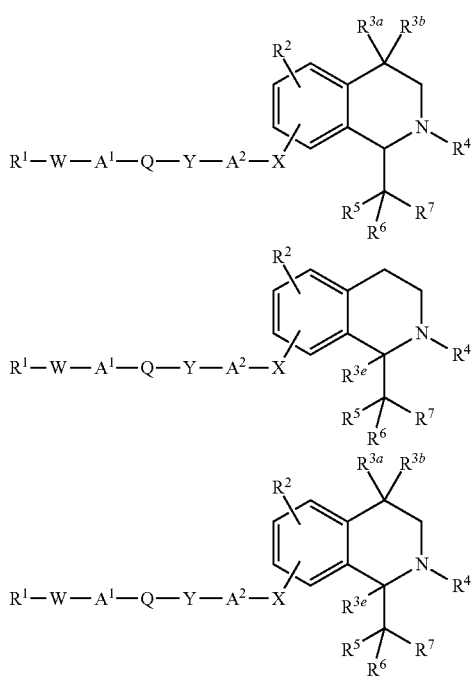

or one of the corresponding formulae wherein the radical $R^1$—W-$A^1$-Q-Y-$A^2$-X— is replaced by the radical —CN, wherein $R^{3a}$, $R^{3b}$, $R^{3e}$ independently have the meaning of $R^3$ and $R^1$, W, $A^1$, Q, Y, $A^2$, X, $R^2$, $R^3$, $R^4$, $R^5$, $R^6$, $R^7$ are as defined herein.

$R^3$ is hydrogen, halogen, $C_1$-$C_6$-alkyl (e.g. 4-methyl or 4,4-dimethyl), $C_1$-$C_6$-alkoxy, or two radicals $R^3$ together with the carbon atom to which they are attached form a carbonyl group.

Preferably, $R^3$ is hydrogen or $C_1$-$C_6$-alkyl (e.g. 4,4-dimethyl).

$R^4$ is hydrogen, $C_1$-$C_6$-alkyl (e.g. methyl, ethy or, isopropyl), halogenated $C_1$-$C_4$-alkyl (e.g. 2,2,2-trifluoroethyl), hydroxy-$C_1$-$C_4$-alkyl, $C_1$-$C_6$-alkoxy-$C_1$-$C_4$-alkyl, amino-$C_1$-$C_4$-alkyl (e.g. aminoethyl), $CH_2CN$, —CHO, $C_1$-$C_4$-alkylcarbonyl (e.g. methylcarbonyl), (halogenated $C_1$-$C_4$-alkyl) carbonyl (e.g. trifluoromethylcarbonyl), $C_6$-$C_{12}$-arylcarbonyl, $C_1$-$C_6$-alkylaminocarbonyl (e.g. methylaminocarbonyl or ethylaminocarbonyl), $C_2$-$C_6$-alkenyl (e.g. 1,2-propenyl), —C(=NH)$NH_2$, —C(=NH)NHCN, $C_1$-$C_6$-alkylsulfonyl (e.g. propylsulfonyl or methylsulfonyl), $C_6$-$C_{12}$-arylsulfonyl (e.g. phenylsulfonyl), amino, —NO or $C_3$-$C_{12}$-heterocyclyl (e.g. 1,3-diazol-2-yl).

Preferably, $R^4$ is hydrogen, $C_1$-$C_6$-alkyl (e.g. methyl), halogenated $C_1$-$C_4$-alkyl (e.g. 2,2,2-trifluoroethyl), amino-$C_1$-$C_4$-alkyl (e.g. aminoethyl), $CH_2CN$, $C_1$-$C_4$-alkylcarbonyl (e.g. methylcarbonyl), (halogenated $C_1$-$C_4$-alkyl)carbonyl (e.g. trifluoromethylcarbonyl), —C(=NH)$NH_2$,—C(=NH)NHCN, $C_1$-$C_6$-alkylsulfonyl (e.g. propylsulfonyl), amino, —NO or $C_3$-$C_{12}$-heterocyclyl (e.g. 1,3-diazol-2-yl).

$R^5$ is optionally substituted $C_1$-$C_6$-alkyl (e.g. methyl or isopropyl), $C_1$-$C_6$-alkylamino-$C_1$-$C_4$-alkyl (e.g. isopropylaminomethyl), di-$C_1$-$C_6$-alkylamino-$C_1$-$C_4$-alkyl (e.g. dimethylaminomethyl or diethylaminomethyl), $C_3$-$C_{12}$-heterocyclyl-$C_1$-$C_6$-alkyl (e.g. N-pyrrolidinylmethyl or N-morpholinylmethyl), optionally substituted $C_6$-$C_{12}$-aryl (e.g. 4-Cl-phenyl) or hydroxy.

$R^6$ is hydrogen, optionally substituted $C_1$-$C_6$-alkyl (e.g. methyl) or hydroxy.

In connection with $R^5$, substituted $C_1$-$C_6$-alkyl in particular includes $C_1$-$C_6$-alkyl substituted with 1, 2 or 3 substituents selected from the group consisting of halogen, hydroxy, $C_1$-$C_4$-alkoxy and amino.

In connection with $R^5$, substituted $C_6$-$C_{12}$-aryl in particular includes $C_6$-$C_{12}$-aryl, such as phenyl, substituted with 1, 2 or 3 substituents selected from the group consisting of $C_1$-$C_4$-alkyl, $C_1$-$C_4$-haloalkyl, cyano, $C_1$-$C_4$-alkoxy and $C_1$-$C_4$-haloalkoxy.

Preferably, $R^5$ is $C_1$-$C_6$-alkyl (e.g. isopropyl, a further example being methyl).

Preferably, $R^6$ is hydrogen or $C_1$-$C_6$-alkyl (e.g. methyl).

According to a particular embodiment, $R^5$ is $C_1$-$C_6$-alkyl (e.g. methyl) and $R^6$ is $C_1$-$C_6$-alkyl (e.g. methyl).

According to a particular embodiment, $R^6$ is hydrogen.

Alternatively, $R^5$ and $R^6$ together are carbonyl or, preferably, optionally substituted $C_1$-$C_4$-alkylene (e.g. ethylene, propylene, butylene, pentylene, 2,2-difluoropropylene or 2,2-dimethylpropylene), wherein one —$CH_2$— of $C_1$-$C_4$-alkylene may be replaced by an oxygen atom or —$NR^{12}$—.

In connection with $R^5$ and $R^6$, substituted $C_1$-$C_4$-alkylene in particular includes $C_1$-$C_4$-alkylene substituted with 1, 2 or 3 substituents selected from the group consisting of halogen, $C_1$-$C_4$-alkyl, $C_1$-$C_4$-haloalkyl, cyano, $C_1$-$C_4$-alkoxy and $C_1$-$C_4$-haloalkoxy.

$R^7$ is optionally substituted $C_6$-$C_{12}$-aryl (e.g. phenyl, 4-F-phenyl, 2-Cl-phenyl, 3-Cl-phenyl, 4-Cl-phenyl, 2,4-di-Cl-phenyl, 2,6-di-Cl-phenyl, 3,4-di-Cl-phenyl, 2-Br-phenyl, 4-Br-phenyl, 2-$CF_3$-phenyl, 4-CN-phenyl, 2-MeO-phenyl, 2-MeO-phenyl, 4-MeO-phenyl, 3-OH-4-Cl-phenyl, 2-Cl-4-MeO-phenyl, 2-MeO-4-Cl-phenyl or 2-Me-phenyl, a further example being 2-F-phenyl, 3-F-phenyl or 2-$NH_2$-3-Cl-phenyl), optionally substituted $C_3$-$C_{12}$-cycloalkyl or optionally substituted $C_3$-$C_{12}$-heterocyclyl (e.g. 2-pyridyl or 3-Cl-pyridyl).

In connection with $R^7$, substituted $C_3$-$C_{12}$-cycloalkyl in particular includes $C_3$-$C_{12}$-cycloalkyl, such as cyclopropyl or cyclohexyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^7$, substituted $C_6$-$C_{12}$-aryl in particular includes $C_6$-$C_{12}$-aryl, such as phenyl, substituted with 1, 2 or 3 substituents selected from the group consisting of halogen (e.g. F, Cl, Br), optionally substituted $C_1$-$C_6$-alkyl (e.g. methyl), halogenated $C_1$-$C_6$-alkyl (e.g. trifluormethyl), CN, hydroxy, $C_1$-$C_6$-alkoxy (e.g. methoxy), halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^7$, substituted $C_3$-$C_{12}$-heterocyclyl in particular includes $C_3$-$C_{12}$-heterocyclyl, such as pyridyl and in particular 2-pyridyl, substituted with 1, 2 or 3 substituents selected from the group consisting of halogen, optionally substituted $C_1$-$C_6$-alkyl, halogenated $C_1$-$C_6$-alkyl, CN, hydroxy, $C_1$-$C_6$-alkoxy, halogenated $C_1$-$C_6$-alkoxy, amino, $C_1$-$C_6$-alkylamino, di-$C_1$-$C_6$-alkylamino and $C_3$-$C_{12}$-heterocyclyl.

In connection with $R^7$, $C_3$-$C_{12}$-heterocyclyl in particular is $C_3$-$C_{12}$-heteroaryl, e.g. pyridyl and in particular 2-pyridyl.

Preferably, $R^7$ is optionally substituted $C_6$-$C_{12}$-aryl, in particular as in the tetrahydroisoquinolines of the formula:

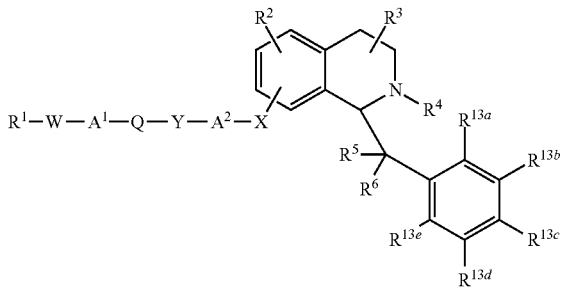

or the corresponding formula wherein the radical $R^1$—W-$A^1$-Q-Y-$A^2$-X— is replaced by the radical —CN,
wherein $R^1$, W, $A^1$, Q, Y, $A^2$, X, $R^2$, $R^3$, $R^4$, $R^5$, $R^6$ are as defined herein, and
$R^{13a}$, $R^{13b}$, $R^{13c}$, $R^{13d}$, $R^{13e}$ independently are hydrogen, halogen (e.g. F, Cl or Br), optionally substituted $C_1$-$C_6$-alkyl (e.g. methyl), halogenated $C_1$-$C_6$-alkyl (e.g. trifluormethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

It is also preferred if $R^7$ is optionally substituted $C_6$-$C_{12}$-heteroaryl, in particular as in the tetrahydroisoquinolines of the formula:

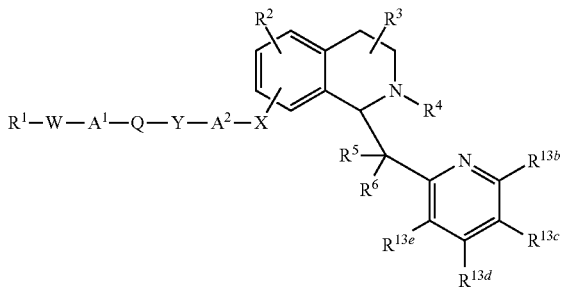

or the corresponding formula wherein the radical $R^1$—W-$A^1$-Q-Y-$A^2$-X— is replaced by the radical —CN,
wherein $R^1$, W, $A^1$, Q, Y, $A^2$, X, $R^2$, $R^3$, $R^4$, $R^5$, $R^6$ are as defined herein, and
$R^{13b}$, $R^{13c}$, $R^{13d}$, $R^{13e}$ independently are hydrogen, halogen (e.g. F, Cl or Br), optionally substituted $C_1$-$C_6$-alkyl (e.g. methyl), halogenated $C_1$-$C_6$-alkyl (e.g. trifluormethyl), CN, hydroxy, $C_1$-$C_6$-alkoxy (e.g. methoxy), amino, $C_1$-$C_6$-alkylamino, di-$C_1$-$C_6$-alkylamino or $C_3$-$C_{12}$-heterocyclyl.

In connection with $R^7$ or $R^{13a}$, $R^{13b}$, $R^{13c}$, $R^{13d}$, $R^{13e}$, substituted $C_1$-$C_6$-alkyl in particular includes $C_1$-$C_6$-alkyl, especially $C_1$-$C_4$-alkyl, substituted with 1, 2 or 3 substituents selected from the group consisting of hydroxy, $C_1$-$C_6$-alkoxy, amino, $C_1$-$C_6$-alkylamino, di-$C_1$-$C_6$-alkylamino and $C_3$-$C_{12}$-heterocyclyl (e.g. morpholinyl or piperidinyl).

According to a particular embodiment, $R^{13a}$, $R^{13b}$, $R^{13d}$, $R^{13e}$ are hydrogen and $R^{13c}$ is different from hydrogen (para-mono-substitution).

According to a further particular embodiment, $R^{13a}$, $R^{13b}$, $R^{13d}$, $R^{13e}$ are hydrogen and $R^{13b}$ is different from hydrogen (meta-mono-substitution).

In connection with $R^{13a}$, $R^{13b}$, $R^{13c}$, $R^{13d}$, $R^{13e}$, $C_3$-$C_{12}$-heterocyclyl in particular includes morpholinyl, imidazolyl and pyrazolyl.

$R^8$ is hydrogen, $C_1$-$C_6$-alkyl. Preferably, $R^8$ is hydrogen.
$R^9$ is hydrogen, $C_1$-$C_6$-alkyl or amino-$C_1$-$C_6$-alkyl (e.g. amino-n-propyl, a further example being 2-aminoethyl). Preferably, $R^9$ is hydrogen.
$R^{10}$ is hydrogen, $C_1$-$C_6$-alkyl or $C_1$-$C_6$-alkylsulfonyl (e.g. n-propylsulfonyl). Preferably, $R^{10}$ is hydrogen.
$R^{11}$ is hydrogen or $C_1$-$C_6$-alkyl. Preferably, $R^{11}$ is hydrogen.
Alternatively, $R^9$, $R^{11}$ together are $C_1$-$C_4$-alkylene (e.g. ethylene).
$R^{12}$ is hydrogen or $C_1$-$C_6$-alkyl. Preferably, $R^{12}$ is hydrogen.
According to a particular embodiment, $A^2$ is $C_1$-$C_4$-alkylene (e.g. ethylene), Y is —$NR^9$—, X is —$NR^{11}$—, and $R^9$, $R^{11}$ together are $C_1$-$C_4$-alkylene (e.g. ethylene).
According to a further particular embodiment, $A^2$ is $C_1$-$C_4$-alkylene-$NR^{10}$—$C_1$-$C_4$-alkylene and —$NR^{10}$— is $C_1$-$C_6$-alkylsulfonyl (e.g. ethylene-N(propylsulfonyl)-ethylene).
Particular embodiments of tetrahydroisoquinolines of the invention result if
$R^1$ is $C_1$-$C_6$-alkyl (e.g. methyl, n-propyl, isopropyl, n-butyl, isobutyl or 2,2-dimethylpropyl), halogenated $C_1$-$C_6$-alkyl (e.g. trifluormethyl, 3-fluoropropyl or 3,3,3-trifluoropropyl), hydroxy-$C_1$-$C_4$-alkyl (e.g. 2-hydroxyethyl or 2-hydroxy-2-methylpropyl), $C_1$-$C_6$-alkoxy-$C_1$-$C_4$-alkyl (e.g. methoxyethyl), amino-$C_1$-$C_4$-alkyl (e.g. aminoethyl, 3-amino-n-propyl or 4-amino-n-butyl), $C_1$-$C_6$-alkylamino-$C_1$-$C_4$-alkyl (e.g. ethylamino-n-propyl, n-propylamino-n-propyl, isopropylamino-n-propyl, isopropylaminoethyl or methylamino-n-propyl), di-$C_1$-$C_6$-alkylamino-$C_1$-$C_4$-alkyl (e.g. dimethylamino-n-propyl, diethylamino-n-propyl or dimethylaminoethyl), $C_1$-$C_6$-alkyloxycarbonylamino-$C_1$-$C_4$-alkyl (e.g. t-butoxycarbonylaminoethyl), $C_1$-$C_6$-alkylaminocarbonylamino-$C_1$-$C_4$-alkyl (e.g. n-propylaminocarbonylaminoethyl), $C_6$-$C_{12}$-aryl-$C_1$-$C_4$-alkyl (e.g. benzyl), $C_3$-$C_{12}$-heterocyclyl-$C_1$-$C_4$-alkyl (e.g. 2-(1-piperidinyl)ethyl), $C_3$-$C_{12}$-cycloalkyl (e.g. cyclopropyl), $C_1$-$C_6$-alkoxycarbonyl (e.g. tert-butyloxycarbonyl), $C_1$-$C_6$-alkylaminocarbonyl (e.g. ethylaminocarbonyl), $C_2$-$C_6$-alkenyl (e.g. prop-1-en-1-yl), optionally substituted $C_6$-$C_{12}$-aryl (e.g. phenyl, naphthyl, 2-CN-phenyl, 3-CN-phenyl, 2-Cl-phenyl, 3-Cl-phenyl, 4-Cl-phenyl, 2,4-di-Cl-phenyl, 2-MeO-phenyl, 3-MeO-phenyl, 4-MeO-phenyl, 4-(2-fluoroethyl)-phenyl, 3-$NH_2$-phenyl, 4-$NH_2$-phenyl or 4-aminocarbonylaminophenyl), hydroxy, $C_1$-$C_6$-alkylamino (e.g. isopropylamino or t-butylamino), di-$C_1$-$C_6$-alkylamino (e.g. diethylamino or dimethylamino) or optionally substituted $C_3$-$C_{12}$-heterocyclyl (e.g. 3-pyridyl, 6-chloro-3-pyridyl, 6-amino-3-pyridyl, 6-propylamino-3-pyridyl, 6-benzylamino-3-pyridyl, 2-thienyl, 5-(3-isoxazolyl)-2-thienyl, 1-methyl-1,2-diazol-4-yl, 1,3-dimethyl-1,2-diazol-4-yl, 1,3-diazol-4-yl, 1-methyl-1,3-diazol-4-yl, 1,2-dimethyl-1,3-diazol-4-yl, 8-quinolinyl, piperidin-1-yl, piperidin-3-yl, 1,4-piperazinyl, 1-ethoxycarbonyl-1,4-piperazinyl, 1-t-butoxycarbonyl-1,4-piperazinyl, 1-propyl-1,4-piperazinyl, 1-propylsulfonyl-1,4-piperazinyl, morpholinyl, 1,3-dioxo-1,3-dihydro-2H-isoindol-2-yl or 6-chloro-imidazo[2,1-b][1,3]thiazole-5-yl, 3-azetidinyl, 1-methylcarbonyl-azetidin-3-yl, 3-pyrrolidinyl, 1-benzyloxycarbonylpyrrolidin-3-yl, 1,2-diazol-4-yl, 1,2,4-triazol-5-yl, 3-amino-1,2,4-triazol-5-yl, 5-methyl-1,2-oxazol-4-yl, 2-amino-1,3-thiazol-5-yl, 2-acetylamino-1,3-thiazol-5-yl, 5-methylamino-1,3-thiadiazol-2-yl, 4-methyl-3,4-dihydro-2H-pyrido[3,2-b][1,4]oxazin-7-yl, 2-pyridyl, 6-methoxy-3-pyridyl, 3-phenoxy-3-pyridyl, 6-amino-3-pyridyl, 6-morpholin-4-yl-3-pyridyl, 2-amino-1,3-pyrimidin-5-yl, 4-piperidinyl or 1-benzyl-piperidin-4-yl);

W is —$NR^8$— or a bond;

$A^1$ is $C_1$-$C_4$-alkylene (e.g. 1,2-ethylene or 1,3 propylene) or a bond;

Q is —$S(O)_2$— or —$C(O)$—;

Y is —$NR^9$—, $C_1$-$C_4$-alkylene (e.g. methylene) or a bond;

$A^2$ is $C_1$-$C_4$-alkylene (e.g. methylene or ethylene), $C_6$-$C_{12}$-arylene (e.g. 1,4-phenylene or 1,2-phenylene) or $C_6$-$C_{12}$-heteroarylene (2,5-pyridylene or 2,3-pyridylene);

X is —O—, —$NR^{11}$— or $C_1$-$C_4$-alkylene;

$R^2$ is hydrogen, halogen (e.g. fluoro or bromo), or $C_1$-$C_6$-alkoxy (e.g. methoxy);

$R^3$ is hydrogen or $C_1$-$C_6$-alkyl (e.g. 4,4-dimethyl);

$R^4$ is hydrogen, $C_1$-$C_6$-alkyl (e.g. methyl), halogenated $C_1$-$C_4$-alkyl (e.g. 2,2,2-trifluoroethyl), amino-$C_1$-$C_4$-alkyl (e.g. aminoethyl), $CH_2CN$, $C_1$-$C_4$-alkylcarbonyl (e.g. methylcarbonyl), (halogenated $C_1$-$C_4$-alkyl)carbonyl (e.g. trifluoromethylcarbonyl), —$C(=NH)NH_2$, —$C(=NH)NHCN$, $C_1$-$C_6$-alkylsulfonyl (e.g. propylsulfonyl, amino), —NO, or $C_3$-$C_{12}$-heterocyclyl (e.g. 1,3-diazol-2-yl);

$R^5$ is $C_1$-$C_6$-alkyl (e.g. methyl or isopropyl) or optionally substituted $C_3$-$C_{12}$-aryl (e.g. 4-Cl-phenyl);

$R^6$ is hydrogen, hydroxy or $C_1$-$C_6$-alkyl, or $R^5$, $R^6$
together are optionally substituted $C_1$-$C_4$-alkylene (e.g. ethylene, propylene or 2,2-difluoropropylene);

$R^7$ is optionally substituted $C_6$-$C_{12}$-aryl (e.g. phenyl, 4-F-phenyl, 2-Cl-phenyl, 3-Cl-phenyl, 4-Cl-phenyl, 2,4-di-Cl-phenyl, 2,6-di-Cl-phenyl, 3,4-di-Cl-phenyl, 2-Br-phenyl, 4-Br-phenyl, 2-$CF_3$-phenyl, 4-CN-phenyl, 2-MeO-phenyl, 2-MeO-phenyl, 4-MeO-phenyl, 3-OH-4-Cl-phenyl, 2-Cl-4-MeO-phenyl, 2-MeO-4-Cl-phenyl, 2-Me-phenyl, 2-F-phenyl, 3-F-phenyl or 2-$NH_2$-3-Cl-phenyl), or optionally substituted $C_3$-$C_{12}$-heteroaryl (e.g. 2-pyridyl or 3-Cl-pyridyl);

$R^8$ is hydrogen;

$R^9$ is hydrogen or amino-$C_1$-$C_6$-alkyl (e.g. 2-aminoethyl);

$R^{10}$ is hydrogen; and $R^{11}$ is hydrogen, or $R^9$, $R^{11}$
together are $C_1$-$C_4$-alkylene (e.g. ethylene).

Further particular embodiments of tetrahydroisoquinolines of the invention result if $R^1$ is $C_1$-$C_6$-alkyl (e.g. methyl, n-propyl, isopropyl, n-butyl, isobutyl or 2,2-dimethylpropyl), halogenated $C_1$-$C_6$-alkyl (e.g. trifluormethyl), $C_1$-$C_6$-alkoxy-$C_1$-$C_4$-alkyl (e.g. methoxyethyl), amino-$C_1$-$C_4$-alkyl (e.g. aminoethyl), $C_1$-$C_6$-alkylamino-$C_1$-$C_4$-alkyl (e.g. ethylamino-n-propyl, n-propylamino-n-propyl or isopropylamino-n-propyl), di-$C_1$-$C_6$-alkylamino-$C_1$-$C_4$-alkyl (e.g. dimethylamino-n-propyl or diethylamino-n-propyl), $C_1$-$C_6$-alkyloxycarbonylamino-$C_1$-$C_4$-alkyl (e.g. t-butoxycarbonylaminoethyl), $C_1$-$C_6$-alkylaminocarbonylamino-$C_1$-$C_4$-alkyl (e.g. n-propylaminocarbonylaminoethyl), $C_6$-$C_{12}$-aryl-$C_1$-$C_4$-alkyl (e.g. benzyl), $C_3$-$C_{12}$-cycloalkyl (e.g. cyclopropyl), optionally substituted $C_6$-$C_{12}$-aryl (e.g. phenyl, naphthyl, 2-CN-phenyl, 3-CN-phenyl, 2-Cl-phenyl, 3-Cl-phenyl, 4-Cl-phenyl, 2,4-di-Cl-phenyl, 2-MeO-phenyl, 3-MeO-phenyl or 4-MeO-phenyl), hydroxy, $C_1$-$C_6$-alkylamino (e.g. isopropylamino), (halogenated $C_1$-$C_6$-alkyl)amino, di-$C_1$-$C_6$-alkylamino (e.g. diethylamino or t-butylamino) or optionally substituted $C_3$-$C_{12}$-heterocyclyl (e.g. 3-pyridyl, 6-chloro-3-pyridyl, 6-amino-3-pyridyl, 6-propylamino-3-pyridyl, 6-benzylamino-3-pyridyl, 2-thienyl, 5-(3-isoxazolyl)-2-thienyl, 1-methyl-1,2-diazol-4-yl, 1,3-dimethyl-1,2-diazol-4-yl, 1,3-diazol-4-yl, 1-methyl-1,3-diazol-4-yl, 1,2-dimethyl-1,3-diazol-4-yl, 8-quinolinyl, piperidin-1-yl, piperidin-3-yl, 1,4-piperazinyl, 1-ethoxycarbonyl-1,4-piperazinyl, 1-t-butoxycarbonyl-1,4-piperazinyl, 1-propyl-1,4-piperazinyl, 1-propylsulfonyl-1,4-piperazinyl, morpholinyl; 1,3-dioxo-1,3-dihydro-2H-isoindol-2-yl or 6-chloro-imidazo[2,1-b][1,3]thiazole-5-yl);

W is —$NR^8$— or a bond;

$A^1$ is a bond;

Q is —$S(O)_2$— or —$C(O)$—;

Y is —$NR^9$— or a bond;

$A^2$ is $C_1$-$C_4$-alkylene (e.g. methylene or ethylene);

X is —O— or —$NR^{11}$—;

$R^2$ is hydrogen, halogen (e.g. fluoro or bromo), or $C_1$-$C_6$-alkoxy (e.g. methoxy);

$R^3$ is hydrogen or $C_1$-$C_6$-alkyl (e.g. 4,4-dimethyl);

$R^4$ is hydrogen, $C_1$-$C_6$-alkyl (e.g. methyl), halogenated $C_1$-$C_4$-alkyl (e.g. 2,2,2-trifluoroethyl), amino-$C_1$-$C_4$-alkyl (e.g. aminoethyl), $CH_2CN$, $C_1$-$C_4$-alkylcarbonyl (e.g. methylcarbonyl), (halogenated $C_1$-$C_4$-alkyl)carbonyl (e.g. trifluoromethylcarbonyl), —$C(=NH)NH_2$, —$C(=NH)NHCN$, $C_1$-$C_6$-alkylsulfonyl (e.g. propylsulfonyl, amino), —NO, or $C_3$-$C_{12}$-heterocyclyl (e.g. 1,3-diazol-2-yl);

$R^5$ is $C_1$-$C_6$-alkyl (e.g. isopropyl);

$R^6$ is hydrogen or $C_1$-$C_6$-alkyl, or $R^5$, $R^6$
together are optionally substituted $C_1$-$C_4$-alkylene (e.g. ethylene, propylene or 2,2-difluoropropylene);

$R^7$ is optionally substituted $C_6$-$C_{12}$-aryl (e.g. phenyl, 4-F-phenyl, 2-Cl-phenyl, 3-Cl-phenyl, 4-Cl-phenyl, 2,4-di-Cl-phenyl, 2,6-di-Cl-phenyl, 3,4-di-Cl-phenyl, 2-Br-phenyl, 4-Br-phenyl, 2-$CF_3$-phenyl, 4-CN-phenyl, 2-MeO-phenyl, 2-MeO-phenyl, 4-MeO-phenyl, 3-OH-4-Cl-phenyl, 2-$C_{1-4}$-MeO-phenyl, 2-MeO-4-Cl-phenyl or 2-Me-phenyl), or optionally substituted $C_3$-$C_{12}$-heteroaryl;

$R^8$ is hydrogen;

$R^9$ is hydrogen;

$R^{10}$ is hydrogen; and $R^{11}$ is hydrogen, or $R^9$, $R^{11}$
together are $C_1$-$C_4$-alkylene (e.g. ethylene).

Particular compounds of the present invention are the tetrahydroisoquinolines disclosed in preparation examples and physiologically tolerated acid addition salts thereof.

The compounds of the formula (I) can be prepared by analogy to methods which are well known in the art. Suitable methods for the preparation of compounds of formula (I) is outlined in the following schemes.

The process depicted in scheme 1 is useful for obtaining tetrahydroisoquinolines, wherein X is —O— or —S—.

Scheme 1:

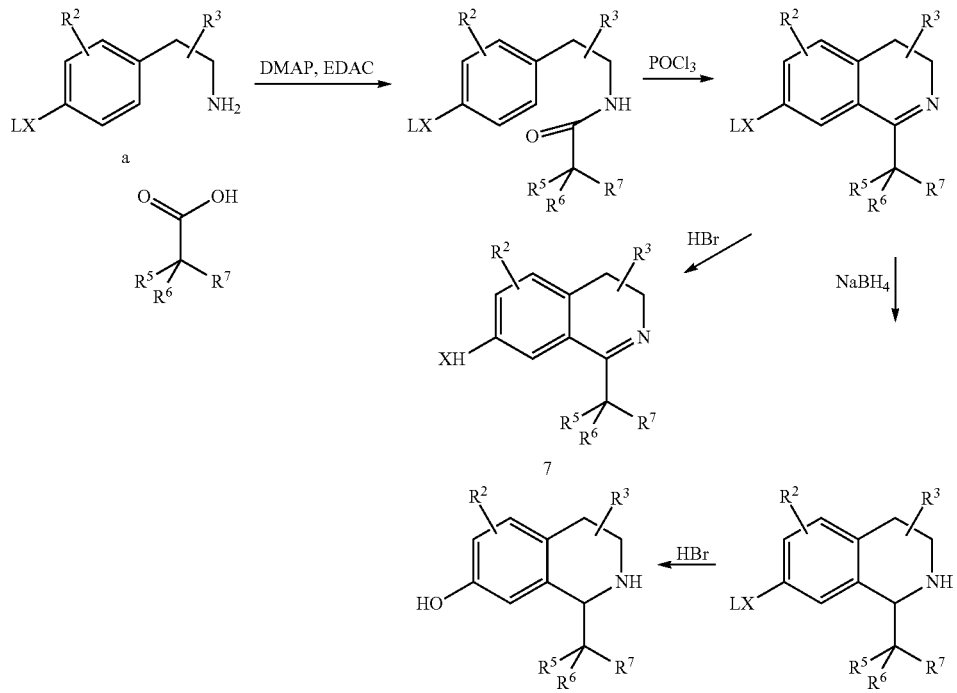

In scheme 1, the variables $R^2$, $R^3$, $R^5$, $R^6$, $R^7$ are as defined herein and L a suitable protecting group (e.g. L=Me).

The amide formation in scheme 1 can also be carried out with other peptide coupling methods (cf. "The Practice of Peptide Synthesis", M. Bodansky, A. Bodansky, Springer Verlag, 1994). In the Bischler-Napieralki cyclization reaction step, $POCl_3$ can be replaced by $PCl_5$, other Lewis acids or combinations thereof.

The process depicted in scheme 1 is also useful for obtaining tetrahydroisoquinolines, wherein X is optionally substituted alkylene. In this case, L is a group that represents, or can be converted into, the desired side chain $R^1$—$W$-$A^1$-$Q$-$Y$-$A^2$-.

The process depicted in scheme 2 is in particular useful for obtaining tetrahydroisoquinolines, wherein X is —O— and $R^5$ and $R^6$ together are —$CH_2CF_2CH_2$—.

Scheme 2:

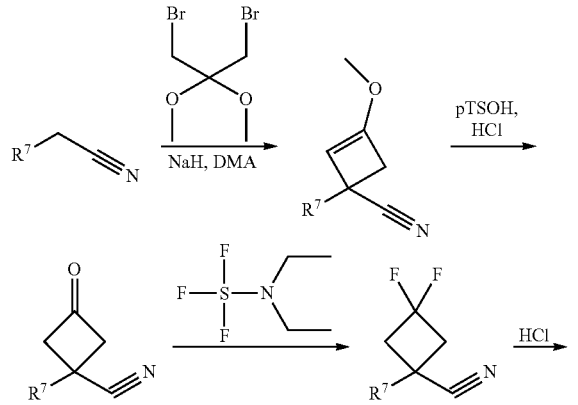

-continued

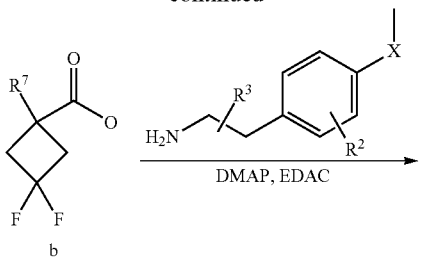

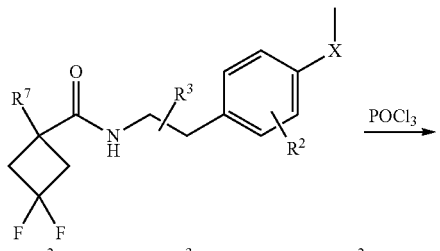

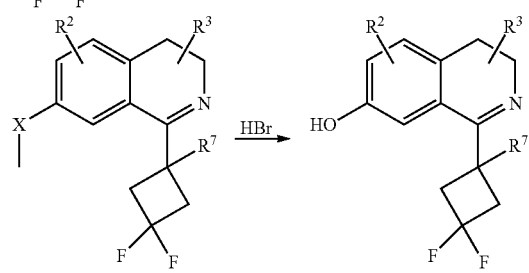

In scheme 2, the variables $R^2$, $R^3$, $R^7$ are as defined herein.

Analogously, intermediates a and b can be converted into the corresponding dihydroisoquinolines of formula (II) and tetrahydroisoquinolines of formula (I).

The process depicted in scheme 3 is in particular useful for obtaining tetrahydroisoquinolines, wherein X is —O—, $R^5$ is hydroxy and $R^6$ is hydrogen.

Scheme 3:

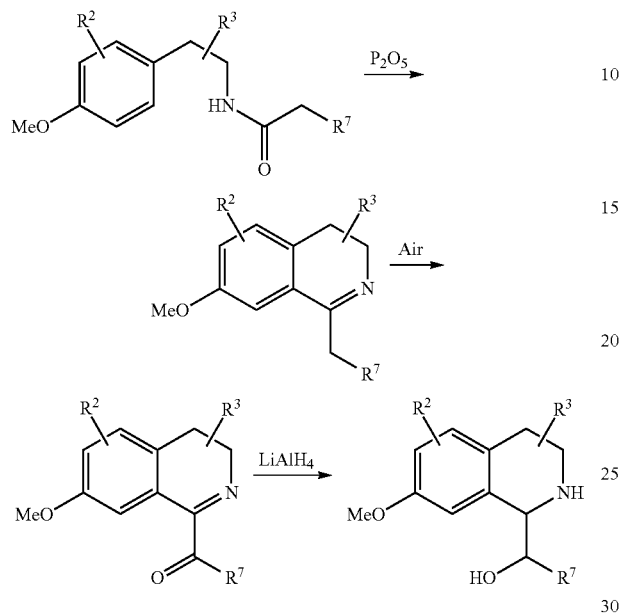

In scheme 3, the variables $R^2$, $R^3$, $R^7$ are as defined herein.

The process depicted in scheme 4 is useful for obtaining tetrahydroisoquinolines, wherein X is —NH—.

Scheme 4:

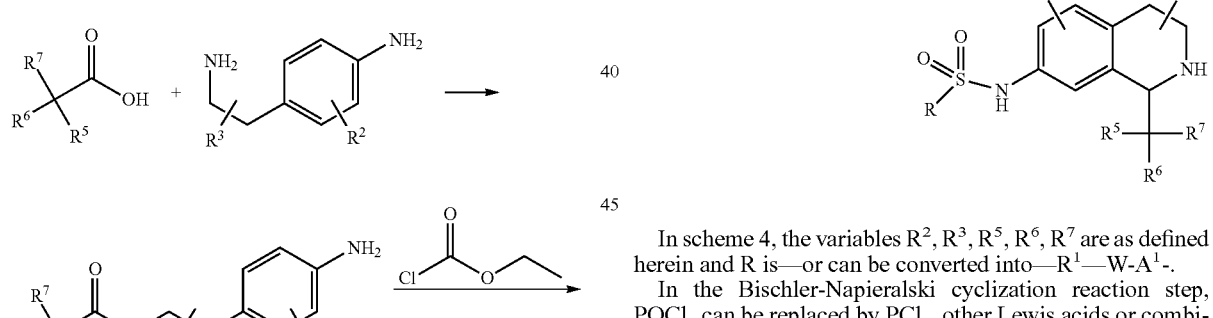

In scheme 4, the variables $R^2$, $R^3$, $R^5$, $R^6$, $R^7$ are as defined herein and R is—or can be converted into—$R^1$—W-$A^1$-.

In the Bischler-Napieralski cyclization reaction step, $POCl_3$ can be replaced by $PCl_5$, other Lewis acids or combinations thereof.

The process depicted in scheme 5 is useful for obtaining tetrahydroisoquinolines, wherein X is —O— or —$NR^{11}$—, and $R^3$ is 1-alkyl.

Scheme 5:

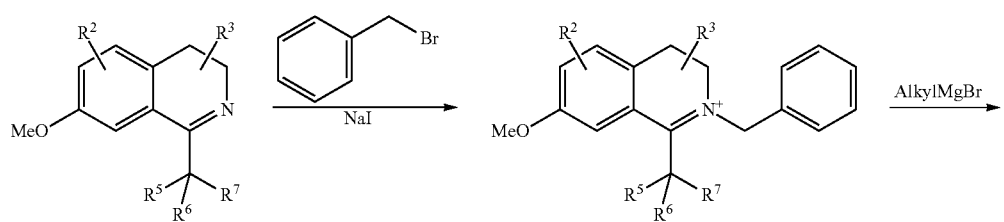

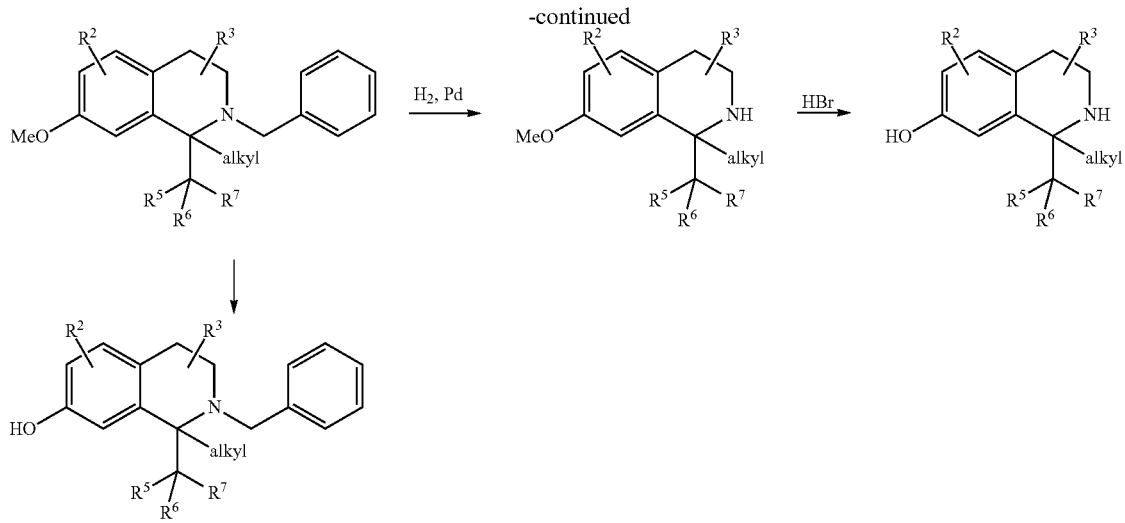

In scheme 5, the variables $R^2$, $R^3$, $R^5$, $R^6$, $R^7$ are as defined herein.

The process depicted in scheme 6 is useful for obtaining tetrahydroisoquinolines, wherein $R^4$ is halogenated alkyl.

The process depicted in scheme 7 is useful for obtaining tetrahydroisoquinolines, wherein X is —O—, $A^2$ is optionally substituted alkylene, Y is —$NR^9$—, and Q is —$S(O)_2$.

Scheme 6:

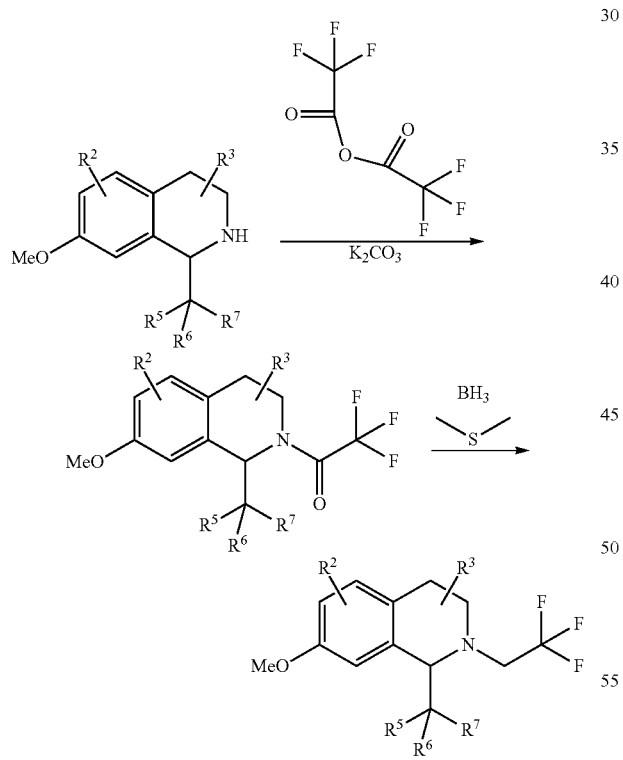

Scheme 7:

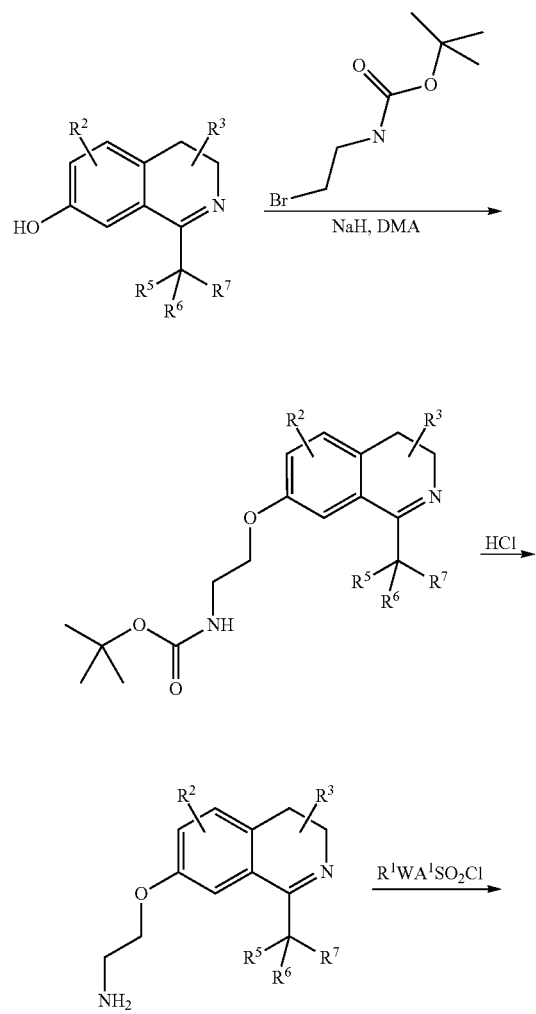

In scheme 6, the variables $R^2$, $R^3$, $R^5$, $R^6$, $R^7$ are as defined herein.

Tetrahydroisoquinolines wherein $R^4$ is —C(=NH)NHCN may be obtained by reacting the intermediate tetrahydroisoquinoline c (wherein $R^1$—W-$A^1$- is e.g. n-propyl) with sodium dicyanamide. Tetrahydroisoquinolines wherein $R^4$ is —C(=NH)$NH_2$ may be obtained by reacting the intermediate tetrahydroisoquinoline c with $(CH_3SC(=NH)NH_3)_2SO_4$.

-continued

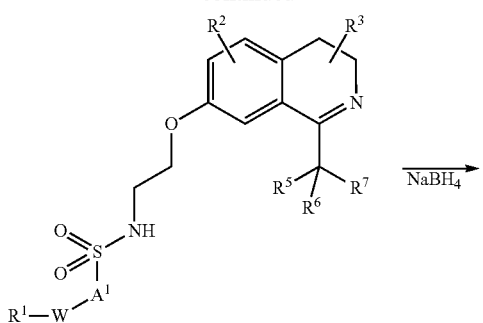

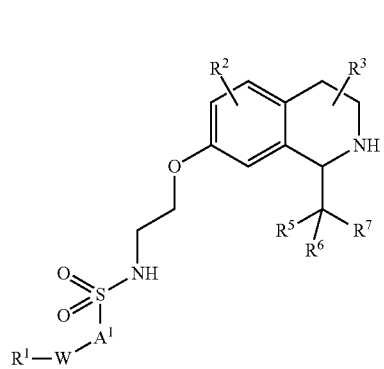

c

In scheme 7, the variables $R^1$, W, $A^1$, $R^2$, $R^3$, $R^5$, $R^6$, $R^7$ are as defined herein.

The process depicted in scheme 8 is useful for obtaining tetrahydroisoquinolines, wherein X is —$NR^{11}$—, $A^2$ is optionally substituted alkylene, Y is —$NR^9$—, $R^9$ and $R^{11}$ together are alkylene, and Q is —$S(O)_2$.

Scheme 8:

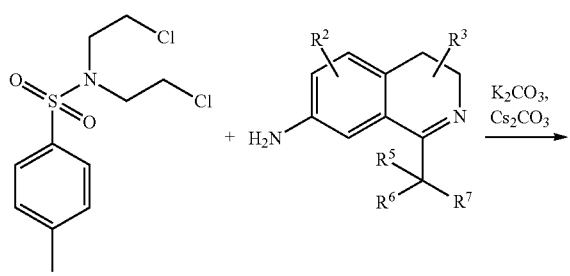

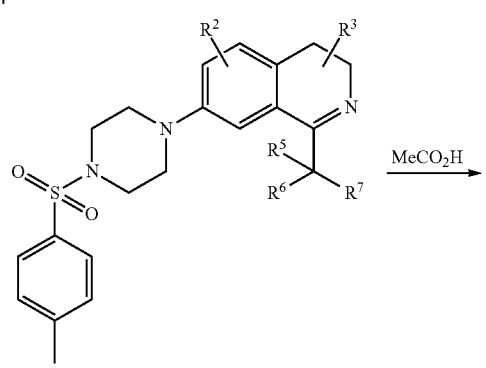

-continued

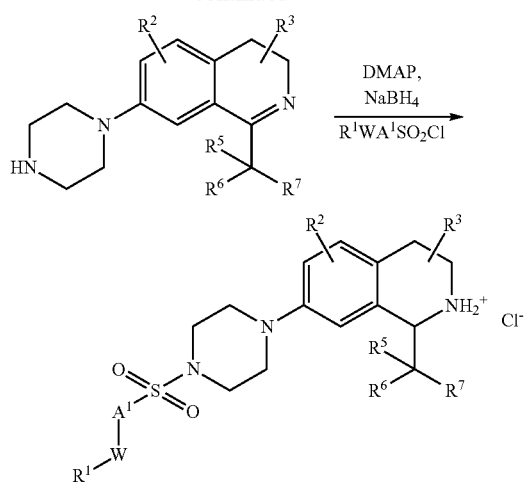

In scheme 8, the variables $R^1$, W, $A^1$, $R^2$, $R^3$, $R^5$, $R^6$, $R^7$ are as defined herein.

The process depicted in scheme 9 is useful for obtaining tetrahydroisoquinolines, wherein $R^7$ is optionally substituted heterocyclyl such as optionally substituted pyridyl.

Scheme 9:

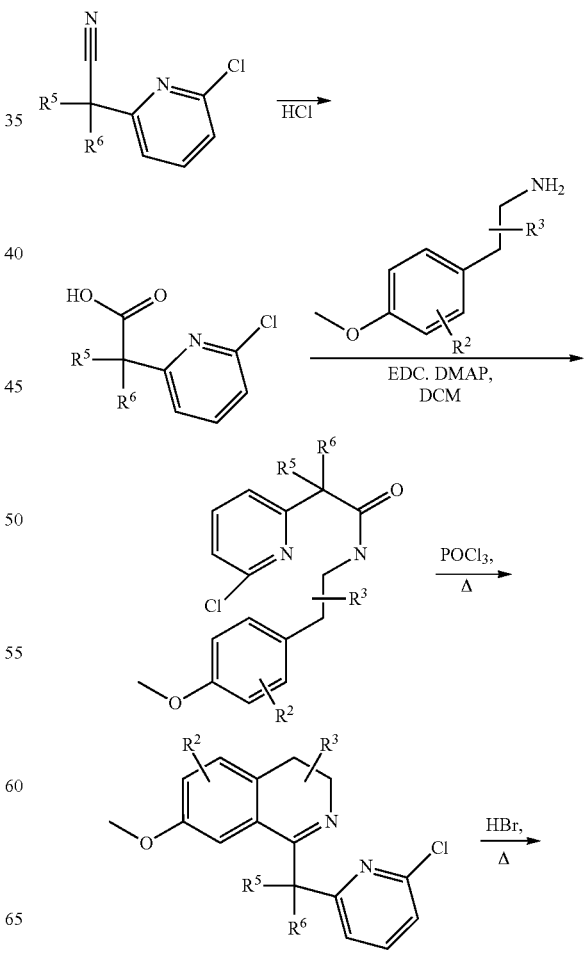

-continued

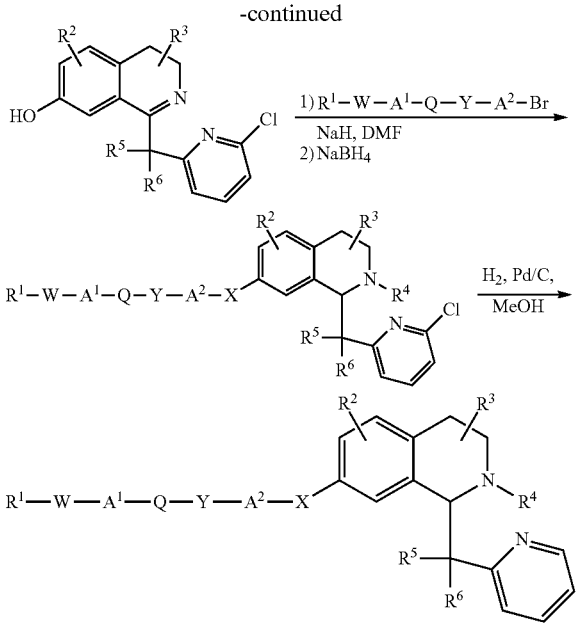

In scheme 9, the variables $R^1$, W, $A^1$, Q, Y, $A^2$, X $R^2$, $R^3$, $R^4$, $R^5$, $R^6$ are as defined herein.

The process depicted in scheme 10 is useful for obtaining tetrahydroisoquinolines, wherein R is —CN or —Y-$A^2$-X— is —$NR^9$—$C_1$-$C_4$-alkylene-.

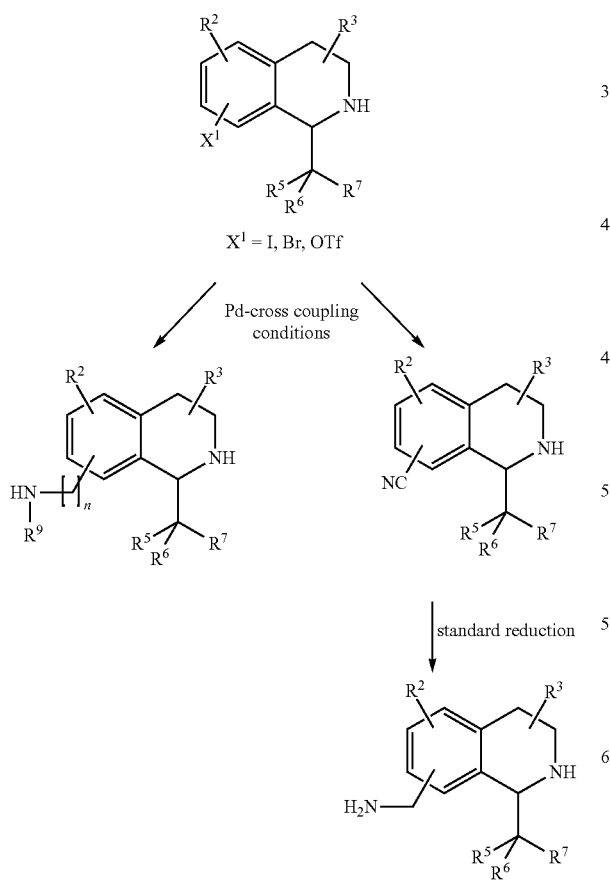

In scheme 10, the variables $R^2$, $R^3$, $R^4$, $R^5$, $R^6$, $R^7$, $R^9$ are as defined herein and n is 1, 2, 3 or 4.

More specifically, the process depicted in scheme 11 is useful for obtaining tetrahydroisoquinolines, wherein R is —CN or —Y-$A^2$-X— is —$NR^9$—$CH_2$—.

Scheme 11:

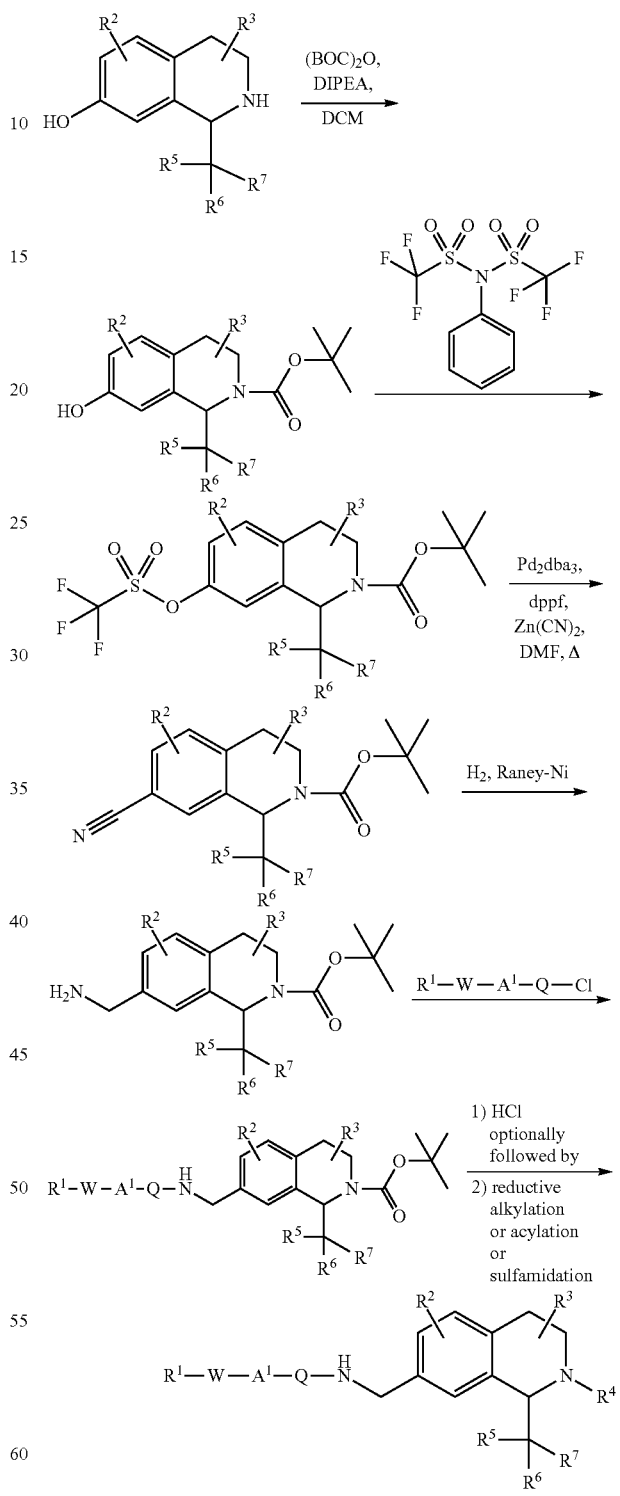

In scheme 11, the variables $R^1$, W, $A^1$, Q, $R^2$, $R^3$, $R^4$, $R^5$, $R^6$, $R^7$ are as defined herein.

Further, the process depicted in scheme 12 is useful for obtaining tetrahydroisoquinolines, wherein —Y-$A^2$-X— is —$NR^9$—$C_1$-$C_4$-alkylene-.

Scheme 12:
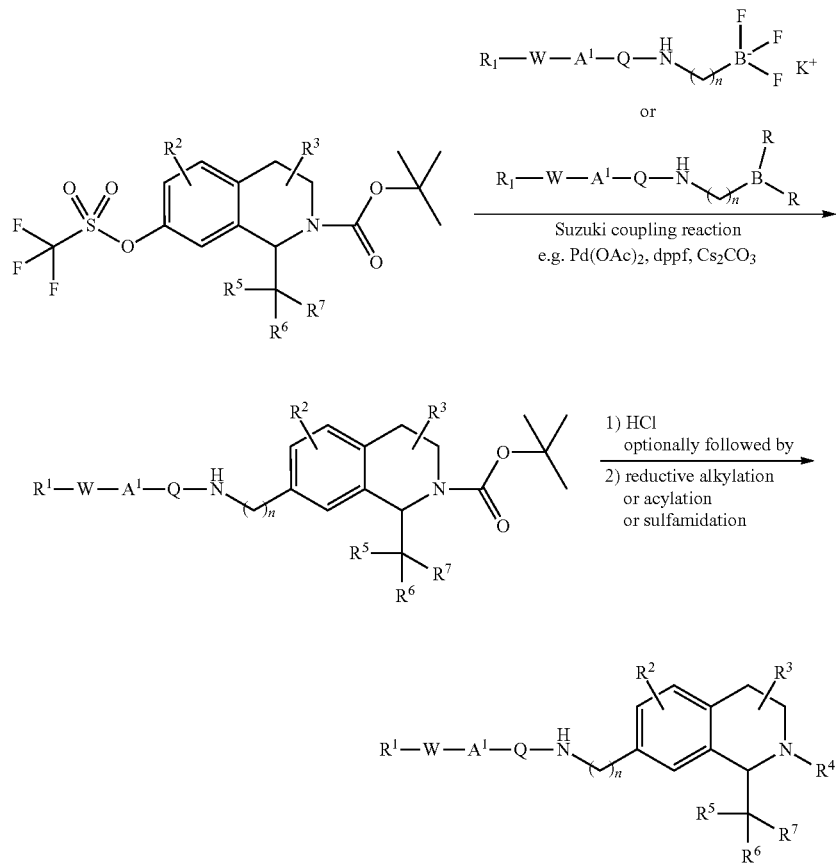
In scheme 12, the variables $R^1$, W, $A^1$, Q, $R^2$, $R^3$, $R^4$, $R^5$, $R^6$, $R^7$ are as defined herein and n is 1, 2, 3 or 4.
Further, the process depicted in scheme 13 is useful for obtaining tetrahydroisoquinolines, wherein —Y-$A^2$-X— is —$NR^9$—$C_1$-$C_4$-alkylene-X—.
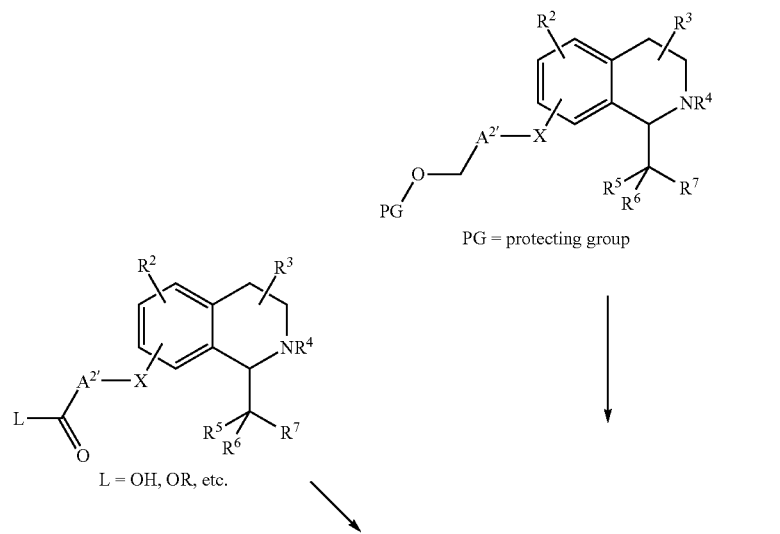

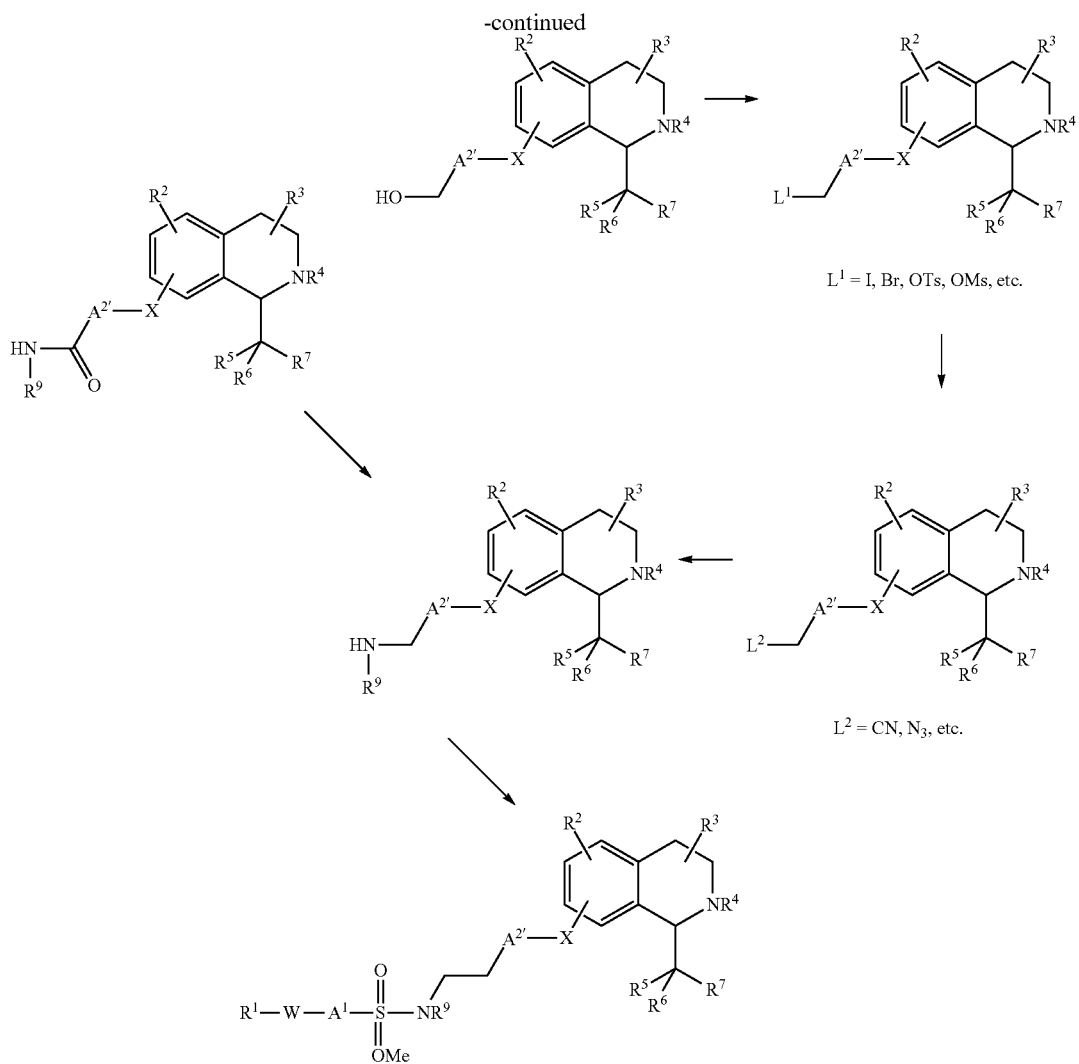

In scheme 13, the variables $R^1$, W, $A^1$, X, $R^2$, $R^3$, $R^4$, $R^5$, $R^6$, $R^7$, $R^9$ are as defined herein and $A^2$ together with the adjacent methylene group is $A^2$.

Protecting group transformations described in scheme 1 to 13 can be replaced by suitable alternatives, cf. "Protective Groups in Organic Synthesis", Theodora W. Greene, Peter G. M. Wuts, John Wiley & Sons, 1999 and "Protecting Groups", Philip J. Kocienski, Georg Thieme Verlag Stuttgart, New York 1994.

Alternatively, tetrahydroisoquinolines can be prepared from isoquinolines (cf. Hetarene II, Teil 1, Houben Weyl, Band E7a, Hrsg. R. P. Kreher, p. 583-726, Thieme Verlag 1991) by reduction (e.g.: Arto; Kanerva, Liisa T.; Fueloep, Ferenc, Tetrahedron: Asymmetry (2007), 18(12), 1428-1433; Reimann, Eberhard; Ettmayr, Christian, Monatshefte fuer Chemie (2004), 135(10), 1289-1295; Pitts, Michael R.; Harrison, Justin R.; Moody, Christopher J., Journal of the Chemical Society, Perkin Transactions 1 (2001), (9), 955-977; Guillonneau, Claude; Pierre, Alain; Charton, Yves; Guilbaud, Nicolas; Kraus-Berthier, Laurence; Leonce, Stephane; Michel, Andre; Bisagni, Emile; Atassi, Ghanem., Journal of Medicinal Chemistry (1999), 42(12), 2191-2203; Clezy, Peter S.; Duncan, Mark W.; Smythe, George A., Australian Journal of Chemistry (1988), 41(4), 483-91; Kaiser, Carl; Oh, Hye Ja; Garcia-Slanga, Blanche J.; Sulpizio, Anthony C.; Hieble, J. Paul; Wawro, Joyce E.; Kruse, Lawrence I., Journal of Medicinal Chemistry (1986), 29(11), 2381-4; Ferles, Miloslav; Sputova, Michaela; Tegza, Marian., Collection of Czechoslovak Chemical Communications (1981), 46(1), 262-5).

Tetrahydroisoquinolines can also be prepared asymmetrically (cf. Chrzanowska, Maria; Rozwadowska, Maria D., Chemical Reviews (Washington, D.C., United States) (2004), 104(7), 3341-3370 and references cited therein).

The acid addition salts of the tetrahydroisoquinolines of formula (I) are prepared in a customary manner by mixing the free base with a corresponding acid, optionally in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds of the formula (I) are capable of inhibiting the activity of glycine transporter, in particular glycine transporter 1 (GlyT1).

The utility of the compounds in accordance with the present invention as inhibiting the glycine transporter activity, in particular GlyT1 activity, may be demonstrated by methodology known in the art. For instance, human GlyT1c expressing recombinant hGlyT1c_5_CHO cells can be used for measuring glycine uptake and its inhibition ($IC_{50}$) by a compound of formula (I).

Amongst the compounds of the formula (I) those are preferred which achieve effective inhibition at low concentrations. In particular, compounds of the formula (I) are preferred which inhibit glycine transporter 1 (GlyT1) at a level of $IC_{50}$<1 µMol, more preferably at a level of $IC_{50}$<0.5 µMol, particularly preferably at a level of $IC_{50}$<0.2 µMol and most preferably at a level of $IC_{50}$<0.1 µMol.

The compounds of the formula (I) according to the present invention are thus useful as pharmaceuticals.

The present invention therefore also relates to pharmaceutical compositions which comprise an inert carrier and a compound of the formula (I).

The present invention also relates to the use of the compounds of the formula (I) in the manufacture of a medicament for inhibiting the glycine transporter GlyT1, and to corresponding methods of inhibiting the glycine transporter GlyT1.

The NMDA receptor is central to a wide range of CNS processes, and its role in a variety of diseases in humans or other species has been described. GlyT1 inhibitors slow the removal of glycine from the synapse, causing the level of synaptic glycine to rise. This in turn increases the occupancy of the glycine binding site on the NMDA receptor, which increases activation of the NMDA receptor following glutamate release from the presynaptic terminal. Glycine transport inhibitors and in particular inhibitors of the glycine transporter GlyT1 are thus known to be useful in treating a variety of neurologic and psychiatric disorders.

The present invention thus further relates to the use of the compounds of the formula (I) for the manufacture of a medicament for treating a neurologic or psychiatric disorder, and to corresponding methods of treating said disorders.

According to a particular embodiment, the disorder is associated with glycinergic or glutamatergic neurotransmission dysfunction.

According to a further particular embodiment, the disorder is one or more of the following conditions or diseases: schizophrenia or a psychotic disorder including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder, including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or cognitive impairment including age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention deficit disorders including attention-deficit hyperactivity disorder (ADHD) and conduct disorder; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writers cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

The compounds of formula (I) are particularly useful in the treatment of schizophrenia, bipolar disorder, depression including unipolar depression, seasonal depression and post-partum depression, premenstrual syndrome (PMS) and premenstrual dysphoric disorder (PDD), learning disorders, pervasive developmental disorder including autistic disorder, attention deficit disorders including Attention-Deficit/Hyperactivity Disorder, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Particular cognitive disorders are dementia, delirium, amnestic disorders and cognitive impartment including age-related cognitive decline.

Particular anxiety disorders are generalized anxiety disorder, obsessive-compulsive disorder and panic attack.

Particular schizophrenia or psychosis pathologies are paranoid, disorganized, catatonic or undifferentiated schizophrenia and substance-induced psychotic disorder.

Particular neurologic disorders that can be treated with the compounds of the formula (I) include in particular a cognitive disorder such as dementia, cognitive impairment, attention deficit hyperactivity disorder.

Particular psychiatric disorders that can be treated with the compounds of the formula (I) include in particular an anxiety disorder, a mood disorder such as depression or a bipolar disorder, schizophrenia, a psychotic disorder.

Within the context of the treatment, the use according to the invention of the compounds of the formula (I) involves a method. In this method, an effective quantity of one or more compounds or the formula (I), as a rule formulated in accordance with pharmaceutical and veterinary practice, is administered to the individual to be treated, preferably a mammal, in particular a human being. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other drugs or drug-containing preparations.

The invention also relates to the manufacture of pharmaceutical compositions for treating an individual, preferably a mammal, in particular a human being. Thus, the compounds of the formula (I) are customarily administered in the form of pharmaceutical compositions which comprise an inert carrier (e.g. a pharmaceutically acceptable excipient) together with at least one compound according to the invention and, where appropriate, other drugs. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Cantor-Verlag, 1996.

The following examples serve to explain the invention without limiting it.

The compounds were characterized by mass spectrometry, generally recorded via HPLC-MS in a fast gradient on C18-material (electrospray-ionisation (ESI) mode).

Preparation Examples

Example 1

2,4-Dichloro-N-(2-{1-[1-(4-chloro-phenyl)-cyclobutyl]-1,2,3,4-tetrahydro-isoquinolin-7-yloxy}-ethyl)-benzamide 1.1 Tert-butyl 2-(1-(1-(4-chlorophenyl)cyclobutyl)-3,4-dihydroisoquinolin-7-yloxy)ethylcarbamate Sodium hydride (60% in paraffin, 1.40 g, 32.1 mmol) was washed with n-hexane. N,N-dimethylacetamide (DMA, 30 ml) was added. 1-[1-(4-chlorophenyl)cyclobutyl]-3,4-dihydroisoquinolin-7-ol (example 82) (5.00 g, 16.0 mmol) dissolved in DMA (70 ml) was added dropwise at RT. After stirring for an additional hour tert-butyl-2-bromoethylcarbamate (10.78 g, 48.1 mmol) was added in portions. The reaction mixture was added to a half concentrated solution of sodium chloride and extracted with ethylacetate. The organic layers were washed with water and then with saturated sodium chloride solution, and dried with magnesium sulphate. The solvent was removed in vacuum to give a residue (11.1 g) that was purified by flash chromatography on silica (heptane/ethylacetate 3:1) to give 6.20 g (13.6 mmol, 85%) of tert-butyl 2-(1-(1-(4-chlorophenyl)cyclobutyl)-3,4-dihydroisoquinolin-7-yloxy)ethylcarbamate.

1.2 2-(1-(1-(4-chlorophenyl)cyclobutyl)-3,4-dihydroisoquinolin-7-yloxy)ethanamine After adding HCl dissolved in isopropanole (15 ml, 6 molar solution) to a solution of tert-butyl 2-(1-(1-(4-chlorophenyl)cyclobutyl)-3,4-dihydroisoquinolin-7-yloxy)ethylcarbamate (6.20 g, 13.6 mmol) in dichloromethane (200 ml) the mixture was stirred for 14 h. The resulting precipitate was removed by filtration and washed with diisopropylether. After drying the filtrate was dissolved in water and basified with 2N NaOH. Extraction with dichloromethane the combined organic layers were washed with water and saturated NaCl solution. Drying with MgSO$_4$ and removal of the solvent gave 2-(1-(1-(4-chlorophenyl)cyclobutyl)-3,4-dihydroisoquinolin-7-yloxy)ethanamine (3.77 g, 10.6 mmol, 78%).

1.3 2,4-Dichloro-N-(2-{1-[1-(4-chloro-phenyl)-cyclobutyl]-1,2,3,4-tetrahydro-isoquinolin-7-yloxy}-ethyl)-benzamide 2-(1-(1-(4-chlorophenyl)cyclobutyl)-3,4-dihydroisoquinolin-7-yloxy)ethanamine (80.0 mg, 0.15 mmol), 2,4-dichloro-benzoyl chloride (44.3 mg, 0.21 mmol), and triethyl amine (48.6 mg, 0.48 mmol) were dissolved in dichloromethane (2 ml) and stirred for 14 h at RT. Water was added and the mixture was extracted with ethyl acetate. The organic layers were washed with water and saturated NaCl solution, dried with MgSO$_4$, and the solvent was removed. The residue was purified by flash chromatography on silica gel using methylenchloride/MeOH 98:2→95:5 to give 2,4-dichloro-N-

(2-{1-[1-(4-chloro-phenyl)-cyclobutyl]-3,4-dihydro-isoquinolin-7-yloxy}-ethyl)-benzamide as a colourless oil (85.0 mg, 0.16 mmol, 84%).

1.4 2,4-Dichloro-N-(2-{1-[1-(4-chloro-phenyl)-cyclobutyl]-1,2,3,4-tetrahydro-isoquinolin-7-yloxy}-ethyl)-benzamide

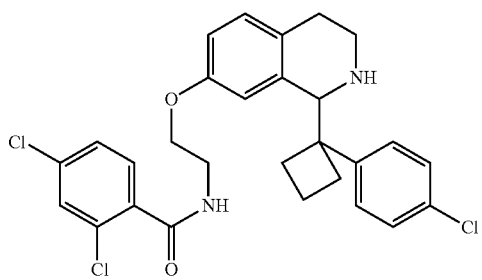 [SMILES: O=C(NCCOc1ccc2c(c1)C(C1(c3ccc(Cl)cc3)CCC1)NCC2)c1ccc(Cl)cc1Cl]

2,4-dichloro-N-(2-{1-[1-(4-chloro-phenyl)-cyclobutyl]-3,4-dihydro-isoquinolin-7-yloxy}-ethyl)-benzamide (80.0 mg, 0.15 mmol) and sodium borohydride (12.0 mg, 0.32 mmol) were dissolved in H$_2$O (10 ml) and MeOH (0.5 ml) and stirred for 14 h at RT. Water was added and the mixture was extracted with ethyl acetate. The organic layers were washed with water and saturated NaCl solution, dried with MgSO$_4$, and the solvent was removed. The residue was transferred into the hydrochloride salt using HCl dissolved in isopropanole (6 molar solution). Crystallization gave 2,4-Dichloro-N-(2-{1-[1-(4-chloro-phenyl)-cyclobutyl]-1,2,3,4-tetrahydro-isoquinolin-7-yloxy}-ethyl)-benzamide (60.0 mg, 0.11 mmol, 70%) as white solid.

ESI-MS [M+H]$^+$=529.1 Calculated for C$_{28}$H$_{27}$Cl$_3$N$_2$O$_2$HCl=528

Example 2

N-(2-{1-[1-(4-Chloro-phenyl)-cyclobutyl]-1,2,3,4-tetrahydro-isoquinolin-7-yloxy}-ethyl)-methanesulfonamide

2.1 N-(2-{1-[1-(4-Chloro-phenyl)-cyclobutyl]-3,4-dihydro-isoquinolin-7-yloxy}-ethyl)-methanesulfonamide 2-(1-(1-(4-chlorophenyl)cyclobutyl)-3,4-dihydroisoquinolin-7-yloxy)ethanamine (example 1, 100 mg, 0.26 mmol), aminopyridine (34.0 mg, 0.28 mmol), and methanesulfonyl chloride (31.9 mg, 0.28 mmol) were dissolved in THF (5 ml) and stirred for 14 h at RT. Water was added and the mixture was extracted with ethyl acetate. The organic layers were washed with water and saturated NaCl solution, dried with MgSO$_4$, and the solvent was removed. The residue was purified by flash chromatography on silica gel using methylenehloride/MeOH 98:2→95:5 to give N-(2-{1-[1-(4-Chlorophenyl)-cyclobutyl]-3,4-dihydroisoquinolin-7-yloxy}-ethyl)-methanesulfonamide (90.0 mg, 0.21 mmol, 78%).

2.2 N-(2-{1-[1-(4-Chloro-phenyl)-cyclobutyl]-1,2,3,4-tetrahydro-isoquinolin-7-yloxy}-ethyl)-methanesulfonamide

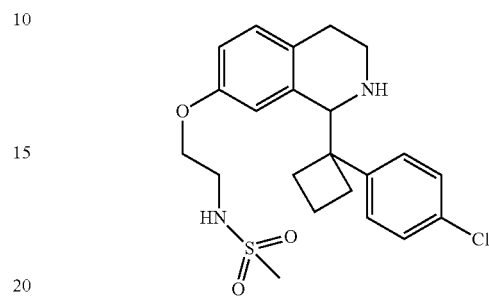

The synthesis was performed in analogy to example 1, procedure 4, to give the final product in 62% yield.

ESI-MS [M+H]$^+$=435 Calculated for C$_{22}$H$_{27}$ClN$_2$O$_3$S=434

Example 3

N-(2-{1-[1-(4-Chloro-phenyl)-cyclobutyl]-1,2,3,4-tetrahydro-isoquinolin-7-yloxy}-ethyl)-benzamide

3.1 N-(2-{1-[1-(4-Chloro-phenyl)-cyclobutyl]-3,4-dihydro-isoquinolin-7-yloxy}-ethyl)-benzamide The synthesis was performed in analogy to example 1 (procedure 3) using benzoyl chloride instead of 2,4-dichlorobenzoyl chloride to give the final product in 74% yield.

3.2 N-(2-{1-[1-(4-Chloro-phenyl)-cyclobutyl]-1,2,3,4-tetrahydro-isoquinolin-7-yloxy}-ethyl)-benzamide hydrochloride

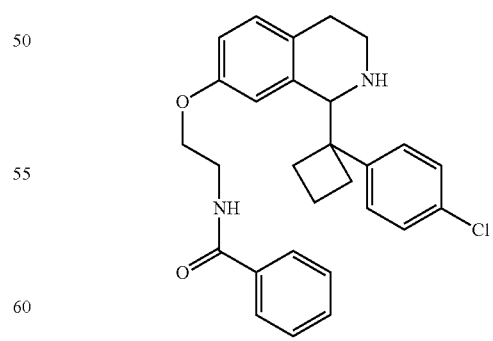

The synthesis was performed in analogy to example 1, procedure 4, to give the final product in 62% yield.

ESI-MS [M+H]$^+$=461.1 Calculated for C$_{28}$H$_{29}$ClN$_2$O$_2$=460

Example 4

Propane-1-sulfonic acid (2-{1-[1-(4-chloro-phenyl)-cyclobutyl]-1,2,3,4-tetrahydro-isoquinolin-7-yloxy}-ethyl)-amide hydrochloride

4.1 Propane-1-sulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using propanesulfonyl chloride instead of methanesulfonyl chloride to give the final product in 74% yield.

ESI-MS [M+H]$^+$=461.1 Calculated for $C_{24}H_{29}ClN_2O_3S$=460

4.2 N-(2-{1-[1-(4-Chloro-phenyl)-cyclobutyl]-1,2,3,4-tetrahydro-isoquinolin-7-yloxy}-ethyl)-benzamide hydrochloride

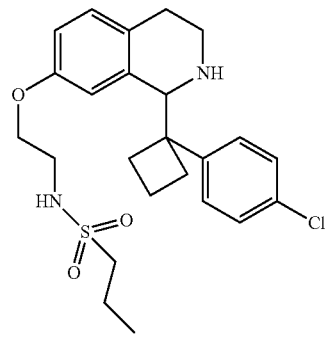 [SMILES: CCCS(=O)(=O)NCCOc1ccc2c(c1)C(C1(c3ccc(Cl)cc3)CCC1)NCC2]

The synthesis was performed in analogy to example 1, procedure 4, to give the final product in 16% yield.

ESI-MS [M+H]$^+$=463.1 Calculated for $C_{24}H_{31}ClN_2O_3S$=462

Example 5

N-(2-{1-[1-(4-Chloro-phenyl)-cyclobutyl]-1,2,3,4-tetrahydro-isoquinolin-7-yloxy}-ethyl)-isobutyramide

5.1 N-(2-{1-[1-(4-Chloro-phenyl)-cyclobutyl]-3,4-dihydro-isoquinolin-7-yloxy}-ethyl)-isobutyramide The synthesis was performed in analogy to example 1 (procedure 3) using isobutyryl chloride instead of 2,4-dichloro-benzoyl chloride to give the final product in 76% yield.

ESI-MS [M+H]$^+$=425.2 Calculated for $C_{25}H_{29}ClN_2O_2$=424

5.2 N-(2-{1-[1-(4-Chloro-phenyl)-cyclobutyl]-1,2,3,4-tetrahydro-isoquinolin-7-yloxy}-ethyl)-isobutyramide

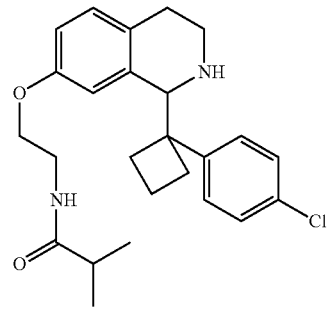 [SMILES: CC(C)C(=O)NCCOc1ccc2c(c1)C(C1(c3ccc(Cl)cc3)CCC1)NCC2]

The synthesis was performed in analogy to example 1, procedure 4, to give the final product in 67% yield.

ESI-MS [M+H]$^+$=427.2 Calculated for $C_{25}H_{31}ClN_2O_2$=426

Example 6

N-(2-{1-[1-(4-Chloro-phenyl)-cyclobutyl]-1,2,3,4-tetrahydro-isoquinolin-7-yloxy}-ethyl)-acetamide

6.1 N-(2-{1-[1-(4-Chloro-phenyl)-cyclobutyl]-3,4-dihydro-isoquinolin-7-yloxy}-ethyl)-acetamide The synthesis was performed in analogy to example 1 (procedure 3) using acetyl chloride instead of 2,4-dichloro-benzoyl chloride to give the final product in 86% yield.

6.2 N-(2-{1-[1-(4-Chloro-phenyl)-cyclobutyl]-1,2,3,4-tetrahydro-isoquinolin-7-yloxy}-ethyl)-acetamide

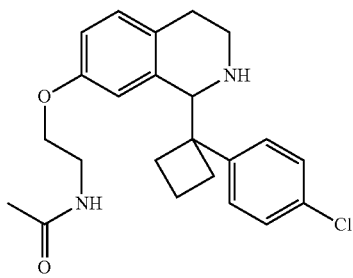 [SMILES: CC(=O)NCCOc1ccc2c(c1)C(C1(c3ccc(Cl)cc3)CCC1)NCC2]

The synthesis was performed in analogy to example 1, procedure 4, to give the final product in 40% yield.

ESI-MS [M+H]$^+$=399.1 Calculated for $C_{23}H_{27}ClN_2O_2$=398

Example 7

Ethanesulfonic acid (2-{1-[1-(4-chloro-phenyl)-cyclobutyl]-1,2,3,4-tetrahydro-isoquinolin-7-yloxy}-ethyl)-amide hydrochloride 7.1 Ethanesulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using ethanesulfonyl chloride instead of methanesulfonyl chloride to give the final product in 84% yield.

7.2 Ethanesulfonic acid (2-{1-[1-(4-chloro-phenyl)-cyclobutyl]-1,2,3,4-tetrahydro-isoquinolin-7-yloxy}-ethyl)-amide hydrochloride

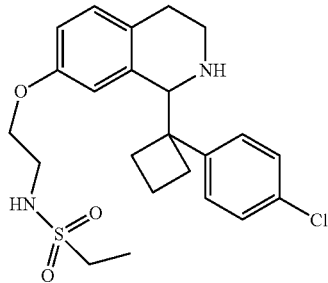 [SMILES: CCS(=O)(=O)NCCOc1ccc2c(c1)C(C1(c3ccc(Cl)cc3)CCC1)NCC2]

The synthesis was performed in analogy to example 1, procedure 4, to give the final product in 59% yield.
ESI-MS [M+H]$^+$=449.1 Calculated for $C_{23}H_{29}ClN_2O_3S$=448

Example 8

2-Methyl-propane-1-sulfonic acid (2-{1-[1-(4-chloro-phenyl)-cyclobutyl]-1,2,3,4-tetrahydro-isoquinolin-7-yloxy}-ethyl)-amide hydrochloride 8.1 2-Methyl-propane-1-sulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using 2-methyl-propane-1-sulfonyl chloride instead of methanesulfonyl chloride to give the final product in 79% yield.

8.2 2-Methyl-propane-1-sulfonic acid (2-{1-[1-(4-chloro-phenyl)-cyclobutyl]-1,2,3,4-tetrahydro-isoquinolin-7-yloxy}-ethyl)-amide hydrochloride

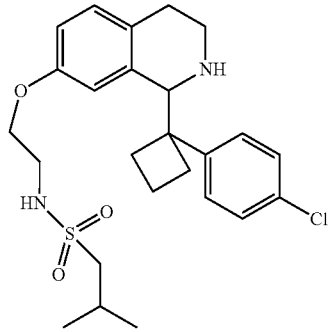 [SMILES: CC(C)CS(=O)(=O)NCCOc1ccc2c(c1)C(C1(c3ccc(Cl)cc3)CCC1)NCC2]

The synthesis was performed in analogy to example 1, procedure 4, to give the final product in 67% yield.
ESI-MS [M+H]$^+$=477.2 Calculated for $C_{25}H_{33}ClN_2O_3S$=476

Example 9

Naphthalene-2-sulfonic acid (2-{1-[1-(4-chloro-phenyl)-cyclobutyl]-1,2,3,4-tetrahydro-isoquinolin-7-yloxy}-ethyl)-amide hydrochloride 9.1 Naphthalene-2-sulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using naphthalene-2-sulfonyl chloride instead of methanesulfonyl chloride to give the final product in 69% yield.

9.2 Naphthalene-2-sulfonic acid (2-{1-[1-(4-chloro-phenyl)-cyclobutyl]-1,2,3,4-tetrahydro-isoquinolin-7-yloxy}-ethyl)-amide hydrochloride The synthesis was performed in analogy to example 1, procedure 4, to give the final product in 66% yield.
ESI-MS [M+H]$^+$=547.2 Calculated for $C_{31}H_{31}ClN_2O_3S$=546

Example 10

Pyridine-3-sulfonic acid (2-{1-[1-(4-chloro-phenyl)-cyclobutyl]-1,2,3,4-tetrahydro-isoquinolin-7-yloxy}-ethyl)-amide hydrochloride 10.1 Pyridine-3-sulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using pyridine-3-sulfonyl chloride instead of methanesulfonyl chloride to give the final product in 76% yield.

10.2 Pyridine-3-sulfonic acid (2-{1-[1-(4-chloro-phenyl)-cyclobutyl]-1,2,3,4-tetrahydro-isoquinolin-7-yloxy}-ethyl)-amide hydrochloride

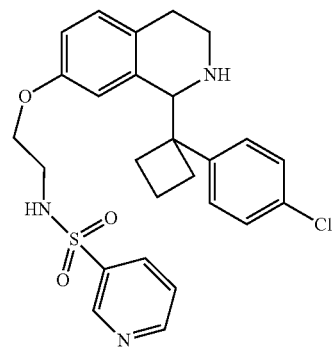 [SMILES: O=S(=O)(NCCOc1ccc2c(c1)C(C1(c3ccc(Cl)cc3)CCC1)NCC2)c1cccnc1]

The synthesis was performed in analogy to example 2, procedure 4, to give the final product in 24% yield.
ESI-MS [M+H]$^+$=498.1 Calculated for $C_{26}H_{28}ClN_3O_3S$=497

Example 11

N-(2-{1-[1-(4-Chloro-phenyl)-cyclobutyl]-1,2,3,4-tetrahydro-isoquinolin-7-yloxy}-ethyl)-C,C,C-trifluoro-methanesulfonamide

11.1 N-(2-{1-[1-(4-Chloro-phenyl)-cyclobutyl]-3,4-dihydro-isoquinolin-7-yloxy}-ethyl)-C,C,C-trifluoro-methanesulfonamide The synthesis was performed in analogy to example 2 (procedure 1) using trifluoro-methanesulfonyl chloride instead of methanesulfonyl chloride to give the final product in 47% yield.

11.2 N-(2-{1-[1-(4-Chloro-phenyl)-cyclobutyl]-1,2,3,4-tetrahydro-isoquinolin-7-yloxy}-ethyl)-C,C,C-trifluoro-methanesulfonamide

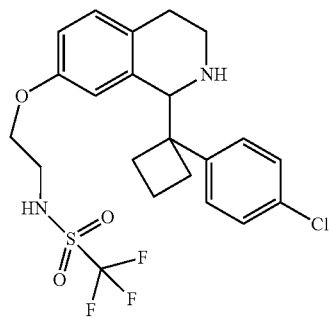 [SMILES: O=S(=O)(NCCOc1ccc2c(c1)C(C1(c3ccc(Cl)cc3)CCC1)NCC2)C(F)(F)F]

The synthesis was performed in analogy to example 1, procedure 4, to give the final product in 78% yield.
ESI-MS [M+H]$^+$=489.1 Calculated for $C_{22}H_{24}ClF_3N_2O_3S$=488

Example 12

N-(2-{1-[1-(4-Chloro-phenyl)-cyclobutyl]-6-fluoro-1,2,3,4-tetrahydro-isoquinolin-7-yloxy}-ethyl)-methanesulfonamide hydrochloride

12.1 2-(3-Fluoro-4-methoxy-phenyl)-ethylamine

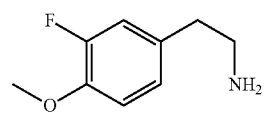

2-(3-Fluoro-4-methoxy-phenyl)-ethylamine was synthesized from (3-fluoro-4-methoxy-phenyl)-acetonitrile following classical reduction methods described e.g. in "M. B. Smith, J. March, March's Advanced Organic Chemistry, 6th Edition, John Wiley & Sons, Hoboken, 2007" and literature cited in there. The product was obtained as colourless oil in a yield of 33%.

12.2 1-(4-Chloro-phenyl)-cyclobutanecarboxylic acid [2-(3-fluoro-4-methoxy-phenyl)-ethyl]-amide

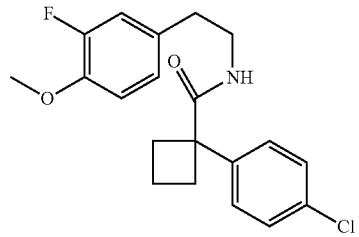 [SMILES: COc1ccc(CCNC(=O)C2(c3ccc(Cl)cc3)CCC2)cc1F]

The synthesis was performed in analogy to example 82, procedure 1, starting from 2-(3-fluoro-4-methoxy-phenyl)-ethylamine to give the final product as a white solid in 100% yield.
ESI-MS [M+H]$^+$=362.1 Calculated for $C_{20}H_{21}ClFNO_2$=361

12.3 1-[1-(4-Chloro-phenyl)-cyclobutyl]-6-fluoro-7-methoxy-3,4-dihydro-isoquinoline

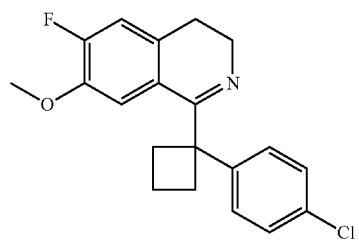 [SMILES: COc1cc2c(cc1F)CCN=C2C1(c2ccc(Cl)cc2)CCC1]

The synthesis was performed in analogy to example 82, procedure 2, starting from 1-(4-Chloro-phenyl)-cyclobutanecarboxylic acid [2-(3-fluoro-4-methoxy-phenyl)-ethyl]-amide to give the final product as a colourless oil in 23% yield.

12.4 1-[1-(4-Chloro-phenyl)-cyclobutyl]-6-fluoro-3,4-dihydro-isoquinolin-7-ol

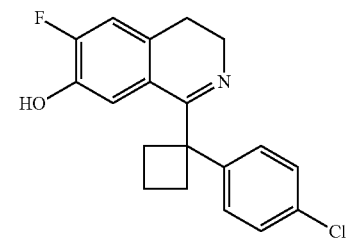 [SMILES: Oc1cc2c(cc1F)CCN=C2C1(c2ccc(Cl)cc2)CCC1]

The synthesis was performed in analogy to example 82, procedure 3, starting from 1-[1-(4-Chloro-phenyl)-cyclobutyl]-6-fluoro-7-methoxy-3,4-dihydro-isoquinoline to give the final product as a white solid in 25% yield.
ESI-MS [M+H]$^+$=330.1 Calculated for $C_{19}H_{17}ClFNO$=329

12.5 (2-{1-[1-(4-Chloro-phenyl)-cyclobutyl]-6-fluoro-3,4-dihydro-isoquinolin-7-yloxy}-ethyl)-carbamic acid tert-butyl ester

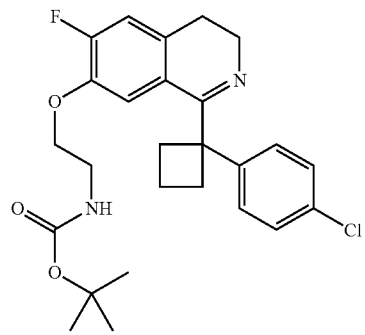 [SMILES: CC(C)(C)OC(=O)NCCOc1cc2c(cc1F)CCN=C2C1(c2ccc(Cl)cc2)CCC1]

The synthesis was performed in analogy to example 1, procedure 1, starting from 1-[1-(4-Chloro-phenyl)-cyclobutyl]-6-fluoro-3,4-dihydro-isoquinolin-7-ol to give the final product in 92% yield.

12.6 2-{1-[1-(4-Chloro-phenyl)-cyclobutyl]-6-fluoro-3,4-dihydro-isoquinolin-7-yloxy}-ethylamine

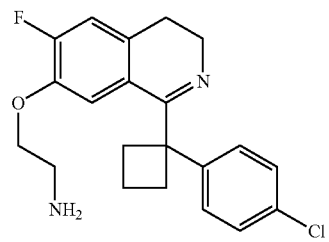 [SMILES: NCCOc1cc2c(cc1F)CCN=C2C1(c2ccc(Cl)cc2)CCC1]

The synthesis was performed in analogy to example 1, procedure 2, starting from (2-{1-[1-(4-Chloro-phenyl)-cyclobutyl]-6-fluoro-3,4-dihydro-isoquinolin-7-yloxy}-ethyl)-carbamic acid tert-butyl ester to give the final product in 90% yield.

ESI-MS [M+H]$^+$=373.1 Calculated for $C_{26}H_{30}ClFN_2O_3$=372

12.7 N-(2-{1-[1-(4-Chloro-phenyl)-cyclobutyl]-6-fluoro-3,4-dihydro-isoquinolin-7-yloxy}-ethyl)-methanesulfonamide

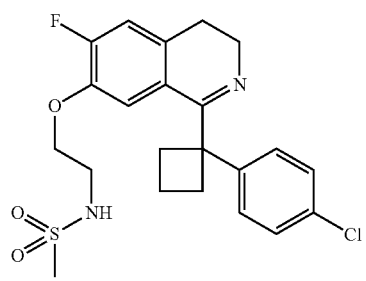 [SMILES: CS(=O)(=O)NCCOc1cc2c(cc1F)CCN=C2C1(c2ccc(Cl)cc2)CCC1]

The synthesis was performed in analogy to example 2, procedure 1, starting from 2-{1-[1-(4-Chloro-phenyl)-cyclobutyl]-6-fluoro-3,4-dihydro-isoquinolin-7-yloxy}-ethylamine to give the final product in 89% yield.

ESI-MS [M+H]$^+$=451.1 Calculated for $C_{22}H_{24}ClFN_2O_3S$=450

12.8 N-(2-{1-[1-(4-Chloro-phenyl)-cyclobutyl]-6-fluoro-1,2,3,4-tetrahydro-isoquinolin-7-yloxy}-ethyl)-methanesulfonamide hydrochloride

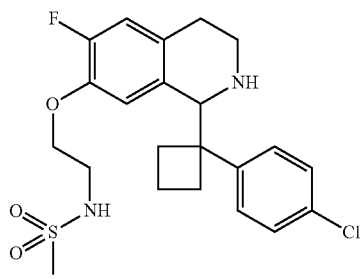 [SMILES: CS(=O)(=O)NCCOc1cc2c(cc1F)CCNC2C1(c2ccc(Cl)cc2)CCC1]

The synthesis was performed in analogy to example 2, procedure 2, starting from N-(2-{1-[1-(4-Chloro-phenyl)-cyclobutyl]-6-fluoro-3,4-dihydro-isoquinolin-7-yloxy}-ethyl)-methanesulfonamide to give the final product in 32% yield.

ESI-MS [M+H]$^+$=453.1 Calculated for $C_{22}H_{26}ClFN_2O_3S$=452

Example 13

N-(2-{1-[1-(4-Chloro-phenyl)-cyclobutyl]-6-fluoro-1,2,3,4-tetrahydro-isoquinolin-7-yloxy}-ethyl)-benzenesulfonamide hydrochloride

13.1 N-(2-{1-[1-(4-Chloro-phenyl)-cyclobutyl]-6-fluoro-3,4-dihydro-isoquinolin-7-yloxy}-ethyl)-benzenesulfonamide The synthesis was performed in analogy to example 2, procedure 1, starting from 2-{1-[1-(4-Chloro-phenyl)-cyclobutyl]-6-fluoro-3,4-dihydro-isoquinolin-7-yloxy}-ethylamine to give the final product in 86% yield.

ESI-MS [M+H]$^+$=513.2 Calculated for $C_{27}H_{26}ClFN_2O_3S$=512

13.2 N-(2-{1-[1-(4-Chloro-phenyl)-cyclobutyl]-6-fluoro-1,2,3,4-tetrahydro-isoquinolin-7-yloxy}-ethyl)-benzenesulfonamide hydrochloride

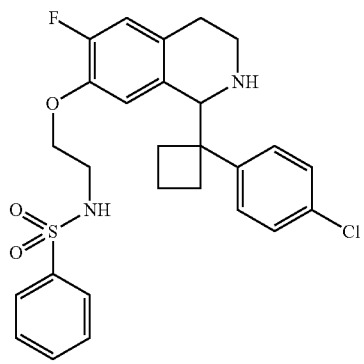 [SMILES: O=S(=O)(NCCOc1cc2c(cc1F)CCNC2C1(c2ccc(Cl)cc2)CCC1)c1ccccc1]

The synthesis was performed in analogy to example 2, procedure 2, starting from N-(2-{1-[1-(4-Chloro-phenyl)-cyclobutyl]-6-fluoro-3,4-dihydro-isoquinolin-7-yloxy}-ethyl)-benzenesulfonamide to give the final product in 35% yield.
ESI-MS [M+H]$^+$=515.2 Calculated for $C_{27}H_{28}ClFN_2O_3S$=514

Example 14

Pyridine-3-sulfonic acid (2-{1-[1-(4-chloro-phenyl)-cyclobutyl]-6-fluoro-1,2,3,4-tetrahydro-isoquinolin-7-yloxy}-ethyl)-amide hydrochloride

14.1 Pyridine-3-sulfonic acid (2-{1-[1-(4-chloro-phenyl)-cyclobutyl]-6-fluoro-3,4-dihydro-isoquinolin-7-yloxy}-ethyl)-amide The synthesis was performed in analogy to example 2, procedure 1, starting from 2-{1-[1-(4-Chloro-phenyl)-cyclobutyl]-6-fluoro-3,4-dihydro-isoquinolin-7-yloxy}-ethylamine to give the final product in 89% yield.
ESI-MS [M+H]$^+$=514.2 Calculated for $C_{26}H_{25}ClFN_3O_3S$=513

14.2 Pyridine-3-sulfonic acid (2-{1-[1-(4-chloro-phenyl)-cyclobutyl]-6-fluoro-1,2,3,4-tetrahydro-isoquinolin-7-yloxy}-ethyl)-amide hydrochloride

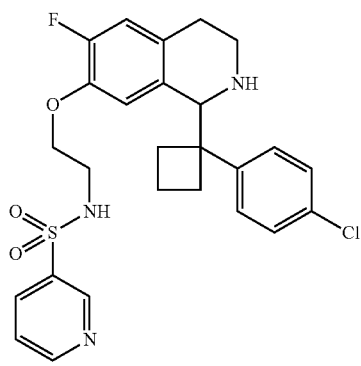 [SMILES: O=S(=O)(NCCOc1cc2c(cc1F)CCNC2C1(c2ccc(Cl)cc2)CCC1)c1cccnc1]

The synthesis was performed in analogy to example 2, procedure 2, starting from N-(2-{1-[1-(4-Chloro-phenyl)-cyclobutyl]-6-fluoro-3,4-dihydro-isoquinolin-7-yloxy}-ethyl)-benzenesulfonamide to give the final product in 35% yield.
ESI-MS [M+H]$^+$=516.2 Calculated for $C_{26}H_{27}ClFN_3O_3S$=515

Example 15

Propane-1-sulfonic acid (2-{1-[1-(4-chloro-phenyl)-cyclobutyl]-6-fluoro-1,2,3,4-tetrahydro-isoquinolin-7-yloxy}-ethyl)-amide hydrochloride

15.1 Propane-1-sulfonic acid (2-{1-[1-(4-chloro-phenyl)-cyclobutyl]-6-fluoro-3,4-dihydro-isoquinolin-7-yloxy}-ethyl)-amide The synthesis was performed in analogy to example 2, procedure 1, starting from 2-{1-[1-(4-Chloro-phenyl)-cyclobutyl]-6-fluoro-3,4-dihydro-isoquinolin-7-yloxy}-ethylamine to give the final product in 89% yield.
ESI-MS [M+H]$^+$=479.1 Calculated for $C_{24}H_{28}ClFN_2O_3S$=478

15.2 Propane-1-sulfonic acid (2-{1-[1-(4-chloro-phenyl)-cyclobutyl]-6-fluoro-1,2,3,4-tetrahydro-isoquinolin-7-yloxy}-ethyl)-amide

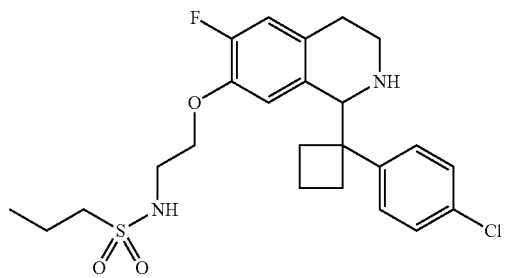 [SMILES: CCCS(=O)(=O)NCCOc1cc2c(cc1F)CCNC2C1(c2ccc(Cl)cc2)CCC1]

The synthesis was performed in analogy to example 2, procedure 2, starting from N-(2-{1-[1-(4-Chloro-phenyl)-cyclobutyl]-6-fluoro-3,4-dihydro-isoquinolin-7-yloxy}-ethyl)-benzenesulfonamide to give the final product in 41% yield.
ESI-MS [M+H]$^+$=481.1 Calculated for $C_{24}H_{30}ClFN_2O_3S$=480

Example 16

Butane-1-sulfonic acid (2-{1-[1-(4-chloro-phenyl)-cyclobutyl]-1,2,3,4-tetrahydro-isoquinolin-7-yloxy}-ethyl)-amide hydrochloride

16.1 Butane-1-sulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using butaneesulfonyl chloride instead of methanesulfonyl chloride to give the final product in 99% yield.
ESI-MS [M+H]$^+$=475.1 Calculated for $C_{25}H_{31}ClN_2O_3S$=474

16.2 Butane-1-sulfonic acid (2-{1-[1-(4-chloro-phenyl)-cyclobutyl]-1,2,3,4-tetrahydro-isoquinolin-7-yloxy}-ethyl)-amide hydrochloride

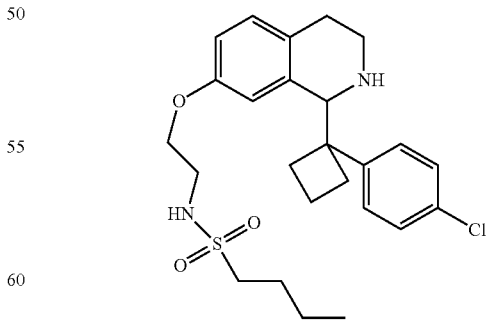

The synthesis was performed in analogy to example 1, procedure 4, to give the final product in 99% yield.
ESI-MS [M+H]$^+$=477.1 Calculated for $C_{25}H_{33}ClN_2O_3S$=476

Example 17

Thiophene-2-sulfonic acid (2-{1-[1-(4-chloro-phenyl)-cyclobutyl]-1,2,3,4-tetrahydro-isoquinolin-7-yloxy}-ethyl)-amide hydrochloride

17.1 Thiophene-2-sulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using thienylsulfonyl chloride instead of methanesulfonyl chloride to give the final product in 97% yield.
ESI-MS [M+H]$^+$=501.0 Calculated for $C_{25}H_{25}ClN_2O_3S_2$=500

17.2 Thiophene-2-sulfonic acid (2-{1-[1-(4-chloro-phenyl)-cyclobutyl]-1,2,3,4-tetrahydro-isoquinolin-7-yloxy}-ethyl)-amide hydrochloride

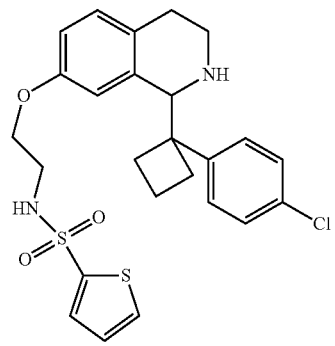 [SMILES: O=S(=O)(NCCOc1ccc2c(c1)C(C1(c3ccc(Cl)cc3)CCC1)NCC2)c1cccs1]

The synthesis was performed in analogy to example 1, procedure 4, to give the final product in 81% yield.
ESI-MS [M+H]$^+$=503.1 Calculated for $C_{25}H_{27}ClN_2O_3S_2$=502

Example 18

N-(2-{1-[1-(4-Chloro-phenyl)-cyclobutyl]-1,2,3,4-tetrahydro-isoquinolin-7-yloxy}-ethyl)-2-methoxy-benzenesulfonamide hydrochloride

18.1 N-(2-{1-[1-(4-Chloro-phenyl)-cyclobutyl]-3,4-dihydro-isoquinolin-7-yloxy}-ethyl)-2-methoxy-benzenesulfonamide The synthesis was performed in analogy to example 2 (procedure 1) using 2-methoxy-benzenesulfonyl chloride instead of methanesulfonyl chloride to give the final product in 99% yield.
ESI-MS [M+H]$^+$=525.1 Calculated for $C_{28}H_{29}ClN_2O_4S$=524

18.2 N-(2-{1-[1-(4-Chloro-phenyl)-cyclobutyl]-1,2,3,4-tetrahydro-isoquinolin-7-yloxy}-ethyl)-2-methoxy-benzenesulfonamide hydrochloride

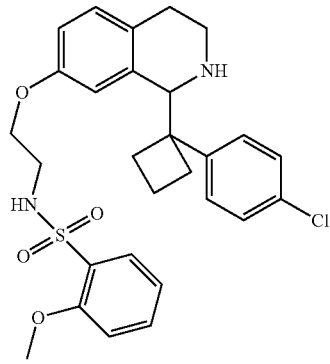 [SMILES: COc1ccccc1S(=O)(=O)NCCOc1ccc2c(c1)C(C1(c3ccc(Cl)cc3)CCC1)NCC2]

The synthesis was performed in analogy to example 1, procedure 4, to give the final product in 78% yield.
ESI-MS [M+H]$^+$=527.1 Calculated for $C_{28}H_{31}ClN_2O_4S$=526

Example 19

N-(2-{1-[1-(4-Chloro-phenyl)-cyclobutyl]-1,2,3,4-tetrahydro-isoquinolin-7-yloxy}-ethyl)-3-methoxy-benzenesulfonamide hydrochloride

19.1 N-(2-{1-[1-(4-Chloro-phenyl)-cyclobutyl]-3,4-dihydro-isoquinolin-7-yloxy}-ethyl)-3-methoxy-benzenesulfonamide The synthesis was performed in analogy to example 2 (procedure 1) using 3-methoxy-benzenesulfonyl chloride instead of methanesulfonyl chloride to give the final product in 99% yield.
ESI-MS [M+H]$^+$=525.1 Calculated for $C_{28}H_{29}ClN_2O_4S$=524

19.2 N-(2-{1-[1-(4-Chloro-phenyl)-cyclobutyl]-1,2,3,4-tetrahydro-isoquinolin-7-yloxy}-ethyl)-3-methoxy-benzenesulfonamide hydrochloride

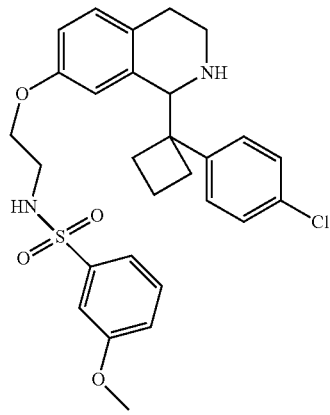 [SMILES: COc1cccc(S(=O)(=O)NCCOc2ccc3c(c2)C(C2(c4ccc(Cl)cc4)CCC2)NCC3)c1]

The synthesis was performed in analogy to example 1, procedure 4, to give the final product in 77% yield.
ESI-MS [M+H]$^+$=527.1 Calculated for $C_{28}H_{31}ClN_2O_4S$=526

Example 22

5-Isoxazol-3-yl-thiophene-2-sulfonic acid (2-{1-[1-(4-chloro-phenyl)-cyclobutyl]-1,2,3,4-tetrahydro-isoquinolin-7-yloxy}-ethyl)-amide hydrochloride

22.1 5-Isoxazol-3-yl-thiophene-2-sulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using 5-isoxazol-3-yl-thiophene-2-sulfonyl chloride instead of methanesulfonyl chloride to give the final product.

22.2 5-Isoxazol-3-yl-thiophene-2-sulfonic acid (2-{1-[1-(4-chloro-phenyl)-cyclobutyl]-1,2,3,4-tetrahydro-isoquinolin-7-yloxy}-ethyl)-amide hydrochloride

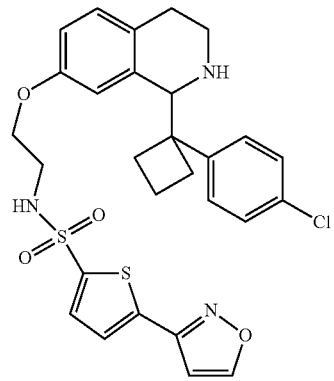 [SMILES: O=S(=O)(NCCOc1ccc2c(c1)C(C1(c3ccc(Cl)cc3)CCC1)NCC2)c1ccc(-c2ccon2)s1]

The synthesis was performed in analogy to example 1, procedure 4, to give the final product in 28% yield.
ESI-MS [M+H]$^+$=570.1 Calculated for $C_{28}H_{28}ClN_3O_4S_2$=569

Example 23

N-(2-{1-[1-(4-Chloro-phenyl)-cyclobutyl]-1,2,3,4-tetrahydro-isoquinolin-7-yloxy}-ethyl)-2-cyano-benzenesulfonamide hydrochloride

23.1 N-(2-{1-[1-(4-Chloro-phenyl)-cyclobutyl]-3,4-dihydro-isoquinolin-7-yloxy}-ethyl)-2-cyano-benzenesulfonamide The synthesis was performed in analogy to example 2 (procedure 1) using 2-cyano-benzenesulfonyl chloride instead of methanesulfonyl chloride to give the final product.

23.2 N-(2-{1-[1-(4-Chloro-phenyl)-cyclobutyl]-1,2,3,4-tetrahydro-isoquinolin-7-yloxy}-ethyl)-2-cyano-benzenesulfonamide hydrochloride

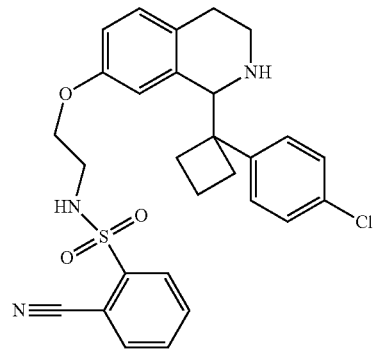 [SMILES: N#Cc1ccccc1S(=O)(=O)NCCOc1ccc2c(c1)C(C1(c3ccc(Cl)cc3)CCC1)NCC2]

The synthesis was performed in analogy to example 1, procedure 4, to give the final product in 27% yield.
ESI-MS [M+H]$^+$=522.1 Calculated for $C_{28}H_{28}ClN_3O_3S$=521

Example 24

N-(2-{1-[1-(4-Chloro-phenyl)-cyclobutyl]-1,2,3,4-tetrahydro-isoquinolin-7-yloxy}-ethyl)-4-cyano-benzenesulfonamide hydrochloride

24.1 N-(2-{1-[1-(4-Chloro-phenyl)-cyclobutyl]-3,4-dihydro-isoquinolin-7-yloxy}-ethyl)-2-cyano-benzenesulfonamide The synthesis was performed in analogy to example 2 (procedure 1) using 4-cyano-benzenesulfonyl chloride instead of methanesulfonyl chloride to give the final product.

24.2 N-(2-{1-[1-(4-Chloro-phenyl)-cyclobutyl]-1,2,3,4-tetrahydro-isoquinolin-7-yloxy}-ethyl)-4-cyano-benzenesulfonamide hydrochloride

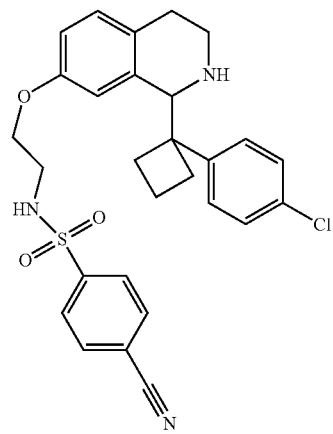 [SMILES: N#Cc1ccc(S(=O)(=O)NCCOc2ccc3c(c2)C(C2(c4ccc(Cl)cc4)CCC2)NCC3)cc1]

The synthesis was performed in analogy to example 1, procedure 4, to give the final product in 32% yield.
ESI-MS [M+H]$^+$=522.1 Calculated for $C_{28}H_{28}ClN_3O_3S$=521

Example 25

2-Chloro-N-(2-{1-[1-(4-chloro-phenyl)-cyclobutyl]-1,2,3,4-tetrahydro-isoquinolin-7-yloxy}-ethyl)-benzenesulfonamide hydrochloride

25.1 2-Chloro-N-(2-{1-[1-(4-chloro-phenyl)-cyclobutyl]-3,4-dihydro-isoquinolin-7-yloxy}-ethyl)-benzenesulfonamide The synthesis was performed in analogy to example 2 (procedure 1) using 2-chloro-benzenesulfonyl chloride instead of methanesulfonyl chloride to give the final product.

25.2 2-Chloro-N-(2-{1-[1-(4-chloro-phenyl)-cyclobutyl]-1,2,3,4-tetrahydro-isoquinolin-7-yloxy}-ethyl)-benzenesulfonamide hydrochloride

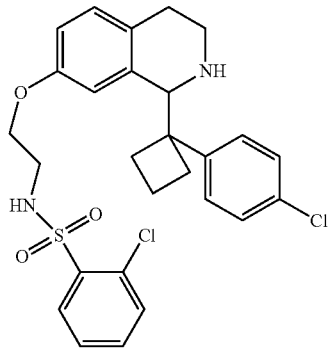 [SMILES: O=S(=O)(NCCOc1ccc2c(c1)C(C1(c3ccc(Cl)cc3)CCC1)NCC2)c1ccccc1Cl]

The synthesis was performed in analogy to example 1, procedure 4, to give the final product in 28% yield.
ESI-MS [M+H]$^+$=531.1 Calculated for $C_{27}H_{28}Cl_2N_2O_3S$=530

Example 26

3-Chloro-N-(2-{1-[1-(4-chloro-phenyl)-cyclobutyl]-1,2,3,4-tetrahydro-isoquinolin-7-yloxy}-ethyl)-benzenesulfonamide hydrochloride

26.1 3-Chloro-N-(2-{1-[1-(4-chloro-phenyl)-cyclobutyl]-3,4-dihydro-isoquinolin-7-yloxy}-ethyl)-benzenesulfonamide The synthesis was performed in analogy to example 2 (procedure 1) using 3-chloro-benzenesulfonyl chloride instead of methanesulfonyl chloride to give the final product.

26.2 3-Chloro-N-(2-{1-[1-(4-chloro-phenyl)-cyclobutyl]-1,2,3,4-tetrahydro-isoquinolin-7-yloxy}-ethyl)-benzenesulfonamide hydrochloride

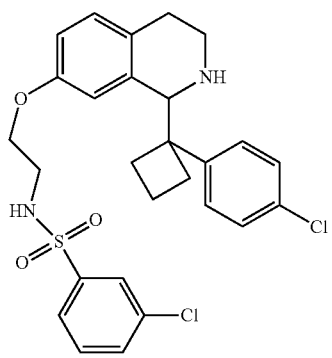 [SMILES: O=S(=O)(NCCOc1ccc2c(c1)C(C1(c3ccc(Cl)cc3)CCC1)NCC2)c1cccc(Cl)c1]

The synthesis was performed in analogy to example 1, procedure 4, to give the final product in 13% yield.
ESI-MS [M+H]$^+$=531.1 Calculated for $C_{27}H_{28}Cl_2N_2O_3S$=530

Example 27

4-Chloro-N-(2-{1-[1-(4-chloro-phenyl)-cyclobutyl]-1,2,3,4-tetrahydro-isoquinolin-7-yloxy}-ethyl)-benzenesulfonamide hydrochloride

27.1 4-Chloro-N-(2-{1-[1-(4-chloro-phenyl)-cyclobutyl]-3,4-dihydro-isoquinolin-7-yloxy}-ethyl)-benzenesulfonamide The synthesis was performed in analogy to example 2 (procedure 1) using 4-chloro-benzenesulfonyl chloride instead of methanesulfonyl chloride to give the final product.

27.2 4-Chloro-N-(2-{1-[1-(4-chloro-phenyl)-cyclobutyl]-1,2,3,4-tetrahydro-isoquinolin-7-yloxy}-ethyl)-benzenesulfonamide hydrochloride

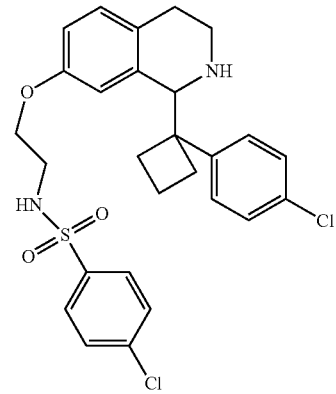 [SMILES: O=S(=O)(NCCOc1ccc2c(c1)C(C1(c3ccc(Cl)cc3)CCC1)NCC2)c1ccc(Cl)cc1]

The synthesis was performed in analogy to example 1, procedure 4, to give the final product in 50% yield.
ESI-MS [M+H]$^+$=531.2 Calculated for $C_{27}H_{28}Cl_2N_2O_3S$=530

Example 28

Cyclopropanesulfonic acid (2-{1-[1-(4-chloro-phenyl)-cyclobutyl]-1,2,3,4-tetrahydro-isoquinolin-7-yloxy}-ethyl)-amide hydrochloride

28.1 Cyclopropanesulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using cyclopropane-sulfonyl chloride instead of methanesulfonyl chloride to give the final product.

28.2 Cyclopropanesulfonic acid (2-{1-[1-(4-chloro-phenyl)-cyclobutyl]-1,2,3,4-tetrahydro-isoquinolin-7-yloxy}-ethyl)-amide hydrochloride

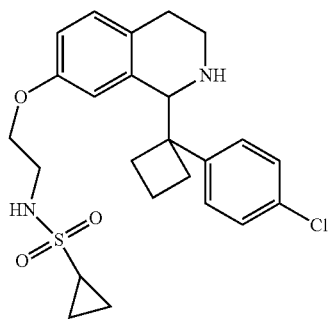 [SMILES: O=S(=O)(NCCOc1ccc2c(c1)C(C1(c3ccc(Cl)cc3)CCC1)NCC2)C1CC1]

The synthesis was performed in analogy to example 1, procedure 4, to give the final product in 36% yield.
ESI-MS [M+H]$^+$=461.1 Calculated for $C_{24}H_{29}ClN_2O_3S$=460

Example 29

6-Chloro-pyridine-3-sulfonic acid (2-{1-[1-(4-chloro-phenyl)-cyclobutyl]-1,2,3,4-tetrahydro-iso-quinolin-7-yloxy}-ethyl)-amide hydrochloride 29.1 6-Chloro-pyridine-3-sulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using 6-chloro-pyridine sulfonyl chloride instead of methanesulfonyl chloride to give the final product.

29.2 6-Chloro-pyridine-3-sulfonic acid (2-{1-[1-(4-chloro-phenyl)-cyclobutyl]-1,2,3,4-tetrahydro-iso-quinolin-7-yloxy}-ethyl)-amide hydrochloride

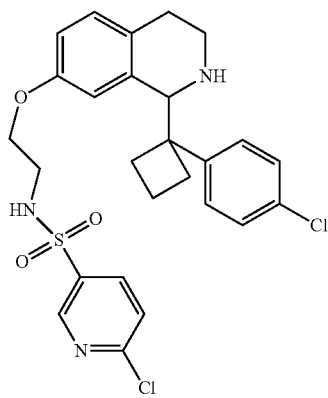 [SMILES: O=S(=O)(NCCOc1ccc2c(c1)C(C1(c3ccc(Cl)cc3)CCC1)NCC2)c1ccc(Cl)nc1]

The synthesis was performed in analogy to example 1, procedure 4, to give the final product in 34% yield.
ESI-MS [M+H]$^+$=532.1 Calculated for $C_{26}H_{27}Cl_2N_3O_3S$=531

Example 30

Quinoline-8-sulfonic acid (2-{1-[1-(4-chloro-phenyl)-cyclobutyl]-1,2,3,4-tetrahydro-isoquinolin-7-yloxy}-ethyl)-amide hydrochloride 30.1 Quinoline-8-sulfonic acid (2-{1-[1-(4-chloro-phenyl)-cyclobutyl]-3,4-dihydro-isoquinolin-7-yloxy}-ethyl)-amide The synthesis was performed in analogy to example 2 (procedure 1) using quinoline-8-sulfonyl chloride instead of methanesulfonyl chloride to give the final product.

30.2 Quinoline-8-sulfonic acid (2-{1-[1-(4-chloro-phenyl)-cyclobutyl]-1,2,3,4-tetrahydro-isoquinolin-7-yloxy}-ethyl)-amide hydrochloride

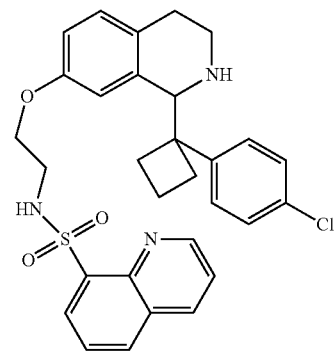 [SMILES: O=S(=O)(NCCOc1ccc2c(c1)C(C1(c3ccc(Cl)cc3)CCC1)NCC2)c1cccc2cccnc12]

The synthesis was performed in analogy to example 1, procedure 4, to give the final product in 42% yield.
ESI-MS [M+H]$^+$=548.1 Calculated for $C_{30}H_{30}ClN_3O_3S$=547

Example 31

N-(2-{1-[1-(4-Chloro-phenyl)-cyclobutyl]-1,2,3,4-tetrahydro-isoquinolin-7-yloxy}-ethyl)-4-methoxy-benzenesulfonamide hydrochloride 31.1 N-(2-{1-[1-(4-Chloro-phenyl)-cyclobutyl]-3,4-dihydro-isoquinolin-7-yloxy}-ethyl)-4-methoxy-benzenesulfonamide The synthesis was performed in analogy to example 2 (procedure 1) using 4-methoxy-benzenesulfonyl chloride instead of methanesulfonyl chloride to give the final product in 99% yield.

31.2 N-(2-{1-[1-(4-Chloro-phenyl)-cyclobutyl]-1,2,3,4-tetrahydro-isoquinolin-7-yloxy}-ethyl)-4-methoxy-benzenesulfonamide hydrochloride

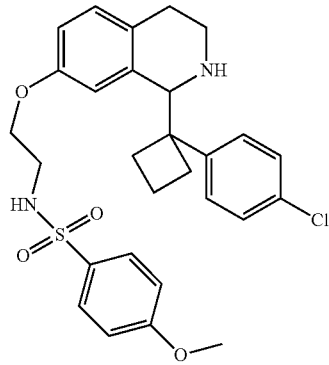 [SMILES: COc1ccc(S(=O)(=O)NCCOc2ccc3c(c2)C(C2(c4ccc(Cl)cc4)CCC2)NCC3)cc1]

The synthesis was performed in analogy to example 1, procedure 4, to give the final product in 50% yield.
ESI-MS [M+H]$^+$=527.1 Calculated for $C_{28}H_{31}ClN_2O_4S$=526

Example 32

N-(2-{1-[1-(4-Chloro-phenyl)-cyclobutyl]-1,2,3,4-tetrahydro-isoquinolin-7-yloxy}-ethyl)-C-phenyl-methanesulfonamide hydrochloride

32.1 N-(2-{1-[1-(4-Chloro-phenyl)-cyclobutyl]-3,4-dihydro-isoquinolin-7-yloxy}-ethyl)-C-phenyl-methanesulfonamide The synthesis was performed in analogy to example 2 (procedure 1) using phenyl-methanesulfonyl chloride instead of methanesulfonyl chloride to give the final product.

32.2 N-(2-{1-[1-(4-Chloro-phenyl)-cyclobutyl]-1,2,3,4-tetrahydro-isoquinolin-7-yloxy}-ethyl)-C-phenyl-methanesulfonamide hydrochloride

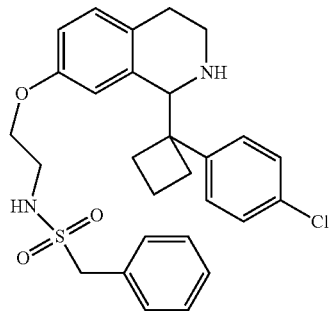 [SMILES: O=S(=O)(Cc1ccccc1)NCCOc1ccc2c(c1)C(C1(c3ccc(Cl)cc3)CCC1)NCC2]

The synthesis was performed in analogy to example 1, procedure 4, to give the final product in 34% yield.
ESI-MS [M+H]$^+$=511.1 Calculated for $C_{28}H_{31}ClN_2O_3S$=510

Example 33

1-(2-{1-[1-(4-Chloro-phenyl)-cyclobutyl]-1,2,3,4-tetrahydro-isoquinolin-7-yloxy}-ethyl)-3-propyl-urea hydrochloride

33.1 1-(2-{1-[1-(4-Chloro-phenyl)-cyclobutyl]-3,4-dihydro-isoquinolin-7-yloxy}-ethyl)-3-propyl-urea 2-(1-(1-(4-chlorophenyl)cyclobutyl)-3,4-dihydroisoquinolin-7-yloxy)ethanamine (example 1, 100 mg, 0.28 mmol) was dissolved in dichloromethane (2 ml) and 1-propyl isocyanate (33.5 mg, 0.39 mmol) was added. The mixture was stirred for 30 min and then the solvent was reduced. After addition of ethylacetate and isopropanol the product precipitated as colourless solid (120 mg, 0.27 mmol, 97%).
ESI-MS [M+H]$^+$=440.2 Calculated for $C_{25}H_{30}ClN_3O_2$=439

33.2 N-(2-{1-[1-(4-Chloro-phenyl)-cyclobutyl]-1,2,3,4-tetrahydro-isoquinolin-7-yloxy}-ethyl)-C-phenyl-methanesulfonamide hydrochloride

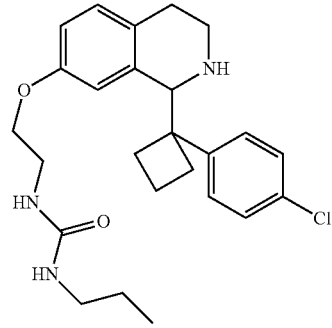 [SMILES: CCCNC(=O)NCCOc1ccc2c(c1)C(C1(c3ccc(Cl)cc3)CCC1)NCC2]

The synthesis was performed in analogy to example 1, procedure 4, to give the final product in 70% yield.
ESI-MS [M+H]$^+$=442.2 Calculated for $C_{25}H_{32}ClN_3O_2$=441

Example 34

1-(2-{1-[1-(4-Chloro-phenyl)-cyclobutyl]-1,2,3,4-tetrahydro-isoquinolin-7-yloxy}-ethyl)-3-propyl-urea hydrochloride

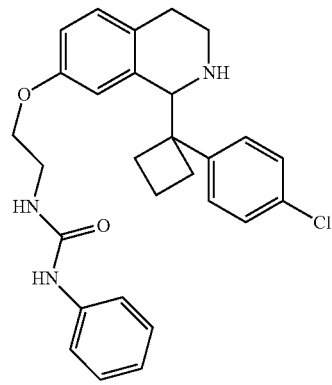 [SMILES: O=C(NCCOc1ccc2c(c1)C(C1(c3ccc(Cl)cc3)CCC1)NCC2)Nc1ccccc1]

The synthesis was performed according to example 33 without further purification of the intermediate 1-(2-{1-[1-(4-chloro-phenyl)-cyclobutyl]-3,4-dihydro-isoquinolin-7-yloxy}-ethyl)-3-phenyl-urea. The final product was isolated as a white solid (48.0 mg, 90.0 mmol, 48%)

ESI-MS [M+H]$^+$=476.2 Calculated for C$_{28}$H$_{30}$ClN$_3$O$_2$=475

Example 35

1,3-Dimethyl-1H-pyrazole-4-sulfonic acid (2-{1-[1-(4-chloro-phenyl)-cyclobutyl]-1,2,3,4-tetrahydro-isoquinolin-7-yloxy}-ethyl)-amide hydrochloride

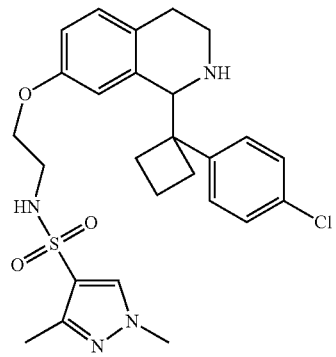 [SMILES: Cc1nn(C)cc1S(=O)(=O)NCCOc1ccc2c(c1)C(C1(c3ccc(Cl)cc3)CCC1)NCC2]

The synthesis was performed according to example 2 without further purification of the intermediate 1,3-dimethyl-1H-pyrazole-4-sulfonic acid (2-{1-[1-(4-chloro-phenyl)-cyclobutyl]-3,4-dihydro-isoquinolin-7-yloxy}-ethyl)-amide. The final product was isolated as a white solid (36.0 mg, 0.07 mmol, 23%).

ESI-MS [M+H]$^+$=515.2 Calculated for C$_{26}$H$_{31}$ClN$_4$O$_3$S=514

Example 36

1-(2-{1-[1-(4-Chloro-phenyl)-cyclobutyl]-1,2,3,4-tetrahydro-isoquinolin-7-yloxy}-ethyl)-3-isopropyl-urea hydrochloride

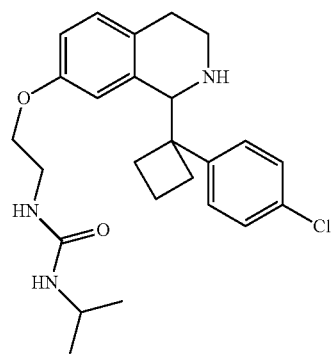 [SMILES: CC(C)NC(=O)NCCOc1ccc2c(c1)C(C1(c3ccc(Cl)cc3)CCC1)NCC2]

The synthesis was performed according to example 33 without further purification of the intermediate 1-(2-{1-[1-(4-chloro-phenyl)-cyclobutyl]-3,4-dihydro-isoquinolin-7-yloxy}-ethyl)-3-isopropyl-urea. The final product was isolated as a white solid (54.0 mg, 0.11 mmol, 57%).

ESI-MS [M+H]$^+$=442.2 Calculated for C$_{25}$H$_{32}$ClN$_3$O$_2$=441

Example 37

1-Methyl-1H-pyrazole-4-sulfonic acid (2-{1-[1-(4-chloro-phenyl)-cyclobutyl]-1,2,3,4-tetrahydro-isoquinolin-7-yloxy}-ethyl)-amide hydrochloride

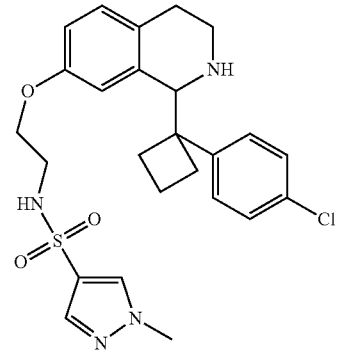 [SMILES: Cn1cc(S(=O)(=O)NCCOc2ccc3c(c2)C(C2(c4ccc(Cl)cc4)CCC2)NCC3)cn1]

The synthesis was performed according to example 2 without further purification of the intermediate 1-methyl-1H-pyrazole-4-sulfonic acid (2-{1-[1-(4-chloro-phenyl)-cyclobutyl]-3,4-dihydro-isoquinolin-7-yloxy}-ethyl)-amide. The final product was isolated as a white solid (21.0 mg, 0.04 mmol, 14%).

ESI-MS [M+H]$^+$=501.2 Calculated for C$_{25}$H$_{29}$ClN$_4$O$_3$S=500

Example 38

Propane-2-sulfonic acid (2-{1-[1-(4-chloro-phenyl)-cyclobutyl]-1,2,3,4-tetrahydro-isoquinolin-7-yloxy}-ethyl)-amide hydrochloride

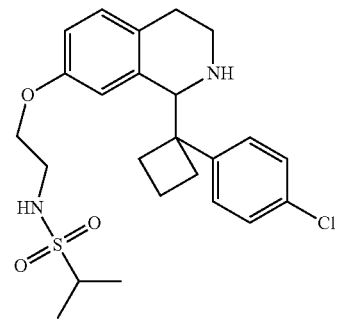 [SMILES: CC(C)S(=O)(=O)NCCOc1ccc2c(c1)C(C1(c3ccc(Cl)cc3)CCC1)NCC2]

The synthesis was performed according to example 2 without further purification of the intermediate propane-2-sulfonic acid (2-{1-[1-(4-chloro-phenyl)-cyclobutyl]-3,4-dihydro-isoquinolin-7-yloxy}-ethyl)-amide. The final product was isolated as a white solid (14.0 mg, 0.03 mmol, 7%).

ESI-MS [M+H]$^+$=463.2 Calculated for C$_{24}$H$_{31}$ClN$_2$O$_3$S=462

Example 39

7-[2-(Butane-1-sulfonylamino)-ethoxy]-1-[1-(4-chloro-phenyl)-cyclobutyl]-3,4-dihydro-1H-isoquinoline-2-carboxylic acid ethylamide hydrochloride

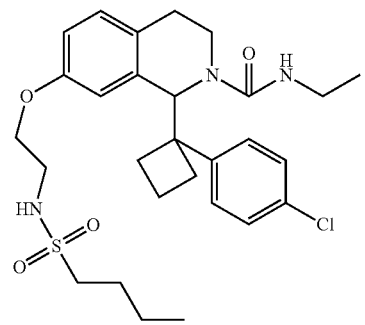 [SMILES: CCCCS(=O)(=O)NCCOc1ccc2c(c1)C(C1(c3ccc(Cl)cc3)CCC1)N(C(=O)NCC)CC2]

The synthesis was performed according to example 33 (procedure 1), starting from butane-1-sulfonic acid (2-{1-[1-(4-chloro-phenyl)-cyclobutyl]-1,2,3,4-tetrahydro-isoquinolin-7-yloxy}-ethyl)-amide hydrochloride (example 16) and ethyl isocyanate instead of 1-propyl isocyanate. The product was obtained as a white solid (16.0 mg, 0.03 mmol, 23%).

ESI-MS [M+H]$^+$=548.2 Calculated for $C_{28}H_{38}ClN_3O_4S$=547

Example 40

Butane-1-sulfonic acid (2-{1-[1-(4-chloro-phenyl)-cyclobutyl]-2-methyl-1,2,3,4-tetrahydro-isoquinolin-7-yloxy}-ethyl)-amide

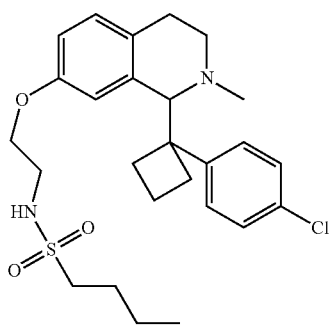 [SMILES: CCCCS(=O)(=O)NCCOc1ccc2c(c1)C(C1(c3ccc(Cl)cc3)CCC1)N(C)CC2]

Butane-1-sulfonic acid (2-{1-[1-(4-chloro-phenyl)-cyclobutyl]-1,2,3,4-tetrahydro-isoquinolin-7-yloxy}-ethyl)-amide hydrochloride (example 16, 50.0 mg, 0.10 mmol) is dissolved in acetone (3 ml) and potassium carbonate (29.0 mg, 0.21 mmol) and methyl iodide (16.4 mg, 0.12 mmol) were added. The mixture was stirred at RT for 14 h. The solvent was reduced, the reaction mixture was diluted with 1 N sodium hydroxid solution and extracted with dichloromethane. The combined organic layers were washed with saturated sodium chloride solution and dried with potassium sulphate. The residue was purified by HPLC with . . . to give the product (50.0 mg, 0.10 mmol, 13%).

ESI-MS [M+H]$^+$=491 Calculated for $C_{26}H_{35}ClN_2O_3S$=490

Example 41

1-[1-(4-Chloro-phenyl)-cyclobutyl]-7-(4-ethanesulfonyl-piperazin-1-yl)-1,2,3,4-tetrahydro-isoquinoline

41.1 1-(4-Chloro-phenyl)-cyclobutanecarboxylic acid [2-(4-amino-phenyl)-ethyl]-amide

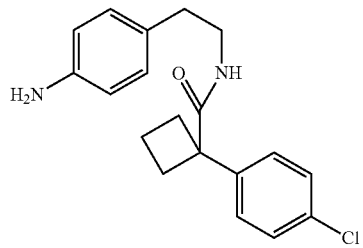 [SMILES: Nc1ccc(CCNC(=O)C2(c3ccc(Cl)cc3)CCC2)cc1]

The synthesis was performed in analogy to example 82, procedure a, starting from 4-(2-amino-ethyl)-phenylamine to give the final product as a white solid in 86% yield.

41.2 [4-(2-{[1-(4-Chloro-phenyl)-cyclobutanecarbonyl]-amino}-ethyl)-phenyl]-carbamic acid ethyl ester

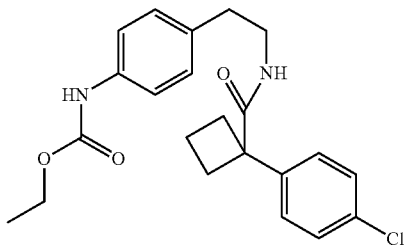 [SMILES: CCOC(=O)Nc1ccc(CCNC(=O)C2(c3ccc(Cl)cc3)CCC2)cc1]

The synthesis followed a procedure described in heterocycles 31(2), 1990, 341-345, using 1-(4-chloro-phenyl)-cyclobutanecarboxylic acid [2-(4-amino-phenyl)-ethyl]-amide as the starting material to give the final product as a white solid (8.60 g, 21.5 mmol, 86%).

41.3 {1-[1-(4-Chloro-phenyl)-cyclobutyl]-3,4-dihydro-isoquinolin-7-yl}-carbamic acid ethyl ester

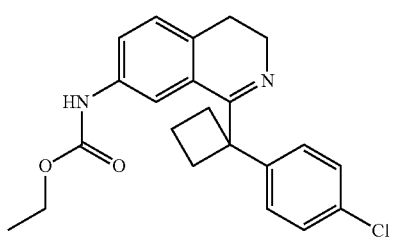 [SMILES: CCOC(=O)Nc1ccc2c(c1)C(C1(c3ccc(Cl)cc3)CCC1)=NCC2]

The synthesis was performed in analogy to example 82, procedure b, starting from [4-(2-{[1-(4-chloro-phenyl)-cyclobutanecarbonyl]-amino}-ethyl)-phenyl]-carbamic acid ethyl ester to give the final product in 21% yield.

ESI-MS [M+H]$^+$=383.1 Calculated for C$_{22}$H$_{23}$ClN$_2$O$_2$=382

41.4 1-[1-(4-Chloro-phenyl)-cyclobutyl]-3,4-dihydro-isoquinolin-7-ylamine

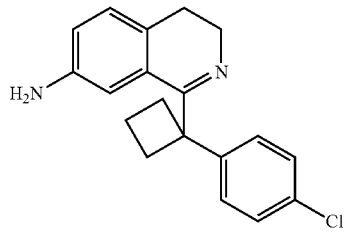 [SMILES: Nc1ccc2c(c1)C(C1(c3ccc(Cl)cc3)CCC1)=NCC2]

{1-[1-(4-Chloro-phenyl)-cyclobutyl]-3,4-dihydro-isoquinolin-7-yl}-carbamic acid ethyl ester (400 mg, 1.04 mmol) in a solution of potassium hydroxid in ethanol (20 ml, 10%) are stirred for 5 h under reflux. The solvent was reduced, the reaction mixture was diluted with water and extracted with ethyl acetate. The combined organic layers were washed with saturated sodium chloride solution and dried with sodium sulphate to give the final product (0.32 mg, 1.04 mmol, 99%) as an orange solid that was used without further purification.

41.5 1-[1-(4-Chloro-phenyl)-cyclobutyl]-3,4-dihydro-isoquinolin-7-ylamine

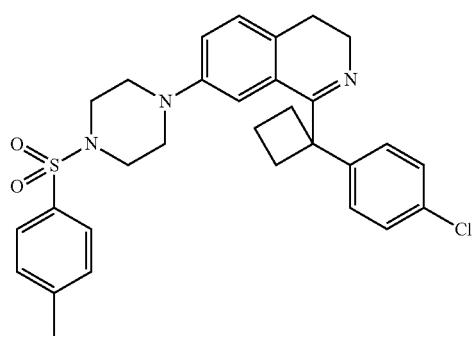 [SMILES: Cc1ccc(S(=O)(=O)N2CCN(c3ccc4c(c3)C(C3(c5ccc(Cl)cc5)CCC3)=NCC4)CC2)cc1]

1-[1-(4-Chloro-phenyl)-cyclobutyl]-3,4-dihydro-isoquinolin-7-ylamine (480 mg, 1.54 mmol), N,N-bis-(2-chloro-ethyl)-4-methyl-benzenesulfonamide (510 mg, 1.72 mmol), cesium carbonate (503 mg, 1.54 mmol) in water (5 ml) and acetonitrile (2 ml) was stirred in a microwave oven at 130° C. for 3 h. The solvent was reduced, the reaction mixture was diluted with 1 N sodium hydroxid solution and extracted with ethyl acetate. The combined organic layers were washed with saturated sodium chloride solution and dried with sodium sulphate. The residue was purified by flash column chromatography on silica with cyclohexane/ethyl acetate 7:3→1:1. The product was obtained as a brown oil (400 mg, 0.75 mmol, 48%) that was sufficiently pure for the next step.

41.6 1-[1-(4-Chloro-phenyl)-cyclobutyl]-7-piperazin-1-yl-3,4-dihydro-isoquinoline

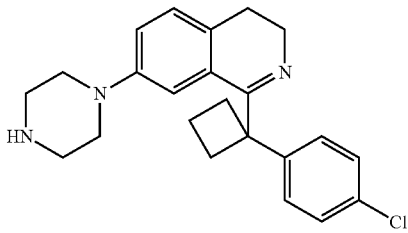 [SMILES: Clc1ccc(C2(C3=NCCc4ccc(N5CCNCC5)cc43)CCC2)cc1]

1-[1-(4-Chloro-phenyl)-cyclobutyl]-3,4-dihydro-isoquinolin-7-ylamine (400 mg, 0.75 mmol) was dissolved in HBr/acetic acid (10 ml, 33%) and stirred for 3 h at 70° C. Another 10 ml of the HBr/acetic acid solution was added and the mixture was stirred for another 8 h at 70° C. The solvent was diluted with 1 N sodium hydroxid solution and extracted with dichloromethane. The combined organic layers were washed with saturated sodium chloride solution and dried with sodium sulphate. The residue was purified by flash column chromatography on silica with dichloromethane/methanol 98:2→95:5. The product was obtained as a brown oil (100 mg, 0.26 mmol, 35%) that was sufficiently pure for the next step.

41.7 1-[1-(4-Chloro-phenyl)-cyclobutyl]-7-(4-ethanesulfonyl-piperazin-1-yl)-1,2,3,4-tetrahydro-isoquinoline hydrochloride

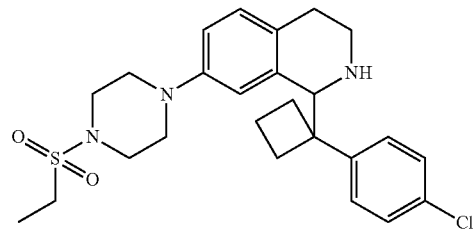 [SMILES: CCS(=O)(=O)N1CCN(c2ccc3c(c2)C(C2(c4ccc(Cl)cc4)CCC2)NCC3)CC1]

The synthesis was performed according to example 2 without further purification of the intermediate 1-[1-(4-chloro-phenyl)-cyclobutyl]-7-(4-ethanesulfonylpiperazin-1-yl)-3,4-dihydro-isoquinoline. The final product was isolated as a brown solid (30.0 mg, 0.06 mmol, 37%)

ESI-MS [M+H]$^+$=474.1 Calculated for C$_{25}$H$_{32}$ClN$_3$O$_2$S=473

Example 42

1-(2-{1-[1-(4-Chloro-phenyl)-cyclobutyl]-1,2,3,4-tetrahydro-isoquinolin-7-yloxy}-ethyl)-3-pyridin-3-yl-urea hydrochloride

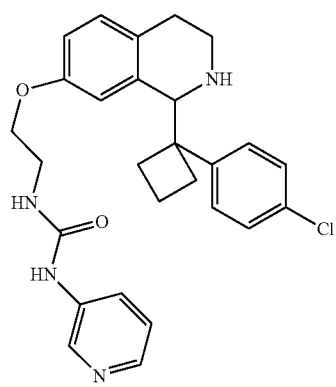 [SMILES: O=C(NCCOc1ccc2c(c1)C(C1(c3ccc(Cl)cc3)CCC1)NCC2)Nc1cccnc1]

The synthesis was performed according to example 33 without further purification of the intermediate 1-(2-{1-[1-(4-Chloro-phenyl)-cyclobutyl]-3,4-dihydro-isoquinolin-7-yloxy}-ethyl)-3-pyridin-3-yl-urea. The final product was isolated as a white solid (25.0 mg, 0.05 mmol, 25%).
ESI-MS [M+H]$^+$=477.2 Calculated for $C_{27}H_{29}ClN_4O_2$=476

Example 43

1-Methyl-1H-pyrazole-4-sulfonic acid (2-{1-[1-(4-chloro-phenyl)-3,3-difluoro-cyclobutyl]-1,2,3,4-tetrahydro-isoquinolin-7-yloxy}-ethyl)-amidehydrochloride 43.1 1-(4-Chloro-phenyl)-3-methoxy-cyclobut-2-enecarbonitrile

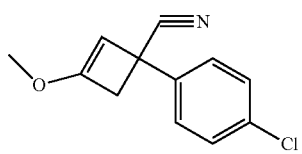

Sodium hydride in paraffin (6.00 g, 24.0 mmol, 55%) was washed with n-hexane, dried, and suspended in N,N-dimethyl-acetamide (50 ml). (4-Chloro-phenyl)-acetonitrile (10.0 g, 66.0 mmol) in N,N-dimethyl-acetamide (50 ml) was added dropwise under exothermic conditions and bubbling. After stirring for 30 min the solution became dark brown and then 1,3-dibromo-2,2-dimethoxy-propane was added in portions and the mixture was stirred over night at RT and then for another 30 min at 65° C. The black reaction mixture was diluted with HCl (16%) and extracted with ethyl acetate. The combined organic layers were washed with water and subsequently with saturated sodium chloride solution and dried with sodium sulphate. The residue was purified by flash column chromatography on silica with cyclohexane/ethyl acetate 95:5. The product was obtained as a brown oil (8.80 g, 40.1 mmol, 61%) that was directly used for the next step.
ESI-MS [M+H]$^+$=220.1 Calculated for $C_{12}H_{10}ClNO$=219

43.2
1-(4-Chloro-phenyl)-3-oxo-cyclobutanecarbonitrile

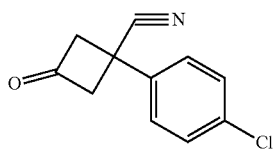 [SMILES: N#CC1(c2ccc(Cl)cc2)CC(=O)C1]

1-(4-Chloro-phenyl)-3-methoxy-cyclobut-2-enecarbonitrile (8.80 g, 40.1 mmol), 4-toluene sulfonic acid (2.30 g, 12.1 mmol), and 2 N HCl were dissolved in acetone/water 100:10 (110 ml) and stirred for 10 h under reflux. The reaction mixture was alkalized with aqueous NaOH and extracted with ethyl acetate. The combined organic layers were washed with water and subsequently with saturated sodium chloride solution and dried with sodium sulphate. The product was obtained as an orange oil (7.40 g, 36.0 mmol) that was sufficiently pure for the next step.
ESI-MS [M+H]$^+$=206.1 Calculated for $C_{11}H_8ClNO$=205

43.3
1-(4-Chloro-phenyl)-3-oxo-cyclobutanecarbonitrile

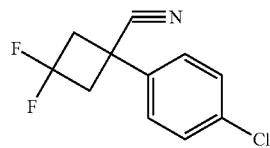 [SMILES: N#CC1(c2ccc(Cl)cc2)CC(F)(F)C1]

1-(4-Chloro-phenyl)-3-oxo-cyclobutanecarbonitrile (7.00 g, 34.0 mmol) is dissolved at 0° C. in dichloromethane (200 ml) and diethylaminosulfur trifluoride (11.0 g, 68.12 mmol) at 0° C. The mixture was allowed to warm up to RT and the stirred for another 14 h. Water was added and the mixture was alkalized with aqueous NaOH and extracted with ethyl acetate. The combined organic layers were washed with water and subsequently with saturated sodium chloride solution and dried with sodium sulphate. The residue was purified by flash column chromatography on silica with cyclohexane/ethyl acetate 8:2→6:4. The product was obtained as an orange oil (4.30 g, 18.9 mmol, 55%) that was directly used for the next step.

43.4 1-(4-Chloro-phenyl)-3,3-difluoro-cyclobutanecarboxylic acid

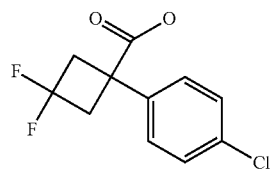 [SMILES: O=C(O)C1(c2ccc(Cl)cc2)CC(F)(F)C1]

1-(4-Chloro-phenyl)-3-oxo-cyclobutanecarbonitrile (4.30 g, 18.9 mmol) is dissolved in aqueous HCl (10 M, 80.0 ml) and stirred for 6 h under reflux. The mixture was extracted with dichloromethane. The combined organic layers were extracted with 2N NaOH. The alkaline layer was acidified with HCl and extracted with dichloromethane. The combined organic layers were dried with sodium sulphate, filtered, and the solvent was removed to obtain a yellow solid (2.70 g, 11.0 mmol, 58%).

43.5 1-(4-Chloro-phenyl)-3,3-difluoro-cyclobutanecarboxylic acid [2-(4-methoxy-phenyl)-ethyl]-amide

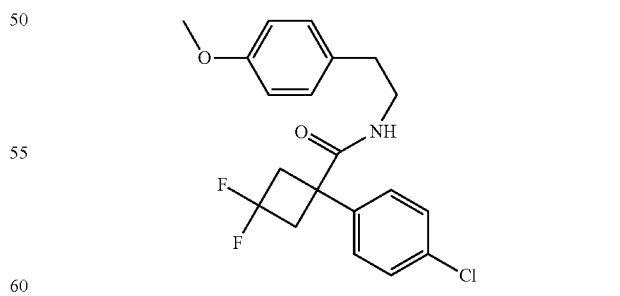

The synthesis was performed in analogy to example 82, procedure a, starting from 1-(4-chloro-phenyl)-3,3-difluoro-cyclobutanecarboxylic acid to give the final product as a white solid in 82% yield.
ESI-MS [M+H]$^+$=380.1 Calculated for $C_{20}H_{20}ClF_2NO_2$=379

43.6 1-[1-(4-Chloro-phenyl)-3,3-difluoro-cyclobutyl]-7-methoxy-3,4-dihydro-isoquinoline

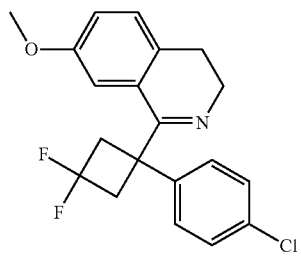 [SMILES: COc1ccc2c(c1)C(C1(c3ccc(Cl)cc3)CC(F)(F)C1)=NCC2]

The synthesis was performed in analogy to example 82, procedure b, starting from 1-(4-chloro-phenyl)-3,3-difluoro-cyclobutanecarboxylic acid [2-(4-meth oxy-phenyl)-ethyl]-amide to give the final product as a colourless oil in 26% yield.

43.7 1-[1-(4-Chloro-phenyl)-3,3-difluoro-cyclobutyl]-3,4-dihydro-isoquinolin-7-ol

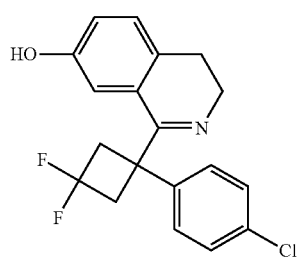 [SMILES: Oc1ccc2c(c1)C(C1(c3ccc(Cl)cc3)CC(F)(F)C1)=NCC2]

The synthesis was performed in analogy to example 82, procedure c, starting from 1-[1-(4-chloro-phenyl)-3,3-difluoro-cyclobutyl]-7-methoxy-3,4-dihydro-isoquinoline to give the final product as a white solid in 89% yield.
ESI-MS [M+H]$^+$=348.1 Calculated for $C_{19}H_{16}ClF_2NO$=347

43.8 (2-{1-[1-(4-Chloro-phenyl)-3,3-difluoro-cyclobutyl]-3,4-dihydro-isoquinolin-7-yloxy}-ethyl)-carbamic acid tert-butyl ester

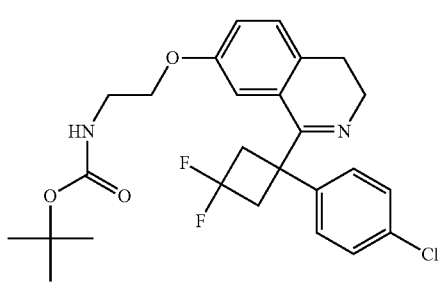 [SMILES: CC(C)(C)OC(=O)NCCOc1ccc2c(c1)C(C1(c3ccc(Cl)cc3)CC(F)(F)C1)=NCC2]

The synthesis was performed in analogy to example 1, procedure 1, starting from 1-[1-(4-chloro-phenyl)-3,3-difluoro-cyclobutyl]-3,4-dihydro-isoquinolin-7-ol to give the final product in 37% yield.
ESI-MS [M+H]$^+$=348.0 Calculated for $C_{26}H_{29}ClF_2N_2O_3$=347

43.9 2-{1-[1-(4-Chloro-phenyl)-3,3-difluoro-cyclobutyl]-3,4-dihydro-isoquinolin-7-yloxy}-ethylamine

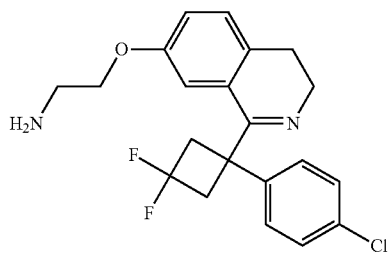 [SMILES: NCCOc1ccc2c(c1)C(C1(c3ccc(Cl)cc3)CC(F)(F)C1)=NCC2]

The synthesis was performed in analogy to example 1, procedure 2, starting from (2-{1-[1-(4-chloro-phenyl)-3,3-difluoro-cyclobutyl]-3,4-dihydro-isoquinolin-7-yloxy}-ethyl)-carbamic acid tert-butyl ester to give the final product in 75% yield.
ESI-MS [M+H]$^+$=391.1 Calculated for $C_{21}H_{21}ClF_2N_2O$=390

43.10 1-Methyl-1H-pyrazole-4-sulfonic acid (2-{1-[1-(4-chloro-phenyl)-3,3-difluoro-cyclobutyl]-1,2,3,4-tetrahydro-isoquinolin-7-yloxy}-ethyl)-amide

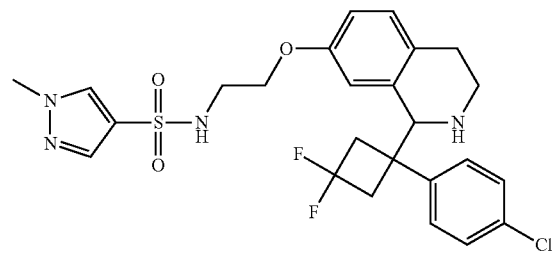 [SMILES: Cn1cc(S(=O)(=O)NCCOc2ccc3c(c2)C(C2(c4ccc(Cl)cc4)CC(F)(F)C2)NCC3)cn1]

The synthesis was performed according to example 2 starting from 2-{1-[1-(4-chloro-phenyl)-3,3-difluoro-cyclobutyl]-3,4-dihydro-isoquinolin-7-yloxy}-ethylamine without further purification of the intermediate 1-methyl-1H-pyrazole-4-sulfonic acid (2-{1-[1-(4-chloro-phenyl)-3,3-difluoro-cyclobutyl]-3,4-dihydro-isoquinolin-7-yloxy}-ethyl)-amide. The final product was isolated as a white solid (130 mg, 0.333 mmol, 61%).
ESI-MS [M+H]$^+$=537.1 Calculated for $C_{25}H_{27}ClF_2N_4O_3S$=536

Example 44

Propane-1-sulfonic acid (2-{1-[1-(4-chloro-phenyl)-3,3-difluoro-cyclobutyl]-1,2,3,4-tetrahydro-isoquinolin-7-yloxy}-ethyl)-amide hydrochloride

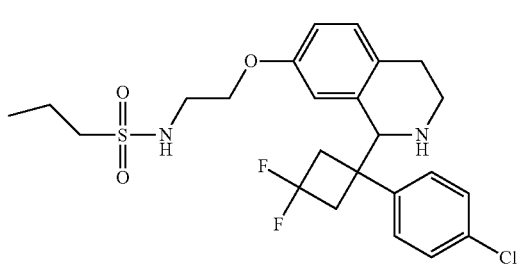 [SMILES: CCCS(=O)(=O)NCCOc1ccc2c(c1)C(C1(c3ccc(Cl)cc3)CC(F)(F)C1)NCC2]

The synthesis was performed according to example 2 starting from 1-methyl-1H-pyrazole-4-sulfonic acid (2-{1-[1-(4-chloro-phenyl)-3,3-difluoro-cyclobutyl]-1,2,3,4-tetrahydro-isoquinolin-7-yloxy}-ethyl)-amide without further purification of the intermediate propane-1-sulfonic acid (2-{1-[1-(4-chloro-phenyl)-3,3-difluoro-cyclobutyl]-3,4-dihydro-isoquinolin-7-yloxy}-ethyl)-amide. The final product was isolated as a white solid (55.0 mg, 0.103 mmol, 67%).

ESI-MS [M+H]$^+$=499.1 Calculated for $C_{24}H_{29}ClF_2N_2O_3S$=498

Example 45

Propane-1-sulfonic acid (2-{1-[1-(4-chloro-phenyl)-cyclobutyl]-1,2,3,4-tetrahydro-isoquinolin-7-yloxy}-ethyl)-[2-(propane-1-sulfonylamino)-ethyl]-amide

45.1 Propane-1-sulfonic acid (2-{1-[1-(4-chloro-phenyl)-cyclobutyl]-3,4-dihydro-isoquinolin-7-yloxy}-ethyl)-[2-(propane-1-sulfonylamino)-ethyl]-amide

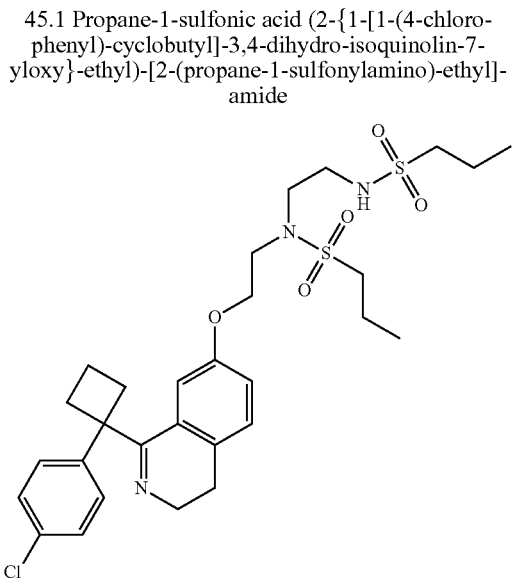

The synthesis was performed in analogy to example 2 (procedure 3) starting from propane-1-sulfonic acid (2-{1-[1-(4-chloro-phenyl)-cyclobutyl]-3,4-dihydro-isoquinolin-7-yloxy}-ethyl)-amide (example 4) and using propanesulfonyl chloride instead of methanesulfonyl chloride to give the final product in 51% yield.

ESI-MS [M+H]$^+$=610 Calculated for $C_{29}H_{40}ClN_3O_5S_2$=609

45.2 Propane-1-sulfonic acid (2-{1-[1-(4-chloro-phenyl)-cyclobutyl]-1,2,3,4-tetrahydro-isoquinolin-7-yloxy}-ethyl)-[2-(propane-1-sulfonylamino)-ethyl]-amide

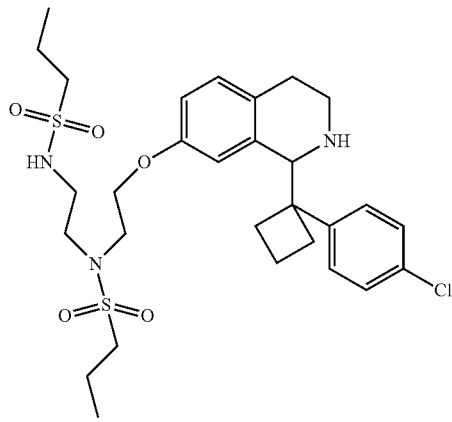 [SMILES: CCCS(=O)(=O)NCCN(CCOc1ccc2c(c1)C(C1(c3ccc(Cl)cc3)CCC1)NCC2)S(=O)(=O)CCC]

The synthesis was performed in analogy to example 1, procedure 4, to give the final product in 56% yield.

ESI-MS [M+H]$^+$=612.2 Calculated for $C_{29}H_{42}ClN_3O_5S_2$=611

Example 46

1-(1-(4-Chlorophenyl)cyclobutyl)-N-cyano-7-(2-(propylsulfonamido)ethoxy)-3,4-dihydroisoquinoline-2(1H)-carboximidamide

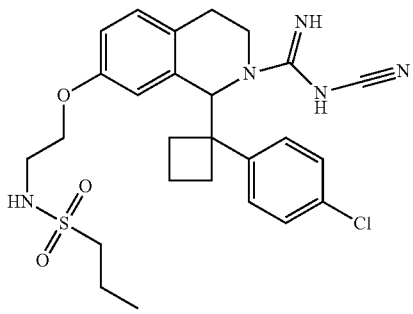 [SMILES: CCCS(=O)(=O)NCCOc1ccc2c(c1)C(C1(c3ccc(Cl)cc3)CCC1)N(C(=N)NC#N)CC2]

Propane-1-sulfonic acid (2-{1-[1-(4-chloro-phenyl)-cyclobutyl]-1,2,3,4-tetrahydro-isoquinolin-7-yloxy}-ethyl)-amide hydrochloride (example 4, 95.0 mg, 0.19 mmol) was dissolved in 1-butanol (10 ml) and sodium dicyanamide (42.3 mg, 0.48 mmol) was added. The reaction mixture was stirred under reflux. After 4 h, the solvent was removed and dichloromethane was added. The resulting precipitate was removed by filtration and purified by flash column chromatography on silica with dichloromethane/methanol 10:0→94:6. The product was obtained as a solid (30.0 mg, 0.06 mmol, 30.0%).

ESI-MS [M+H]$^+$=530 Calculated for $C_{26}H_{32}ClN_5O_3S$=529

Example 47

1-[1-(4-Chloro-phenyl)-cyclobutyl]-7-[2-(propane-1-sulfonylamino)-ethoxy]-3,4-dihydro-1H-isoquinoline-2-carboxamidine

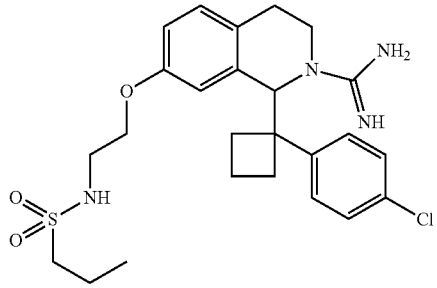 [SMILES: CCCS(=O)(=O)NCCOc1ccc2c(c1)C(C1(c3ccc(Cl)cc3)CCC1)N(C(=N)N)CC2]

Propane-1-sulfonic acid (2-{1-[1-(4-chloro-phenyl)-cyclobutyl]-1,2,3,4-tetrahydro-isoquinolin-7-yloxy}-ethyl)-amide hydrochloride (example 4, 100 mg, 0.216 mmol) and 2-methylisothiouronium sulphate (180 mg, 648 mmol) were dissolved in water/2-propanole 5:1 (2.4 ml) and stirred in microwave oven at 150° C. and 10 bar for 45 min. Another 90 mg (324 mmol) were added and the mixture was stirred for 20 min. Another 90 mg (324 mmol) were added and the mixture was stirred for 30 min. The solvent was reduced and the mixture was extracted with dichloromethane. The combined organic layers were dried with sodium sulphate, filtered, and the solvent was removed. The residue was purified by HPLC (RP-18, water/MeOH) to obtain the product as a solid (98.0 mg, 0.194 mmol, 90.0%).

ESI-MS [M+H]$^+$=506.2 Calculated for $C_{25}H_{33}ClN_4O_3S$=504

Example 48

2-{1-[1-(4-Chloro-phenyl)-cyclobutyl]-1,2,3,4-tetrahydro-isoquinolin-7-yloxy}-1-piperazin-1-yl-ethanone

48.1 4-(2-{1-[1-(4-Chloro-phenyl)-cyclobutyl]-3,4-dihydro-isoquinolin-7-yloxy}-acetyl)-piperazine-1-carboxylic acid tert-butyl ester

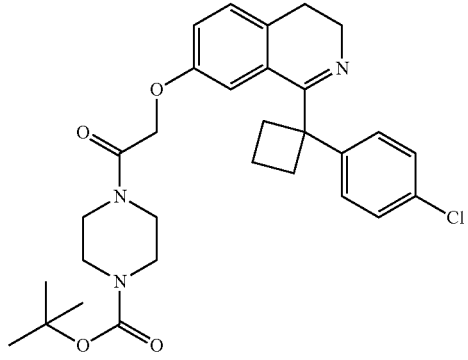 [SMILES: CC(C)(C)OC(=O)N1CCN(C(=O)COc2ccc3c(c2)C(C2(c4ccc(Cl)cc4)CCC2)=NCC3)CC1]

1-[1-(4-chlorophenyl)cyclobutyl]-3,4-dihydroisoquinolin-7-ol (example 82) (400 mg, 1.18 mmol) and 4-(2-chloro-acetyl)-piperazine-1-carboxylic acid tert-butyl ester (404 mg, 1.54 mmol) were dissolved in N,N-dimethyl-formamide (10 ml). After addition of potassium carbonate (355 mg, 2.57 mmol) the mixture was stirred for 2 h under reflux. The solvent was removed and the residue (690 mg) was used in the next step without further purification.

48.2 2-{1-[1-(4-Chloro-phenyl)-cyclobutyl]-3,4-dihydro-isoquinolin-7-yloxy}-1-piperazin-1-yl-ethanone

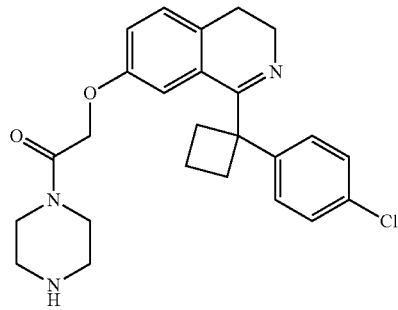 [SMILES: O=C(COc1ccc2c(c1)C(C1(c3ccc(Cl)cc3)CCC1)=NCC2)N1CCNCC1]

4-(2-{1-[1-(4-Chloro-phenyl)-cyclobutyl]-3,4-dihydro-isoquinolin-7-yloxy}-acetyl)-piperazine-1-carboxylic acid tert-butyl ester (690 mg, 1.28 mmol) was dissolved in dichloro-methane. A 5 M solution of HCl in 2-propanol (5 mol) was added and the mixture was stirred for 14 h at RT. The solvent was removed and the residue (230 mg) was used in the next step without further purification.

48.3 2-{1-[1-(4-Chloro-phenyl)-cyclobutyl]-1,2,3,4-tetrahydro-isoquinolin-7-yloxy}-1-piperazin-1-yl-ethanone

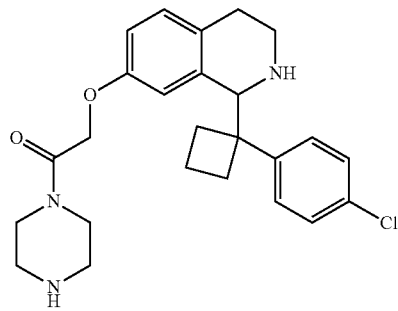 [SMILES: O=C(COc1ccc2c(c1)C(C1(c3ccc(Cl)cc3)CCC1)NCC2)N1CCNCC1]

The reaction was performed according to example 1 (procedure 4) starting from 2-{1-[1-(4-chloro-phenyl)-cyclobutyl]-3,4-dihydro-isoquinolin-7-yloxy}-1-piperazin-1-yl-ethanone and the product was obtained as a white solid (17.0 mg, 16%).

ESI-MS [M+H]$^+$=440.2 Calculated for $C_{25}H_{30}ClN_3O_2$=439

Example 49

Propane-1-sulfonic acid (2-{1-[1-(3-chloro-phenyl)-cyclobutyl]-1,2,3,4-tetrahydro-isoquinolin-7-yloxy}-ethyl)-amide

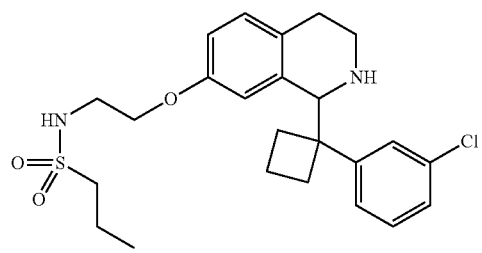 [SMILES: CCCS(=O)(=O)NCCOc1ccc2c(c1)C(C1(c3cccc(Cl)c3)CCC1)NCC2]

The synthesis was performed in analogy to example 4 and the product was obtained as a white solid.

ESI-MS [M+H]$^+$=463 Calculated for $C_{24}H_{31}ClN_2O_3$=462

Example 50

1-(1-Phenylcyclobutyl)-7-(2-(propylsulfonamido)ethoxy)-1,2,3,4-tetrahydroisoquinolinium chloride

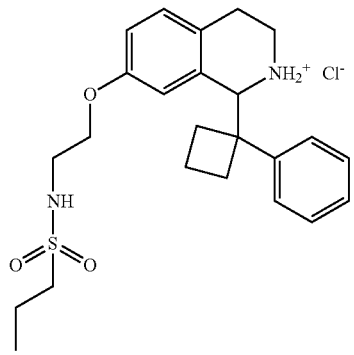 [SMILES: CCCS(=O)(=O)NCCOc1ccc2c(c1)C(C1(c3ccccc3)CCC1)[NH2+]CC2 ; [Cl-]]

1-(1-(4-Chlorophenyl)cyclobutyl)-7-(2-(propylsulfonamido)ethoxy)-1,2,3,4-tetrahydroisoquinolinium chloride (187 mg, 0.374 mmol, example 4), triethylamine (91 mg, 0.897 mmol), Pd/C (11.95 mg, 0.011 mmol) were suspended in dry MeOH (5 ml) and treated with hydrogen gas at ambient pressure for 14 h. The solvent was removed and the residue was purified by column chromatography using silica gel dichloromethane/methanol (97:3→95:5) as the eluent. The product was transferred into the hydrochloride with isopropylether and HCl dissolved in isopropanol (6%). The product was obtained as a white powder (68.0 mg, 0.146 mmol, 39%.)

ESI-MS [M+H]$^+$=429.2 Calculated for $C_{24}H_{32}N_2O_3S$=428

Example 51

1-(1-(4-Chlorophenyl)cyclobutyl)-7-(2-(1-methyl-1H-imidazole-4-sulfonamido)ethoxy)-1,2,3,4-tetrahydroisoquinolinium chloride

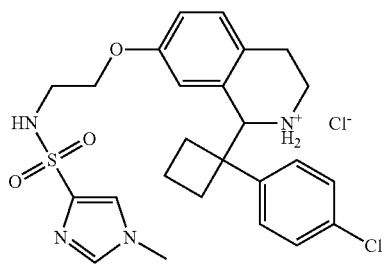

The synthesis was performed according to example 2 without further purification of the intermediate 2-{1-[1-(4-chloro-phenyl)-cyclobutyl]-3,4-dihydro-isoquinolin-7-yloxy}-ethylamine. The final product was isolated as a colourless oil (106 mg, 0.197 mmol).

ESI-MS [M+H]$^+$=501.2 Calculated for $C_{25}H_{30}ClN_4O_3S$=501

Example 52

1-(1-(4-Chlorophenyl)cyclobutyl)-7-(2-(1,2-dimethyl-1H-imidazole-4-sulfonamido)ethoxy)-1,2,3,4-tetrahydroisoquinolinium chloride

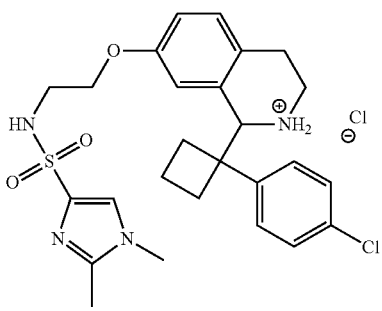 [SMILES: Cc1nc(S(=O)(=O)NCCOc2ccc3c(c2)C(C2(c4ccc(Cl)cc4)CCC2)[NH2+]CC3)cn1C ; [Cl-]]

The synthesis was performed according to example 2 without further purification of the intermediate 1,2-dimethyl-1H-imidazole-4-sulfonic acid (2-{1-[1-(4-chloro-phenyl)-cyclobutyl]-3,4-dihydro-isoquinolin-7-yloxy}-ethyl)-amide. The final product was isolated as a white solid (35.0 mg, 0.063 mmol, 32%).

ESI-MS [M+H]$^+$=515.2 Calculated for $C_{26}H_{31}ClN_4O_3S$=514

Example 54

Ethyl 4-(N-(2-(1-(1-(4-chlorophenyl)cyclobutyl)-1,2,3,4-tetrahydroisoquinolin-7-yloxy)ethyl)sulfamoyl)piperazine-1-carboxylate hydrochloride 54.1 4-(2-{1-[1-(4-Chloro-phenyl)-cyclobutyl]-3,4-dihydro-isoquinolin-7-yloxy}-ethylsulfamoyl)-piperazine-1-carboxylic acid ethyl ester

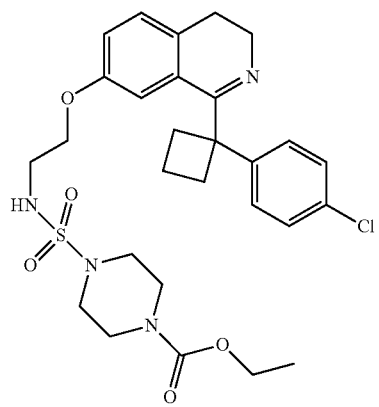 [SMILES: CCOC(=O)N1CCN(S(=O)(=O)NCCOc2ccc3c(c2)C(C2(c4ccc(Cl)cc4)CCC2)=NCC3)CC1]

The synthesis was performed according to example 2 (procedure 1). The final product was isolated as a white solid (729 mg, 0.887 mmol, 70%).

ESI-MS [M+H]⁺=575.2 Calculated for $C_{28}H_{35}ClN_4O_5S$=574

54.2 Ethyl 4-(N-(2-(1-(1-(4-chlorophenyl)cyclobutyl)-1,2,3,4-tetrahydroisoquinolin-7-yloxy)ethyl)sulfamoyl)piperazine-1-carboxylate hydrochloride

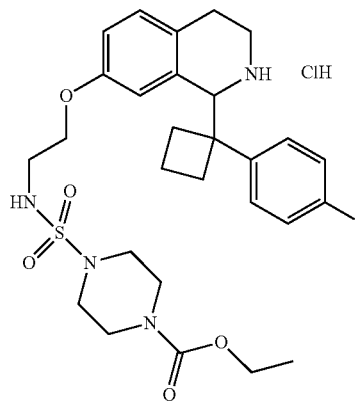

The synthesis was performed according to example 2 (procedure 2). The final product was isolated as a white solid (20.0 mg, 0.033 mmol, 38%).
ESI-MS [M+H]⁺=577.2 Calculated for $C_{28}H_{37}ClN_4O_5S$=576

Example 55

N-(2-(1-(1-(4-Chlorophenyl)cyclobutyl)-1,2,3,4-tetrahydroisoquinolin-7-yloxy)ethyl)piperazine-1-sulfonamide dihydrochloride 55.1 N-(2-(1-(1-(4-Chlorophenyl)cyclobutyl)-3,4-dihydroisoquinolin-7-yloxy)ethyl)piperazine-1-sulfonamide

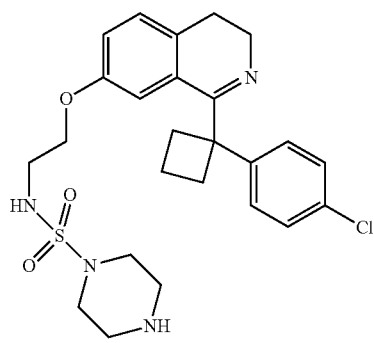 [SMILES: O=S(=O)(NCCOc1ccc2c(c1)C(C1(c3ccc(Cl)cc3)CCC1)=NCC2)N1CCNCC1]

4-(2-{1-[1-(4-Chloro-phenyl)-cyclobutyl]-3,4-dihydro-isoquinolin-7-yloxy}-ethylsulfamoyl)-piperazine-1-carboxylic acid ethyl ester (450 mg, 0.782 mmol, example 54, procedure 1) and a 10% solution of potassium hydroxid in ethanol (20 ml) were heated under reflux for 15 h. The solvent was reduced and water was added to the residue. The mixture was extracted with dichloromethane. The combined organic layers were washed with sodium chloride, dried with potassium sulphate and evaporated. The residue was purified by column chromatography with silica gel using dichloromethane/methanol 3%→5% as the eluent to give the desired product as a yellow oil (394 mg, 0.782 mmol, 61%).
ESI-MS [M+H]⁺=503.2 Calculated for $C_{25}H_{31}ClN_4O_3S$=502

55.2 N-(2-(1-(1-(4-Chlorophenyl)cyclobutyl)-1,2,3,4-tetrahydroisoquinolin-7-yloxy)ethyl)piperazine-1-sulfonamide dihydrochloride

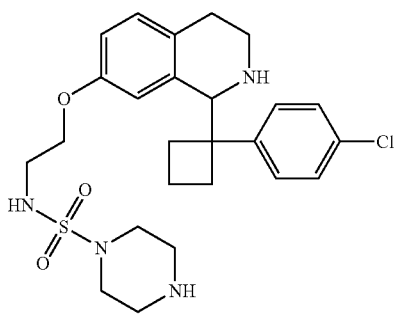 [SMILES: O=S(=O)(NCCOc1ccc2c(c1)C(C1(c3ccc(Cl)cc3)CCC1)NCC2)N1CCNCC1]

The synthesis was performed according to example 2 (procedure 2). The final product was isolated as a white solid (35.0 mg, 0.060 mmol, 73%).
ESI-MS [M+H]⁺=505.2 Calculated for $C_{25}H_{33}ClN_4O_3S$=504

Example 56

N-(2-(1-(1-(4-Chlorophenyl)cyclobutyl)-1,2,3,4-tetrahydroisoquinolin-7-yloxy)ethyl)-4-(propylsulfonyl)piperazine-1-sulfonamide hydrochloride

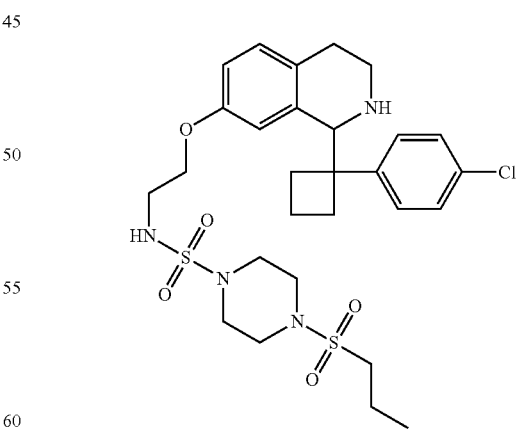

The synthesis was performed according to example 2 (procedure 2) starting from N-(2-(1-(1-(4-chlorophenyl)cyclobutyl)-3,4-dihydroisoquinolin-7-yloxy)ethyl)piperazine-1-sulfonamide (example 55, procedure 1). The final product was isolated as a white solid (35.0 mg, 0.054 mmol, 39%).

ESI-MS [M+H]$^+$=611.2 Calculated for C$_{28}$H$_{39}$ClN$_4$O$_5$S$_2$=610

Example 57

N-(2-(1-(1-(4-Chlorophenyl)cyclobutyl)-1,2,3,4-tetrahydroisoquinolin-7-yloxy)ethyl)-1H-imidazole-4-sulfonamide hydrochloride

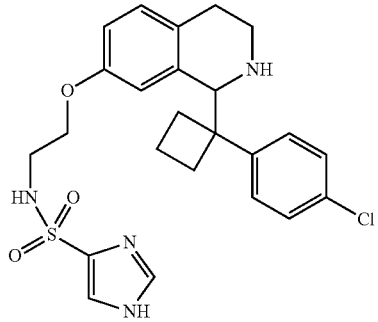 [SMILES: O=S(=O)(NCCOc1ccc2c(c1)C(C1(c3ccc(Cl)cc3)CCC1)NCC2)c1c[nH]cn1]

The synthesis was performed according to example 2 without further purification of the intermediate N-(2-(1-(1-(4-chlorophenyl)cyclobutyl)-3,4-dihydroisoquinolin-7-yloxy)ethyl)-1H-imidazole-4-sulfonamide. The final product was isolated as a white solid (221 mg, 0.423 mmol, 52%).

ESI-MS [M+H]$^+$=487.2 Calculated for C$_{24}$H$_{27}$ClN$_4$O$_3$S=486

Example 58

6-(Benzylamino)-N-(2-(1-(1-(4-chlorophenyl)cyclobutyl)-1,2,3,4-tetrahydroisoquinolin-7-yloxy)ethyl)pyridine-3-sulfonamide hydrochloride

58.1 6-Chloro-N-(2-(1-(1-(4-chlorophenyl)cyclobutyl)-3,4-dihydroisoquinolin-7-yloxy)ethyl)pyridine-3-sulfonamide

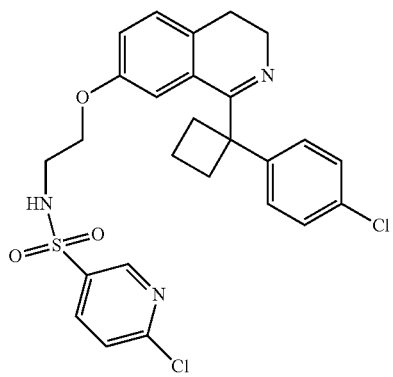 [SMILES: O=S(=O)(NCCOc1ccc2c(c1)C(C1(c3ccc(Cl)cc3)CCC1)=NCC2)c1ccc(Cl)nc1]

The synthesis was performed according to example 2 (procedure 1). The final product was isolated as a white solid (598 mg, 1.13 mmol, 92%).

ESI-MS [M+H]$^+$=530.1 Calculated for C$_{26}$H$_{25}$Cl$_2$N$_3$O$_3$S=529

58.2 6-(Benzylamino)-N-(2-(1-(1-(4-chlorophenyl)cyclobutyl)-3,4-dihydroisoquinolin-7-yloxy)ethyl)pyridine-3-sulfonamide

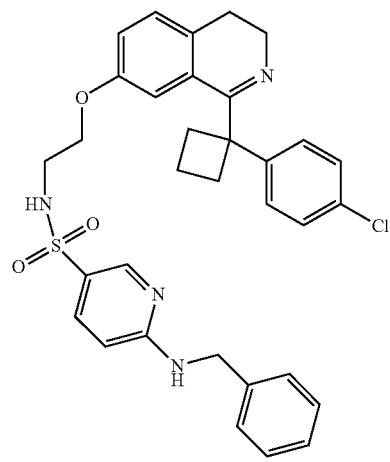 [SMILES: O=S(=O)(NCCOc1ccc2c(c1)C(C1(c3ccc(Cl)cc3)CCC1)=NCC2)c1ccc(NCc2ccccc2)nc1]

6-Chloro-N-(2-(1-(1-(4-chlorophenyl)cyclobutyl)-3,4-dihydroisoquinolin-7-yloxy)ethyl)pyridine-3-sulfonamide (70.0 mg, 0.132 mmol) and benzylamine (14.2 mg, 0.133 mmol) were dissolved in dry ethanol (3 ml) and stirred in a microwave oven at 150° C. for 1 h. The solvent was reduced under vacuo and the residue was purified by column chromatography using silica gel and heptan/ethyl acetate (3:7→7:3) as the eluent. The product was obtained as a white solid (79 mg, 0.132 mmol, 20%).

ESI-MS [M+H]$^+$=601.2 Calculated for C$_{33}$H$_{33}$ClN$_4$O$_3$S=600

58.3 6-(Benzylamino)-N-(2-(1-(1-(4-chlorophenyl)cyclobutyl)-1,2,3,4-tetrahydroisoquinolin-7-yloxy)ethyl)pyridine-3-sulfonamide hydrochloride

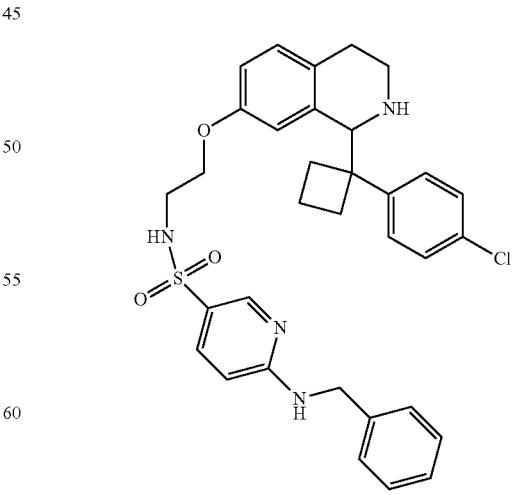

The synthesis was performed according to example 2 (procedure 2). The final product was isolated as a white solid (17.0 mg, 0.023 mmol, 88%).

ESI-MS [M+H]⁺=603.3 Calculated for $C_{33}H_{35}ClN_4O_3S$=602

Example 59

N-(2-(1-(1-(4-Chlorophenyl)cyclobutyl)-1,2,3,4-tetrahydroisoquinolin-7-yloxy)ethyl)-6-(propylamino)pyridine-3-sulfonamide hydrochloride

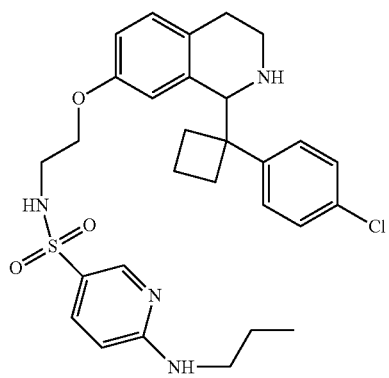 [SMILES: CCCNc1ccc(S(=O)(=O)NCCOc2ccc3c(c2)C(C2(c4ccc(Cl)cc4)CCC2)NCC3)cn1]

The synthesis was performed according to example 29 starting from 6-Chloro-pyridine-3-sulfonic acid (2-{1-[1-(4-chloro-phenyl)-cyclobutyl]-1,2,3,4-tetrahydro-isoquinolin-7-yloxy}-ethyl)-amide hydrochloride. The final product was isolated as a white solid (55 mg, 0.097 mmol, 64%).

ESI-MS [M+H]⁺=555.3 Calculated for $C_{29}H_{35}ClN_4O_3S$=554

Example 60

N-(2-(1-(1-(4-Chlorophenyl)cyclobutyl)-1,2,3,4-tetrahydroisoquinolin-7-yloxy)ethyl)piperidine-3-sulfonamide dihydrochloride

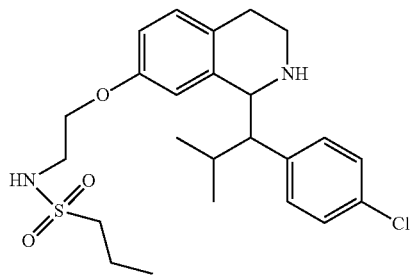 [SMILES: CCCS(=O)(=O)NCCOc1ccc2c(c1)C(C(c1ccc(Cl)cc1)C(C)C)NCC2]

The synthesis was performed according to example 12 to yield the final product as a yellow powder (53 mg, 0.106 mmol, 47%).

ESI-MS [M+H]⁺=465.2 Calculated for $C_{24}H_{33}ClN_2O_3S$=464

Example 61

N-(2-(1-(1-(4-Chlorophenyl)cyclobutyl)-1,2,3,4-tetrahydroisoquinolin-7-yloxy)ethyl)piperidine-3-sulfonamide dihydrochloride

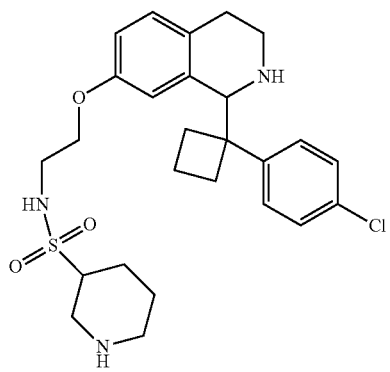 [SMILES: O=S(=O)(NCCOc1ccc2c(c1)C(C1(c3ccc(Cl)cc3)CCC1)NCC2)C1CCCNC1]

N-(2-(1-(1-(4-chlorophenyl)cyclobutyl)-1,2,3,4-tetrahydroisoquinolin-7-yloxy)ethyl)pyridine-3-sulfonamide (110 mg, 0.221 mmol, example 10) and a 6 molar solution of HCl in 2-propanol were dissolved in methanol (10 ml) and treated in an hydrogenation flow reactor (H-Cube®, Platinium (IV) oxide cartridge THS02119, ThalesNano) at 30 bar and 30° C. with a flow of 0.5 ml/min under circulating conditions for 14 h. The final product was purified by HPLC using . . . to yield the final product as a white powder (25.0 mg, 0.043 mmol, 20%).

ESI-MS [M+H]⁺=504.2 Calculated for $C_{26}H_{34}ClN_3O_3S$=503

Example 62

N-(2-{1-[1-(4-Chloro-phenyl)-cyclobutyl]-1,2,3,4-tetrahydro-isoquinolin-7-yloxy}-ethyl)-benzene-sulfonamide hydrochloride

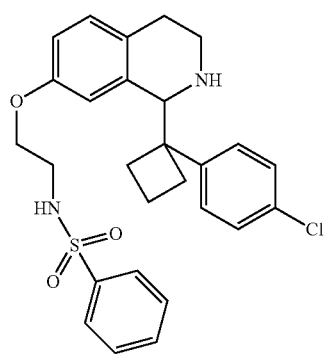 [SMILES: O=S(=O)(NCCOc1ccc2c(c1)C(C1(c3ccc(Cl)cc3)CCC1)NCC2)c1ccccc1]

The synthesis was performed according to example 2 to yield the final product as a white powder (108 mg, 0.20 mmol, 91%).

ESI-MS [M+H]⁺=497 Calculated for $C_{27}H_{29}ClN_2O_3S$=496

Example 63

N-[2-({1-[1-(4-Chlorophenyl)cyclobutyl]-1,2,3,4-tetrahydroisoquinolin-6-yl}oxy)ethyl]propane-2-sulfonamide hydrochloride

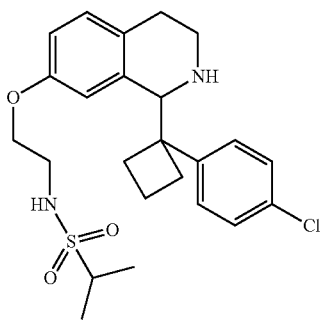 [SMILES: CC(C)S(=O)(=O)NCCOc1ccc2c(c1)C(C1(c3ccc(Cl)cc3)CCC1)NCC2]

N-[2-({1-[1-(4-Chlorophenyl)cyclobutyl]-1,2,3,4-tetrahydroisoquinolin-6-yl}oxy)ethyl]propane-2-sulfonamide hydrochloride was prepared analogously to example 68 using propane-2-sulfonyl chloride in place of propane-1-sulfonyl chloride.

ESI-MS [M+H⁺]=463 Calculated for $C_{24}H_{31}ClN_2O_3S$=462.

Example 64

N-[2-({1-[1-(4-Chlorophenyl)cyclobutyl]-1,2,3,4-tetrahydroisoquinolin-6-yl}oxy)ethyl]pyridine-3-sulfonamide dihydrochloride

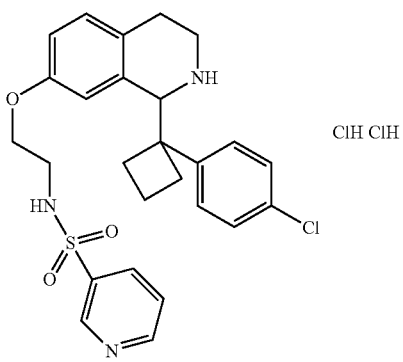 [SMILES: O=S(=O)(NCCOc1ccc2c(c1)C(C1(c3ccc(Cl)cc3)CCC1)NCC2)c1cccnc1 ; "ClH ClH"]

N-[2-({1-[1-(4-Chlorophenyl)cyclobutyl]-1,2,3,4-tetrahydroisoquinolin-6-yl}oxy)ethyl]pyridine-3-sulfonamide dihydrochloride was prepared analogously to example 68 using pyridine-2-sulfonyl chloride in place of propane-1-sulfonyl chloride.

ESI-MS [M+H⁺]=498 Calculated for $C_{26}H_{28}ClN_3O_3S$=497.

Example 65

N-[2-({1-[1-(4-Fluorophenyl)cyclobutyl]-1,2,3,4-tetrahydroisoquinolin-7-yl}oxy)ethyl]propane-1-sulfonamide hydrochloride

65.1 1-[1-(4-Fluorophenyl)cyclobutyl]-3,4-dihydroisoquinolin-7-ol

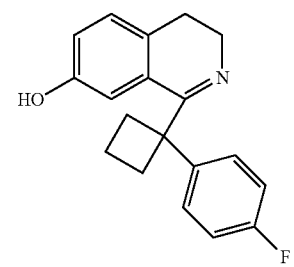 [SMILES: Oc1ccc2c(c1)C(C1(c3ccc(F)cc3)CCC1)=NCC2]

The compound was prepared analogously to 1-[1-(4-chlorophenyl)cyclobutyl]-3,4-dihydroisoquinolin-7-ol (cf. example 82) starting from 1-(4-fluorophenyl)cyclobutanecarboxylic acid.

65.2 tert-Butyl[2-({1-[1-(4-fluorophenyl)cyclobutyl]-3,4-dihydroisoquinolin-7-yl}oxy)ethyl]carbamate

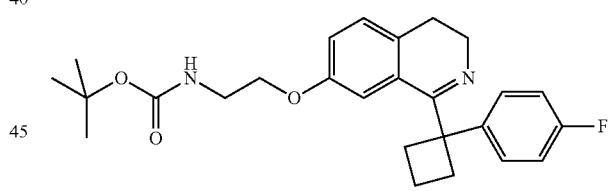

Sodium hydride (0.626 g, 15.64 mmol, 60% suspension in mineral oil) was washed under dry conditions under nitrogen atmosphere with n-hexane. Dimethylformamide (20 mL) was added followed by 1-[1-(4-fluorophenyl)cyclobutyl]-3,4-dihydroisoquinolin-7-ol (2.1 g, 7.11 mmol) under stirring. After the exothermic reaction had ceased stirring was continued at room temperature for 1 h before tert-butyl (2-bromoethyl)carbamate (4.78 g, 21.33 mmol) was added dropwise as a solution in dimethylformamide (10 mL). The reaction mixture was stirred at room temperature over night. The solvent was evaporated in vacuo. Ice water was added (60 mL) and the aqueous phase was extracted with ethyl acetate. The combined organic layers were dried (MgSO₄) and the solvent was evaporated in vacuo. The crude product was purified by flash chromatography (silica, dichloromethane:methanol=100:1). Yield: 2.5 g (5.7 mmol, 36%).

65.3 2-({1-[1-(4-Fluorophenyl)cyclobutyl]-3,4-dihydroisoquinolin-7-yl}oxy)ethanamine

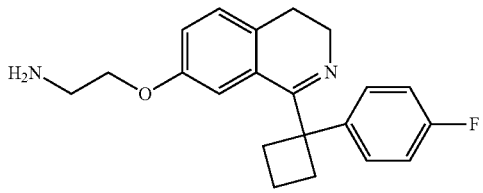 [SMILES: NCCOc1ccc2c(c1)C(C1(c3ccc(F)cc3)CCC1)=NCC2]

tert-Butyl[2-({1-[1-(4-fluorophenyl)cyclobutyl]-3,4-dihydroisoquinolin-7-yl}oxy)ethyl]carbamate (2.5 g, 5.7 mmol) was dissolved in dichloromethane (30 mL) and 5N hydrochloric acid in isopropanol (20 mL) was added. After stirring over night at room temperature the solvent was evaporated in vacuo. Water (30 mL) was added and the aqueous phase was neutralized with saturated aqueous $NaHCO_3$ and extracted with dichloromethane. The combined organic layers were washed with brine (20 mL), dried ($MgSO_4$) and concentrated in vacuo. The crude product (1.76 g) was used without purification for the next step.

65.4 N-[2-({1-[1-(4-Fluorophenyl)cyclobutyl]-3,4-dihydroisoquinolin-7-yl}oxy)ethyl]propane-1-sulfonamide

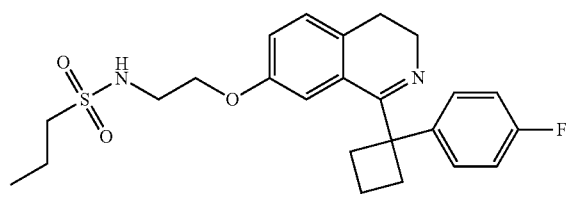 [SMILES: CCCS(=O)(=O)NCCOc1ccc2c(c1)C(C1(c3ccc(F)cc3)CCC1)=NCC2]

2-({1-[1-(4-Fluorophenyl)cyclobutyl]-3,4-dihydroisoquinolin-7-yl}oxy)ethanamine (298 mg, 0.88 mmol) was dissolved in dichloromethane (10 mL) and N,N-dimethylpyridin-4-amine (118 mg, 0.97 mmol) was added. After dropwise addition of a solution of propane-1-sulfonyl chloride (138 mg, 0.97 mmol) in dichloromethane (2 mL) stirring was continued over night. The reaction mixture was diluted with dichloromethane (20 mL), washed with an aqueous ammonium chloride solution (30 mL). The organic layer was dried ($MgSO_4$) and concentrated in vacuo. The crude product was purified by flash chromatography (silica, ethyl acetate:dichloromethane=1:10). Yield: 200 mg (0.45 mmol, 51%).

65.5 N-[2-({1-[1-(4-Fluorophenyl)cyclobutyl]-1,2,3,4-tetrahydroisoquinolin-7-yl}oxy)ethyl]propane-1-sulfonamide hydrochloride

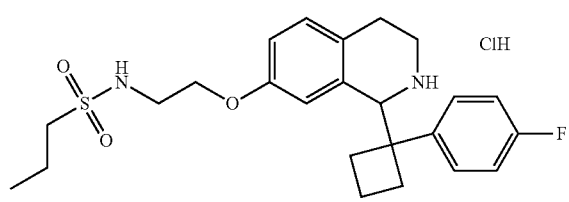 [SMILES: CCCS(=O)(=O)NCCOc1ccc2c(c1)C(C1(c3ccc(F)cc3)CCC1)NCC2 ; Cl]

N-[2-({1-[1-(4-Fluorophenyl)cyclobutyl]-3,4-dihydroisoquinolin-7-yl}oxy)ethyl]propane-1-sulfonamide (180 mg, 0.4 mmol) was dissolved in methanol (4 mL) and water (0.1 mL) and sodiumborohydride (30.6 mg, 0.81 mmol) was added in small portions under stirring at room temperature. Stirring was continued over night. The solvent was evaporated in vacuo. The residue was treated with dichloromethane. The organic layer was washed with saturated aqueous NaHCO3 (2×10 mL) and water (1×10 mL). After drying ($MgSO_4$) and evaporation of the solvent in vacuo the product was treated with 2N hydrochloric acid in diethylether. The diethylether was removed by destillation and the product was dried in vacuo. Yield: 153 mg (0.34 mmol, 85%, colorless solid).

ESI-MS [M+H$^{+}$]=447 Calculated for $C_{24}H_{31}FN_2O_3S$=446.

Example 66

N-[2-({1-[1-(4-Fluorophenyl)cyclobutyl]-1,2,3,4-tetrahydroisoquinolin-7-yl}oxy)ethyl]pyridine-3-sulfonamide hydrochloride

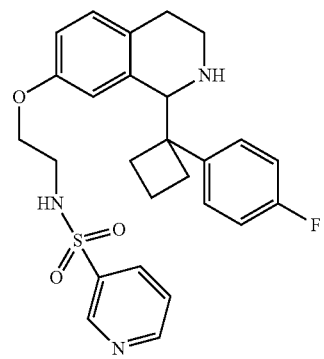 [SMILES: O=S(=O)(NCCOc1ccc2c(c1)C(C1(c3ccc(F)cc3)CCC1)NCC2)c1cccnc1]

N-[2-({1-[1-(4-Fluorophenyl)cyclobutyl]-1,2,3,4-tetrahydroisoquinolin-7-yl}oxy)ethyl]pyridine-3-sulfonamide hydrochloride was prepared analogously to example 65 using pyridine-3-sulfonyl chloride in place of propane-1-sulfonyl chloride.

ESI-MS [M+H$^{+}$]=482 Calculated for $C_{26}H_{28}FN_3O_3S$=481.

Example 67

N-[2-({1-[1-(4-Chlorophenyl)cyclobutyl]-4,4-dimethyl-1,2,3,4-tetrahydroisoquinolin-7-yl}oxy)ethyl]propane-1-sulfonamide hydrochloride

67.1 2-(4-Methoxyphenyl)-2-methylpropanenitrile

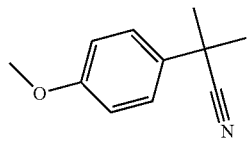

To a suspension of sodium tert-butylate (21.54 g, 217.4 mmol) in dimethylformamide (37 mL) and tetrahydrofuran (37 mL) was added (4-methoxyphenyl)acetonitrile (8.00 g, 54.36 mmol) at 5° C. At the same temperature methyl iodide (13.54 mL) was added dropwise resulting in the formation of a light brown solid. The reaction mixture was diluted with dimethylformamide (15 mL) and tetrahydrofuran (15 mL). Stirring was continued at 10° C. for 1.5 h. The reaction mixture was cooled in a ice bath and 2N aqueous hydrochloric acid (100 mL) was added. The reaction mixture was extracted with ethyl acetate (3×100 mL). The combined extracts were washed with aqueous saturated NaHCO$_3$ solution (2×50 mL) and brine (50 mL). The extracts were dried (MgSO$_4$) and the solvent was evaporated in vacuo. The crude product was purified by flash chromatography (silica, n-heptane:dichloromethane=1:1). Yield: 7.6 g (43.4 mmol, 79.8%).

67.2 2-(4-Methoxyphenyl)-2-methylpropan-1-amine

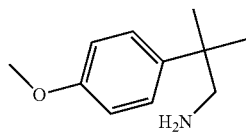

A reaction vessel was charged with lithiumaluminium hydride (0.433 g, 11.41 mmol) and dry diethyl ether (20 mL). After cooling to 5° C. a solution of 2-(4-methoxyphenyl)-2-methylpropanenitrile (2.00 g, 11.41 mmol) in dry diethylether (10 mL) was added dropwise. The reaction mixture was stirred at 5° C. for 2 h. The reaction mixture was then cooled in an ice bath and 2N aqueous sodium hydroxide solution (0.8 mL) and water (1.5 mL) were added. After stirring for 20 min additional water (40 mL) was added and the reaction mixture was extracted with ethyl acetate (2×30 mL). The combined extracts were dried (MgSO$_4$) and the solvent was evaporated in vacuo. The crude product (1.94 g, 10.82 mmol) was used without further purification for the next step.

67.3 2-({1-[1-(4-Chlorophenyl)cyclobutyl]-4,4-dimethyl-3,4-dihydroisoquinolin-7-yl}oxy)ethanamine

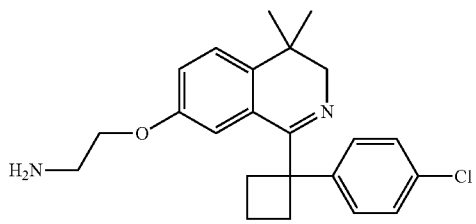 [SMILES: CC1(C)CN=C(C2(c3ccc(Cl)cc3)CCC2)c2cc(OCCN)ccc21]

2-({1-[1-(4-Chlorophenyl)cyclobutyl]-4,4-dimethyl-3,4-dihydroisoquinolin-7-yl}oxy)ethanamine was prepared analogously to 2-({1-[1-(4-fluorophenyl)cyclobutyl]-3,4-dihydroisoquinolin-7-yl}oxy)ethanamine (cf. example 65) using 2-(4-methoxyphenyl)-2-methylpropan-1-amine and 1-(4-chlorophenyl)cyclobutanecarboxylic acid in place of 2-(4-methoxyphenyl)ethanamine and 1-(4-fluorophenyl)cyclobutanecarboxylic acid, respectively.

67.4 N-[2-({1-[1-(4-Chlorophenyl)cyclobutyl]-4,4-dimethyl-1,2,3,4-tetrahydroisoquinolin-7-yl}oxy)ethyl]propane-1-sulfonamide hydrochloride

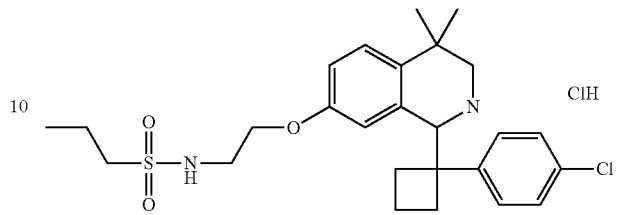

N-[2-({1-[1-(4-Chlorophenyl)cyclobutyl]-4,4-dimethyl-1,2,3,4-tetrahydroisoquinolin-7-yl}oxy)ethyl]propane-1-sulfonamide hydrochloride was prepared analogously to N-[2-({1-[1-(4-fluorophenyl)cyclobutyl]-1,2,3,4-tetrahydroisoquinolin-7-yl}oxy)ethyl]propane-1-sulfonamide hydrochloride (cf. example 65) using 2-({1-[1-(4-chlorophenyl)cyclobutyl]-4,4-dimethyl-3,4-dihydroisoquinolin-7-yl}oxy)ethanamine in place of 2-({1-[1-(4-fluorophenyl)cyclobutyl]-3,4-dihydroisoquinolin-7-yl}oxy)ethanamine.

ESI-MS [M+H$^+$]=491 Calculated for C$_{26}$H$_{35}$ClN$_2$O$_3$S=490.

Example 68

N-[2-({1-[1-(4-Chlorophenyl)cyclobutyl]-1,2,3,4-tetrahydroisoquinolin-6-yl}oxy)ethyl]propane-1-sulfonamide hydrochloride 68.1 1-[1-(4-Chlorophenyl)cyclobutyl]-3,4-dihydroisoquinolin-6-ol

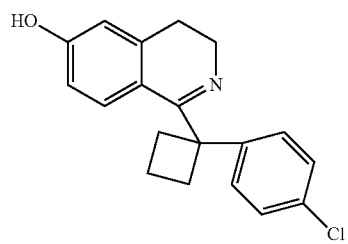 [SMILES: Oc1ccc2c(c1)CCN=C2C1(c2ccc(Cl)cc2)CCC1]

1-[1-(4-Chlorophenyl)cyclobutyl]-3,4-dihydroisoquinolin-6-ol was prepared analogously to 1-[1-(4-chlorophenyl)cyclobutyl]-3,4-dihydroisoquinolin-7-ol (cf. example 82) using 2-(3-methoxyphenyl)ethanamine in place of 2-(4-methoxyphenyl)ethanamine.

68.2 2-({1-[1-(4-Chlorophenyl)cyclobutyl]-3,4-dihydroisoquinolin-6-yl}oxy)ethanamine

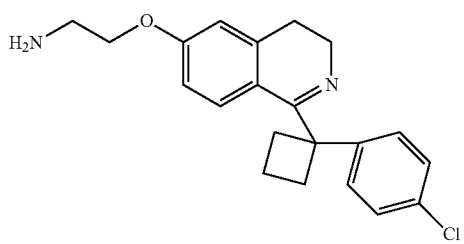 [SMILES: NCCOc1ccc2c(c1)CCN=C2C1(c2ccc(Cl)cc2)CCC1]

2-({1-[1-(4-Chlorophenyl)cyclobutyl]-3,4-dihydroisoquinolin-6-yl}oxy)ethanamine was prepared analogously to 2-({1-[1-(4-fluorophenyl)cyclobutyl]-3,4-dihydroisoquinolin-7-yl}oxy)ethanamine using 1-[1-(4-chlorophenyl)cyclobutyl]-3,4-dihydroisoquinolin-6-ol in place of 1-[1-(4-fluorophenyl)cyclobutyl]-3,4-dihydroisoquinolin-7-ol (cf. example 65).

68.3 N-[2-({1-[1-(4-Chlorophenyl)cyclobutyl]-3,4-dihydroisoquinolin-6-yl}oxy)ethyl]propane-1-sulfonamide

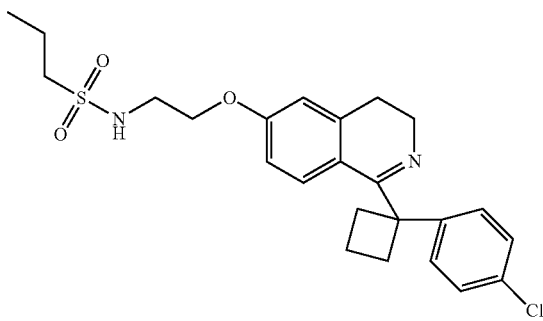 [SMILES: CCCS(=O)(=O)NCCOc1ccc2c(c1)CCN=C2C1(c2ccc(Cl)cc2)CCC1]

2-({1-[1-(4-Chlorophenyl)cyclobutyl]-3,4-dihydroisoquinolin-6-yl}oxy)ethanamine (0.40 g, 0.90 mmol) was dissolved in dichloromethane (8 mL) and propane-1-sulfonyl chloride (0.169 g, 1.18 mmol) and N,N-dimethylpyridin-4-amine (0.152 g, 1.24 mmol) were added. The reaction mixture was stirred at room temperature over night. Water was added and the aqueous phase was extracted several time with dichloromethane. The combined organic layers were dried (Na₂SO₄) and concentrated in vacuo. The crude product was purified by flash chromatography (silica, dichloromethane:methanol=99:1). Yield: 0.35 g (0.68 mmol, 76%, colorless oil).

68.4 N-[2-({1-[1-(4-Chlorophenyl)cyclobutyl]-1,2,3,4-tetrahydroisoquinolin-6-yl}oxy)ethyl]propane-1-sulfonamide hydrochloride

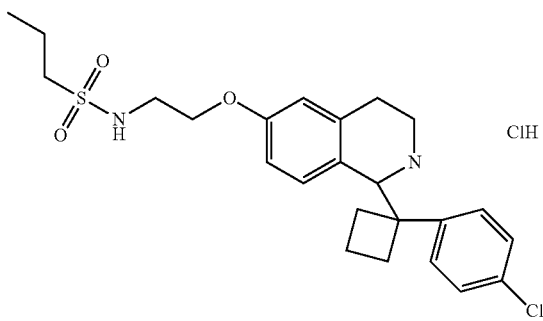 [SMILES: CCCS(=O)(=O)NCCOc1ccc2c(c1)CCNC2C1(c2ccc(Cl)cc2)CCC1 ; Cl]

N-[2-({1-[1-(4-Chlorophenyl)cyclobutyl]-3,4-dihydroisoquinolin-6-yl}oxy)ethyl]propane-1-sulfonamide (320 mg, 0.62 mmol) was dissolved in methanol (5 mL) and water (0.1 mL) and sodiumborohydride (47 mg, 1.25 mmol) was added at 4° C. in small portions. The reaction mixture was allowed to warm to room temperature and stirring was continued over night. The solvent was evaporated in vacuo, the residue was treated with dichloromethane and water. The aqueous layer was extracted several times with dichloromethane. The combined organic layers were dried (Na₂SO₄) and concentrated in vacuo. The crude product was purified by preparative HPLC (RP, acetonitrile, water). The purified amine was then converted into the corresponding hydrochloric acid salt by adding 5M isoporpanolic hydrochloric acid followed by concentration in vacuo. Yield: 35 mg (0.07 mmol, 11%, colorless solid).

ESI-MS [M+H⁺]=463 Calculated for C₂₄H₃₁ClN₂O₃S=462.

Example 69

N'-[2-({1-[1-(4-Chlorophenyl)cyclobutyl]-4,4-dimethyl-1,2,3,4-tetrahydroisoquinolin-7-yl}oxy)ethyl]-N,N-diethylsulfuric diamide hydrochloride

69.1 N'-[2-({1-[1-(4-Chlorophenyl)cyclobutyl]-4,4-dimethyl-3,4-dihydroisoquinolin-7-yl}oxy)ethyl]-N,N-diethylsulfuric diamide

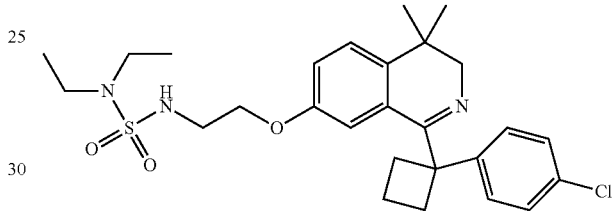

2-({1-[1-(4-Chlorophenyl)cyclobutyl]-4,4-dimethyl-3,4-dihydroisoquinolin-7-yl}oxy)ethanamine (145 mg, 0.38 mmol, cf. example 67) was dissolved in dry dichloromethane (8 mL). Triethylamine (60 μL, 0.45 mmol). The solution was cooled to 0-5° C. and diethylsulfamoyl chloride (71.5 mg, 0.42 mmol) was added. The reaction mixture was stirred at room temperature over night. The reaction mixture was diluted with dichloromethane (20 mL) and washed with a 1:1 mixture of water and saturated ammonium chloride solution (20 mL). The organic layer was dried (MgSO₄) and the solvent was evaporated in vacuo. The crude product was purified by flash chromatography (silica, dichloromethane then dichloromethane:ethyl acetate=180:5). Yield: 96 mg (0.19 mmol, 48.9%).

69.2 N'-[2-({1-[1-(4-Chlorophenyl)cyclobutyl]-4,4-dimethyl-1,2,3,4-tetrahydroisoquinolin-7-yl}oxy)ethyl]-N,N-diethylsulfuric diamide hydrochloride

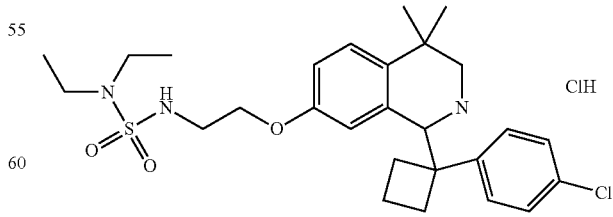

N'-[2-({1-[1-(4-Chlorophenyl)cyclobutyl]-4,4-dimethyl-1,2,3,4-tetrahydroisoquinolin-7-yl}oxy)ethyl]-N,N-diethylsulfuric diamide hydrochloride was prepared analogously to example 65 using N'-[2-({1-[1-(4-chlorophenyl)cyclobutyl]-

4,4-dimethyl-3,4-dihydroisoquinolin-7-yl}oxy)ethyl]-N,N-diethylsulfuric diamide (68 mg, 0.13 mmol) and sodiumborohydride (10 mg, 0.26 mmol). Yield: 60 mg (0.11 mmol, 82%, colorless foam).

ESI-MS [M+H$^+$]=520 Calculated for $C_{27}H_{38}ClN_3O_3S$=519.

Example 70

N-[2-({1-[1-(4-Fluorophenyl)cyclobutyl]-2-(trifluoroacetyl)-1,2,3,4-tetrahydroisoquinolin-7-yl}oxy)ethyl]propane-1-sulfonamide

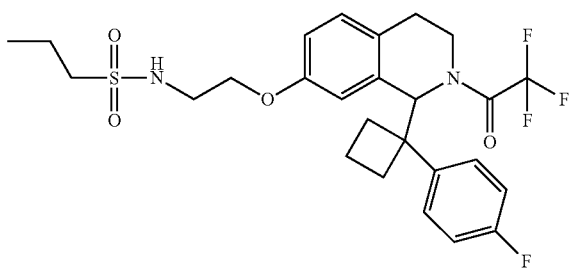 [SMILES: CCCS(=O)(=O)NCCOc1ccc2c(c1)C(C1(c3ccc(F)cc3)CCC1)N(C(=O)C(F)(F)F)CC2]

N-[2-({1-[1-(4-Fluorophenyl)cyclobutyl]-1,2,3,4-tetrahydroisoquinolin-7-yl}oxy)ethyl]propane-1-sulfonamide hydrochloride (135 mg, 0.30 mmol, cf. example 65) was dissolved in dichloromethane (9 mL). Triethylamine (92 mg, 0.91 mmol) and trifluoro-acetic acid anhydride (95 mg, 0.45 mmol) were added. The reaction mixture was stirred at room temperature until TLC indicated complete conversion of the starting material. Aqueous saturated NaHCO$_3$ solution (12 mL) and water (20 mL) was added. After stirring at room temperature for 15 min the layers were separated and the aqueous layer was extracted several times with dichloromethane. The combined organic layers were dried (Na$_2$SO$_4$), concentrated in vacuo and the crude product was purified by flash chromatographie (silica, dichloromethane then dichloromethane:ethyl acetate=20:1). Yield: 80 mg (0.15 mmol, 49%).

ESI-MS [M+H$^+$]=543 Calculated for $C_{26}H_{30}F_4N_2O_4S$=542.

Example 71

N-[2-({1-[1-(4-Fluorophenyl)cyclobutyl]-2-(2,2,2-trifluoroethyl)-1,2,3,4-tetrahydroisoquinolin-7-yl}oxy)ethyl]propane-1-sulfonamide hydrochloride

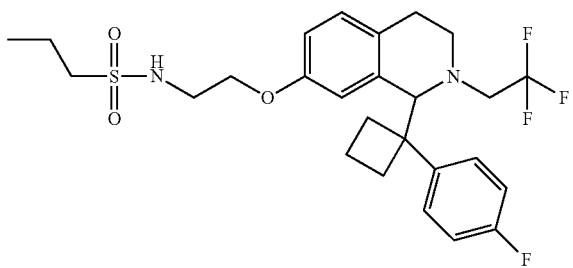 [SMILES: CCCS(=O)(=O)NCCOc1ccc2c(c1)C(C1(c3ccc(F)cc3)CCC1)N(CC(F)(F)F)CC2]

N-[2-({1-[1-(4-Fluorophenyl)cyclobutyl]-2-(trifluoroacetyl)-1,2,3,4-tetrahydroisoquinolin-7-yl}oxy)ethyl]propane-1-sulfonamide (49 mg, 0.09 mmol) was dissolved in dry tetrahydrofuran (0.6 mL) under an atmosphere of nitrogen. The solution was cooled to 0° C. and a 1M solution of borane in tetrahydrofuran (0.181 mL, 0.181 mmol) was added dropwise. The reaction mixture was warmed to room temperature and then heated under reflux for 2 h. The solvent was evaporated in vacuo, the residue was dissolved in dichloromethane (20 mL) and washed with water (10 mL). The organic layer was dried (MgSO$_4$) and concentrated in vacuo. The product was dissolved in dichloromethane (2 mL) and treated with 5N isopropanolic hydrochloric acid (27 µL, 0.135 mmol). The solvents were evaporated and the product was dried in vacuo. Yield: 45 mg (0.08 mmol, 88%).

ESI-MS [M+H$^+$]=529 Calculated for $C_{26}H_{32}F_4N_2O_3S$=528.

Example 72

1-[1-(4-Fluorophenyl)cyclobutyl]-7-{2-[(propylsulfonyl)amino]ethoxy}-3,4-dihydroisoquinoline-2(1H)-carboximidamide acetate 72.1 Dibenzyl[(E)-{1-[1-(4-fluorophenyl)cyclobutyl]-7-{2-[(propylsulfonyl)amino]ethoxy}-3,4-dihydroisoquinolin-2(1H)-yl}methylylidene]biscarbamate

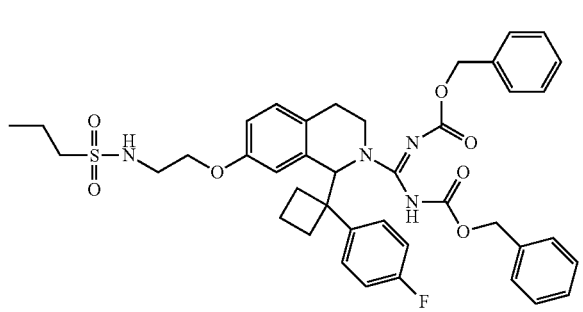 [SMILES: CCCS(=O)(=O)NCCOc1ccc2c(c1)C(C1(c3ccc(F)cc3)CCC1)N(/C(=N/C(=O)OCc1ccccc1)NC(=O)OCc1ccccc1)CC2]

N-[2-({1-[1-(4-Fluorophenyl)cyclobutyl]-1,2,3,4-tetrahydroisoquinolin-7-yl}oxy)ethyl]propane-1-sulfonamide (100 mg, 0.224 mmol, cf. example 65) and dibenzyl [(methylsulfanyl)methylylidene]biscarbamate (104 mg, 0.291 mmol) were dissolved in dry dimethylformamide (1 mL). Triethylamine (0.094 mL, 0.672 mmol) was added followed by silver trifluoromethanesulfonate (81 mg, 0.313 mmol). A yellow precipitate was formed and the reaction mixture turned dark brown. Stirring was continued at room temperature for 3 h. The solvent was evaporated in vacuo. Dichloromethane (15 mL) was added, the solid was removed by filtration and washed with dichloromethane. The combined dichloromethane phases were concentrated in vacuo and the crude product was purified by flash chromatography (silica, dichloromethane then dichlorometane:methanol=100:1). Yield: 100 mg (0.132 mmol, 59%).

72.2 1-[1-(4-Fluorophenyl)cyclobutyl]-7-{2-[(propylsulfonyl)amino]ethoxy}-3,4-dihydroisoquinoline-2(1H)-carboximidamide acetate

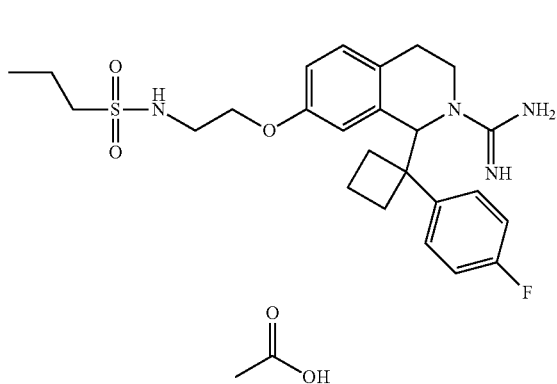

Dibenzyl[(E)-{1-[1-(4-fluorophenyl)cyclobutyl]-7-{2-[(propylsulfonyl)amino]ethoxy}-3,4-dihydroisoquinolin-2(1H)-yl}methylylidene]biscarbamate (95 mg, 0.126 mmol) was dissolved in methanol (8 mL) under an atmosphere of nitrogen. Acetic acid (0.4 mL) was added followed by 10% palladium on charcoal (40 mg, 0.038 mmol). The nitrogen was replaced by one atmosphere of hydrogen and the reaction mixture was stirred at room temperature for 3 h. The catalyst was removed by filtration and the solution of the product was concentrated in vacuo. The product was dissolved in ethanol (0.5 mL) and water (15 mL) and was lyophilized. Yield: 61 mg (0.125 mmol, 99%).

ESI-MS [M+H$^+$]=489 Calculated for $C_{25}H_{33}FN_4O_3S$=488.

Example 73

N-[2-({5-Bromo-1-[1-(4-fluorophenyl)cyclobutyl]-1,2,3,4-tetrahydroisoquinolin-8-yl}oxy)ethyl]propane-1-sulfonamide hydrochloride

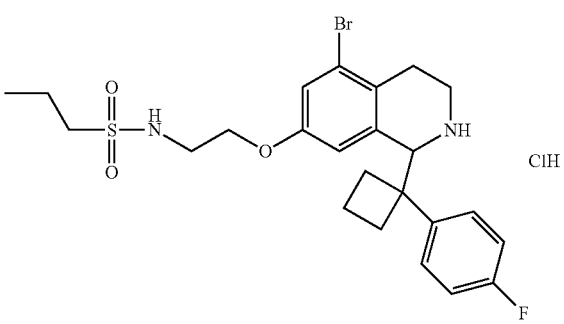 [SMILES: CCCS(=O)(=O)NCCOc1cc(Br)c2c(c1)C(C1(c3ccc(F)cc3)CCC1)NCC2 ; Cl]

N-[2-({5-Bromo-1-[1-(4-fluorophenyl)cyclobutyl]-1,2,3,4-tetrahydroisoquinolin-8-yl}oxy)ethyl]propane-1-sulfonamide hydrochloride was prepared analogously to N-[2-({1-[1-(4-fluorophenyl)cyclobutyl]-1,2,3,4-tetrahydroisoquinolin-7-yl}oxy)ethyl]propane-1-sulfonamide hydrochloride (cf. example 65) using 2-(2-bromo-5-methoxyphenyl)ethanamine in place of 2-(4-methoxyphenyl)ethanamine.

ESI-MS [M+H$^+$]=526 Calculated for $C_{24}H_{30}BrFN_2O_3S$=525.

Example 74

N-[2-({1-[1-(4-Fluorophenyl)cyclobutyl]-2-nitroso-1,2,3,4-tetrahydroisoquinolin-7-yl}oxy)ethyl]propane-1-sulfonamide

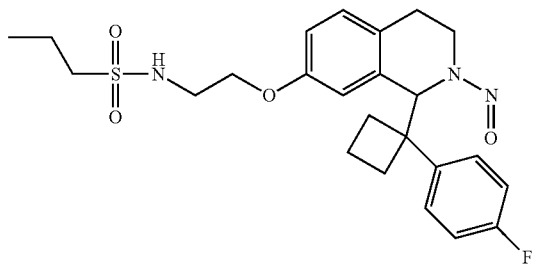 [SMILES: CCCS(=O)(=O)NCCOc1ccc2c(c1)C(C1(c3ccc(F)cc3)CCC1)N(N=O)CC2]

N-[2-({1-[1-(4-Fluorophenyl)cyclobutyl]-1,2,3,4-tetrahydroisoquinolin-7-yl}oxy)ethyl]propane-1-sulfonamide (92 mg, 0.206 mmol, cf. example 65) was dissolved in tetrahydrofuran (1 mL) under an atmosphere of nitrogen. Tert-butyl nitrite (32 mg, 0.309 mmol) were added and the reaction mixture was stirred under reflux for 3 h. After that time additional tert-butyl nitrite (32 mg, 0.309 mmol) was added and stirring under reflux was continued for 2 h. The solvent was evaporated in vacuo and the crude product was purified by flash chromatography (silica, dichloromethane then dichloromethane:methanol=100:1). Yield: 56 mg (0.118 mmol, 57%).

ESI-MS [M+H$^+$]=476 Calculated for $C_{24}H_{30}FN_3O_4S$=475.

Example 75

N-[2-({2-Amino-1-[1-(4-fluorophenyl)cyclobutyl]-1,2,3,4-tetrahydroisoquinolin-7-yl}oxy)ethyl]propane-1-sulfonamide

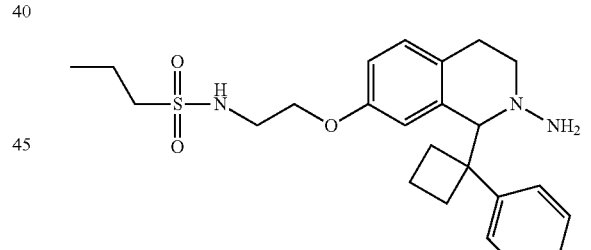

A reaction vessel was charged with lithiumaluminium hydride (23.5 mg, 0.618 mmol) and dry tetrahydrofuran (1 mL). N-[2-({1-[1-(4-fluorophenyl)cyclobutyl]-2-nitroso-1,2,3,4-tetrahydroisoquinolin-7-yl}oxy)ethyl]propane-1-sulfonamide (49 mg, 0.103 mmol, cf. example 75) was added dropwise as a solution in dry tetrahydrofuran (1 mL) at 0° C. After the addition was completed the reaction mixture was stirred at room temperature for 1 h and then at 40-50° C. for 1 h. After cooling to room temperature the reaction mixture was poured on ice water (15 mL) and the aqueous phase was extracted with ethyl acetate (3×10 mL). The combined extracts were dried (MgSO$_4$) and concentrated in vacuo. The crude product was purified by preparative HPLC (RP, acetonitrile, water). Yield: 1 mg (2.2 µmol, 2%)

ESI-MS [M+H$^+$]=462 Calculated for $C_{24}H_{32}FN_3O_3S$=461.

Example 76

N-[2-({1-[1-(4-Chloro-2-methoxyphenyl)cyclobutyl]-1,2,3,4-tetrahydroisoquinolin-7-yl}oxy)ethyl]propane-1-sulfonamide hydrochloride

76.1 1-(4-Chloro-2-methoxyphenyl)cyclobutanecarbonitrile

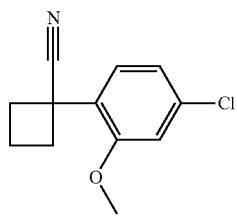

1-(4-Chloro-2-methoxyphenyl)cyclobutanecarbonitrile can be prepared analogously to procedure described in Organic Letters (2006), 8(17), 3745ff starting from (4-chloro-2-methoxyphenyl)acetonitrile. Alternatively sodium hydride can be used as a base and di-methylsuloxide as solvent.

76.2 1-(4-Chloro-2-methoxyphenyl)cyclobutanecarboxylic acid

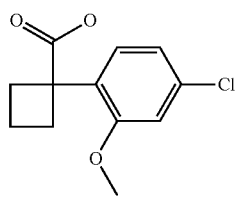 [SMILES: COc1cc(Cl)ccc1C1(C(=O)O)CCC1]

1-(4-Chloro-2-methoxyphenyl)cyclobutanecarboxylic acid can be obtained by heating 1-(4-chloro-2-methoxyphenyl)cyclobutanecarbonitrile in the presence of potassium hydroxide in ethylene glycol (cf. J. Am. Chem. Soc. 1956, 78, 5413ff or Org. Synth. Coll. Vol. 4, 1963, 93ff).

76.3 N-{2-[4-(Benzyloxy)phenyl]ethyl}-1-(4-chloro-2-methoxyphenyl)cyclobutanecarboxamide

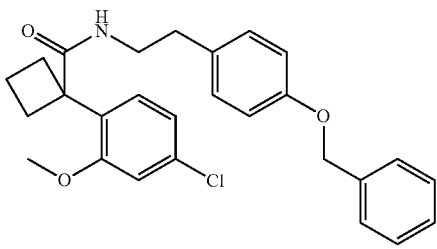 [SMILES: COc1cc(Cl)ccc1C1(C(=O)NCCc2ccc(OCc3ccccc3)cc2)CCC1]

N-{2-[4-(Benzyloxy)phenyl]ethyl}-1-(4-chloro-2-methoxyphenyl)cyclobutanecarboxamide was prepared analogously to example 65 from 1-(4-chloro-2-methoxyphenyl)cyclobutanecarboxylic acid (3.45 g, 14.3 mmol) and 2-[4-(benzyloxy)phenyl]ethanamine (4.2 g, 15.92 mmol). Yield: 4.7 g (10.45 mmol, 66%).

76.4 7-(Benzyloxy)-1-[1-(4-chloro-2-methoxyphenyl)cyclobutyl]-3,4-dihydroisoquinoline

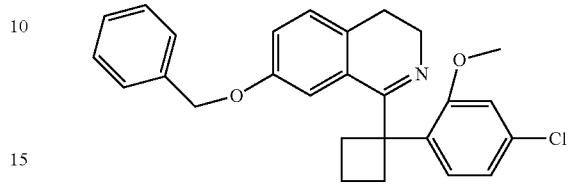

7-(Benzyloxy)-1-[1-(4-chloro-2-methoxyphenyl)cyclobutyl]-3,4-dihydroisoquinoline was prepared analogously to example 65 using N-{2-[4-(benzyloxy)phenyl]ethyl}-1-(4-chloro-2-methoxyphenyl)cyclobutanecarboxamide (1.1 g, 2.445 mmol) and phosphoric trichloride (3.75 g, 24.45 mmol). Yield: 65 mg (0.15 mmol, 6%).

76.5 1-[1-(4-Chloro-2-methoxyphenyl)cyclobutyl]-3,4-dihydroisoquinolin-7-ol

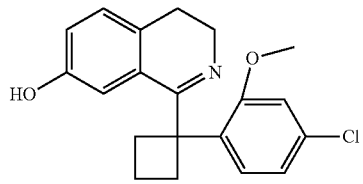 [SMILES: COc1cc(Cl)ccc1C1(C2=NCCc3ccc(O)cc32)CCC1]

7-(benzyloxy)-1-[1-(4-chloro-2-methoxyphenyl)cyclobutyl]-3,4-dihydroisoquinoline (460 mg, 1.065 mmol) were dissolved in 33% hydrobromic acid in acetic acid. The reaction mixture was stirred at room temperature for 15 min. The solvent was evaporated in vacuo. Toluene was added and evaporated in vacuo (repeated three times). The crude product was purified by flash chromatography (silica, dichloromethane then dichloromethane:methanol=4:1). Yield: 322 mg (0.942 mmol, 88%).

76.5 N-[2-({1-[1-(4-Chloro-2-methoxyphenyl)cyclobutyl]-1,2,3,4-tetrahydroisoquinolin-7-yl}oxy)ethyl]propane-1-sulfonamide hydrochloride

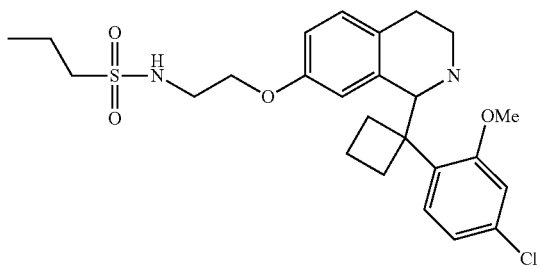 [SMILES: CCCS(=O)(=O)NCCOc1ccc2c(c1)C(C1(c3ccc(Cl)cc3OC)CCC1)NCC2]

N-[2-({1-[1-(4-Chloro-2-methoxyphenyl)cyclobutyl]-1,2,3,4-tetrahydroisoquinolin-7-yl}oxy)ethyl]propane-1-sulfonamide hydrochloride was prepared analogously to example 65 starting from 1-[1-(4-chloro-2-methoxyphenyl)cyclobutyl]-3,4-dihydroisoquinolin-7-ol.

ESI-MS [M+H$^+$]=493 Calculated for $C_{25}H_{33}ClN_2O_4S$=492.

Example 77

N-[2-({1-[1-(3-Chlorophenyl)cyclobutyl]-2-(cyanomethyl)-1,2,3,4-tetrahydroisoquinolin-7-yl}oxy)ethyl]propane-1-sulfonamide

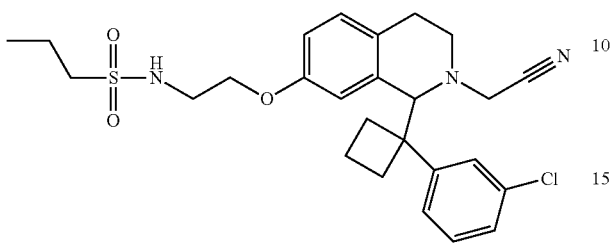

N-[2-({1-[1-(3-Chlorophenyl)cyclobutyl]-1,2,3,4-tetrahydroisoquinolin-7-yl}oxy)ethyl]propane-1-sulfonamide (70 mg, 0.14 mmol, cf. example 49) was dissolved in dry dichloromethane (0.5 mL). Triethylamine (35.5 mg, 0.35 mmol) was added and the reaction mixture was stirred at room temperature for 30 min. After addition of 2-bromoacetonitrile (20 mg, 0.168 mmol) stirring at room temperature was continued over night. The reaction mixture was diluted with dichloromethane and washed with aqueous saturated NaHCO$_3$ solution (5 mL) and water (5 mL). The organic phase was dried (MgSO$_4$) and the solvent was evaporated in vacuo. The crude product was purified by flash chromatography (silica, dichloromethane then dichloromethane:methanol=200:1). Yield: 35 mg (0.07 mmol, 50%).

ESI-MS [M+H$^+$]=502 Calculated for C$_{26}$H$_{32}$ClN$_3$O$_3$S=501.

Example 78

N-[2-({2-(2-Aminoethyl)-1-[1-(3-chlorophenyl)cyclobutyl]-1,2,3,4-tetrahydroisoquinolin-7-yl}oxy)ethyl]propane-1-sulfonamide bis(trifluoroacetate)

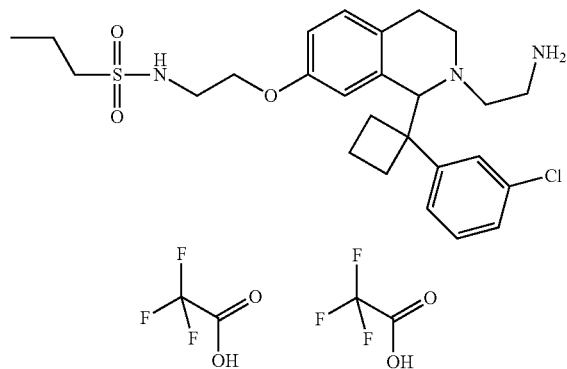

A reaction vessel was charged with lithiumaluminium hydride (3.3 mg, 0.087 mmol) and dry diethyl ether (3.5 mL). At −5° C. a solution of N-[2-({1-[1-(3-chlorophenyl)cyclobutyl]-2-(cyanomethyl)-1,2,3,4-tetrahydroisoquinolin-7-yl}oxy)ethyl]propane-1-sulfonamide (29 mg, 0.058 mmol) in dry diethyl ether (0.5 mL) was added dropwise. After stirring at −5° C. for 1 h another portion of lithiumaluminium hydride (3.3 mg, 0.087 mmol) was added. The reaction mixture was allowed warm to room temperature and stirring was continued for 5 h. 2N aqueous sodium hydroxide solution (10 mL) was added dropwise. After stirring for 10 min the reaction mixture was diluted with water (5 mL) and extracted with ethyl acetate (2×15 mL). The combined extracts were dried (MgSO4) and the solvent was evaporated in vacuo. The crude product was purified by preparative HPLC (RP, acetonitrile, water). Yield: 12 mg (0.016 mmol, 28%).

ESI-MS [M+H$^+$]=506 Calculated for C$_{26}$H$_{36}$ClN$_3$O$_3$S=505.

Example 79

N-[2-({1-[1-(4-Fluorophenyl)cyclobutyl]-2-(1H-imidazol-2-yl)-1,2,3,4-tetrahydroisoquinolin-7-yl}oxy)ethyl]propane-1-sulfonamide 79.1 N-(2,2-Dimethoxyethyl)-1-[1-(4-fluorophenyl)cyclobutyl]-7-{2-[(propylsulfonyl)amino]ethoxy}-3,4-dihydroisoquinoline-2(1H)-carboximidamide

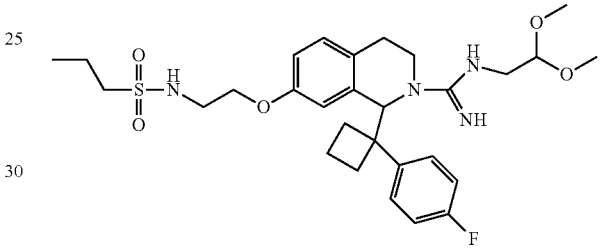

1-[1-(4-Fluorophenyl)cyclobutyl]-7-{2-[(propylsulfonyl)amino]ethoxy}-3,4-dihydroisoquinoline-2(1H)-carboximidamide acetate (140 mg, 0.255 mmol, cf. example 72) was suspended in ethanol (2 mL). Sodium methylate (138 mg, 0.142 mmol) and 2-bromo-1,1-dimethoxyethane (65 mg, 0.383 mmol) were added. The reaction mixture was stirred at 120° C. in the microwave (80 W) for 80 min. The solvent was evaporated in vacuo and the crude product was used without further purification for the next step.

79.2 N-[2-({1-[1-(4-Fluorophenyl)cyclobutyl]-2-(1H-imidazol-2-yl)-1,2,3,4-tetrahydroisoquinolin-7-yl}oxy)ethyl]propane-1-sulfonamide

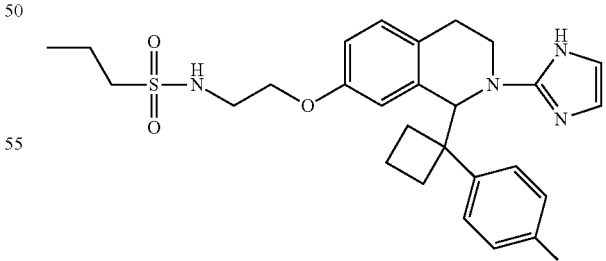

The crude N-(2,2-dimethoxyethyl)-1-[1-(4-fluorophenyl)cyclobutyl]-7-{2-[(propylsulfonyl)amino]ethoxy}-3,4-dihydroisoquinoline-2(1H)-carboximidamide (see above) was dissolved in acetonitrile (5 mL). Concentrated aqueous hydrochloric acid was added until the reaction mixture remained at pH 1. After stirring at room temperature over night the solvent was evaporated in vacuo. Water (10 mL) was added and the mixture was neutralized with aqueous saturated NaHCO₃ solution. The mixture was extracted with dichloromethane (2×10 mL). The combined organic layers were dried (MgSO₄) and the solvent was evaporated in vacuo. The crude product was purified by flash chromatography (silica, dichloromethane then dichloromethane:methanol=80:1). Yield: 2.8 mg (5.5 μmol, 2%).

ESI-MS [M+H⁺]=513 Calculated for $C_{27}H_{33}FN_4O_3S$=512.

Example 80

N-[2-({1-[1-(4-cChlorophenyl)cyclobutyl]-2-(cyanomethyl)-1,2,3,4-tetrahydroisoquinolin-7-yl}oxy)ethyl]propane-1-sulfonamide hydrochloride

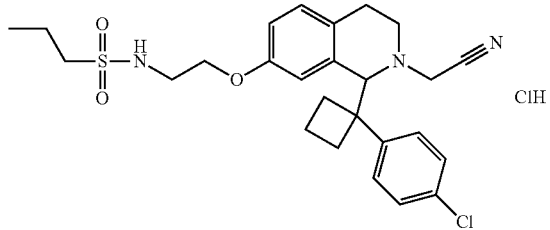 [SMILES: CCCS(=O)(=O)NCCOc1ccc2c(c1)C(C1(c3ccc(Cl)cc3)CCC1)N(CC#N)CC2 ; Cl]

N-[2-({1-[1-(4-Chlorophenyl)cyclobutyl]-1,2,3,4-tetrahydroisoquinolin-7-yl}oxy)ethyl]propane-1-sulfonamide (80 mg, 0.173 mmol, cf. example 4) was dissolved in dimethylformamide (2 mL). Triethylamine (70 mg, 0.414 mmol) and 2-bromoacetonitrile (50 mg, 0.414 mmol) were added and the reaction mixture was heated in the microwave at 120° C. for 20 min (100 W). The solvent was evaporated in vacuo, the crude product was diluted with dichloromethane (10 mL) and washed with water (2×10 mL). The organic layer was dried (MgSO₄) and concentrated in vacuo. The crude product was purified by flash chromatography (silica, dichloromethane, methanol). The purified product was dissolved in dichloromethane (1 mL) treated with 6 M hydrochloric acid in isopropanol. The solvent was evaporated in vacuo. Yield: 13 mg (0.024 mmol, 14%).

ESI-MS [M+H⁺]=502 Calculated for $C_{26}H_{32}ClN_3O_3S$=501.

Example 81

1-[1-(4-Chlorophenyl)cyclobutyl]-7-[3-(morpholin-4-ylsulfonyl)propoxy]-1,2,3,4-tetrahydroisoquinoline hydrochloride

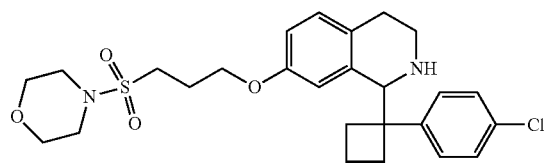 [SMILES: O=S(=O)(CCCOc1ccc2c(c1)C(C1(c3ccc(Cl)cc3)CCC1)NCC2)N1CCOCC1]

The compound was prepared analogously to example 82 from 3-({1-[1-(4-chlorophenyl)cyclobutyl]-3,4-dihydroisoquinolin-7-yl}oxy)propane-1-sulfonyl chloride using morpholine in place of 1-propylamine.

ESI-MS [M+H⁺]=505 Calculated for $C_{26}H_{33}ClN_2O_4S$=504.

Example 82

3-({1-[1-(4-Chlorophenyl)cyclobutyl]-1,2,3,4-tetrahydroisoquinolin-7-yl}oxy)-N-propylpropane-1-sulfonamide hydrochloride

82.1 1-(4-Chlorophenyl)-N-[2-(4-methoxyphenyl)ethyl]cyclobutanecarboxamide

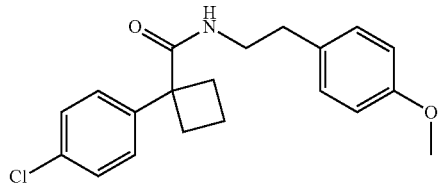 [SMILES: COc1ccc(CCNC(=O)C2(c3ccc(Cl)cc3)CCC2)cc1]

1-(4-Chlorophenyl)cyclobutanecarboxylic acid (6.63 g, 31.492 mmol) and 2-(4-methoxyphenyl)ethanamine (5.00 g, 33.067 mmol) were treated with dichloromethane (470 mL). The suspension was cooled to 3° C. and N,N-dimethylpyridin-4-amine (4.04 g, 33.1 mmol) and N-[3-(dimethylamino)propyl]-N'-ethylcarbodiimide hydrochloride (6.35 g, 33.1 mmol) were added. The reaction mixture was allowed to warm to room temperature and was stirred over night. The reaction mixture was washed successively with 2N hydrochloric acid (2×) and water (2×). The organic layer was dried (MgSO₄) and concentrated in vacuo. The crude product was purified by flash-chromatography (silica, dichloromethane:methanol=9:1) to give a pale yellow solid. Yield: 10.58 g (30.8 mmol, 98%).

82.2 1-[1-(4-Chlorophenyl)cyclobutyl]-7-methoxy-3,4-dihydroisoquinoline

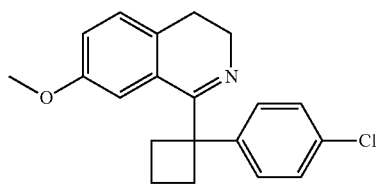 [SMILES: COc1ccc2c(c1)C(C1(c3ccc(Cl)cc3)CCC1)=NCC2]

1-(4-Chlorophenyl)-N-[2-(4-methoxyphenyl)ethyl]cyclobutanecarboxamide (10.58 g, 30.8 mmol) was treated with toluene (100 mL). Phosphoryl trichloride (4.72 g, 30.8 mmol) was added and the reaction mixture was heated under reflux for 8 h. After cooling to room temperature the reaction mixture was concentrated in vacuo and then slowly poured in ice water. Ethyl acetate was added and the organic layer was

82.3 1-[1-(4-Chlorophenyl)cyclobutyl]-3,4-dihydroisoquinolin-7-ol

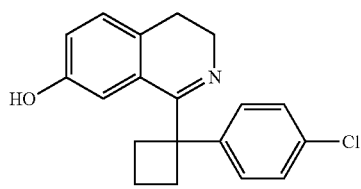 [SMILES: Oc1ccc2c(c1)C(C1(c3ccc(Cl)cc3)CCC1)=NCC2]

The crude 1-[1-(4-chlorophenyl)cyclobutyl]-7-methoxy-3,4-dihydroisoquinoline (10.25 g, 30.8 mmol) was treated with 47% aqueous hydrobromic acid (109 mL) and stirred at 120° C. for 4 h. The reaction mixture was cooled to room temperature. The aqueous layer was decanted. The crude product was treated with dichloromethan, methanol and water and the pH was adjusted to 10 with aqueous 1N sodium hydroxide solution. The product precipitated and the solid was collected by filtration. The product was washed with water and dried in vacuo at 30° C. Yield: 3.56 g (30.3, 12.38 mmol).

82.4 3-({1-[1-(4-Chlorophenyl)cyclobutyl]-3,4-dihydroisoquinolin-7-yl}oxy)propane-1-sulfonic acid

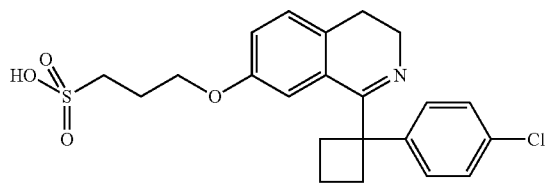 [SMILES: O=S(=O)(O)CCCOc1ccc2c(c1)C(C1(c3ccc(Cl)cc3)CCC1)=NCC2]

The crude 1-[1-(4-chlorophenyl)cyclobutyl]-3,4-dihydroisoquinolin-7-ol (3.5 g, 11.22 mmol) was added to a suspension of sodium hydride (60% in mineral oil, 471 mg, 11.79 mmol) in dimethylformamide (25 mL). After stirring for 30 min at room temperature 1,3-propanesultone (1.44 g, 11.79 mmol) was added dropwise. The reaction mixture was stirred over night at room temperature. The dimethylformamide was removed in vacuo. The crude product (8.4 g) was used for the next step without further purification.

82.5 3-({1-[1-(4-Chlorophenyl)cyclobutyl]-3,4-dihydroisoquinolin-7-yl}oxy)propane-1-sulfonyl chloride

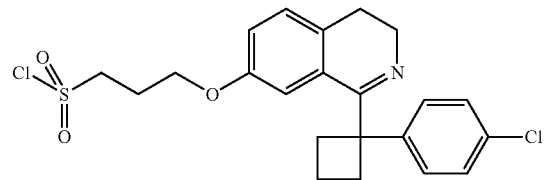 [SMILES: O=S(=O)(Cl)CCCOc1ccc2c(c1)C(C1(c3ccc(Cl)cc3)CCC1)=NCC2]

3-({1-[1-(4-Chlorophenyl)cyclobutyl]-3,4-dihydroisoquinolin-7-yl}oxy)propane-1-sulfonic acid (8.4 g) were dissolved in dichloromethane (70 mL). Pentachloro-$\lambda^5$-phosphane (6.05 g, 29 mmol) were added at room temperature and the reaction mixture was heated under reflux for 3 h. The reaction mixture was poured on ice water and the aqueous layer was extracted with dichloromethane. The combined organic layers were concentrated in vacuo (11 g). The crude product was used for the next step without further purification. For test purposes a sample of the crude product (3.8 g) was purified by flash chromatography (silica, methanol:acetonitrile=1:1) to yield a pale yellow foam (1.5 g).

82.6 3-({1-[1-(4-Chlorophenyl)cyclobutyl]-3,4-dihydroisoquinolin-7-yl}oxy)-N-propylpropane-1-sulfonamide

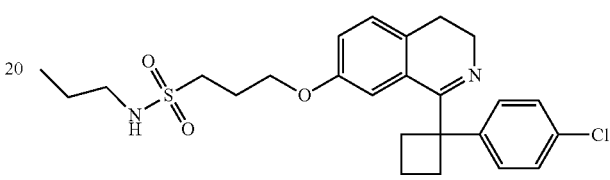

1-Propylamine (314 mg, 5.31 mmol) was dissolved in dichloromethane (3 mL) and a solution of 3-({1-[1-(4-chlorophenyl)cyclobutyl]-3,4-dihydroisoquinolin-7-yl}oxy)propane-1-sulfonyl chloride (200 mg, 0.442 mmol) in dichloromethane (2 mL) was added dropwise. After 1 h stirring at room temperature the reaction mixture was diluted with dichloromethane (10 mL) and was washed with aqueous ammonium chloride solution (2×) and water (1×), dried (MgSO₄) and concentrated in vacuo. The crude product (265 mg) was used for the next step without purification.

82.7 3-({1-[1-(4-Chlorophenyl)cyclobutyl]-1,2,3,4-tetrahydroisoquinolin-7-yl}oxy)-N-propylpropane-1-sulfonamide hydrochloride

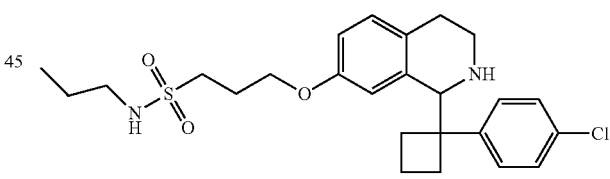

3-({1-[1-(4-Chlorophenyl)cyclobutyl]-3,4-dihydroisoquinolin-7-yl}oxy)-N-propylpropane-1-sulfonamide (260 mg, 0.547 mmol) was dissolved in methanol (5 mL) and water (0.2 mL). Sodiumborohydride (41.4 mg, 1.095 mmol) was added in small portions at room temperature and the reaction mixture was stirred over night. 5N Hydrochloric acid in isopropanol was added until the reaction mixture became acidic. Stirring was continued for 30 min at room temperature. The reaction mixture was concentrated in vacuo. The crude product was dissolved in dichloromethane. Aqueous saturated NaHCO₃ solution (10 mL) and water (10 mL) were added and the aqueous layer was extracted with dichloromethane (2×). The combined organic layers were dried (MgSO₄) and concentrated in vacuo. The crude product was purified by flash chromatography (silica, first dichloromethane, then dichloromethane:methanol=80:1). The purified product was treated with 2N hydrochloric acid in diethylether. The diethylether was removed by destillation. Yield: 120 mg (0.234 mmol, 42.7%, colorless foam).

ESI-MS [M+H$^+$]=477 Calculated for $C_{25}H_{33}ClN_2O_3S$=476.

Example 83

1-[1-(4-Chlorophenyl)cyclobutyl]-7-methoxy-6-[4-(propylsulfonyl)piperazin-1-yl]-1,2,3,4-tetrahydroisoquinoline

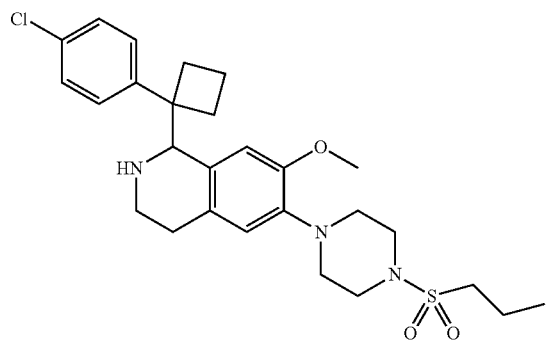 [SMILES: CCCS(=O)(=O)N1CCN(c2cc3c(cc2OC)C(C2(c4ccc(Cl)cc4)CCC2)NCC3)CC1]

83.1 N-[2-(3-Bromo-4-methoxyphenyl)ethyl]-1-(4-chlorophenyl)cyclobutanecarboxamide Prepared from 1-(4-chlorophenyl)cyclobutanecarboxylic acid and 2-(3-bromo-4-methoxyphenyl)ethanamine following the procedure described in example 85, step 1.

83.2 6-Bromo-1-[1-(4-chlorophenyl)cyclobutyl]-7-methoxy-3,4-dihydroisoquinoline Prepared from N-[2-(3-bromo-4-methoxyphenyl)ethyl]-1-(4-chlorophenyl)cyclobutanecarboxamide following the procedure described in example 85, step 2.

83.3 6-Bromo-1-[1-(4-chlorophenyl)cyclobutyl]-7-methoxy-1,2,3,4-tetrahydroisoquinoline Prepared from 6-bromo-1-[1-(4-chlorophenyl)cyclobutyl]-7-methoxy-3,4-dihydroisoquinoline following the procedure described in example 85, step 7.

83.4 tert-Butyl 4-{1-[1-(4-chlorophenyl)cyclobutyl]-7-methoxy-1,2,3,4-tetrahydroisoquinolin-6-yl}piperazine-1-carboxylate A solution of 6-bromo-1-[1-(4-chlorophenyl)cyclobutyl]-7-methoxy-1,2,3,4-tetrahydroisoquinoline (203 mg, 0.5 mmol), Boc-piperazine (93 mg, 0.5 mmol), tris(benzylideaceton)dipalladium (18 mg, 0.02 mmol), sodium-tert-butylate (48 mg, 0.5 mmol) and 2'-(dicyclohexylphosphino)-N,N-dimethylbiphenyl-2-amine 815.7 mg, 0.04 mmol) under nitrogen in toluene (5 ml) was heated in the microwave to 120° C. for 10 minutes. The solvent was removed, the residue dissolved in methylenehloride and extracted with water. The methylenehloride was evaporated and the remaining solid purified by chromatography. Yield: 56 mg (0.1 mmol, 20%)

ESI-MS [M+H$^+$]=512 Calc. for $C_{25}H_{24}ClN_3O_3S$=511

83.5 1-[1-(4-Chlorophenyl)cyclobutyl]-7-methoxy-6-piperazin-1-yl-1,2,3,4-tetrahydroisoquinoline Prepared from tert-butyl 4-{1-[1-(4-chlorophenyl)cyclobutyl]-7-methoxy-1,2,3,4-tetrahydroisoquinolin-6-yl}piperazine-1-carboxylate (56 mg, 0.11 mmol) following the procedure described in example 85, step 5. Yield: 42 mg (0.1 mmol, 93%)

ESI-MS [M+H$^+$]=412 Calc. for $C_{25}H_{24}ClN_3O_3S$=411

83.6 1-[1-(4-chlorophenyl)cyclobutyl]-7-methoxy-6-[4-(propylsulfonyl)piperazin-1-yl]-1,2,3,4-tetrahydroisoquinoline Prepared from 1-[1-(4-chlorophenyl)cyclobutyl]-7-methoxy-6-piperazin-1-yl-1,2,3,4-tetrahydroisoquinoline (31 mg, 0.07 mmol) following the procedure described in example 85, step 6. Yield: 8.8 mg (0.02 mmol, 23%)

ESI-MS [M+H$^+$]=518 Calc. for $C_{25}H_{24}ClN_3O_3S$=517

Example 84

1-[1-(4-Chlorophenyl)cyclobutyl]-7-methoxy-2-(propylsulfonyl)-6-[4-(propylsulfonyl)-piperazin-1-yl]-1,2,3,4-tetrahydroisoquinoline

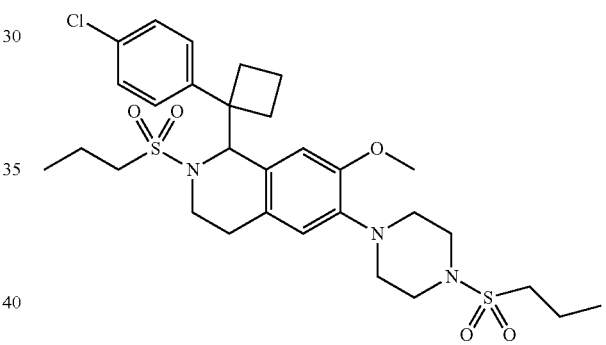

Prepared from 1-[1-(4-chlorophenyl)cyclobutyl]-7-methoxy-6-piperazin-1-yl-1,2,3,4-tetrahydroisoquinoline (31 mg, 0.07 mmol) following the procedure described in example 85, step 6. Yield: 9.2 mg (0.015 mmol, 20%)

ESI-MS [M+H$^+$]=624 Calc. for $C_{30}H_{42}ClN_3O_5S_2$=623

Example 85

N-[2-({1-[1-(4-Chlorophenyl)cyclopropyl]-1,2,3,4-tetrahydroisoquinolin-7-yl}oxy)ethyl]pyridine-3-sulfonamide

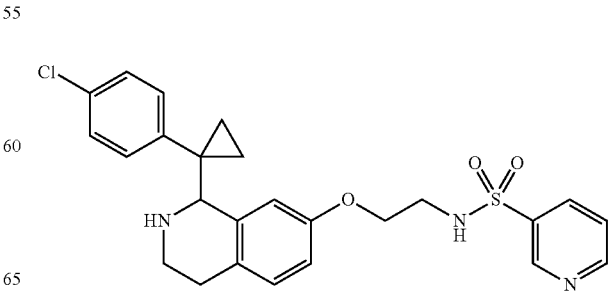

85.1 1-(4-chlorophenyl)-N-[2-(4-methoxyphenyl) ethyl]cyclopropanecarboxamide A solution of 1-(4-chlorophenyl)cyclopropanecarboxylic acid (5.0 g, 25.3 mmol), 2-(4-methoxyphenyl)ethanamine (4.2 g, 28 mmol) and 4-N,N-Dimethylaminopyridin (3.3 g; 28 mmol) in methylenehloride (200 ml) was cooled to −10° C. N-ethyl-N'-(3-Dimethylaminopropyl)-carbodiimid hydrochloride (EDC, 5.3 g, 28 mmol) was added in several portions and the resulting mixture stirred overnight. The reaction mixture was poured into water and consecutively extracted with water, 2N NaOH and 1N HCl. Evaporation of the dried (NaSO$_4$) extract yielded an oily residue that crystallized upon addition of n-heptan, which was used without further purification. Yield 7.0 g (21.2 mmol, 83%).

ESI-MS [M+H$^+$]=330 Calc. for $C_{13}H_{20}ClNO_2$=329

85.2 41-[1-(4-Chlorophenyl)cyclopropyl]-7-methoxy-3,4-dihydroisoquinoline

A solution of 1-(4-chlorophenyl)-N-[2-(4-methoxyphenyl)ethyl]cyclopropane-carboxamide (7.0 g, 21.2 mmol) in phosphoroxytrichloride (POCl$_3$, 50 ml) was heated under reflux for 3 days. Evaporation of POCl$_3$ yielded an oily residue that was dissolved in ethylacetate (100 ml). The mixture was poured into ice and basified with NaOH (50%), extracted with water and dried (Na$_2$SO$_4$). Removal of the solvents afforded a residue which was further purified by column chromatography. Yield: 2.5 g (8.1 mmol, 38%).

ESI-MS [M+H$^+$]=312 Calc. for $C_{19}H_{18}ClNO$=311

85.3 1-[1-(4-Chlorophenyl)cyclopropyl]-3,4-dihydroisoquinolin-7-ol

A solution of 1-[1-(4-chlorophenyl)cyclopropyl]-7-methoxy-3,4-dihydroisoquinoline (700 mg, 2.2 mmol) in methylenehloride (10 ml) under nitrogen was cooled to −78° C. Borontribromide (BBr$_3$, 4.2 ml 1M in methyleneloride, 4.2 mmol) was added dropwise. The reaction was allowed to warm up to room temperature and stirred overnight. Methanol was added (5 ml) and the resulting mixture poured into water neutralized with 1M sodiumbicarbonate and extracted consecutively with methylenehloride and water. The organic layer was dried (Na$_2$SO$_4$), the solvents removed and the black residue purified by chromatography. Yield: 320 mg, (1.1 mmol, 48%).

ESI-MS [M+H$^+$]=297 Calc. for $C_{18}H_{16}ClNO$=298

85.4 tert-Butyl[2-({1-[1-(4-chlorophenyl)cyclopropyl]-3,4-dihydroisoquinolin-7-yl}oxy)ethyl]carbamate 1-[1-(4-chlorophenyl)cyclopropyl]-3,4-dihydroisoquinolin-7-ol (120 mg, 0.4 mmol) was added in several portions to a suspension of sodium hydrid (NaH, 1.3 mmol, activated by removal of oil) in dimethylformamide (DMF, 5 ml). 2-(Boc-amino)ethyl bromide was added after one hour and the resulting mixture stirred for 3 days at room temperature. DMF was evaporated, the residue diluted with ethylacetate and extracted with water. Removal of the solvents from the dried (Na$_2$SO$_4$) extract afforded an oil which was further purified by chromatography. Yield: 100 mg (0.23 mmol, 56%)

85.5 2-({1-[1-(4-Chlorophenyl)cyclopropyl]-3,4-dihydroisoquinolin-7-yl}oxy)ethanamine hydrochloride A solution of tert-butyl[2-({1-[1-(4-chlorophenyl)cyclopropyl]-3,4-dihydroisoquinolin-7-yl}oxy)ethyl]carbamate (440 mg, 1 mmol) methylenehloride (10 ml) was treated with 5N HCl in dimethylether (0.5 ml) and stirred over night at room temperature. The solvent was removed, the residue triturated with diisopropyl ether and the insoluble slid collected. Yield: 370 mg (0.98 mmol, 98%)

ESI-MS [M+H$^+$]=341 Calc. for $C_{20}H_{21}ClN_2O$=340

85.6 N-[2-({1-[1-(4-Chlorophenyl)cyclopropyl]-3,4-dihydroisoquinolin-7-yl}oxy)ethyl]-1-methyl-1H-pyrazole-4-sulfonamide A solution of 2-({1-[1-(4-chlorophenyl)cyclopropyl]-3,4-dihydroisoquinolin-7-yl}oxy)ethanamine (free base, 63 mg, 0.18 mmol), 4-N,N-Dimethylaminopyridin (47 mg, 0.39 mmol), 3-(chlorosulfonyl)pyridiniumchloride in tetrahydrofuran (THF, 10 ml) was stirred at room temperature for 3 days. The solvent was removed, the residue dissolved in ethyl acetate and extracted with water. The ethyl acetate was evaporated and the oily residue purified by chromatography. Yield: 46 mg (0.09 mmol, 52%).

ESI-MS [M+H$^+$]=482 Calc. for $C_{25}H_{24}ClN_3O_3S$=481

85.7 N-[2-({1-[1-(4-Chlorophenyl)cyclopropyl]-1,2,3,4-tetrahydroisoquinolin-7-yl}oxy)ethyl]pyridine-3-sulfonamide A solution of N-[2-({1-[1-(4-chlorophenyl)cyclopropyl]-3,4-dihydroisoquinolin-7-yl}oxy)ethyl]-1-methyl-1H-pyrazole-4-sulfonamide (46 mg, 0.09 mmol), sodium borohydrid (7.2 mg, 0.19 mmol) in water (0.25 ml) and methanol (2 ml) was stirred for 3 days at room temperature. The solvent was removed, the residue dissolved in methylenehloride and extracted with water. The methylenehloride was evaporated and the remaining solid purified by chromatography. Yield: 20 mg (0.04 mmol, 43%)

ESI-MS [M+H$^+$]=484 Calc. for $C_{25}H_{24}ClN_3O_3S$=483

Example 86

N-[2-({1-[1-(4-Chlorophenyl)cyclopropyl]-1,2,3,4-tetrahydroisoquinolin-7-yl}oxy)ethyl]-1-methyl-1H-pyrazole-4-sulfonamide

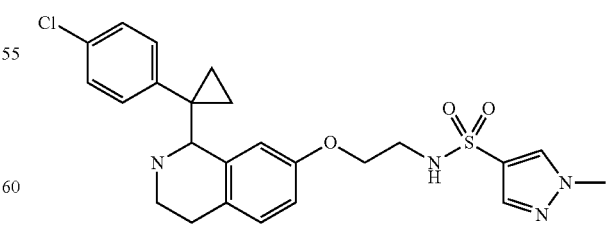

Prepared following the procedure described in example 85 using 1-methyl-1H-pyrazole-4-sulfonyl chloride instead of 3-(chlorosulfonyl)-pyridiniumchloride in step 6.

ESI-MS [M+H$^+$]=487 Calc. for $C_{24}H_{27}ClN_4O_3S$=486

Example 87

N-[2-({1-[1-(4-Chlorophenyl)cyclopropyl]-1,2,3,4-tetrahydroisoquinolin-7-yl}oxy)ethyl]propane-1-sulfonamide hydrochloride

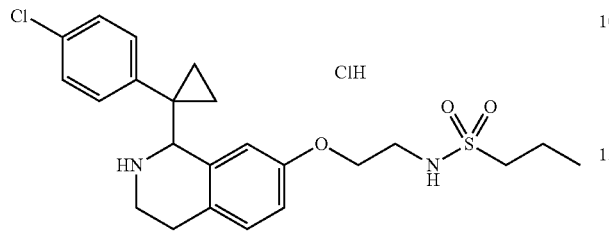

Prepared following the procedure described in example 85 using propane-1-sulfonyl chloride instead of 3-(chlorosulfonyl)pyridiniumchloride in step 6.

ESI-MS [M+H$^+$]=449 Calc. for $C_{23}H_{29}ClN_2O_3S$=448

The following compounds of the invention were prepared in an analogous manner:

Example 88

(1E)-N-[2-({1-[1-(4-Chlorophenyl)cyclobutyl]-1,2,3,4-tetrahydroisoquinolin-7-yl}oxy)ethyl]prop-1-ene-1-sulfonamide hydrochloride

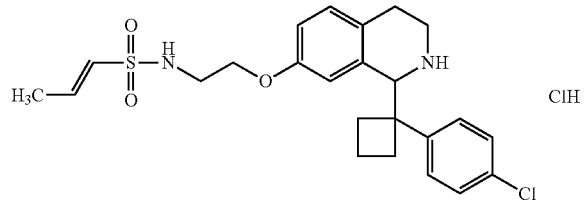 [SMILES: C/C=C/S(=O)(=O)NCCOc1ccc2c(c1)C(C1(c3ccc(Cl)cc3)CCC1)NCC2 ; Cl]

ESI-MS [M+H$^+$]=461

Example 89

N-[2-({1-[1-(4-Chlorophenyl)cyclobutyl]-1,2,3,4-tetrahydroisoquinolin-7-yl}amino)ethyl]propane-1-sulfonamide dihydrochloride

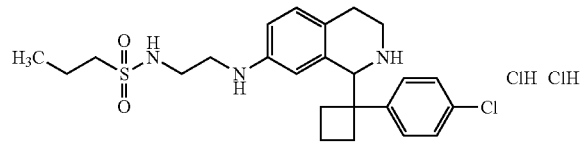 [SMILES: CCCS(=O)(=O)NCCNc1ccc2c(c1)C(C1(c3ccc(Cl)cc3)CCC1)NCC2 ; Cl ; Cl]

ESI-MS [M+H$^+$]=462

Example 90

N-({1-[1-(4-Chlorophenyl)cyclobutyl]-1,2,3,4-tetrahydroisoquinolin-7-yl}methyl)propane-1-sulfonamide hydrochloride

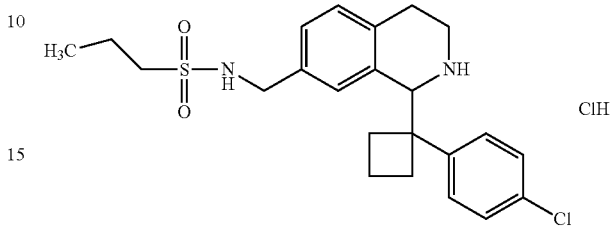

ESI-MS [M+H$^+$]=433

Example 91

N-({1-[1-(4-Chlorophenyl)cyclobutyl]-1,2,3,4-tetrahydroisoquinolin-7-yl}methyl)-1-methyl-1H-pyrazole-4-sulfonamide trifluoroacetate

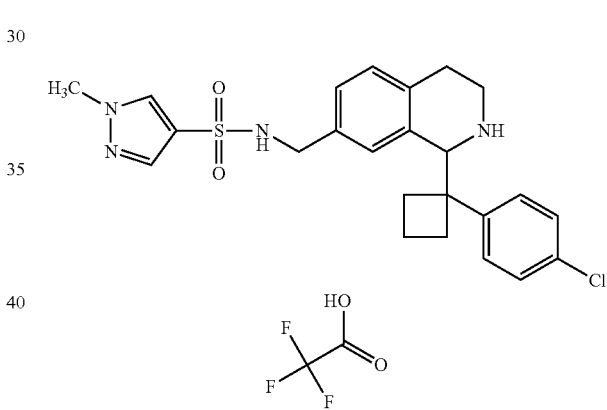

ESI-MS [M+H$^+$]=471

Example 92

1-[1-(4-Chlorophenyl)cyclobutyl]-1,2,3,4-tetrahydroisoquinoline-7-carbonitrile hydrochloride

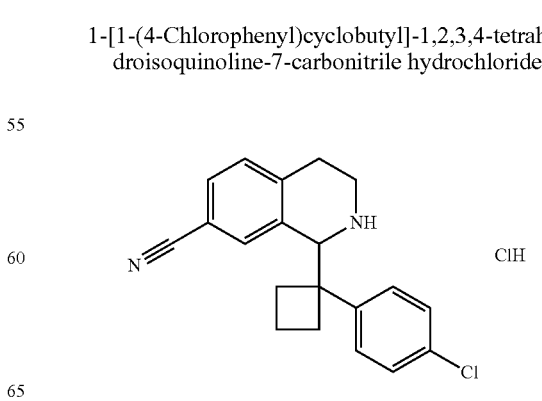

ESI-MS [M+H$^+$]=323

Example 93

N-({1-[1-(4-Chlorophenyl)cyclobutyl]-1,2,3,4-tetrahydroisoquinolin-7-yl}methyl)-1-methyl-1H-imidazole-4-sulfonamide hydrochloride

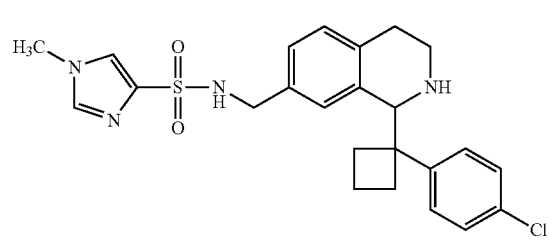

ESI-MS [M+H⁺]=471

Example 94

N-({1-[1-(4-Chlorophenyl)cyclobutyl]-1,2,3,4-tetrahydroisoquinolin-7-yl}methyl)-3-fluoropropane-1-sulfonamide hydrochloride

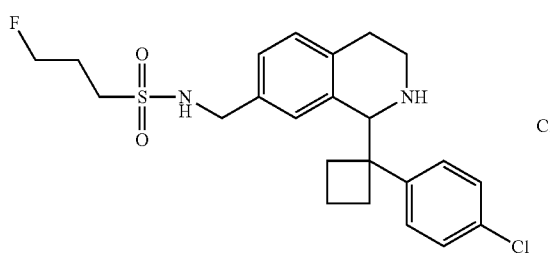

ESI-MS [M+H⁺]=451

Example 95

N-[2-({1-[1-(3-Fluorophenyl)cyclobutyl]-1,2,3,4-tetrahydroisoquinolin-7-yl}oxy)ethyl]propane-1-sulfonamide hydrochloride

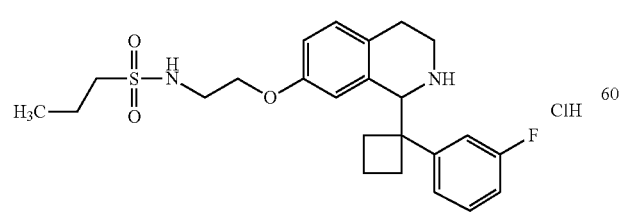

ESI-MS [M+H⁺]=477

Example 96

N-({1-[2-(4-Chlorophenyl)propan-2-yl]-1,2,3,4-tetrahydroisoquinolin-7-yl}methyl)propane-1-sulfonamide hydrochloride

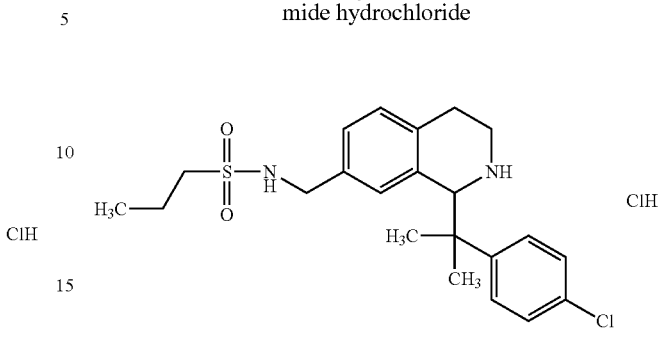

ESI-MS [M+H⁺]=421

Example 97

N-[2-({1-[1-(4-Chlorophenyl)cyclobutyl]-1,2,3,4-tetrahydroisoquinolin-7-yl}oxy)ethyl]-2-hydroxyethanesulfonamide hydrochloride

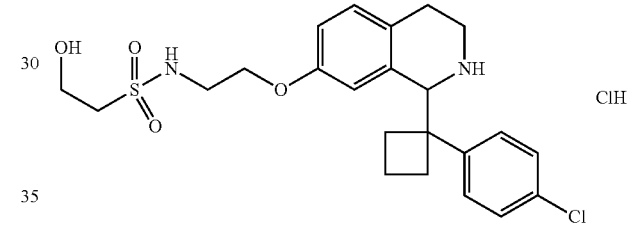

ESI-MS [M+H⁺]=465.2

Example 98

N-[2-({1-[1-(Pyridin-2-yl)cyclobutyl]-1,2,3,4-tetrahydroisoquinolin-7-yl}oxy)ethyl]propane-1-sulfonamide dihydrochloride

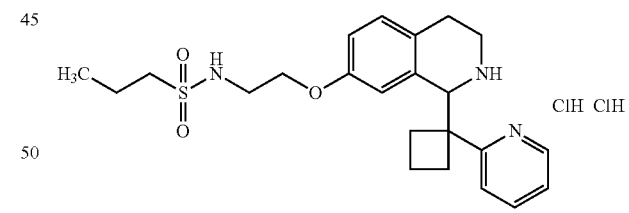

98.1
1-(6-Chloropyridin-2-yl)cyclobutanecarbonitrile

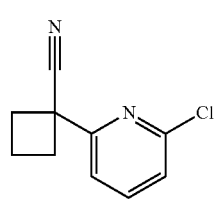 [SMILES: N#CC1(c2cccc(Cl)n2)CCC1]

2-(6-Chloropyridin-2-yl)acetonitrile (5.7 g, 37.4 mmol) was dissolved in dichloromethane (25 ml). 50% aqueous sodium hydroxide solution (26.5 mL) was added dropwise. Benzyl-triethylammonium chloride (0.17 g, 0.747 mmol) was added. 1,3-Dibromopropane (7.54 g, 37.4 mmol) were added dropwise and the reaction mixture was stirred over night at room temperature. The reaction mixture was diluted with dichloromethane and washed with water (3×). The organic layer was dried (MgSO$_4$) and concentrated in vacuo. The crude product was purified by flash chromatography (silica, dichloromethane, methanol). Yield: 2.4 g (10.9 mmol, 29%).

98.2 1-(6-Chloropyridin-2-yl)cyclobutanecarboxylic acid hydrochloride

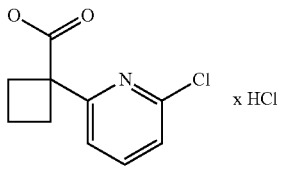 [SMILES: O=C(O)C1(c2cccc(Cl)n2)CCC1]

1-(6-Chloropyridin-2-yl)cyclobutanecarbonitrile (2.4 g, 12.46 mmol) was suspended in concentrated aqueous hydrochloric acid (15.1 ml) and the reaction mixture heated to 100° C. for 30 min in the microwave. The solvent was evaporated in vacuo. Toluol was added and the solvent was evaporated in vacuo. The crude product was used for the next step without further purification. Yield: 2.68 g (10.8 mmol, 87%).

98.3 N-[2-(4-methoxyphenyl)ethyl]-1-(pyridin-2-yl)cyclobutanecarboxamide

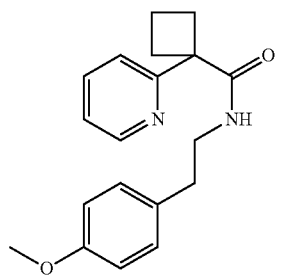 [SMILES: COc1ccc(CCNC(=O)C2(c3ccccn3)CCC2)cc1]

1-(6-Chloropyridin-2-yl)cyclobutanecarboxylic acid hydrochloride (2.6 g, 10.48 mmol) was suspended in dichloromethane (30 ml). 2-(4-Methoxyphenyl)ethanamine (1.743 g, 11.53 mmol) and 4-dimethylaminopyridine (2.56 g, 20.96 mmol) were added and stirring at room temperature was continued for 30 min. The reaction mixture was cooled to 0° C. and 1-ethyl-3-(3-dimethylaminopropyl)carbodiimide hydrochloride (2.21 g, 11.53 mmol) was added in small portions. The reaction mixture was allowed to warm to room temperature and stirring was continued over night. The reaction mixture was poured on water. The aqueous layer was extracted with dichloromethane (3×). The combined organic layers were washed with 5% aqueous citric acid and dried (MgSO$_4$). The solvent was evaporated in vacuo and the crude product purified by flash chromatography (silica, heptane, ethyl acetate). Yield: 709 mg (2.056 mmol, 19.6%).

98.4 1-[1-(6-chloropyridin-2-yl)cyclobutyl]-7-methoxy-3,4-dihydroisoquinoline

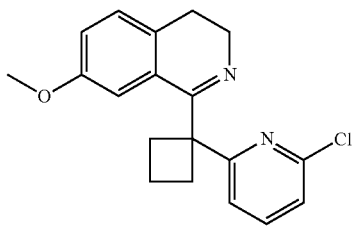 [SMILES: COc1ccc2c(c1)C(C1(c3cccc(Cl)n3)CCC1)=NCC2]

N-[2-(4-methoxyphenyl)ethyl]-1-(pyridin-2-yl)cyclobutanecarboxamide (679 mg, 1.969 mmol) was reacted with phosphorusoxychloride (2.7 ml, 29.5 mmol) in the microwave at 140° C. for 60 min. The reaction mixture was poured on ice water. After 10 min 10% aqueous sodium hydroxide solution was added until pH 8 was reached. The aqueous layer was extracted with dichloromethane. The combined extracts were dried (MgSO$_4$), concentrated in vacuo and the crude product was purified by flash chromatography (silica, dichloromethane, methanol). Yield: 560 mg (1.71 mmol, 87%).

98.5 1-[1-(6-Chloropyridin-2-yl)cyclobutyl]-3,4-dihydroisoquinolin-7-ol

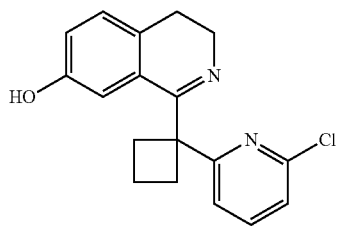 [SMILES: Oc1ccc2c(c1)C(C1(c3cccc(Cl)n3)CCC1)=NCC2]

1-[1-(6-Chloropyridin-2-yl)cyclobutyl]-7-methoxy-3,4-dihydroisoquinoline (550 mg, 1.68 mmol) in 48% aqueous hydrobromic acid (3.8 ml) was heated under reflux for 4 hours. After cooling to room temperature the reaction mixture was poured on ice water. 10% aqueous sodium hydroxide solution was added until pH 8 was reached. The mixture was extracted with dichloromethane (3×). The combined organic extracts were dried (MgSO$_4$), concentrated in vacuo and purified by flash chromatography (silica, dichloromethane, methanol). Yield: 220 mg (0.70 mmol, 42%).

98.6 tert-Butyl[2-({1-[1-(6-chloropyridin-2-yl)cyclobutyl]-3,4-dihydroisoquinolin-7-yl}oxy)ethyl]carbamate

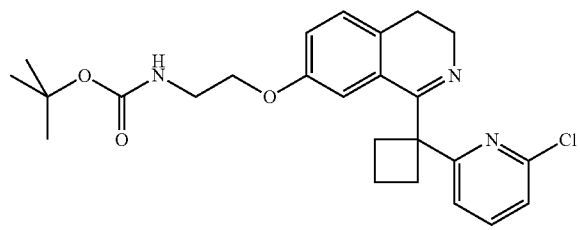 [SMILES: CC(C)(C)OC(=O)NCCOc1ccc2c(c1)C(C1(c3cccc(Cl)n3)CCC1)=NCC2]

90% suspension of sodium hydride in oil (37 mg, 1.387 mmol) was washed with n-pentane and suspended in dry dimethylformamide (5 ml). (1-[1-(6-Chloropyridin-2-yl)cyclobutyl]-3,4-dihydroisoquinolin-7-ol (217 mg, 0.69 mmol) dissolved in dimethylformamide (1 ml) was added dropwise. After stirring at room temperature for 1 hour a solution of tert-butyl-2-bromoethylcarbamate (466 mg, 2.08 mmol) in dimethylformamide (2 ml) was added dropwise. The reaction mixture was heated to 40° C. for 4 hours. The reaction mixture was diluted with water (30 ml) and extracted with dichloromethane (3×). The combined organic extracts were washed with brine twice, dried ($MgSO_4$) and concentrated in vacuo. The crude product was used for the next step without further purification.

98.7 2-({1-[1-(6-Chloropyridin-2-yl)cyclobutyl]-3,4-dihydroisoquinolin-7-yl}oxy)ethanamine

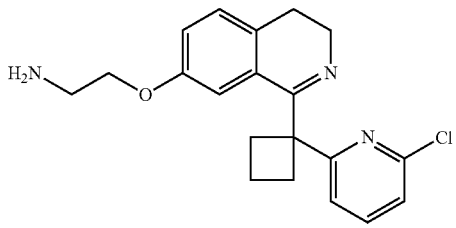 [SMILES: NCCOc1ccc2c(c1)C(C1(c3cccc(Cl)n3)CCC1)=NCC2]

tert-Butyl[2-({1-[1-(6-chloropyridin-2-yl)cyclobutyl]-3,4-dihydroisoquinolin-7-yl}oxy)ethyl]carbamate (300 mg, 0.658 mmol) were dissolved in isopropanole (4 ml). 5N isopropanolic hydrochloric acid (2 ml) was added and the reaction mixture stirred at room temperature for 4 hours. The solvent was evaporated in vacuo and dichloromethane (20 mL) was added. 1N aqueous sodium hydroxide solution was added dropwise until pH 10 was reached. The phases were separated and the aqueous layer was extracted twice with dichloromethane. The combined organich layers were dried ($MgSO_4$) and concentrated in vacuo. The crude product was used for the next step without further purification. Yield: 150 mg (0.422 mmol, 64%).

98.8 N-[2-({1-[1-(6-Chloropyridin-2-yl)cyclobutyl]-3,4-dihydroisoquinolin-7-yl}oxy)ethyl]propane-1-sulfonamide

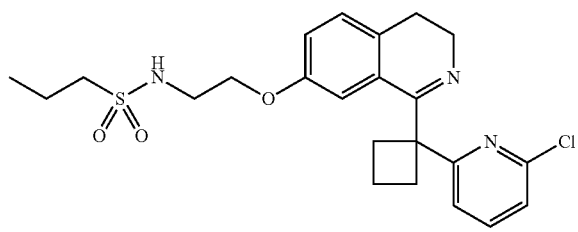 [SMILES: CCCS(=O)(=O)NCCOc1ccc2c(c1)C(C1(c3cccc(Cl)n3)CCC1)=NCC2]

2-({1-[1-(6-Chloropyridin-2-yl)cyclobutyl]-3,4-dihydroisoquinolin-7-yl}oxy)ethanamine (80 mg, 0.225 mmol) was dissolved in pyridine and propane-1-sulfonyl chloride (29 µl, 0.25 mmol) were added. The reaction mixture was stirred at room temperature over night. The solvent was evaporated in vacuo. Toluene was added to the residue and the solvent was evaporated in vacuo (repeated twice). The crude product was purified by flash chromatography (silica, dichloromethane, methanol). Yield: 36 mg (0.078 mmol, 35%).

98.9 N-[2-({1-[1-(6-Chloropyridin-2-yl)cyclobutyl]-1,2,3,4-tetrahydroisoquinolin-7-yl}oxy)ethyl]propane-1-sulfonamide

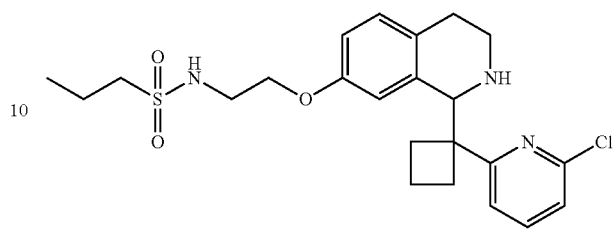

N-[2-({1-[1-(6-Chloropyridin-2-yl)cyclobutyl]-3,4-dihydroisoquinolin-7-yl}oxy)ethyl]propane-1-sulfonamide (36 mg, 0.78 mmol) was dissolved in methanol (1 ml). Sodiumborohydride (12 mg, 0.31 mmol) was added and stirring was continued at room temperature over night. The solvent was evaporated in vacuo and the residue partitioned between dichloromethane and 1N aqueous sodium hydroxide solution. The layers were separated and the organic layer was dried ($MgSO_4$) and concentrated in vacuo. The crude product was used for the next step without further purification. Yield: 9 mg.

98.10 N-[2-({1-[1-(Pyridin-2-yl)cyclobutyl]-1,2,3,4-tetrahydroisoquinolin-7-yl}oxy)ethyl]propane-1-sulfonamide dihydrochloride

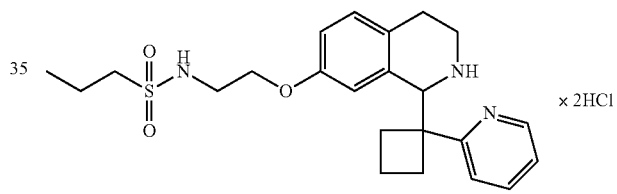

N-[2-({1-[1-(6-Chloropyridin-2-yl)cyclobutyl]-1,2,3,4-tetrahydroisoquinolin-7-yl}oxy)ethyl]propane-1-sulfonamide (9 mg) were dissolved in methanol (1 ml). 10% Palladium on charcoal (5 mg) was added and the reaction mixture was stirred under an atmosphere of hydrogen at room temperature for 36 hours. The catalyst was removed by filtration and washed with methanol. The solvent was evaporated in vacuo. 5N isopropanolic hydrochloric acid (0.5 ml) was added. The solvent was evaporated in vacuo. Yield: 9 mg.
ESI-MS [M+H$^+$]=430 Calculated for $C_{23}H_{31}N_3O_3S$=429.

Example 99

N-{1-[1-(4-Chlorophenyl)cyclobutyl]-1,2,3,4-tetrahydroisoquinolin-7-yl}-N~2~-(propylsulfonyl)glycinamide hydrochloride

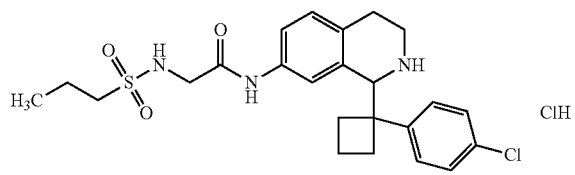 [SMILES: CCCS(=O)(=O)NCC(=O)Nc1ccc2c(c1)C(C1(c3ccc(Cl)cc3)CCC1)NCC2 ; Cl]

ESI-MS [M+H$^+$]=476

Example 100

N-({1-[2-(4-Chlorophenyl)propan-2-yl]-1,2,3,4-tetrahydroisoquinolin-7-yl}methyl)-1-methyl-1H-pyrazole-4-sulfonamide hydrochloride

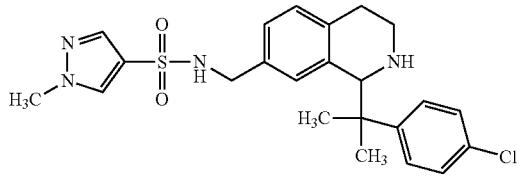

ESI-MS [M+H$^+$]=459

Example 101

N-[2-({1-[1-(3-fluorophenyl)cyclobutyl]-1,2,3,4-tetrahydroisoquinolin-7-yl}oxy)ethyl]pyridine-3-sulfonamide dihydrochloride

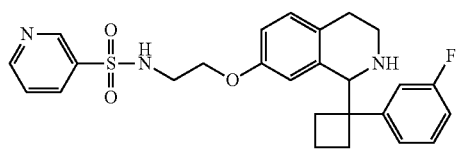

ESI-MS [M+H$^+$]=482

Example 102

N-({1-[2-(4-Chlorophenyl)propan-2-yl]-1,2,3,4-tetrahydroisoquinolin-7-yl}methyl)-1-methyl-1H-imidazole-4-sulfonamide hydrochloride

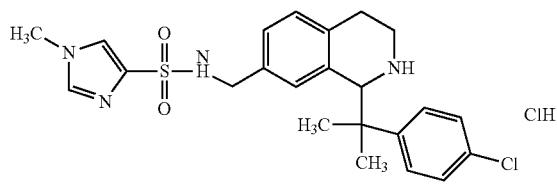 [SMILES: Cn1cnc(S(=O)(=O)NCc2ccc3c(c2)C(C(C)(C)c2ccc(Cl)cc2)NCC3)c1 ; Cl]

ESI-MS [M+H$^+$]=459

Example 103

N-[2-({1-[1-(4-Chlorophenyl)cyclobutyl]-1,2,3,4-tetrahydroisoquinolin-7-yl}oxy)ethyl]-2-hydroxy-2-methylpropane-1-sulfonamide hydrochloride

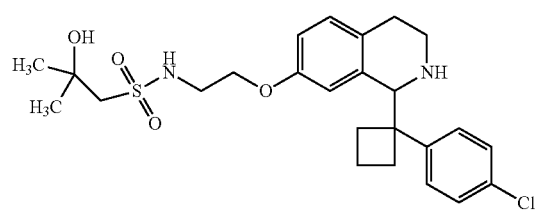

ESI-MS [M+H$^+$]=493.2

Example 104

3-Fluoro-N-[2-({1-[1-(pyridin-2-yl)cyclobutyl]-1,2,3,4-tetrahydroisoquinolin-7-yl}oxy)ethyl]propane-1-sulfonamide hydrochloride

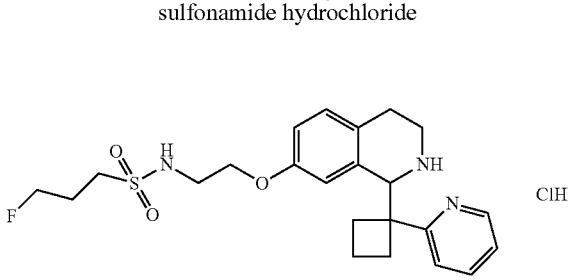

ESI-MS [M+H$^+$]=448.2

Example 105

N-[2-({1-[1-(6-Chloropyridin-2-yl)cyclobutyl]-1,2,3,4-tetrahydroisoquinolin-7-yl}oxy)ethyl]propane-1-sulfonamide dihydrochloride

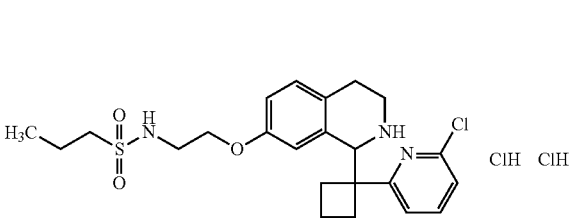 [SMILES: CCCS(=O)(=O)NCCOc1ccc2c(c1)C(C1(c3cccc(Cl)n3)CCC1)NCC2 ; Cl ; Cl]

ESI-MS [M+H$^+$]=464.2

Example 106

N-[2-({1-[1-(3-Fluorophenyl)cyclobutyl]-1,2,3,4-tetrahydroisoquinolin-7-yl}oxy)ethyl]thiophene-2-sulfonamide hydrochloride

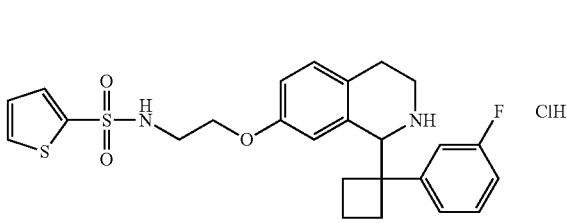 [SMILES: O=S(=O)(NCCOc1ccc2c(c1)C(C1(c3cccc(F)c3)CCC1)NCC2)c1cccs1 ; Cl]

ESI-MS [M+H$^+$]=487

Example 107

1-[2-(4-Chlorophenyl)propan-2-yl]-1,2,3,4-tetrahydroisoquinoline-7-carbonitrile hydrochloride

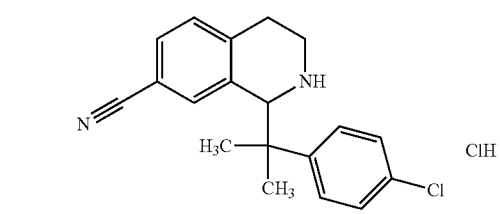 [SMILES: CC(C)(c1ccc(Cl)cc1)C1NCCc2ccc(C#N)cc21 ; Cl]

ESI-MS [M+H$^+$]=311

Example 108

N-({1-[1-(4-Chlorophenyl)cyclobutyl]-1,2,3,4-tetrahydroisoquinolin-7-yl}methyl)pyridine-3-sulfonamide dihydrochloride

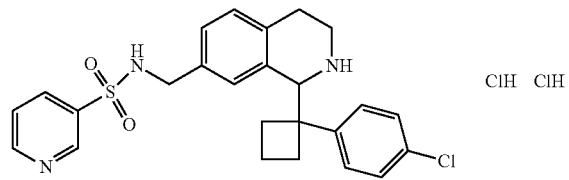 [SMILES: O=S(=O)(NCc1ccc2c(c1)C(C1(c3ccc(Cl)cc3)CCC1)NCC2)c1cccnc1 ; Cl ; Cl]

ESI-MS [M+H⁺]=468

Example 109

3-({1-[1-(4-Chlorophenyl)cyclobutyl]-1,2,3,4-tetrahydroisoquinolin-7-yl}oxy)-N-(pyridin-2-yl)propane-1-sulfonamide dihydrochloride

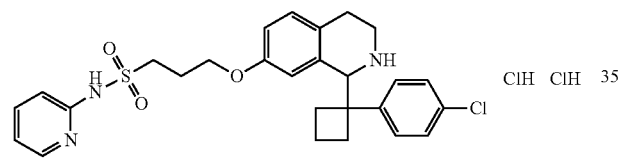

ESI-MS [M+H⁺]=512

Example 110

N-[2-({1-[1-(4-Chlorophenyl)cyclobutyl]-1,2,3,4-tetrahydroisoquinolin-7-yl}oxy)ethyl]-4-(2-fluoroethyl)benzenesulfonamide hydrochloride

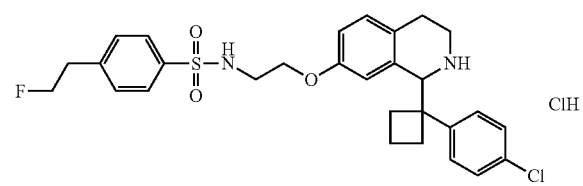 [SMILES: O=S(=O)(NCCOc1ccc2c(c1)C(C1(c3ccc(Cl)cc3)CCC1)NCC2)c1ccc(CCF)cc1 ; Cl]

ESI-MS [M+H⁺]=543

Example 111

N-{1-[1-(4-Chlorophenyl)cyclobutyl]-1,2,3,4-tetrahydroisoquinolin-7-yl}-N~2~-[(1-methyl-1H-imidazol-4-yl)sulfonyl]glycinamide dihydrochloride

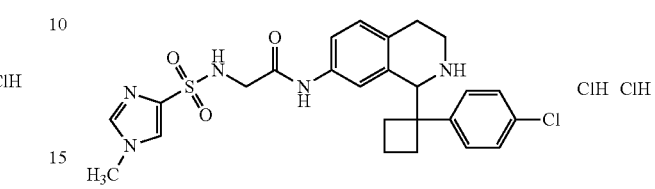

ESI-MS [M+H⁺]=514.2

Example 112

3-({1-[1-(4-Chlorophenyl)cyclobutyl]-1,2,3,4-tetrahydroisoquinolin-7-yl}oxy)-N-phenylpropane-1-sulfonamide hydrochloride

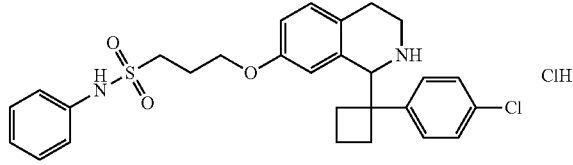 [SMILES: O=S(=O)(CCCOc1ccc2c(c1)C(C1(c3ccc(Cl)cc3)CCC1)NCC2)Nc1ccccc1 ; Cl]

ESI-MS [M+H⁺]=511

Example 113

N-{1-[1-(4-Chlorophenyl)cyclobutyl]-1,2,3,4-tetrahydroisoquinolin-7-yl}-N~2~-[(1-methyl-1H-pyrazol-4-yl)sulfonyl]glycinamide hydrochloride

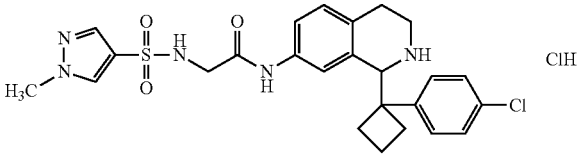 [SMILES: Cn1cc(S(=O)(=O)NCC(=O)Nc2ccc3c(c2)C(C2(c4ccc(Cl)cc4)CCC2)NCC3)cn1 ; Cl]

ESI-MS [M+H⁺]=514.2

Example 114

N-[2-({1-[1-(4-Chlorophenyl)cyclobutyl]-1,2,3,4-tetrahydroisoquinolin-7-yl}oxy)ethyl]-4-(3-fluoropropyl)benzenesulfonamide hydrochloride

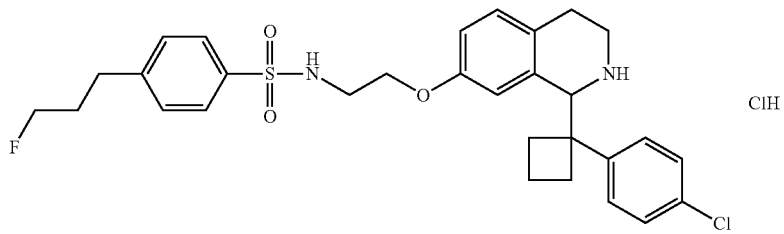 [SMILES: O=S(=O)(NCCOc1ccc2c(c1)C(C1(c3ccc(Cl)cc3)CCC1)NCC2)c1ccc(CCCF)cc1 ; Cl]

ESI-MS [M+H$^+$]=557

Example 115

N-[4-({1-[1-(4-Chlorophenyl)cyclobutyl]-1,2,3,4-tetrahydroisoquinolin-7-yl}oxy)phenyl]thiophene-2-sulfonamide hydrochloride

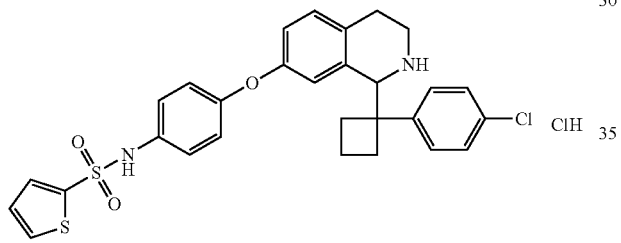

ESI-MS [M+H$^+$]=551

Example 116

N-[2-({1-[1-(4-Chlorophenyl)cyclobutyl]-1,2,3,4-tetrahydroisoquinolin-7-yl}oxy)phenyl]thiophene-2-sulfonamide hydrochloride

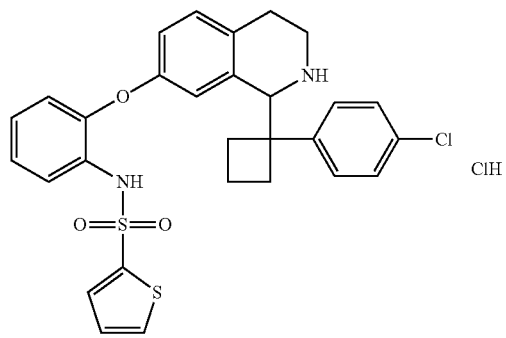 [SMILES: O=S(=O)(Nc1ccccc1Oc1ccc2c(c1)C(C1(c3ccc(Cl)cc3)CCC1)NCC2)c1cccs1 ; Cl]

ESI-MS [M+H$^+$]=551

Example 117

3-({1-[1-(4-Chlorophenyl)cyclobutyl]-1,2,3,4-tetrahydroisoquinolin-7-yl}oxy)-N-(propan-2-yl)propane-1-sulfonamide hydrochloride

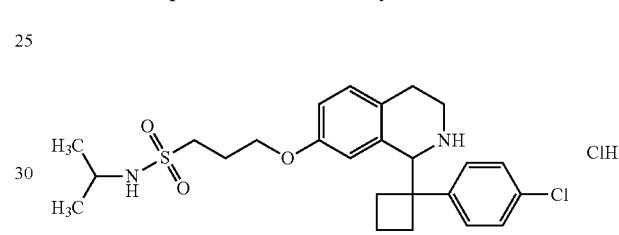

ESI-MS [M+H$^+$]=477

Example 118

N-tert-Butyl-3-({1-[1-(4-chlorophenyl)cyclobutyl]-1,2,3,4-tetrahydroisoquinolin-7-yl}oxy)propane-1-sulfonamide hydrochloride

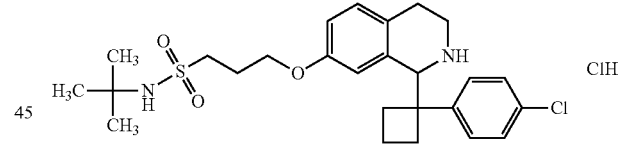

ESI-MS [M+H$^+$]=491

Example 119

N-[6-({1-[1-(4-Chlorophenyl)cyclobutyl]-1,2,3,4-tetrahydroisoquinolin-7-yl}oxy)pyridin-3-yl]propane-1-sulfonamide dihydrochloride

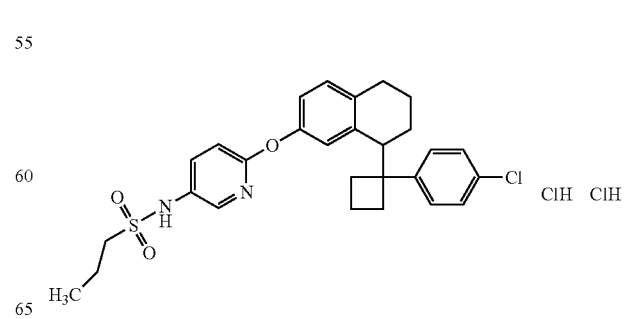

ESI-MS [M+H$^+$]=512

Example 120

1-[1-(3-Fluorophenyl)cyclobutyl]-1,2,3,4-tetrahydroisoquinolin-7-yl propane-1-sulfonate hydrochloride

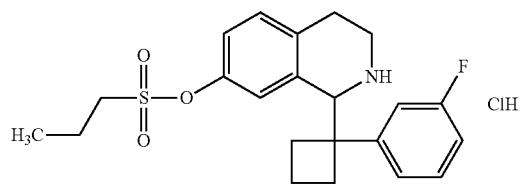 [SMILES: CCCS(=O)(=O)Oc1ccc2c(c1)C(C1(c3cccc(F)c3)CCC1)NCC2 ; Cl]

ESI-MS [M+H⁺]=404

Example 121

3-({1-[1-(4-Chlorophenyl)cyclobutyl]-1,2,3,4-tetrahydroisoquinolin-7-yl}oxy)-N-(2-methoxyphenyl)propane-1-sulfonamide hydrochloride

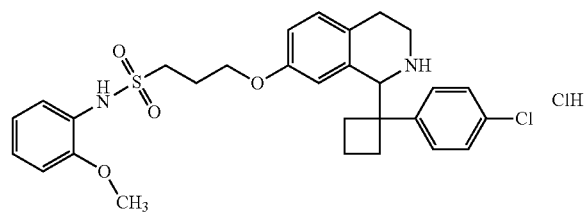 [SMILES: COc1ccccc1NS(=O)(=O)CCCOc1ccc2c(c1)C(C1(c3ccc(Cl)cc3)CCC1)NCC2 ; Cl]

ESI-MS [M+H⁺]=541

Example 122

N-[2-({1-[1-(4-Chlorophenyl)cyclobutyl]-1,2,3,4-tetrahydroisoquinolin-7-yl}oxy)phenyl]pyridine-3-sulfonamide dihydrochloride

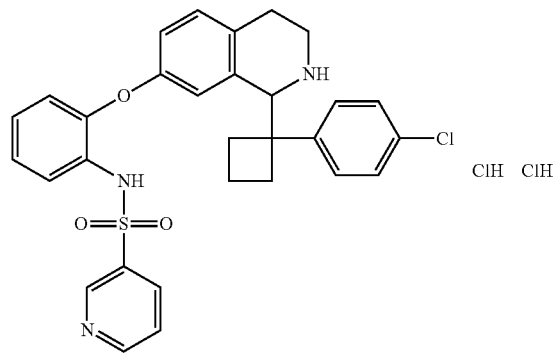 [SMILES: O=S(=O)(Nc1ccccc1Oc1ccc2c(c1)C(C1(c3ccc(Cl)cc3)CCC1)NCC2)c1cccnc1 ; Cl ; Cl]

ESI-MS [M+H⁺]=546

Example 123 tert-Butyl 4-{[3-({1-[1-(4-chlorophenyl)cyclobutyl]-1,2,3,4-tetrahydroisoquinolin-7-yl}oxy)propyl]sulfonyl}piperazine-1-carboxylate

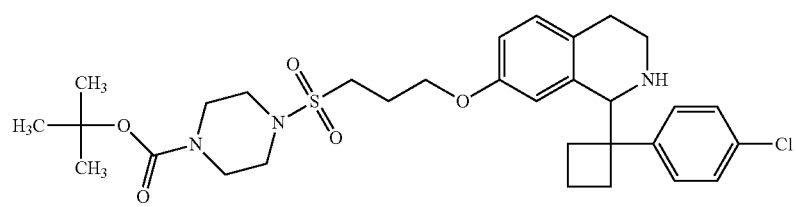 [SMILES: CC(C)(C)OC(=O)N1CCN(S(=O)(=O)CCCOc2ccc3c(c2)C(C2(c4ccc(Cl)cc4)CCC2)NCC3)CC1]

ESI-MS [M+H⁺]=604

Example 124

N-[6-({1-[1-(4-Chlorophenyl)cyclobutyl]-1,2,3,4-tetrahydroisoquinolin-7-yl}oxy)pyridin-3-yl]thiophene-2-sulfonamide dihydrochloride

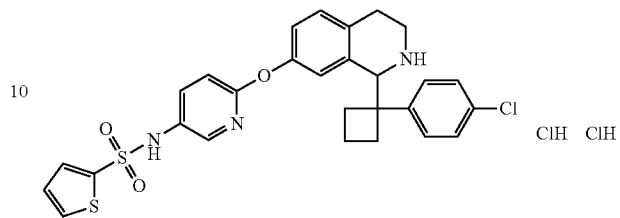

ESI-MS [M+H⁺]=552

Example 125

N-({1-[1-(Pyridin-2-yl)cyclobutyl]-1,2,3,4-tetrahydroisoquinolin-7-yl}methyl)propane-1-sulfonamide trifluoroacetate

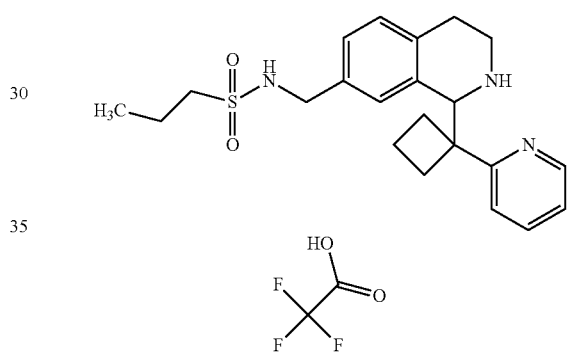

125.1 1-[1-(Pyridin-2-yl)cyclobutyl]-1,2,3,4-tetrahydroisoquinolin-7-ol

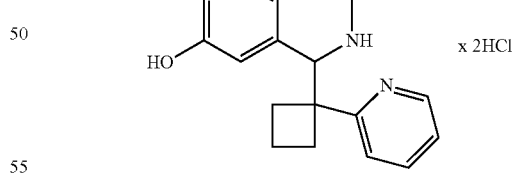

1-[1-(6-Chloropyridin-2-yl)cyclobutyl]-3,4-dihydroisoquinolin-7-ol (1.93 g, 6.17 mmol) were dissolved in methanol (100 ml) under an atmosphere of nitrogen. 10% Pd/C (0.19 g) were added and the reaction mixture stirred at room temperature under an atmosphere of hydrogen for 48 hours. The catalyst was removed by filtration and the solvent was evaporated in vacuo. The crude product was used without further purification for the next step. Yield: 1.75 g (5.52 mmol, 90%).

125.2 tert-Butyl 7-hydroxy-1-[1-(pyridin-2-yl)cyclobutyl]-3,4-dihydroisoquinoline-2(1H)-carboxylate

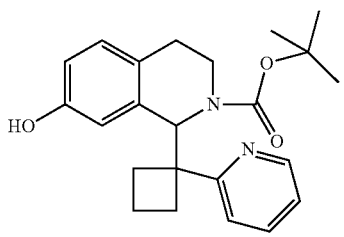 [SMILES: CC(C)(C)OC(=O)N1CCc2ccc(O)cc2C1C1(c2ccccn2)CCC1]

1-[1-(Pyridin-2-yl)cyclobutyl]-1,2,3,4-tetrahydroisoquinolin-7-ol (1.75 g, 5.52 mmol) was suspended in dichloromethane (200 ml). Diisopropylethylamine (2.89 ml, 16.57 mmol) were added at 0° C. followed by di-tert-butyl dicarbonate (1.21 g, 5.52 mmol). The reaction mixture was allowed to warm to room temperature and stirring was continued over night. The reaction mixture was washed successively with aqueous ammonium chloride solution (3×) and aqueous sodium hydrogencarbonate. The organic layer was dried (MgSO4) and concentrated in vacuo. The crude product was used without further purification for the next step. Yield: 2.1 g.

125.3 tert-Butyl 1-[1-(pyridin-2-yl)cyclobutyl]-7-{[(trifluoromethyl)sulfonyl]oxy}-3,4-dihydroisoquinoline-2(1H)-carboxylate

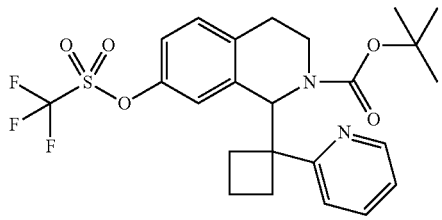 [SMILES: CC(C)(C)OC(=O)N1CCc2ccc(OS(=O)(=O)C(F)(F)F)cc2C1C1(c2ccccn2)CCC1]

tert-Butyl 7-hydroxy-1-[1-(pyridin-2-yl)cyclobutyl]-3,4-dihydroisoquinoline-2(1H)-carboxylate (2.1 g, 5.52 mmol) was dissolved in dichloromethane (200 ml). 1,1,1-Trifluoro-N-phenyl-N-(trifluoromethylsulfonyl)methanesulfonamide (2.07 g, 5.8 mmol) was added in small portions at 5° C. followed by dropwise addition of triethylamine (2.3 ml, 16.56 mmol) in dichloromethane (46 mL). The reaction mixture was stirred for 6 hours at room temperature and then washed successively with aqueous ammonium chloride solution (3×) and aqueous sodium hydrogencarbonate solution. The organic layer was dried (MgSO4) and concentrated in vacuo. The crude product was purified by flash chromatography (silica, dichloromethane, methanol). Yield: 1.735 g (61%).

125.4 tert-Butyl 7-cyano-1-[1-(pyridin-2-yl)cyclobutyl]-3,4-dihydroisoquinoline-2(1H)-carboxylate

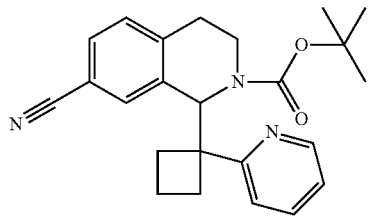 [SMILES: CC(C)(C)OC(=O)N1CCc2ccc(C#N)cc2C1C1(c2ccccn2)CCC1]

Dipalladium trisdibenzylidene acetone (0.14 g, 0.153 mmol) and diphenylphosphinoferrocene (0.338 g, 0.61 mmol) were suspended in dimethylformamide (15 ml) under an argon atmosphere. tert-Butyl 1-[1-(pyridin-2-yl)cyclobutyl]-7-{[(trifluoromethyl)sulfonyl]oxy}-3,4-dihydroisoquinoline-2(1H)-carboxylate (0.782 g, 1.562 mmol) was added and the reaction mixture was heated to 90° C. Zinc cyanide (0.215 g, 1.831 mmol) was added over 30 min in small portions. Stirring at 90° C. was continued for 15 min. After cooling to room temperature the catalyst was removed by filtration and washed with dimethylformamide. The dimethylformamide filtrate was poured in water (200 ml). The water was extracted with dichloromethane (3×). The combined organic extracts were washed with water, dried (MgSO$_4$) and concentrated in vacuo. The crude product was purified by flash chromatography (silica, dichloromethane, methanol). Yield: 197 mg (0.506 mmol, 33%).

125.5 tert-Butyl 7-(aminomethyl)-1-[1-(pyridin-2-yl)cyclobutyl]-3,4-dihydroisoquinoline-2(1H)-carboxylate

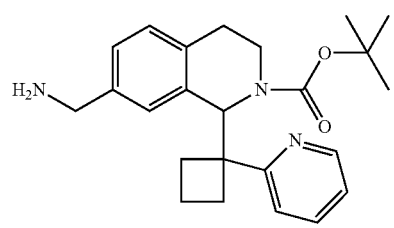 [SMILES: CC(C)(C)OC(=O)N1CCc2ccc(CN)cc2C1C1(c2ccccn2)CCC1]

tert-Butyl 7-cyano-1-[1-(pyridin-2-yl)cyclobutyl]-3,4-dihydroisoquinoline-2(1H)-carboxylate (169 mg, 0.434 mmol) was dissolved in methanol (15 mL) under an atmosphere of nitrogen. Raney nickel (100 mg) was added and the reaction mixture stirred at room temperature under an atmosphere of hydrogen for 9 hours. The catalyst was removed by filtration. The filtrate was concentrated in vacuo and the crude product was purified by flash chromatography (silica, dichloromethane, methanol). Yield: 103 mg (0.262 mmol, 60%).

125.6 tert-Butyl 7-{[(propylsulfonyl)amino]methyl}-1-[1-(pyridin-2-yl)cyclobutyl]-3,4-dihydroisoquinoline-2(1H)-carboxylate

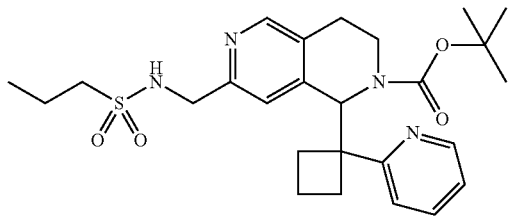 [SMILES: CCCS(=O)(=O)NCc1cc2c(cn1)CCN(C(=O)OC(C)(C)C)C2C1(c2ccccn2)CCC1]

tert-Butyl 7-(aminomethyl)-1-[1-(pyridin-2-yl)cyclobutyl]-3,4-dihydroisoquinoline-2(1H)-carboxylate (33 mg, 0.084 mmol) was dissolved in dichloromethane. 4-Dimethylaminopyridine (30.7 mg, 0.252 mmol) was added. After stirring for 5 min propane-1-sulfonyl chloride (12 mg, 0.084 mmol) was added and stirring was continued over night. The reaction mixture was diluted with dichloromethane (30 ml) and washed with aqueous ammonium chloride solution. The organic layer was washed with water, dried (MgSO$_4$) and concentrated in vacuo. The crude product was used for the next step without further purification. Yield: 37 mg.

125.7 N-({1-[1-(Pyridin-2-yl)cyclobutyl]-1,2,3,4-tetrahydroisoquinolin-7-yl}methyl)propane-1-sulfonamide bistrifluoroacetate

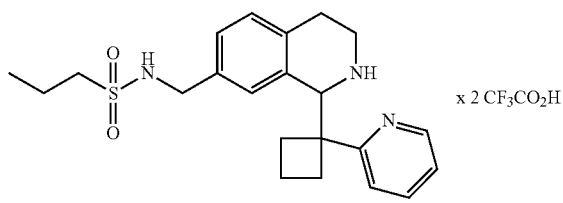 [SMILES: CCCS(=O)(=O)NCc1ccc2c(c1)C(C1(c3ccccn3)CCC1)NCC2]

tert-Butyl 7-{[(propylsulfonyl)amino]methyl}-1-[1-(pyridin-2-yl)cyclobutyl]-3,4-dihydroisoquinoline-2(1H)-carboxylate (30 mg, 0.060 mmol) was dissolved in 5N isopropanolic hydrochloride solution (1 ml). After deprotection was completed (TLC) the solvent was evaporated in vacuo. The crude product was purified by preparative HPLC (RP18, acetonitrile, water, 0.1% TFA). Yield: 1.5 mg (3.75 µmol, 6.3%).

ESI-MS [M+H$^+$]=400 Calculated for C$_{22}$H$_{29}$N$_3$O$_2$S=399.

Example 126 tert-Butyl[2-({[3-({1-[1-(4-chlorophenyl)cyclobutyl]-1,2,3,4-tetrahydroisoquinolin-7-yl}oxy)propyl]sulfonyl}amino)ethyl]carbamate

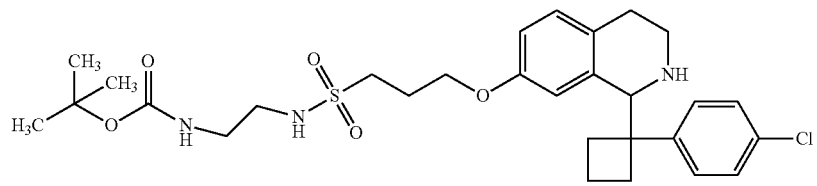 [SMILES: CC(C)(C)OC(=O)NCCNS(=O)(=O)CCCOc1ccc2c(c1)C(C1(c3ccc(Cl)cc3)CCC1)NCC2]

ESI-MS [M+H$^+$]=578

Example 127

N-[2-({1-[1-(4-Chlorophenyl)cyclobutyl]-1,2,3,4-tetrahydroisoquinolin-7-yl}oxy)pyridin-3-yl]thiophene-2-sulfonamide dihydrochloride

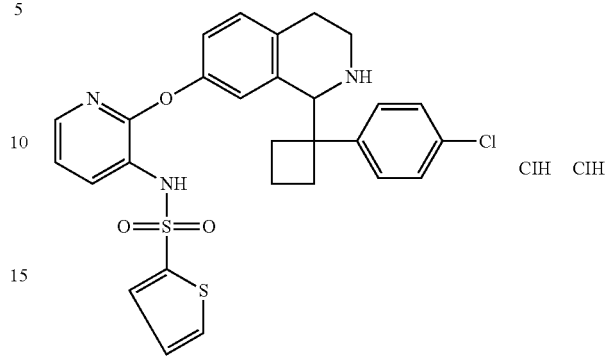

ESI-MS [M+H$^+$]=552

Example 128

N-[2-({1-[1-(4-Chlorophenyl)cyclobutyl]-1,2,3,4-tetrahydroisoquinolin-7-yl}oxy)pyridin-3-yl]propane-1-sulfonamide dihydrochloride

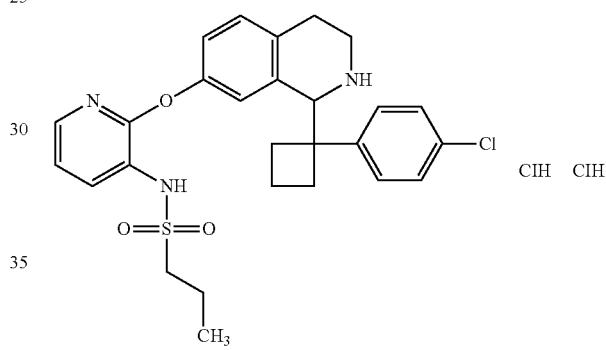

ESI-MS [M+H$^+$]=512

Example 129

1-[1-(Pyridin-2-yl)cyclobutyl]-1,2,3,4-tetrahydroisoquinoline-7-carbonitrile hydrochloride

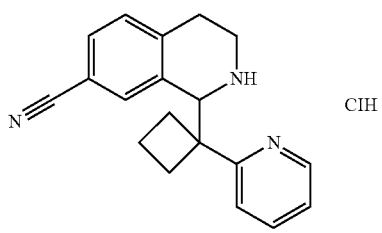 [SMILES: N#Cc1ccc2c(c1)C(C1(c3ccccn3)CCC1)NCC2 ; "CIH"]

ESI-MS [M+H$^+$]=290.2

Example 130

N-(2-Aminoethyl)-3-({1-[1-(4-chlorophenyl)cy-clobutyl]-1,2,3,4-tetrahydroisoquinolin-7-yl}oxy)propane-1-sulfonamide dihydrochloride

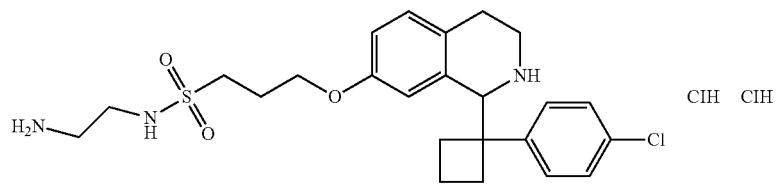

ESI-MS [M+H⁺]=478

Example 131

N-[6-({1-[1-(4-Chlorophenyl)cyclobutyl]-1,2,3,4-tetrahydroisoquinolin-7-yl}oxy)pyridin-3-yl]pyridine-3-sulfonamide trihydrochloride

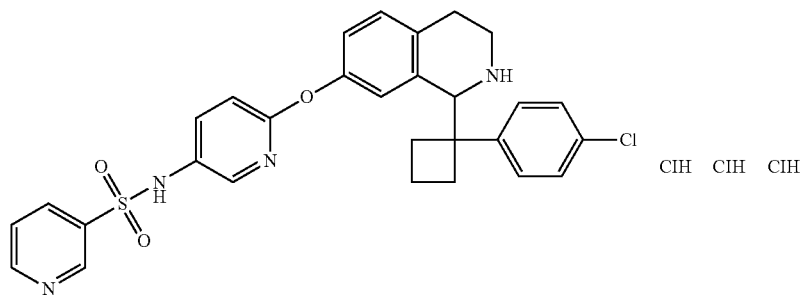

ESI-MS [M+H⁺]=547

Example 132

3-({1-[1-(4-Chlorophenyl)cyclobutyl]-1,2,3,4-tetrahydroisoquinolin-7-yl}oxy)-N-[2-(dimethylamino)ethyl]propane-1-sulfonamide dihydrochloride

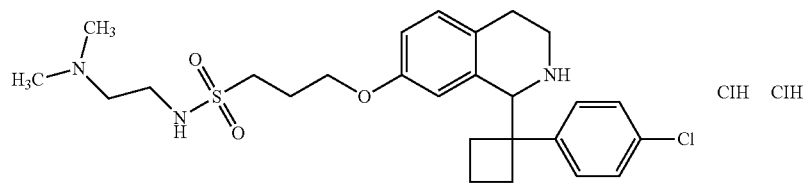

ESI-MS [M+H⁺]=506

Example 133

1-[1-(4-Chlorophenyl)cyclobutyl]-7-[3-(piperazin-1-ylsulfonyl)propoxy]-1,2,3,4-tetrahydroisoquinoline dihydrochloride

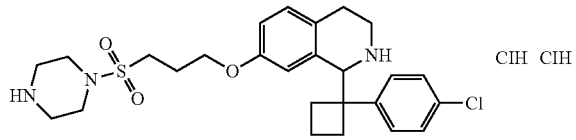 [SMILES: O=S(=O)(CCCOc1ccc2c(c1)C(C1(c3ccc(Cl)cc3)CCC1)NCC2)N1CCNCC1 ; "CIH" ; "CIH"]

ESI-MS [M+H⁺]=504

Example 134

1-Cyclopropyl-N-({1-[1-(pyridin-2-yl)cyclobutyl]-1,2,3,4-tetrahydroisoquinolin-7-yl}methylmethanesulfonamide trifluoroacetate

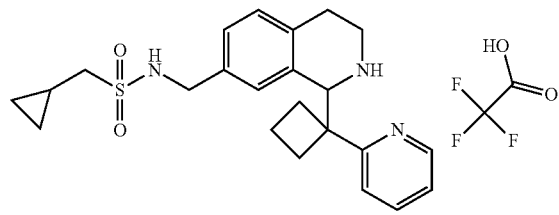

ESI-MS [M+H⁺]=412.2

Example 135

3-({1-[1-(4-Chlorophenyl)cyclobutyl]-1,2,3,4-tetrahydroisoquinolin-7-yl}oxy)-N-(2-methoxyethyl)propane-1-sulfonamide hydrochloride

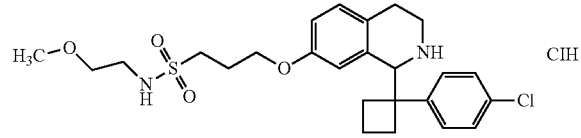 [SMILES: COCCNS(=O)(=O)CCCOc1ccc2c(c1)C(C1(c3ccc(Cl)cc3)CCC1)NCC2 ; "CIH"]

ESI-MS [M+H⁺]=493

Example 136

N-[2-({1-[1-(4-Chlorophenyl)cyclobutyl]-1,2,3,4-tetrahydroisoquinolin-7-yl}oxy)pyridin-3-yl]pyridine-3-sulfonamide trihydrochloride

ESI-MS [M+H⁺]=547

Example 137

N-(3-Aminopropyl)-3-({1-[1-(4-chlorophenyl)cyclobutyl]-1,2,3,4-tetrahydroisoquinolin-7-yl}oxy)propane-1-sulfonamide dihydrochloride

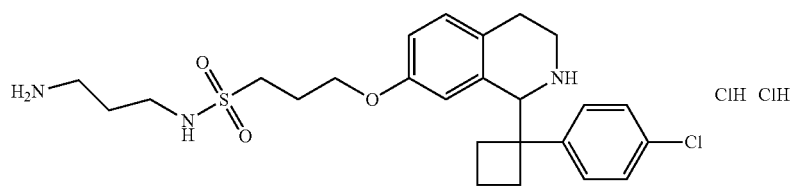 [SMILES: NCCCNS(=O)(=O)CCCOc1ccc2c(c1)C(C1(c3ccc(Cl)cc3)CCC1)NCC2 ; Cl ; Cl]

ESI-MS [M+H⁺]=492

Example 138

N-[2-({1-[1-(4-Chlorophenyl)-3,3-difluorocyclobutyl]-1,2,3,4-tetrahydroisoquinolin-7-yl}oxy)ethyl]-1-methyl-1H-pyrazole-4-sulfonamide (isomer 1)

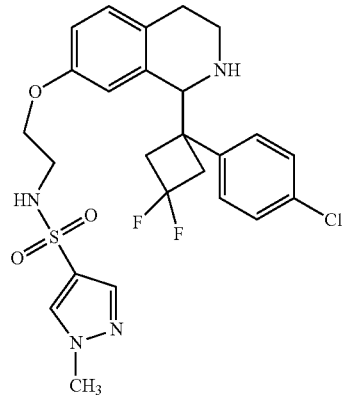 [SMILES: Cn1cc(S(=O)(=O)NCCOc2ccc3c(c2)C(C2(c4ccc(Cl)cc4)CC(F)(F)C2)NCC3)cn1]

ESI-MS [M+H$^+$]=537.1

Example 139

N-[2-({1-[2-(4-Chlorophenyl)propan-2-yl]-1,2,3,4-tetrahydroisoquinolin-7-yl}oxy)ethyl]propane-1-sulfonamide

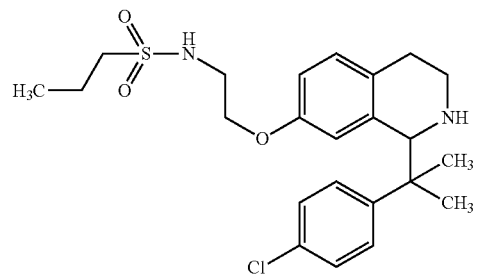 [SMILES: CCCS(=O)(=O)NCCOc1ccc2c(c1)C(C(C)(C)c1ccc(Cl)cc1)NCC2]

ESI-MS [M+H$^+$]=451.2

Example 140

N-[2-({1-[1-(4-Chlorophenyl)cyclobutyl]-1,2,3,4-tetrahydroisoquinolin-7-yl}oxy)ethyl]-3-fluoropropane-1-sulfonamide hydrochloride

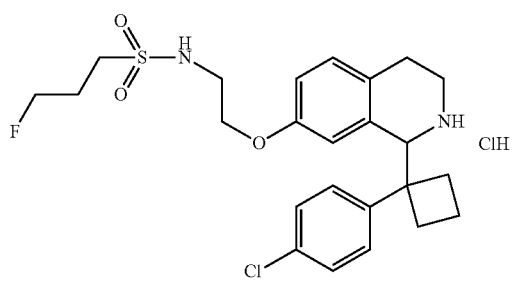 [SMILES: O=S(=O)(CCCF)NCCOc1ccc2c(c1)C(C1(c3ccc(Cl)cc3)CCC1)NCC2 ; Cl]

ESI-MS [M+H$^+$]=481.2

Example 141

N-[2-({(1S)-1-[1-(4-Chlorophenyl)cyclobutyl]-1,2,3,4-tetrahydroisoquinolin-7-yl}oxy)ethyl]pyridine-3-sulfonamide hydrochloride

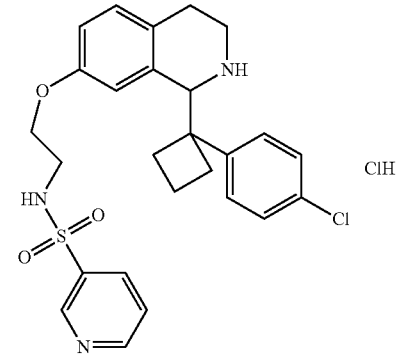 [SMILES: O=S(=O)(NCCOc1ccc2c(c1)C(C1(c3ccc(Cl)cc3)CCC1)NCC2)c1cccnc1 ; Cl]

ESI-MS [M+H$^+$]=498.2

Example 142

N-[2-({1-[1-(3-Amino-4-chlorophenyl)cyclobutyl]-1,2,3,4-tetrahydroisoquinolin-7-yl}oxy)ethyl]propane-1-sulfonamide dihydrochloride

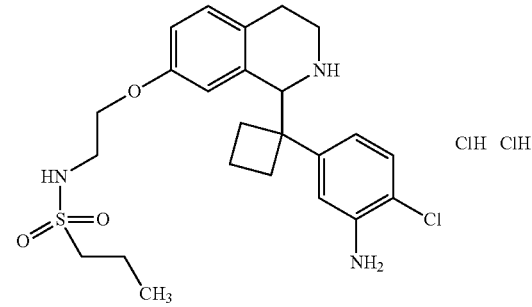 [SMILES: CCCS(=O)(=O)NCCOc1ccc2c(c1)C(C1(c3ccc(Cl)c(N)c3)CCC1)NCC2 ; Cl ; Cl]

ESI-MS [M+H$^+$]=478.2

Example 143

N'-[2-({1-[1-(4-Chlorophenyl)cyclobutyl]-1,2,3,4-tetrahydroisoquinolin-7-yl}oxy)ethyl]-N,N-dimethylsulfuric diamide hydrochloride

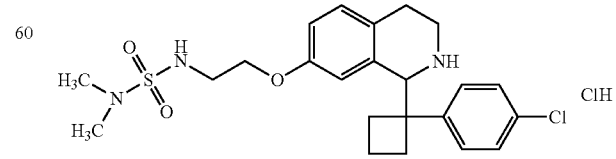

ESI-MS [M+H$^+$]=464.2

Example 144

N-[2-({1-[1-(4-Chlorophenyl)cyclobutyl]-1,2,3,4-tetrahydroisoquinolin-7-yl}oxy)ethyl]-3,3,3-trifluoropropane-1-sulfonamide hydrochloride

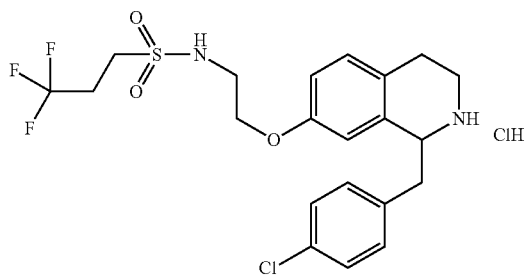 [SMILES: O=S(=O)(CCC(F)(F)F)NCCOc1ccc2c(c1)C(Cc1ccc(Cl)cc1)NCC2 ; Cl]

ESI-MS [M+H$^+$]=517.1

Example 145

N-[2-({1-[1-(4-Chlorophenyl)ethyl]-1,2,3,4-tetrahydroisoquinolin-7-yl}oxy)ethyl]propane-1-sulfonamide hydrochloride

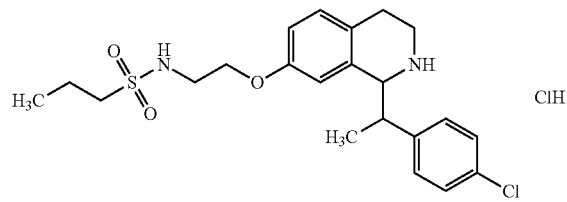 [SMILES: CCCS(=O)(=O)NCCOc1ccc2c(c1)C(C(C)c1ccc(Cl)cc1)NCC2 ; Cl]

ESI-MS [M+H$^+$]=437.1

Example 146

2-Amino-N-[2-({(1S)-1-[1-(4-chlorophenyl)cyclobutyl]-1,2,3,4-tetrahydroisoquinolin-7-yl}oxy)ethyl]ethanesulfonamide dihydrochloride

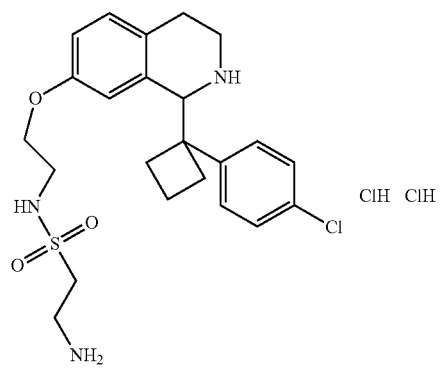 [SMILES: NCCS(=O)(=O)NCCOc1ccc2c(c1)C(C1(c3ccc(Cl)cc3)CCC1)NCC2 ; Cl ; Cl]

ESI-MS [M+H$^+$]=464.2

Example 147

4-Amino-N-[2-({1-[1-(4-chlorophenyl)cyclobutyl]-1,2,3,4-tetrahydroisoquinolin-7-yl}oxy)ethyl]benzenesulfonamide dihydrochloride

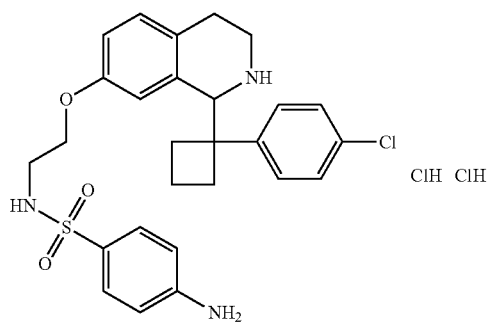 [SMILES: Nc1ccc(S(=O)(=O)NCCOc2ccc3c(c2)C(C2(c4ccc(Cl)cc4)CCC2)NCC3)cc1 ; Cl ; Cl]

ESI-MS [M+H$^+$]=512.2

Example 148

N-[2-({1-[1-(4-Chlorophenyl)cyclobutyl]-1,2,3,4-tetrahydroisoquinolin-7-yl}oxy)ethyl]pyrrolidine-3-sulfonamide dihydrochloride (isomer 1)

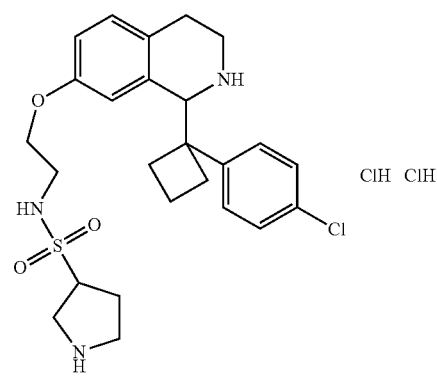 [SMILES: O=S(=O)(NCCOc1ccc2c(c1)C(C1(c3ccc(Cl)cc3)CCC1)NCC2)C1CCNC1 ; Cl ; Cl]

ESI-MS [M+H$^+$]=490.2

Example 149

N-[2-({1-[1-(4-Chlorophenyl)cyclobutyl]-1,2,3,4-tetrahydroisoquinolin-7-yl}oxy)ethyl]-2-(dimethylamino)ethanesulfonamide(2E)-but-2-enedioate

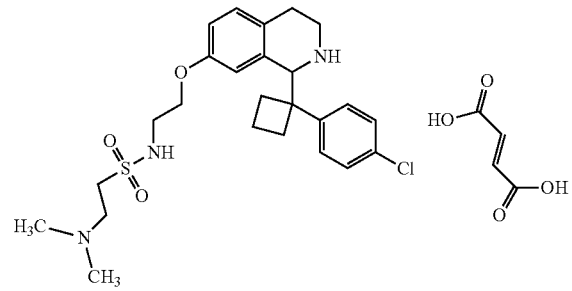 [SMILES: CN(C)CCS(=O)(=O)NCCOc1ccc2c(c1)C(C1(c3ccc(Cl)cc3)CCC1)NCC2 ; O=C(O)/C=C/C(=O)O]

ESI-MS [M+H$^+$]=492.2

Example 150

2-Amino-N-[2-({1-[1-(4-chlorophenyl)cyclobutyl]-1,2,3,4-tetrahydroisoquinolin-7-yl}oxy)ethyl]pyrimidine-5-sulfonamide

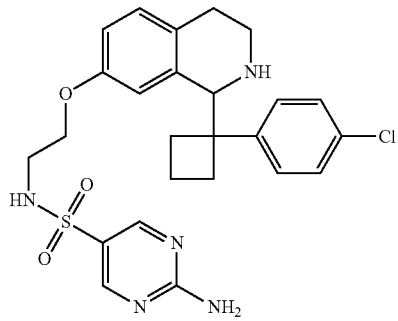 [SMILES: Nc1ncc(S(=O)(=O)NCCOc2ccc3c(c2)C(C2(c4ccc(Cl)cc4)CCC2)NCC3)cn1]

ESI-MS [M+H$^+$]=514.2

Example 151

N-[2-({1-[1-(4-Chlorophenyl)cyclobutyl]-1,2,3,4-tetrahydroisoquinolin-7-yl}oxy)ethyl]pyrrolidine-3-sulfonamide dihydrochloride (isomer 2)

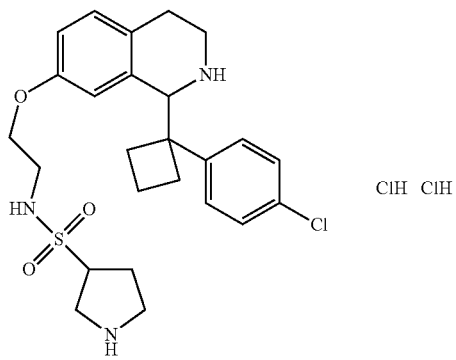 [SMILES: O=S(=O)(NCCOc1ccc2c(c1)C(C1(c3ccc(Cl)cc3)CCC1)NCC2)C1CCNC1 ; Cl ; Cl]

ESI-MS [M+H$^+$]=490.2

Example 152

2-Amino-N-[2-({1-[1-(4-Chlorophenyl)cyclobutyl]-1,2,3,4-tetrahydroisoquinolin-7-yl}oxy)ethyl]ethane-sulfonamide dihydrochloride (isomer 1)

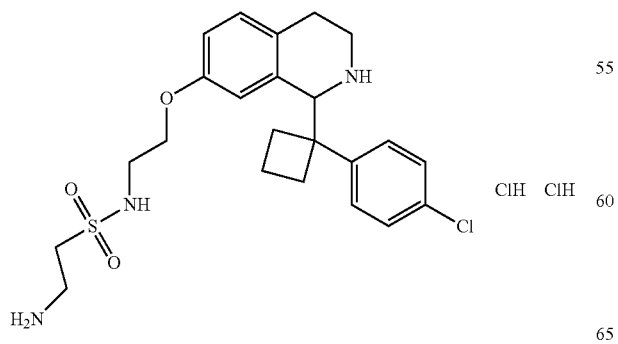

ESI-MS [M+H$^+$]=464.2

Example 153

N-[2-({1-[1-(4-Chlorophenyl)cyclobutyl]-1,2,3,4-tetrahydroisoquinolin-7-yl}oxy)ethyl]-1H-pyrazole-4-sulfonamide hydrochloride

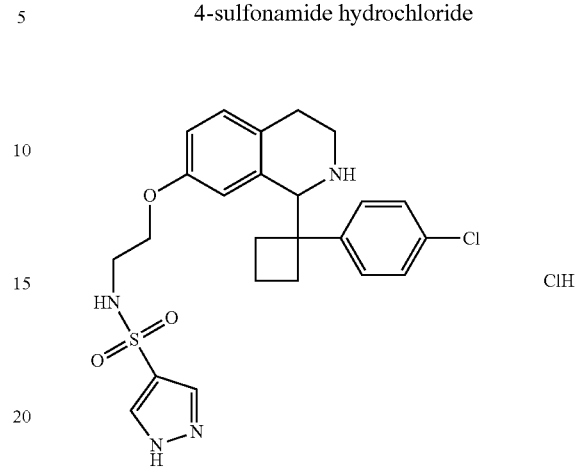

ESI-MS [M+H$^+$]=487.2

Example 154

2-Amino-N-[2-({1-[1-(4-chlorophenyl)cyclobutyl]-1,2,3,4-tetrahydroisoquinolin-7-yl}oxy)ethyl]ethanesulfonamide

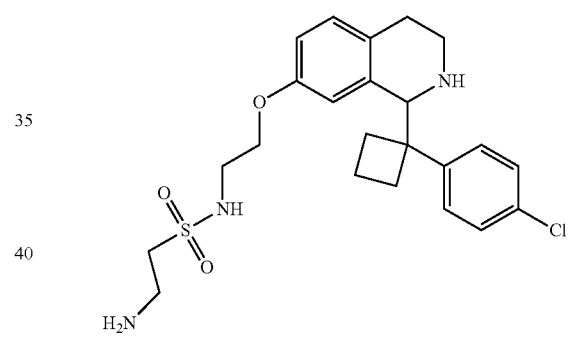

ESI-MS [M+H$^+$]=464.2

Example 155

N-[2-({1-[1-(4-Chlorophenyl)cyclobutyl]-1,2,3,4-tetrahydroisoquinolin-7-yl}oxy)ethyl]-2,2-dimethyl-propane-1-sulfonamide hydrochloride

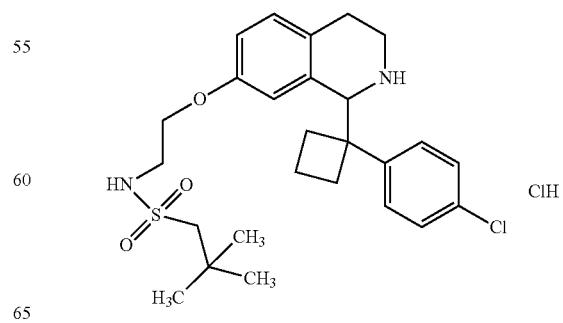

ESI-MS [M+H$^+$]=491.2

Example 156

N-[2-({1-[1-(4-Chlorophenyl)cyclobutyl]-1,2,3,4-tetrahydroisoquinolin-7-yl}oxy)ethyl]-6-methoxypyridine-3-sulfonamide hydrochloride

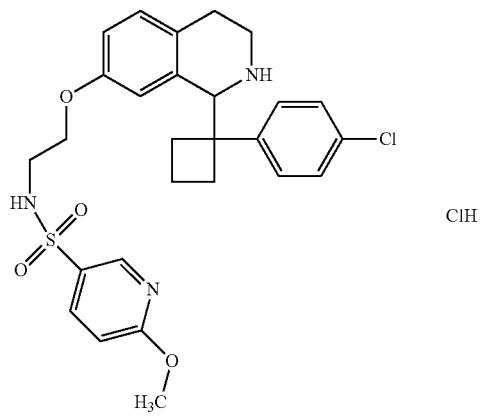 [SMILES: COc1ccc(S(=O)(=O)NCCOc2ccc3c(c2)C(C2(c4ccc(Cl)cc4)CCC2)NCC3)cn1 ; Cl]

ESI-MS [M+H⁺]=528.2

Example 157

3-Amino-N-[2-({1-[1-(4-chlorophenyl)cyclobutyl]-1,2,3,4-tetrahydroisoquinolin-7-yl}oxy)ethyl]benzenesulfonamide dihydrochloride

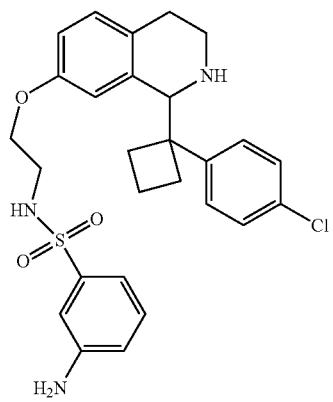 [SMILES: Nc1cccc(S(=O)(=O)NCCOc2ccc3c(c2)C(C2(c4ccc(Cl)cc4)CCC2)NCC3)c1]

ESI-MS [M+H⁺]=512.2

Example 158

2-Amino-N-[2-({1-[1-(4-chlorophenyl)cyclobutyl]-1,2,3,4-tetrahydroisoquinolin-7-yl}oxy)ethyl]ethanesulfonamide dihydrochloride (isomer 2)

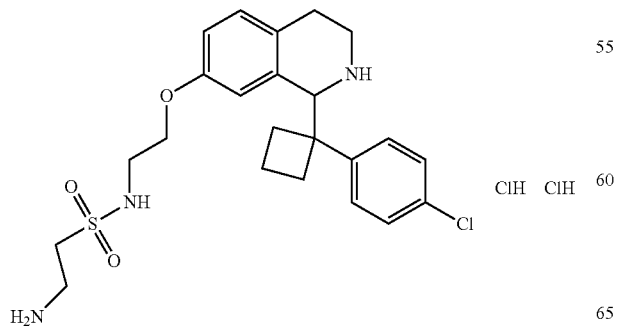

ESI-MS [M+H⁺]=464.4

Example 159

N-[2-({1-[1-(4-Chlorophenyl)cyclobutyl]-1,2,3,4-tetrahydroisoquinolin-7-yl}oxy)ethyl]pyrrolidine-3-sulfonamide dihydrochloride

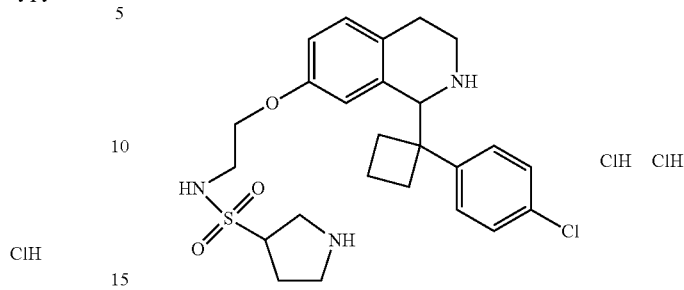

ESI-MS [M+H⁺]=490.2

Example 160

N-[2-({1-[1-(4-Chlorophenyl)cyclobutyl]-1,2,3,4-tetrahydroisoquinolin-7-yl}oxy)ethyl]piperidine-3-sulfonamide dihydrochloride (isomer 1)

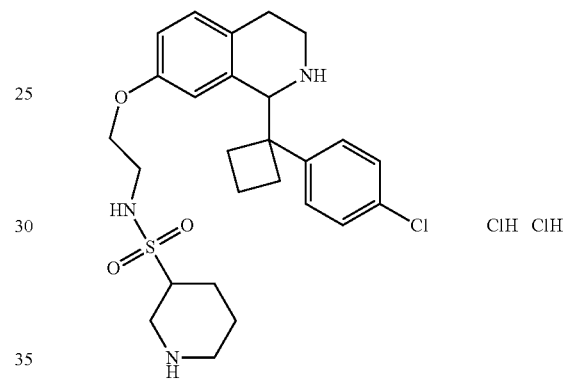

ESI-MS [M+H⁺]=504.2

Example 161

N-[2-({1-[1-(4-Chlorophenyl)cyclobutyl]-1,2,3,4-tetrahydroisoquinolin-7-yl}oxy)ethyl]-2-(piperidin-1-yl)ethanesulfonamide(2E)-but-2-enedioate

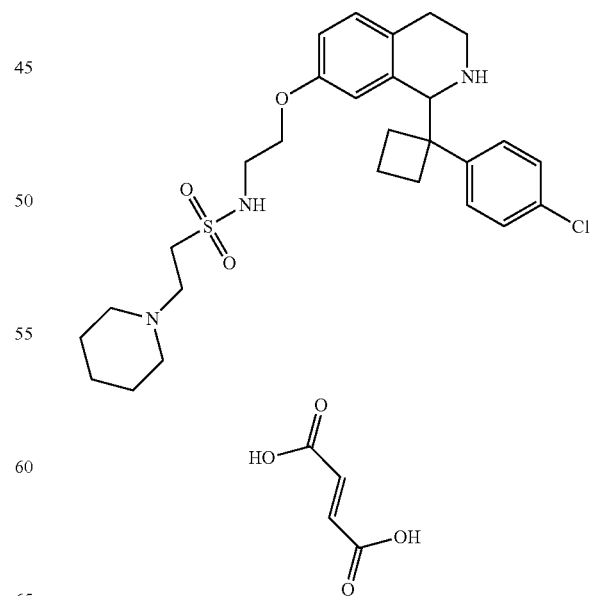

ESI-MS [M+H⁺]=532.3

Example 162

N-[2-({1-[1-(4-Chlorophenyl)cyclobutyl]-1,2,3,4-tetrahydroisoquinolin-7-yl}oxy)ethyl]-5-(methylamino)-1,3,4-thiadiazole-2-sulfonamide hydrochloride

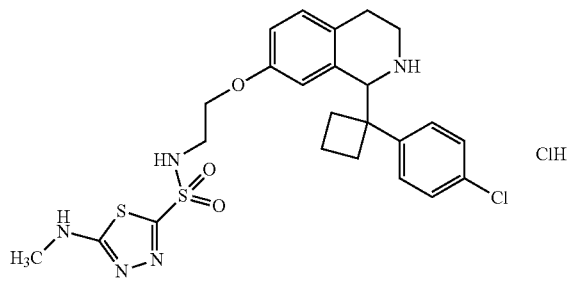 [SMILES: CNc1nnc(S(=O)(=O)NCCOc2ccc3c(c2)C(C2(c4ccc(Cl)cc4)CCC2)NCC3)s1 ; Cl]

ESI-MS [M+H$^+$]=534.2

Example 163

2-Amino-N-[2-({1-[1-(4-chlorophenyl)cyclobutyl]-1,2,3,4-tetrahydroisoquinolin-7-yl}oxy)ethyl]-1,3-thiazole-5-sulfonamide dihydrochloride

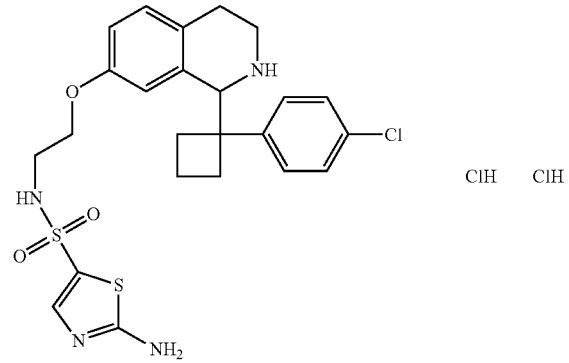 [SMILES: Nc1ncc(S(=O)(=O)NCCOc2ccc3c(c2)C(C2(c4ccc(Cl)cc4)CCC2)NCC3)s1 ; Cl ; Cl]

ESI-MS [M+H$^+$]=519.1

Example 164

N-[2-({1-[1-(4-Chlorophenyl)cyclobutyl]-1,2,3,4-tetrahydroisoquinolin-7-yl}oxy)ethyl]piperidine-3-sulfonamide dihydrochloride (isomer 2)

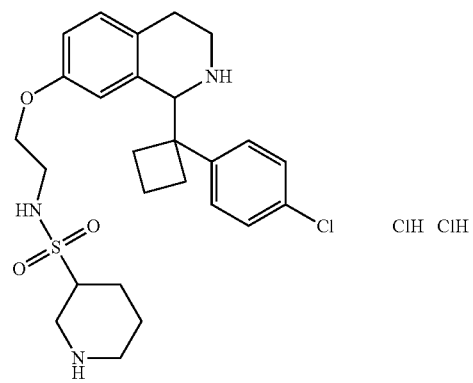 [SMILES: O=S(=O)(NCCOc1ccc2c(c1)C(C1(c3ccc(Cl)cc3)CCC1)NCC2)C1CCCNC1 ; Cl ; Cl]

ESI-MS [M+H$^+$]=504.2

Example 165

6-Amino-N-[2-({1-[1-(4-chlorophenyl)cyclobutyl]-1,2,3,4-tetrahydroisoquinolin-7-yl}oxy)ethyl]pyridine-3-sulfonamide

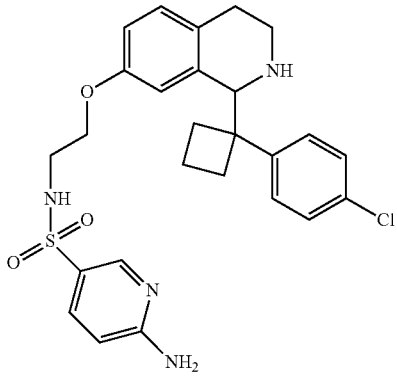 [SMILES: Nc1ccc(S(=O)(=O)NCCOc2ccc3c(c2)C(C2(c4ccc(Cl)cc4)CCC2)NCC3)cn1]

ESI-MS [M+H$^+$]=513.2

Example 166

N-[2-({1-[1-(4-Chlorophenyl)cyclobutyl]-1,2,3,4-tetrahydroisoquinolin-7-yl}oxy)ethyl]azetidine-3-sulfonamide(2E)-but-2-enedioate

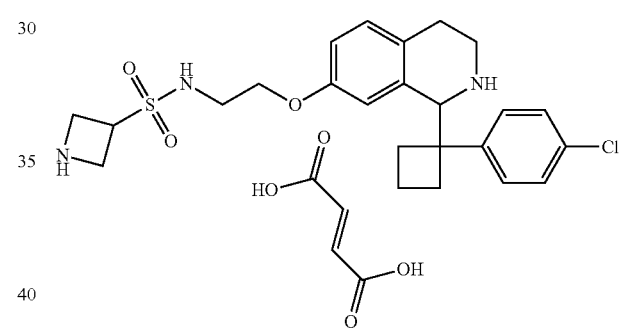

ESI-MS [M+H$^+$]=476.2

Example 167

6-Chloro-N-[2-({1-[1-(4-Chlorophenyl)cyclobutyl]-1,2,3,4-tetrahydroisoquinolin-7-yl}oxy)ethyl]imidazo[2,1-b][1,3]thiazole-5-sulfonamide hydrochloride

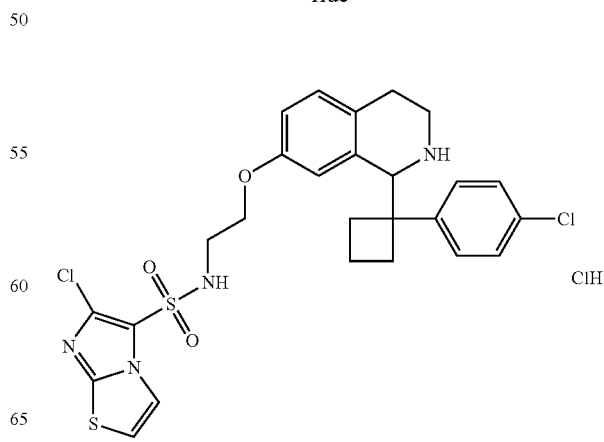

ESI-MS [M+H$^+$]=577.1

Example 168

N-[2-({1-[1-(4-Chlorophenyl)-3,3-difluorocyclobutyl]-1,2,3,4-tetrahydroisoquinolin-7-yl}oxy)ethyl]-1-methyl-1H-pyrazole-4-sulfonamide (isomer 2)

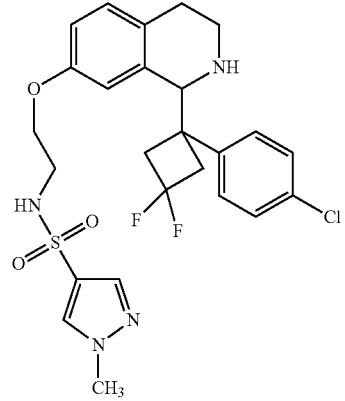 [SMILES: Cn1cc(S(=O)(=O)NCCOc2ccc3c(c2)C(C2(c4ccc(Cl)cc4)CC(F)(F)C2)NCC3)cn1]

ESI-MS [M+H$^+$]=537.1

Example 169

N-[2-({1-[1-(4-Chlorophenyl)cyclobutyl]-1,2,3,4-tetrahydroisoquinolin-7-yl}oxy)ethyl]-2-(propan-2-ylamino)ethanesulfonamide

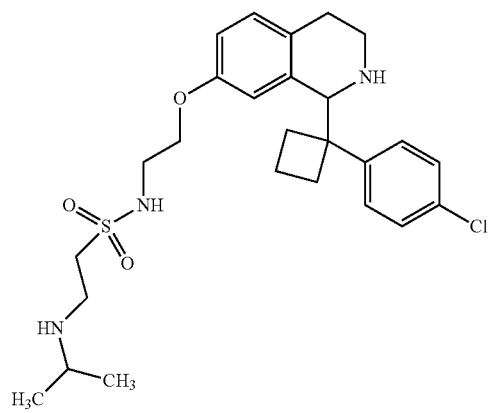 [SMILES: CC(C)NCCS(=O)(=O)NCCOc1ccc2c(c1)C(C1(c3ccc(Cl)cc3)CCC1)NCC2]

ESI-MS [M+H$^+$]=506.2

Example 170

Benzyl 3-{[2-({1-[1-(4-chlorophenyl)cyclobutyl]-1,2,3,4-tetrahydroisoquinolin-7-yl}oxy)ethyl]sulfamoyl}pyrrolidine-1-carboxylate

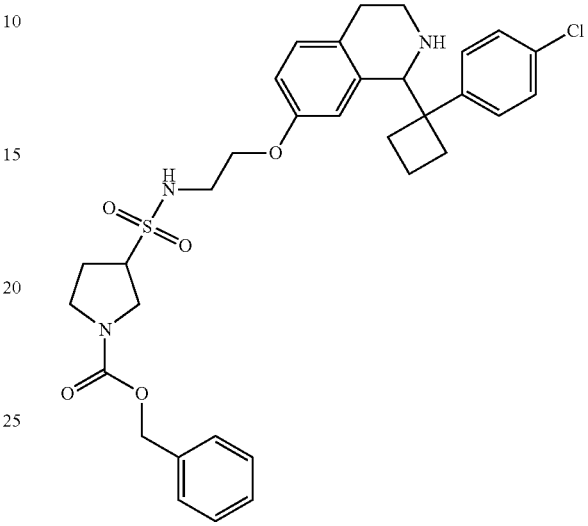

ESI-MS [M+H$^+$]=624.3

Example 171

N-[2-({2-Acetyl-1-[1-(4-chlorophenyl)cyclobutyl]-1,2,3,4-tetrahydroisoquinolin-7-yl}oxy)ethyl]propane-1-sulfonamide

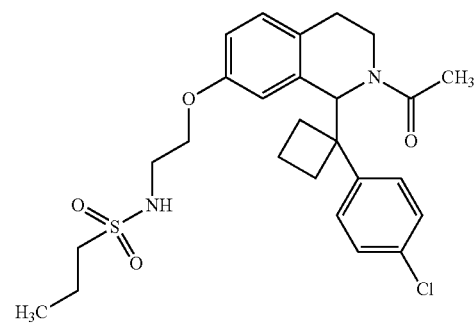 [SMILES: CCCS(=O)(=O)NCCOc1ccc2c(c1)C(C1(c3ccc(Cl)cc3)CCC1)N(C(C)=O)CC2]

ESI-MS [M+H$^+$]=505.2

Example 172

N-[2-({1-[1-(4-Chlorophenyl)cyclobutyl]-1,2,3,4-tetrahydroisoquinolin-7-yl}oxy)ethyl]pyrrolidine-3-sulfonamide dihydrochloride (isomer 3)

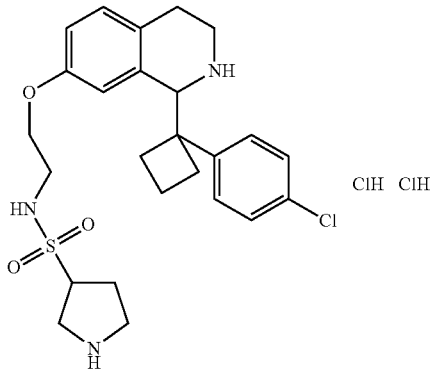 [SMILES: O=S(=O)(NCCOc1ccc2c(c1)C(C1(c3ccc(Cl)cc3)CCC1)NCC2)C1CCNC1 ; Cl ; Cl]

ESI-MS [M+H$^+$]=490.2

Example 173

N-[2-({1-[1-(4-Chlorophenyl)cyclobutyl]-1,2,3,4-tetrahydroisoquinolin-7-yl}oxy)ethyl]-6-phenoxypyridine-3-sulfonamide hydrochloride

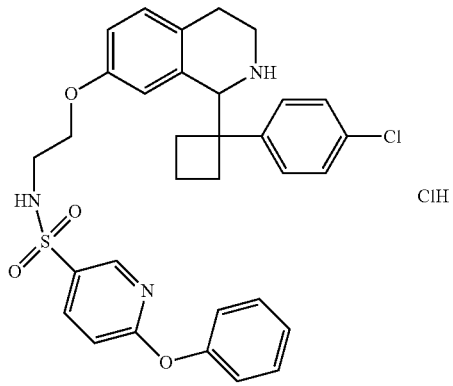 [SMILES: O=S(=O)(NCCOc1ccc2c(c1)C(C1(c3ccc(Cl)cc3)CCC1)NCC2)c1ccc(Oc2ccccc2)nc1 ; Cl]

ESI-MS [M+H$^+$]=590.2

Example 174

N-(2-Aminoethyl)-N-[2-({1-[1-(4-chlorophenyl)cyclobutyl]-1,2,3,4-tetrahydroisoquinolin-7-yl}oxy)ethyl]propane-1-sulfonamide dihydrochloride

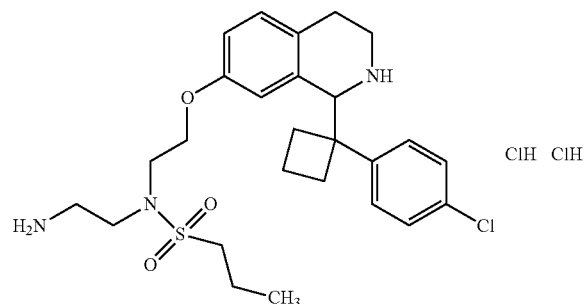

ESI-MS [M+H$^+$]=506.2

Example 175

N-[2-({1-[1-(4-Chlorophenyl)cyclobutyl]-1,2,3,4-tetrahydroisoquinolin-7-yl}oxy)ethyl]pyrrolidine-3-sulfonamide dihydrochloride (isomer 4)

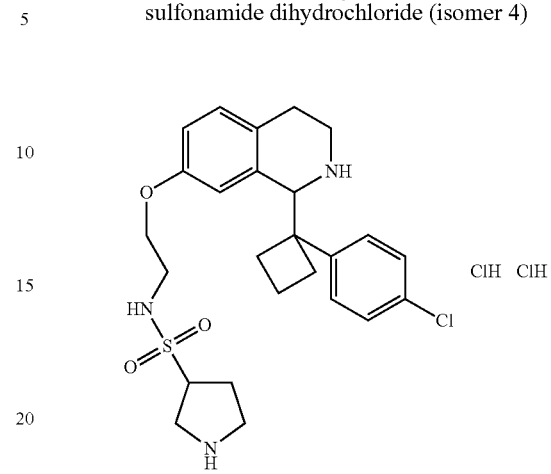

ESI-MS [M+H$^+$]=490.2

Example 176

N-[2-({1-[Bis(4-chlorophenyl)(hydroxy)methyl]-1,2,3,4-tetrahydroisoquinolin-7-yl}oxy)ethyl]propane-1-sulfonamide hydrochloride

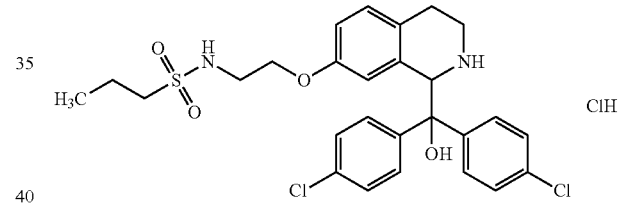

ESI-MS [M+H$^+$]=549.1

Example 177

1-Benzyl-N-[2-({1-[1-(4-chlorophenyl)cyclobutyl]-1,2,3,4-tetrahydroisoquinolin-7-yl}oxy)ethyl]piperidine-4-sulfonamide hydrochloride

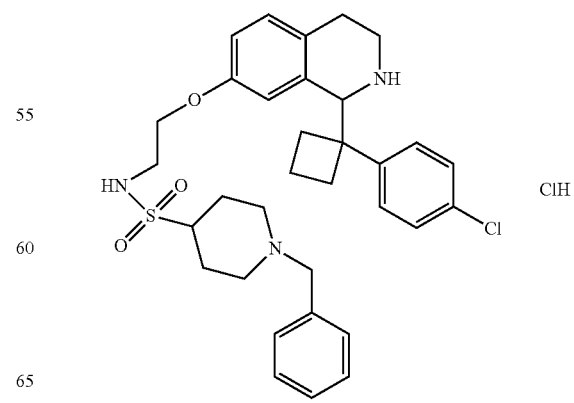

ESI-MS [M+H$^+$]=594.3

Example 178

N-[2-({1-[1-(4-Chlorophenyl)cyclobutyl]-1,2,3,4-tetrahydroisoquinolin-7-yl}oxy)ethyl]-3-(methylamino)propane-1-sulfonamide(2E)-but-2-enedioate

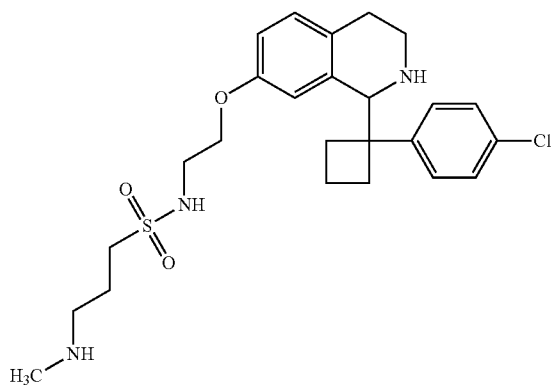

ESI-MS [M+H$^+$]=492.2

Example 179

N-[2-({1-[1-(4-Chlorophenyl)cyclobutyl]-1,2,3,4-tetrahydroisoquinolin-7-yl}oxy)ethyl]-2-(1,3-dioxo-1,3-dihydro-2H-isoindol-2-yl)ethanesulfonamide

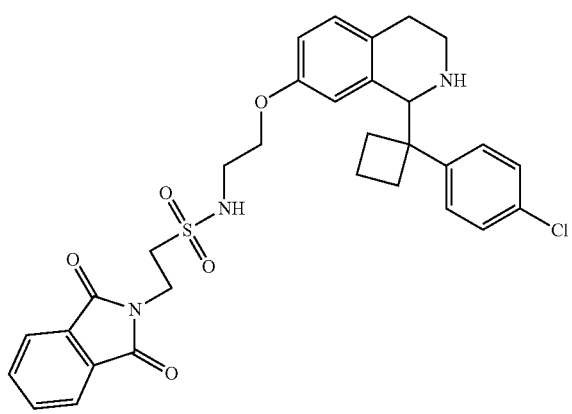 [SMILES: O=C1c2ccccc2C(=O)N1CCS(=O)(=O)NCCOc1ccc2c(c1)C(C1(c3ccc(Cl)cc3)CCC1)NCC2]

ESI-MS [M+H$^+$]=594.2

Example 180

1-Acetyl-N-[2-({1-[1-(4-chlorophenyl)cyclobutyl]-1,2,3,4-tetrahydroisoquinolin-7-yl}oxy)ethyl]azetidine-3-sulfonamide di[(2E)-but-2-enedioate]

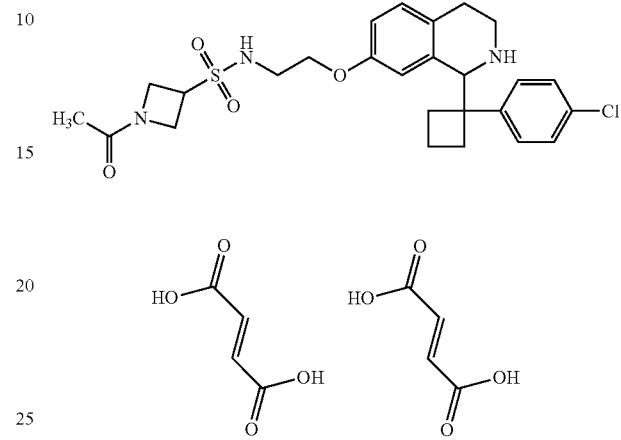

ESI-MS [M+H$^+$]=518.2

Example 181

N-[2-({1-[1-(4-Chlorophenyl)cyclobutyl]-1,2,3,4-tetrahydroisoquinolin-7-yl}oxy)ethyl]-3-(dimethylamino)propane-1-sulfonamide(2E)-but-2-enedioate

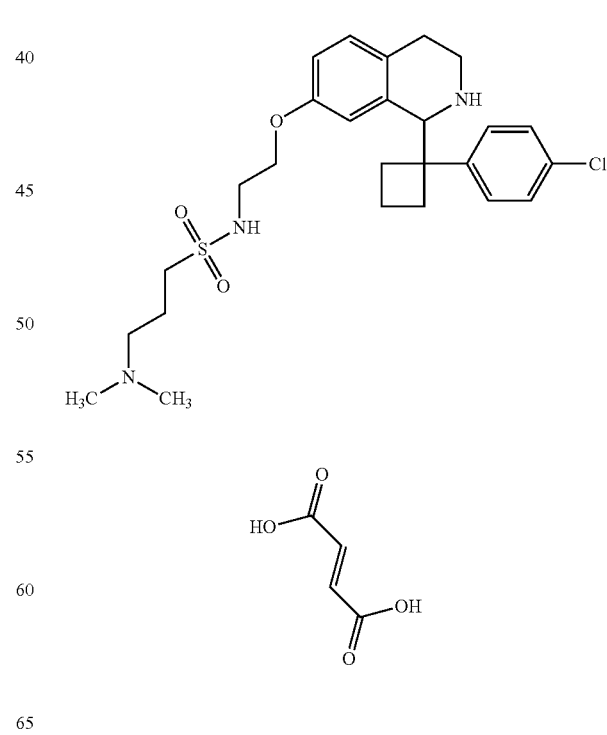

ESI-MS [M+H$^+$]=506.2

Example 182

N-[2-({(1R)-1-[1-(4-Chlorophenyl)cyclobutyl]-1,2,3,4-tetrahydroisoquinolin-7-yl}oxy)ethyl]pyridine-3-sulfonamide hydrochloride

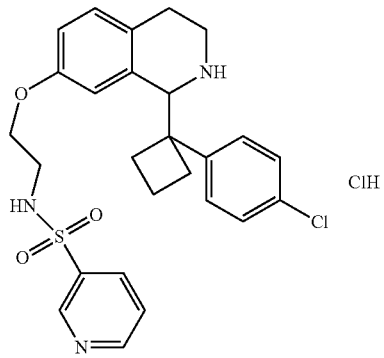 [SMILES: O=S(=O)(NCCOc1ccc2c(c1)C(C1(c3ccc(Cl)cc3)CCC1)NCC2)c1cccnc1 ; Cl]

ESI-MS [M+H$^+$]=498.1

Example 183

N-[2-({1-[1-(4-Chlorophenyl)cyclobutyl]-1,2,3,4-tetrahydroisoquinolin-7-yl}oxy)ethyl]-4-propylpiperazine-1-sulfonamide dihydrochloride

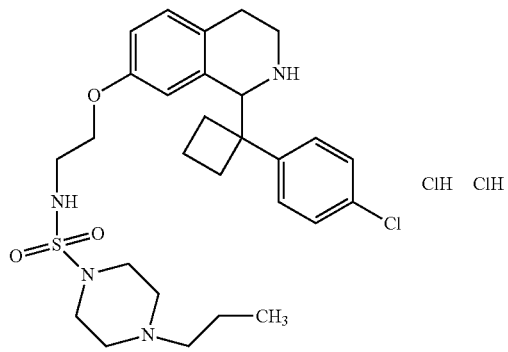 [SMILES: CCCN1CCN(S(=O)(=O)NCCOc2ccc3c(c2)C(C2(c4ccc(Cl)cc4)CCC2)NCC3)CC1 ; Cl ; Cl]

ESI-MS [M+H$^+$]=547.2

Example 184

4-Amino-N-[2-({1-[1-(4-chlorophenyl)cyclobutyl]-1,2,3,4-tetrahydroisoquinolin-7-yl}oxy)ethyl]butane-1-sulfonamide(2E)-but-2-enedioate

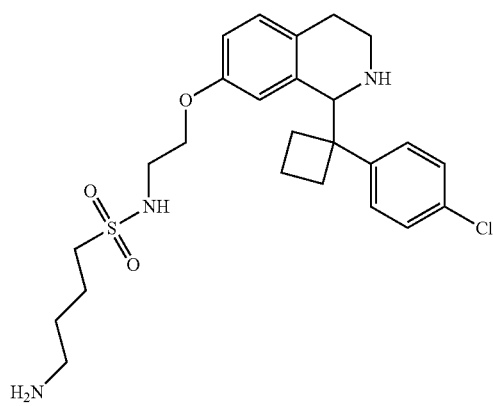

-continued

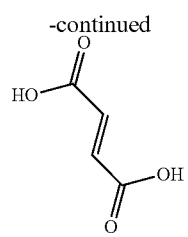

ESI-MS [M+H$^+$]=492.2

Example 185

N-[2-({1-[1-(4-Chlorophenyl)cyclobutyl]-1,2,3,4-tetrahydroisoquinolin-7-yl}oxy)ethyl]-4-methyl-3,4-dihydro-2H-pyrido[3,2-b][1,4]oxazine-7-sulfonamide hydrochloride

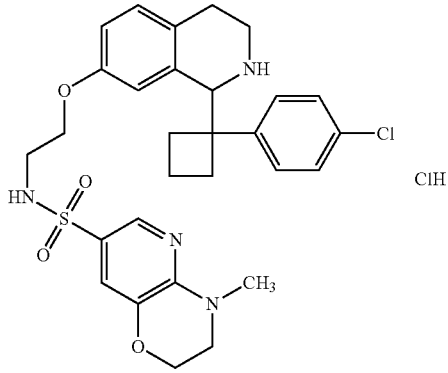 [SMILES: CN1CCOc2cc(S(=O)(=O)NCCOc3ccc4c(c3)C(C3(c5ccc(Cl)cc5)CCC3)NCC4)cnc21 ; Cl]

ESI-MS [M+H$^+$]=569.3

Example 186

N-[2-({1-[1-(4-Chlorophenyl)cyclobutyl]-1,2,3,4-tetrahydroisoquinolin-7-yl}oxy)ethyl]-3-(propylamino)propane-1-sulfonamide(2E)-but-2-enedioate

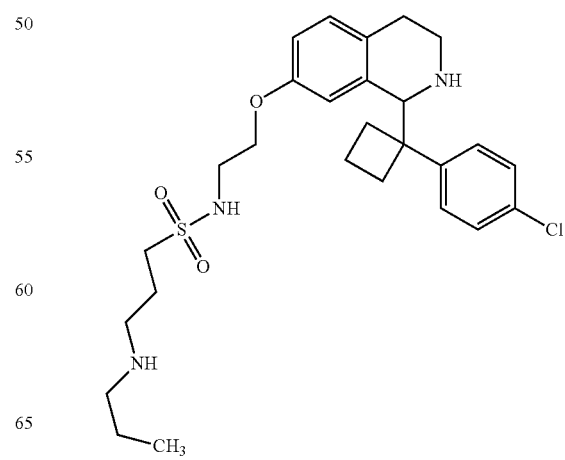

-continued

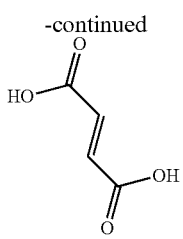

ESI-MS [M+H⁺]=520.2

Example 187

N-[2-({1-[1-(4-Chlorophenyl)cyclobutyl]-1,2,3,4-tetrahydroisoquinolin-7-yl}oxy)ethyl]-3-(ethylamino)propane-1-sulfonamide

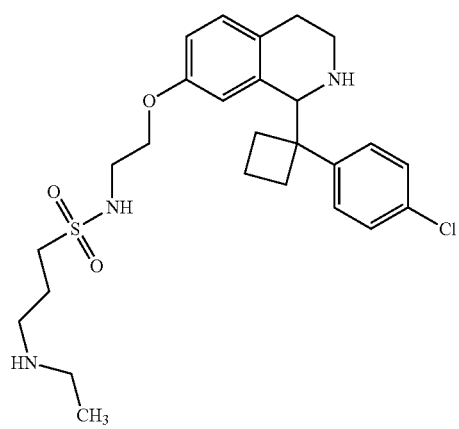 [SMILES: CCNCCCS(=O)(=O)NCCOc1ccc2c(c1)C(C1(c3ccc(Cl)cc3)CCC1)NCC2]

ESI-MS [M+H⁺]=506.2

Example 188

N-(5-{[2-({1-[1-(4-Chlorophenyl)cyclobutyl]-1,2,3,4-tetrahydroisoquinolin-7-yl}oxy)ethyl]sulfamoyl}-1,3-thiazol-2-yl)acetamide hydrochloride

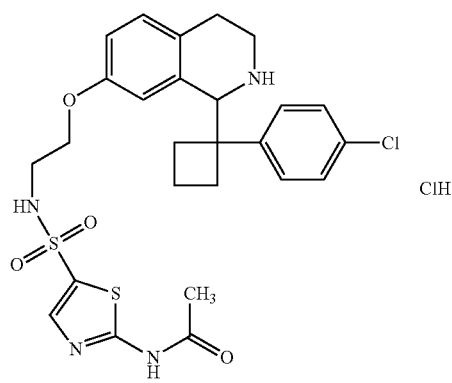 [SMILES: CC(=O)Nc1ncc(S(=O)(=O)NCCOc2ccc3c(c2)C(C2(c4ccc(Cl)cc4)CCC2)NCC3)s1 ; Cl]

ESI-MS [M+H⁺]=561.2

Example 189

N-[2-({1-[1-(4-Chlorophenyl)cyclobutyl]-1,2,3,4-tetrahydroisoquinolin-7-yl}oxy)ethyl]-6-(morpholin-4-yl)pyridine-3-sulfonamide hydrochloride

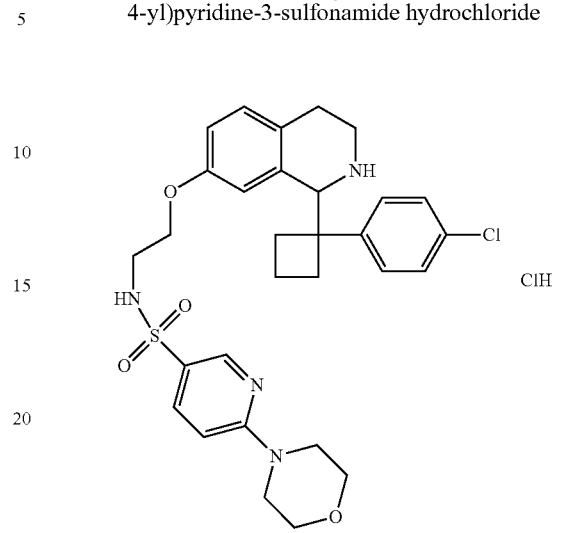

ESI-MS [M+H⁺]=583.3

Example 190

N-[2-({1-[1-(4-Chlorophenyl)cyclobutyl]-1,2,3,4-tetrahydroisoquinolin-7-yl}oxy)ethyl]piperidine-4-sulfonamide dihydrochloride

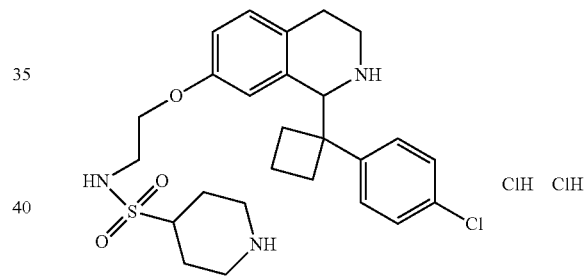

ESI-MS [M+H⁺]=504.2

Example 191

4-(Carbamoylamino)-N-[2-({1-[1-(4-chlorophenyl)cyclobutyl]-1,2,3,4-tetrahydroisoquinolin-7-yl}oxy)ethyl]benzenesulfonamide hydrochloride

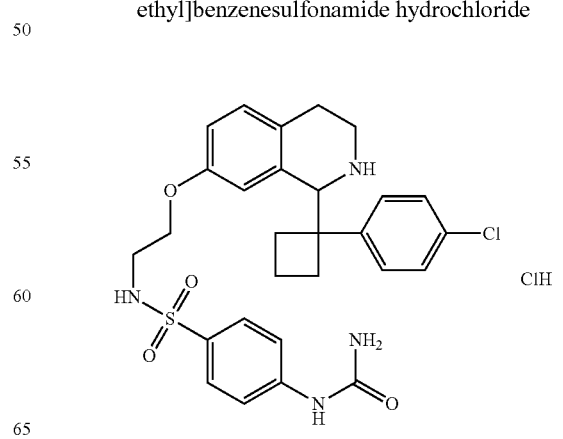

ESI-MS [M+H⁺]=555.2

Example 192

N-[2-({1-[1-(4-Chlorophenyl)cyclobutyl]-1,2,3,4-tetrahydroisoquinolin-7-yl}oxy)ethyl]piperidine-3-sulfonamide dihydrochloride (isomer 3)

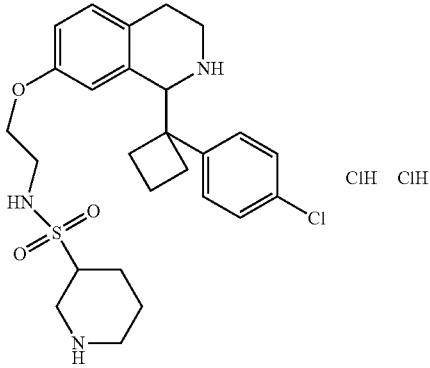 [SMILES: O=S(=O)(NCCOc1ccc2c(c1)C(C1(c3ccc(Cl)cc3)CCC1)NCC2)C1CCCNC1 ; Cl ; Cl]

ESI-MS [M+H$^+$]=504.2

Example 193

N-[2-({1-[1-(4-Chlorophenyl)cyclobutyl]-1,2,3,4-tetrahydroisoquinolin-7-yl}oxy)ethyl]piperidine-3-sulfonamide dihydrochloride (isomer 4)

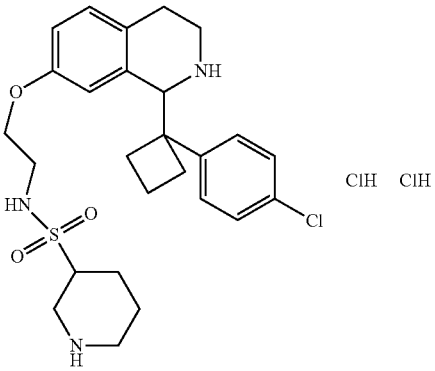 [SMILES: O=S(=O)(NCCOc1ccc2c(c1)C(C1(c3ccc(Cl)cc3)CCC1)NCC2)C1CCCNC1 ; Cl ; Cl]

ESI-MS [M+H$^+$]=504.3

Example 194

N-[2-({1-[1-(4-Chlorophenyl)cyclobutyl]-1,2,3,4-tetrahydroisoquinolin-7-yl}oxy)ethyl]-3-(diethylamino)propane-1-sulfonamide

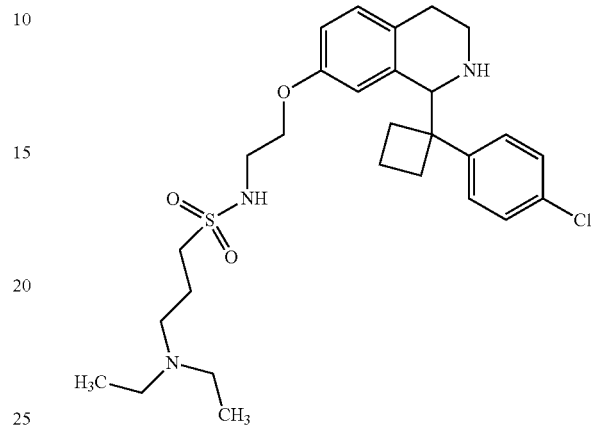

ESI-MS [M+H$^+$]=534.2

Example 195

N-[2-({1-[1-(4-Chlorophenyl)cyclobutyl]-1,2,3,4-tetrahydroisoquinolin-7-yl}oxy)ethyl]-3-(diethylamino)propane-1-sulfonamide(2E)-but-2-enedioate

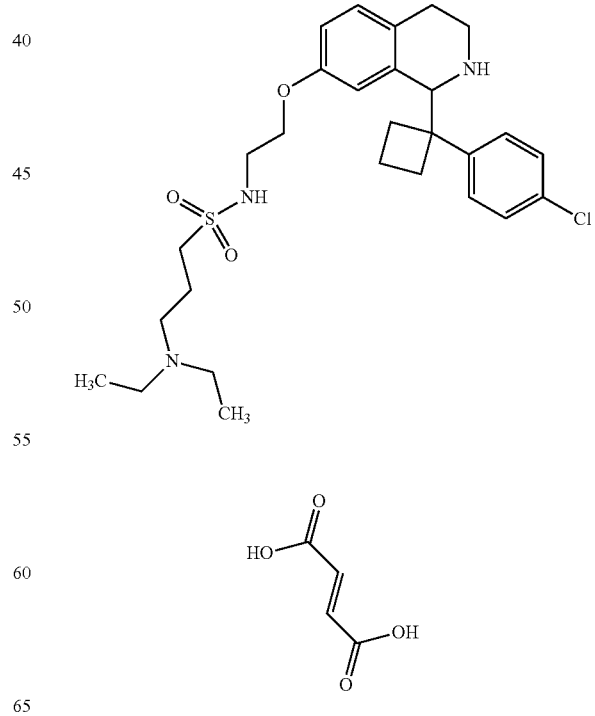

ESI-MS [M+H$^+$]=534.3

Example 196

N-[2-({1-[1-(4-Chlorophenyl)cyclobutyl]-1,2,3,4-tetrahydroisoquinolin-7-yl}oxy)ethyl]-3-(ethylamino)propane-1-sulfonamide(2E)-but-2-enedioate

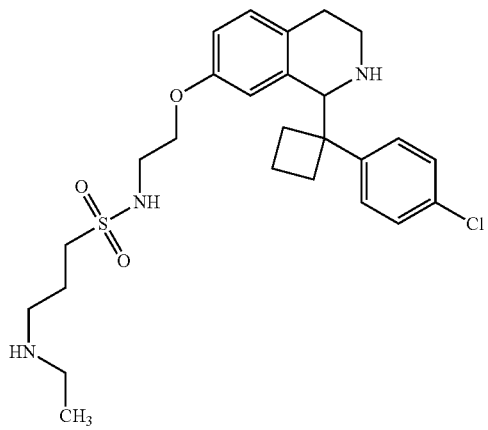

ESI-MS [M+H⁺]=506.3

Example 197

N-[2-({1-[1-(4-Chlorophenyl)cyclobutyl]-1,2,3,4-tetrahydroisoquinolin-7-yl}oxy)ethyl]-3-(propan-2-ylamino)propane-1-sulfonamide(2E)-but-2-enedioate

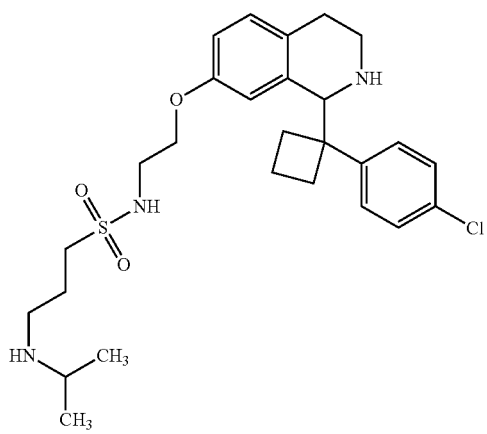

-continued

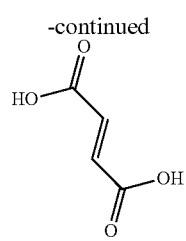

ESI-MS [M+H⁺]=520.2

Example 198

N-[2-({1-[1-(4-Chlorophenyl)cyclobutyl]-1,2,3,4-tetrahydroisoquinolin-7-yl}oxy)ethyl]-5-methylisoxazole-4-sulfonamide

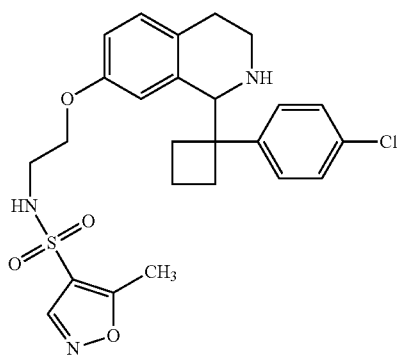 [SMILES: Cc1oncc1S(=O)(=O)NCCOc1ccc2c(c1)C(C1(c3ccc(Cl)cc3)CCC1)NCC2]

ESI-MS [M+H⁺]=502.2

Example 199

N-[2-({1-[1-(4-Chlorophenyl)cyclobutyl]-1,2,3,4-tetrahydroisoquinolin-7-yl}oxy)ethyl]-1H-1,2,4-triazole-5-sulfonamide

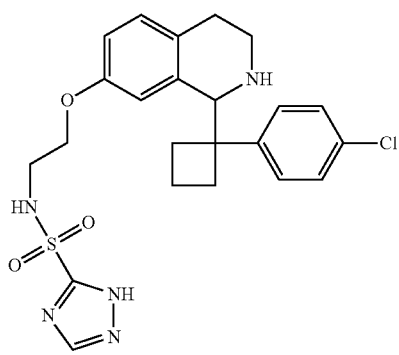 [SMILES: O=S(=O)(NCCOc1ccc2c(c1)C(C1(c3ccc(Cl)cc3)CCC1)NCC2)c1ncn[nH]1]

ESI-MS [M+H⁺]=488.1

Example 200

N-[2-({1-[1-(4-Chlorophenyl)cyclobutyl]-1,2,3,4-tetrahydroisoquinolin-7-yl}oxy)ethyl]-3-(piperidin-1-yl)propane-1-sulfonamide(2E)-but-2-enedioate

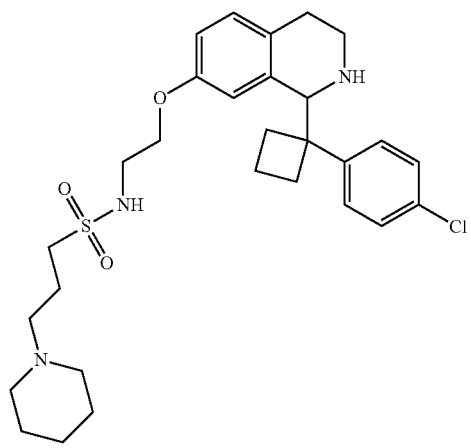

ESI-MS [M+H⁺]=546.2

Example 201

N-[2-({1-[1-(4-Chlorophenyl)cyclobutyl]-1,2,3,4-tetrahydroisoquinolin-7-yl}oxy)ethyl]-3-(morpholin-4-yl)propane-1-sulfonamide(2E)-but-2-enedioate

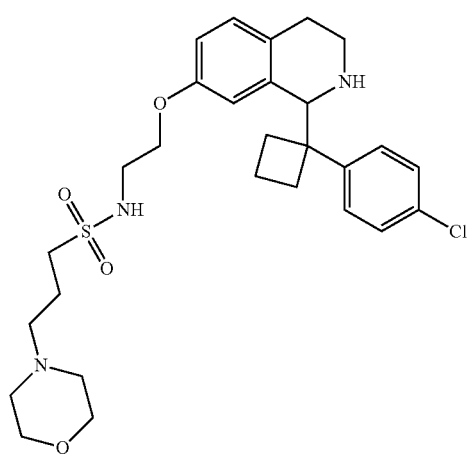

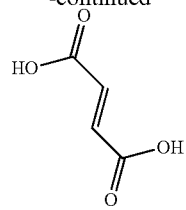

ESI-MS [M+H⁺]=548.2

Example 202

N-[2-({1-[1-(4-Chlorophenyl)cyclobutyl]-1,2,3,4-tetrahydroisoquinolin-7-yl}oxy)ethyl]-2-[(ethylcarbamoyl)amino]ethanesulfonamide(2E)-but-2-enedioate

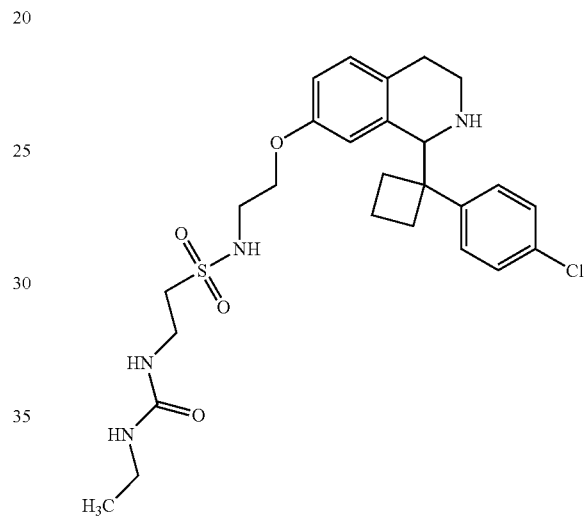

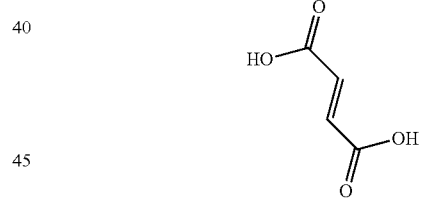

ESI-MS [M+H⁺]=535.3

Example 203

3-Amino-N-[2-({1-[1-(4-chlorophenyl)cyclobutyl]-1,2,3,4-tetrahydroisoquinolin-7-yl}oxy)ethyl]-1H-1,2,4-triazole-5-sulfonamide dihydrochloride

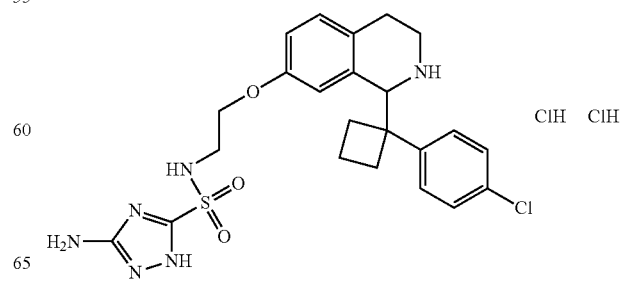

ESI-MS [M+H⁺]=503.2

Example 204

N-[2-({1-[1-(4-Chlorophenyl)cyclobutyl]-1,2,3,4-tetrahydroisoquinolin-7-yl}oxy)ethyl]-1H-1,2,4-triazole-5-sulfonamide

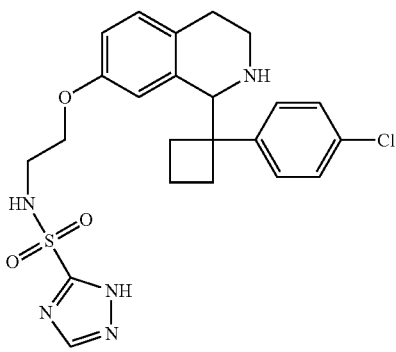 [SMILES: O=S(=O)(NCCOc1ccc2c(c1)C(C1(c3ccc(Cl)cc3)CCC1)NCC2)c1ncn[nH]1]

ESI-MS [M+H$^+$]=488.1

Biological Testing

1. [$^3$H]-Glycine Uptake into Recombinant CHO Cells Expressing Human GlyT1:

Human GlyT1c expressing recombinant hGlyT1c_5_CHO cells were plated at 20,000 cells per well in 96 well Cytostar-T scintillation microplates (Amersham Biosciences) and cultured to sub-confluency for 24 h. For glycine uptake assays the culture medium was aspirated and the cells were washed once with 100 μl HBSS (Gibco BRL, #14025-050) with 5 mM L-Alanine (Merck #1007). 80 μl HBSS buffer were added, followed by 10 μl inhibitor or vehicle (10% DMSO) and 10 μl [$^3$H]-glycine (TRK71, Amersham Biosciences) to a final concentration of 200 nM for initiation of glycine uptake. The plates were placed in a Wallac Microbeta (PerkinElmer) and continuously counted by solid phase scintillation spectrometry during up to 3 hours. Nonspecific uptake was determined in the presence of 10 μM Org24598. IC$_{50}$ calculations were made by four-parametric logistic non-linear regression analysis (GraphPad Prism) using determinations within the range of linear increase of [$^3$H]-glycine incorporation between 60 and 120 min.

2. Radioligand Binding Assays Using Recombinant CHO Cell Membranes Expressing Human GlyT1:

Radioligand binding to human GlyT1c transporter-expressing membranes was carried out as described in Mezler et al., Molecular Pharmacology 74:1705-1715, 2008.

More specifically, [$^3$H]-(R)-NPTS radioligand binding to human GlyT1c transporter-expressing membranes was measured in duplicate in a total volume of 200 μl in 96-well plates. To 100 μl of membrane suspension (yielding a final membrane protein concentration of 50 μg/ml) in assay buffer (120 mM NaCl, 2 mM KCl, 10 mM Hepes, 1 mM MgCl2, 1 mM CaCl2, pH 7.5) 80 μl of [$^3$H]-(R)-NPTS (0.5 nM final) were added in assay buffer. For competition experiments 10 μl of buffer or unlabeled compound solution obtained from dilution series of test compounds in DMSO followed. An intermediate 1:10 dilution in assay buffer yielded a final DMSO concentration of 1%. Non-specific binding was determined in the presence of 10 μM Org24598 (or its racemate Org24461) for [$^3$H]-(R)-NPTS. After incubation at room temperature for 1 h, the incubation mixture was harvested (Tomtec Mach III U Harvester) through 96-well GF/B filter plates (PerkinElmer), presoaked for 1 h with 40 μl per well of 0.1% polyethylene-imine (PEI). After washing twice with ice-cold 50 mM Tris-HCl pH 7.4 buffer, drying and addition of 35 μl scintillator (BetaplateScint, PerkinElmer) per well followed. The radioactivity was determined by liquid scintillation spectrometry in a MicroBeta (PerkinElmer) plate counter.

Data analysis: For binding of [$^3$H]-(R)-NPTS to cell membranes, the calculation of Kd and Bmax values from the saturation binding assays and the IC$_{50}$ values from the displacement binding was performed by iterative non-linear regression analysis adapted from the 'Ligand' program (Munson and Rodbard, 1980). Radioligand displacement curves in absence or in presence of increasing concentrations of tested compounds were fitted using a one-site fit and the apparent Ki values were calculated from the IC$_{50}$ values using the Cheng-Prusoff equation (Cheng and Prusoff 1973).

The following results were obtained with the compounds disclosed in the examples:

TABLE 1

| Example | Glycine uptake IC$_{50}$ [μmol] | radioligand binding[1] K$_{iapp}$ [μmol] |
|---|---|---|
| 1 | ≤10 | ≤10 |
| 2 | ≤0.1 | ≤0.1 |
| 3 | ≤10 | n.d. |
| 4 | ≤0.1 | ≤0.1 |
| 5 | ≤100 | n.d. |
| 6 | ≤10 | n.d. |
| 7 | ≤0.1 | ≤0.1 |
| 8 | ≤0.1 | ≤0.1 |
| 9 | ≤10 | ≤10 |
| 10 | ≤0.1 | ≤0.1 |
| 11 | ≤10 | ≤10 |
| 12 | ≤0.1 | ≤1 |
| 13 | ≤1 | ≤1 |
| 14 | ≤0.1 | ≤0.1 |
| 15 | ≤0.1 | ≤0.1 |
| 16 | ≤0.1 | ≤0.1 |
| 17 | ≤0.1 | ≤1 |
| 18 | ≤1 | ≤10 |
| 19 | ≤10 | ≤10 |
| 22 | ≤10 | ≤100 |
| 23 | ≤10 | ≤10 |
| 24 | ≤1 | ≤10 |
| 25 | ≤1 | ≤1 |
| 26 | ≤1 | ≤10 |
| 27 | ≤1 | ≤1 |
| 28 | ≤0.1 | ≤0.1 |
| 29 | ≤1 | ≤1 |
| 30 | ≤1 | ≤10 |
| 31 | ≤1 | ≤1 |
| 32 | ≤10 | ≤10 |
| 33 | ≤10 | n.d. |
| 34 | ≤10 | n.d. |
| 35 | ≤1 | n.d. |
| 36 | ≤100 | n.d. |
| 37 | ≤0.1 | n.d. |
| 38 | ≤0.1 | n.d. |
| 39 | ≤100 | n.d. |
| 40 | ≤1 | n.d. |
| 41 | ≤100 | n.d. |
| 42 | ≤100 | n.d. |
| 43 | ≤0.1 | n.d. |
| 44 | ≤0.1 | n.d. |
| 45 | ≤1 | n.d. |
| 46 | ≤1 | n.d. |
| 47 | ≤10 | n.d. |
| 48 | ≤10 | n.d. |
| 49 | ≤0.1 | n.d. |
| 50 | ≤0.1 | n.d. |
| 51 | ≤0.1 | n.d. |
| 52 | ≤10 | n.d. |
| 54 | ≤10 | n.d. |
| 55 | ≤10 | n.d. |
| 56 | ≤10 | n.d. |
| 57 | ≤0.1 | n.d. |

TABLE 1-continued

| Example | Glycine uptake IC$_{50}$ [μmol] | radioligand binding[1] K$_{iapp}$ [μmol] |
|---|---|---|
| 58 | ≤1 | n.d. |
| 59 | ≤10 | n.d. |
| 60 | ≤10 | n.d. |
| 61 | ≤0.1 | n.d. |
| 62 | ≤1 | ≤1 |
| 63 | ≤100 | ≤100 |
| 64 | ≤10 | n.d. |
| 65 | ≤0.1 | ≤0.1 |
| 66 | ≤0.1 | n.d. |
| 67 | ≤0.1 | n.d. |
| 68 | ≤10 | n.d. |
| 69 | ≤1 | n.d. |
| 70 | ≤100 | n.d. |
| 71 | ≤1 | n.d. |
| 72 | ≤1 | ≤10 |
| 73 | ≤1 | n.d. |
| 74 | ≤10 | n.d. |
| 75 | ≤1 | n.d. |
| 76 | ≤0.1 | n.d. |
| 77 | ≤1 | n.d. |
| 78 | ≤10 | n.d. |
| 79 | ≤1 | n.d. |
| 80 | ≤0.1 | n.d. |
| 81 | ≤10 | n.d. |
| 82 | ≤1 | n.d. |
| 83 | n.d | n.d |
| 84 | ≤100 | ≤10 |
| 85 | ≤0.1 | n.d. |
| 86 | ≤0.1 | n.d. |
| 87 | ≤0.1 | n.d. |
| 88 | n.d. | ≤0.1 |
| 89 | n.d. | ≤0.1 |
| 90 | n.d. | ≤0.1 |
| 91 | n.d. | ≤0.1 |
| 92 | n.d. | ≤0.1 |
| 93 | n.d. | ≤0.1 |
| 94 | n.d. | ≤0.1 |
| 95 | ≤0.1 | ≤0.1 |
| 96 | n.d. | ≤0.1 |
| 97 | n.d. | ≤0.1 |
| 98 | n.d. | ≤0.1 |
| 99 | n.d. | ≤0.1 |
| 100 | n.d. | ≤0.1 |
| 101 | ≤1 | ≤0.1 |
| 102 | n.d. | ≤0.1 |
| 103 | ≤0.1 | ≤0.1 |
| 104 | n.d. | ≤0.1 |
| 105 | n.d. | ≤0.1 |
| 106 | ≤10 | ≤1 |
| 107 | n.d. | ≤1 |
| 108 | ≤10 | ≤1 |
| 109 | n.d. | ≤1 |
| 110 | n.d. | ≤1 |
| 111 | n.d. | ≤1 |
| 112 | ≤10 | ≤1 |
| 113 | n.d. | ≤1 |
| 114 | n.d. | ≤1 |
| 115 | n.d. | ≤1 |
| 116 | ≤100 | ≤1 |
| 117 | ≤10 | ≤1 |
| 118 | ≤10 | ≤1 |
| 119 | n.d. | ≤10 |
| 120 | n.d. | ≤10 |
| 121 | ≤10 | ≤10 |
| 122 | n.d. | ≤10 |
| 123 | ≤100 | ≤10 |
| 124 | n.d. | ≤10 |
| 125 | n.d. | ≤10 |
| 126 | ≤10 | ≤10 |
| 127 | n.d. | ≤10 |
| 128 | n.d. | ≤10 |
| 129 | n.d. | ≤10 |
| 130 | ≤100 | ≤10 |
| 131 | n.d. | ≤10 |
| 132 | ≤10 | ≤10 |
| 133 | ≤10 | ≤10 |
| 134 | n.d. | ≤10 |
| 135 | ≤100 | ≤10 |
| 136 | n.d. | ≤10 |
| 137 | n.d. | ≤10 |
| 138 | n.d. | ≤0.1 |
| 139 | n.d. | ≤0.1 |
| 140 | n.d. | ≤0.1 |
| 141 | n.d. | ≤0.1 |
| 142 | ≤0.1 | ≤0.1 |
| 143 | n.d. | ≤0.1 |
| 144 | n.d. | ≤0.1 |
| 145 | ≤0.1 | ≤0.1 |
| 146 | n.d. | ≤0.1 |
| 147 | n.d. | ≤0.1 |
| 148 | n.d. | ≤0.1 |
| 149 | n.d. | ≤0.1 |
| 150 | n.d. | ≤0.1 |
| 151 | n.d. | ≤0.1 |
| 152 | ≤10 | ≤0.1 |
| 153 | n.d. | ≤0.1 |
| 154 | ≤1 | ≤0.1 |
| 155 | ≤10 | ≤0.1 |
| 156 | n.d. | ≤0.1 |
| 157 | n.d. | ≤0.1 |
| 158 | n.d. | ≤0.1 |
| 159 | n.d. | ≤0.1 |
| 160 | n.d. | ≤0.1 |
| 161 | n.d. | ≤1 |
| 162 | n.d. | ≤1 |
| 163 | n.d. | ≤1 |
| 164 | n.d. | ≤1 |
| 165 | ≤10 | ≤1 |
| 166 | n.d. | ≤1 |
| 167 | ≤10 | ≤1 |
| 168 | n.d. | ≤1 |
| 169 | n.d. | ≤1 |
| 170 | n.d. | ≤1 |
| 171 | n.d. | ≤10 |
| 172 | n.d. | ≤10 |
| 173 | n.d. | ≤10 |
| 174 | n.d. | ≤10 |
| 175 | n.d. | ≤10 |
| 176 | ≤10 | ≤10 |
| 177 | n.d. | ≤10 |
| 178 | n.d. | ≤10 |
| 179 | ≤100 | ≤10 |
| 180 | n.d. | ≤10 |
| 181 | ≤10 | ≤10 |
| 182 | ≤10 | ≤10 |
| 183 | ≤10 | ≤10 |
| 184 | n.d. | ≤10 |
| 185 | n.d. | ≤10 |
| 186 | ≤10 | ≤10 |
| 187 | ≤10 | ≤10 |
| 188 | n.d. | ≤10 |
| 189 | n.d. | ≤10 |
| 190 | n.d. | ≤10 |
| 191 | n.d. | ≤10 |
| 192 | n.d. | ≤10 |
| 193 | n.d. | ≤10 |
| 194 | ≤10 | ≤10 |
| 195 | n.d. | ≤10 |
| 196 | n.d. | ≤10 |
| 197 | ≤100 | ≤10 |
| 198 | n.d. | ≤10 |
| 199 | n.d. | ≤10 |
| 200 | ≤10 | ≤100 |
| 201 | ≤100 | ≤100 |
| 202 | ≤10 | ≤100 |
| 203 | n.d. | ≤100 |
| 204 | n.d. | ≤100 |

[1] for examples 1-19, 22-52, and 54-87 the radioligand was [$^3$H]—(R)—NPTS.

We claim:
1. A tetrahydroisoquinoline compound of the formula (I)

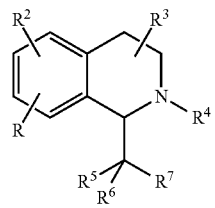

wherein
R is —CN;
R² is hydrogen, halogen, C₁-C₆-alkyl, halogenated C₁-C₄-alkyl, hydroxy-C₁-C₄-alkyl, —CN, C₂-C₆-alkenyl, C₂-C₆-alkynyl, optionally substituted C₆-C₁₂-aryl, hydroxy, C₁-C₆-alkoxy, halogenated C₁-C₆-alkoxy, C₂-C₆-alkenyloxy, C₆-C₁₂-aryl-C₁-C₄-alkoxy, C₁-C₆-alkylcarbonyloxy, C₁-C₆-alkylthio, C₁-C₆-alkylsulfinyl, C₁-C₆-alkylsulfonyl, aminosulfonyl, amino, C₁-C₆-alkylamino, C₂-C₆-alkenylamino or optionally substituted C₃-C₁₂-heterocyclyl;
R³ is hydrogen, halogen, C₁-C₆-alkyl or C₁-C₆-alkoxy, or two radicals R³ together with the carbon atom to which they are attached form a carbonyl group;
R⁴ is hydrogen, C₁-C₆-alkyl, halogenated C₁-C₄-alkyl, hydroxy-C₁-C₄-alkyl, C₁-C₆-alkoxy-C₁-C₄-alkyl, amino-C₁-C₄-alkyl, CH₂CN, —CHO, C₁-C₄-alkylcarbonyl, (halogenated C₁-C₄-alkyl)carbonyl, C₆-C₁₂-arylcarbonyl, C₁-C₆-alkylaminocarbonyl, C₂-C₆-alkenyl, —C(=NH)NH₂, —C(=NH)NHCN, C₁-C₆-alkylsulfonyl, C₆-C₁₂-arylsulfonyl, amino, —NO or C₃-C₁₂-heterocyclyl;
R⁵ is optionally substituted C₁-C₆-alkyl, C₁-C₆-alkylamino-C₁-C₄-alkyl, di-C₁-C₆-alkylamino-C₁-C₄-alkyl, C₃-C₁₂-heterocyclyl-C₁-C₆-alkyl, optionally substituted C₆-C₁₂-aryl or hydroxy;
R⁶ is hydrogen, optionally substituted C₁-C₆-alkyl or hydroxy, or
R⁵, R⁶
together are carbonyl or optionally substituted C₁-C₄-alkylene, wherein one —CH₂— of C₁-C₄-alkylene may be replaced by an oxygen atom or —NR¹²—;
R⁷ is optionally substituted C₆-C₁₂-aryl, optionally substituted C₃-C₁₂-cycloalkyl or optionally substituted C₃-C₁₂-heterocyclyl; and
R¹² is hydrogen or C₁-C₆-alkyl;
or a physiologically tolerated salt thereof.

2. The compound as claimed in claim 1, having one of the formulae

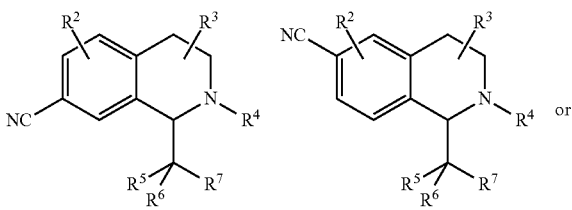

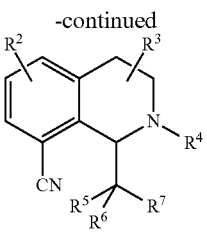

wherein R², R³, R⁴, R⁵, R⁶, R⁷ are as defined in claim 1.

3. The compound as claimed in claim 1, wherein R² is hydrogen, halogen or C₁-C₆-alkoxy.

4. The compound as claimed in claim 1, having one of the formulae

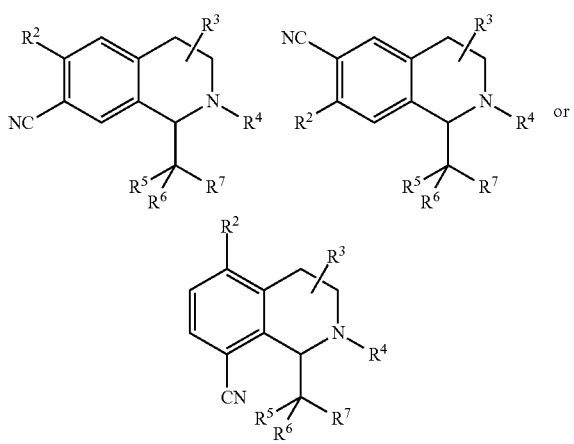

wherein R², R³, R⁴, R⁵, R⁶, R⁷ are as defined in claim 1.

5. The compound as claimed in claim 1, wherein R³ is hydrogen or C₁-C₆-alkyl.

6. The compound as claimed in claim 1, wherein R⁴ is hydrogen, C₁-C₆-alkyl, halogenated C₁-C₄-alkyl, amino-C₁-C₄-alkyl, CH₂CN, C₁-C₄-alkylcarbonyl, (halogenated C₁-C₄-alkyl)carbonyl, —C(=NH)NH₂, —C(=NH)NHCN, C₁-C₆-alkylsulfonyl, amino, —NO or C₃-C₁₂-heterocyclyl.

7. The compound as claimed in claim 1, wherein R⁵ is C₁-C₆-alkyl and R⁶ is hydrogen or C₁-C₆-alkyl, or wherein R⁵, R⁶ together are optionally substituted C₁-C₄-alkylene.

8. The compound as claimed in claim 1, wherein R⁷ is optionally substituted C₆-C₁₂-aryl.

9. The compound as claimed in claim 8, having the formula

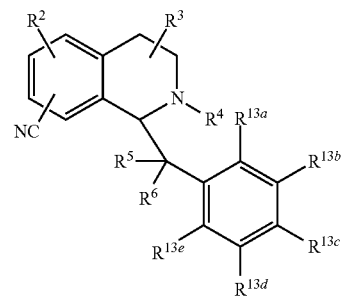

wherein R¹³ᵃ, R¹³ᵇ, R¹³ᶜ, R¹³ᵈ, R¹³ᵉ
independently are hydrogen, halogen, optionally substituted C₁-C₆-alkyl, halogenated C₁-C₆-alkyl, CN, hydroxy, $C_1$-$C_6$-alkoxy, amino, $C_1$-$C_6$-alkylamino, di-$C_1$-$C_6$-alkylamino or $C_3$-$C_{12}$-heterocyclyl.

10. The compound as claimed in claim 1, wherein $R^7$ is optionally substituted $C_3$-$C_{12}$-heterocyclyl.

11. The compound as claimed in claim 10, having the formula

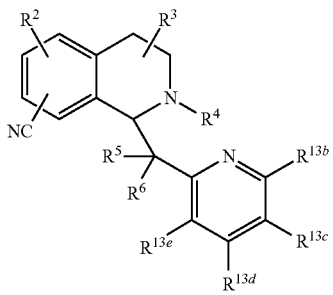

wherein $R^{13b}$, $R^{13c}$, $R^{13d}$, $R^{13e}$
independently are hydrogen, halogen, optionally substituted $C_1$-$C_6$-alkyl, halogenated $C_1$-$C_6$-alkyl, CN, hydroxy, $C_1$-$C_6$-alkoxy, amino, $C_1$-$C_6$-alkylamino, di-$C_1$-$C_6$-alkylamino or $C_3$-$C_{12}$-heterocyclyl.

12. The compound as claimed in claim 1, which is:
1-[1-(4-Chlorophenyl)cyclobutyl]-1,2,3,4-tetrahydroisoquinoline-7-carbonitrile;
1-[2-(4-Chlorophenyl)propan-2-yl]-1,2,3,4-tetrahydroisoquinoline-7-carbonitrile; or
1-[1-(Pyridin-2-yl)cyclobutyl]-1,2,3,4-tetrahydroisoquinoline-7-carbonitrile.

13. A pharmaceutical composition which comprises a carrier and a compound of claim 1.

14. A method for treating a neurologic or psychiatric disorder in a mammalian patient in need thereof which comprises administering to the patient a therapeutically effective amount of a compound of claim 1, wherein the neurologic disorder is selected from the group consisting of dementia, cognitive impairment, and attention deficit disorder, and wherein the psychiatric disorder is selected from the group consisting of anxiety disorder, depression, bipolar disorder, schizophrenia, and psychosis.

15. A dihydroisoquinoline compound of the formula (II)

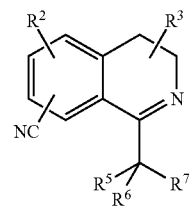

(II)

wherein
$R^2$ is hydrogen, halogen, $C_1$-$C_6$-alkyl, halogenated $C_1$-$C_4$-alkyl, hydroxy-$C_1$-$C_4$-alkyl, —CN, $C_2$-$C_6$-alkenyl, $C_2$-$C_6$-alkynyl, optionally substituted $C_6$-$C_{12}$-aryl, hydroxy, $C_1$-$C_6$-alkoxy, halogenated $C_1$-$C_6$-alkoxy, $C_2$-$C_6$-alkenyloxy, $C_6$-$C_{12}$-aryl-$C_1$-$C_4$-alkoxy, $C_1$-$C_6$-alkylcarbonyloxy, $C_1$-$C_6$-alkylthio, $C_1$-$C_6$-alkylsulfinyl, $C_1$-$C_6$-alkylsulfonyl, aminosulfonyl, amino, $C_1$-$C_6$-alkylamino, $C_2$-$C_6$-alkenylamino or optionally substituted $C_3$-$C_{12}$-heterocyclyl;
$R^3$ is hydrogen, halogen, $C_1$-$C_6$-alkyl or $C_1$-$C_6$-alkoxy, or two radicals $R^3$ together with the carbon atom to which they are attached form a carbonyl group;
$R^5$ is optionally substituted $C_1$-$C_6$-alkyl, $C_1$-$C_6$-alkylamino-$C_1$-$C_4$-alkyl, di-$C_1$-$C_6$-alkylamino-$C_1$-$C_4$-alkyl, $C_3$-$C_{12}$-heterocyclyl-$C_1$-$C_6$-alkyl, optionally substituted $C_6$-$C_{12}$-aryl or hydroxy;
$R^6$ is hydrogen, optionally substituted $C_1$-$C_6$-alkyl or hydroxy, or
$R^5$, $R^6$
together are carbonyl or optionally substituted $C_1$-$C_4$-alkylene, wherein one —$CH_2$— of $C_1$-$C_4$-alkylene may be replaced by an oxygen atom or —$NR^{12}$—;
$R^7$ is optionally substituted $C_6$-$C_{12}$-aryl, optionally substituted $C_3$-$C_{12}$-cycloalkyl or optionally substituted $C_3$-$C_{12}$-heterocyclyl; and
$R^{12}$ is hydrogen or $C_1$-$C_6$-alkyl;
or a physiologically tolerated salt thereof.

* * * * *